US010968277B2

(12) United States Patent
Reeves et al.

(10) Patent No.: US 10,968,277 B2
(45) Date of Patent: Apr. 6, 2021

(54) GENE SIGNATURES FOR DETERMINING ICOS EXPRESSION

(71) Applicant: Jounce Therapeutics, Inc., Cambridge, MA (US)

(72) Inventors: Jason Windham Reeves, Boston, MA (US); Igor Feldman, Jamaica Planin, MA (US); Christopher Harvey, Boston, MA (US); Sriram Sathyanarayanan, Lexington, MA (US); Heather Hirsch, Brookline, MA (US); Lauren Pepper MacKenzie, Cambridge, MA (US); Amit Deshpande, Cambridge, MA (US); Stephen Sazinsky, Melrose, MA (US); Jennifer S. Michaelson, Brighton, MA (US); Kutlu Goksu Elpek, Arlington, MA (US)

(73) Assignee: Jounce Therapeutics, Inc., Cambridge, MA (US)

( * ) Notice: Subject to any disclaimer, the term of this patent is extended or adjusted under 35 U.S.C. 154(b) by 341 days.

(21) Appl. No.: 15/767,172

(22) PCT Filed: Oct. 21, 2016

(86) PCT No.: PCT/US2016/058032
§ 371 (c)(1),
(2) Date: Apr. 10, 2018

(87) PCT Pub. No.: WO2017/070423
PCT Pub. Date: Apr. 27, 2017

(65) Prior Publication Data
US 2018/0371091 A1 Dec. 27, 2018

Related U.S. Application Data

(60) Provisional application No. 62/395,970, filed on Sep. 16, 2016, provisional application No. 62/359,069, filed on Jul. 6, 2016, provisional application No. 62/311,486, filed on Mar. 22, 2016, provisional application No. 62/245,180, filed on Oct. 22, 2015.

(51) Int. Cl.
| C07K 16/00 | (2006.01) |
| C12P 21/08 | (2006.01) |
| A61P 35/00 | (2006.01) |
| C07K 16/28 | (2006.01) |
| C12Q 1/6886 | (2018.01) |
| A61K 39/00 | (2006.01) |
| A61K 39/395 | (2006.01) |

(52) U.S. Cl.
CPC .......... *C07K 16/2818* (2013.01); *A61P 35/00* (2018.01); *C12Q 1/6886* (2013.01); *A61K 39/0011* (2013.01); *A61K 39/39558* (2013.01); *A61K 2039/505* (2013.01); *A61K 2039/507* (2013.01); *C07K 2317/20* (2013.01); *C07K 2317/24* (2013.01); *C07K 2317/33* (2013.01); *C07K 2317/73* (2013.01); *C07K 2317/75* (2013.01); *C07K 2317/76* (2013.01); *C07K 2317/92* (2013.01); *C12Q 2600/106* (2013.01); *C12Q 2600/158* (2013.01)

(58) Field of Classification Search
CPC ............ C07K 16/2818; C07K 2317/24; C07K 2317/33; C07K 2317/73; C07K 2317/75; C07K 2317/76; C07K 2317/92; A61P 35/00; C12Q 1/6886; C12Q 2600/106; C12Q 2600/158; A61K 39/0011
See application file for complete search history.

(56) References Cited

U.S. PATENT DOCUMENTS

| 6,051,227 | A | 4/2000 | Allison et al. |
| 6,521,749 | B1 | 2/2003 | Ling et al. |
| 6,808,710 | B1 | 10/2004 | Wood et al. |
| 6,984,720 | B1 | 1/2006 | Korman et al. |
| 7,132,099 | B2 | 11/2006 | Kroczek |
| 7,259,247 | B1 | 8/2007 | Kroczek |
| 7,521,051 | B2 | 4/2009 | Collins et al. |
| 7,595,048 | B2 | 9/2009 | Honjo et al. |
| 7,722,872 | B2 | 5/2010 | Kroczek |
| 8,017,114 | B2 | 9/2011 | Korman et al. |
| 8,168,179 | B2 | 5/2012 | Honjo et al. |
| 8,652,465 | B2 | 2/2014 | Freeman et al. |
| 8,709,417 | B2 | 4/2014 | Allison et al. |
| 8,728,474 | B2 | 5/2014 | Honjo et al. |
| 9,005,619 | B2 | 4/2015 | Kohrt et al. |
| 9,375,475 | B2 | 6/2016 | Allison et al. |
| 10,023,635 | B2 | 7/2018 | Sazinsky et al. |

(Continued)

FOREIGN PATENT DOCUMENTS

| EP | 2 796 465 A1 | 10/2014 |
| JP | 2006-265155 | 10/2006 |

(Continued)

OTHER PUBLICATIONS

Handbook of Chemistry and Physics, 49th Edition, 1968, Weast (ed.), The Chemical Rubber Co., Cleveland, Ohio, p. A-245.*

(Continued)

*Primary Examiner* — James Martinell
(74) *Attorney, Agent, or Firm* — McNeill Baur PLLC

(57) ABSTRACT

Gene expression signatures correlating to ICOS expression levels are provided. Methods of treatment comprising determining ICOS expression levels using gene signatures in patients and administering anti-ICOS antibodies are also provided.

21 Claims, 43 Drawing Sheets
Specification includes a Sequence Listing.

(56) References Cited

U.S. PATENT DOCUMENTS

| | | |
|---|---|---|
| 2003/0124149 A1 | 7/2003 | Shalaby et al. |
| 2005/0085433 A1 | 4/2005 | Breidenstein |
| 2007/0122378 A1 | 5/2007 | Freeman et al. |
| 2008/0069795 A1 | 3/2008 | Rabb |
| 2011/0275089 A1 | 11/2011 | Bogunovic et al. |
| 2012/0251556 A1 | 10/2012 | Allison |
| 2012/0321646 A1 | 12/2012 | Kohrt et al. |
| 2013/0058868 A1 | 3/2013 | Kroczek |
| 2013/0071409 A1 | 3/2013 | Riley et al. |
| 2013/0142783 A1 | 6/2013 | Coyle et al. |
| 2014/0086923 A1 | 3/2014 | Faget et al. |
| 2014/0314714 A1 | 10/2014 | Honjo et al. |
| 2015/0093380 A1 | 4/2015 | Honjo et al. |
| 2016/0304610 A1 | 10/2016 | Sazinsky et al. |

FOREIGN PATENT DOCUMENTS

| | | |
|---|---|---|
| WO | WO 91/10737 A1 | 7/1991 |
| WO | 2000032231 A1 | 6/2000 |
| WO | WO 2000/32231 | 6/2000 |
| WO | 2001014424 A2 | 3/2001 |
| WO | WO 2001/14557 A1 | 3/2001 |
| WO | WO 2002/00692 A2 | 1/2002 |
| WO | WO 2002/00730 A2 | 1/2002 |
| WO | WO 2004/004771 A1 | 1/2004 |
| WO | WO 2005/103086 A1 | 11/2005 |
| WO | WO 2006/133396 A2 | 12/2006 |
| WO | WO 2007/113648 A2 | 10/2007 |
| WO | WO 2008/137915 A2 | 11/2008 |
| WO | WO2011020024 | 2/2011 |
| WO | WO 2011/041613 A2 | 4/2011 |
| WO | WO 2012/131004 A2 | 10/2012 |
| WO | WO 2014/009535 A2 | 1/2014 |
| WO | WO 2014/151006 A2 | 9/2014 |
| WO | WO 2016/120789 A1 | 8/2016 |
| WO | WO2017070423 | 4/2017 |
| WO | WO2018187191 A1 | 10/2018 |

OTHER PUBLICATIONS

Ara et al., "Potent Activity of Soluble B7rp-1-Fc in Therapy of Murine Tumors in Syngeneic Hosts," Int. J. Cancer: 103, pp. 501-507 (2003).

Arimura et al., "A co-stimulatory molecule on activated T cells, H4/ICOS, delivers specific signals in $T_h$ and regulates their responses," International Immunology, vol. 4, No. 6, pp. 555-566 (2002).

Bakkour et al., "Mapping of the ICOS binding surface of murine B7h using an unbiased, cellular library of B7h mutants created by cyclical packaging rescue," Journal of Immunological Methods:332, pp. 151-161 (2008).

Beck et al., "Enterocolitis in Patients with Cancer After Antibody Blockade of Cytotoxic T-Lymphocyte-Associated Antigen 4" J Clin Oncol 24: pp. 2283-2289 (2006).

Beier et al., "Induction, binding specificity and function of human ICOS," Eur. J. Immunol: 30, pp. 3707-3717 (2000).

Bertino et al., "Roquin Paralogs Add a New Dimension to ICOS Regulation," Immunity 38, pp. 624-626 (Apr. 18, 2013).

Biolegend Product Data sheet: APC Anti-human/mouse/rat CD278 ICOS Antibody—C398.4A, pp. 1-4 (Oct. 29, 2014).

Biolegend Product Data Sheet: PE anti-human/mouse/rat CD278 (ICOS), 1 pg. (2013).

Blazar, B.R., "Infusion of anti-B7.1 (CD80) and anti-B7.2 (CD86) monoclonal antibodies inhibits murine graft-versus-host disease lethality in part via direct effects on CD4+ and CD8+ T cells," J. Immunol., 157(8): pp. 3250-3259 (1996).

Boon, T., et al., "Human T cell responses against melanoma," Annu. Rev. Immunol., 24: pp. 175-208 (2006).

Bruhns et al., "Specificity and affinity of human Fcgamma receptors and their polymorphic variants for human IgG subclasses," Blood 113: pp. 3716-25 (2009).

Callahan, M.K., et al., "Anti-CTLA-4 antibody therapy: Immune monitoring during clinical development of a novel immunotherapy," Semin. Oncol., 37(5): pp. 473-484 (2010).

Carlesso et al. "Arthritis & Rheumatism Abstract Supplement," The 2009 ACR/ARNP Annual Scientific Meeting, vol. 60, Philadelphia Oct. 16-21, 2009.

Carlesso, "Presentation: Memory T Lymphocytes Expressing the Inducible Costimulator (icos) Are Required to Maintain the Secondary Lymphoid Tissue Architecture In Non Human Primates," American College of Rheumatology Annual Scientific Meeting (2008).

Carthon et al., "Preoperative CTLA-4 Blockade: Tolerability and Immune Monitoring in the Setting of a Presurgical Clinical Trial," Clin Cancer Res; 16(10), pp. 2861-2871 (May 15, 2010).

Chattopadhyay et al., "Structural Basis of Inducible Costimulator Ligand Costimulatory Function: State and Functional Mapping of the Determination of the Cell Surface Oligomeric Receptor Binding Site of the Protein," J Immunol; 177:3920-3929 (2006).

Chen et al., "Anti-CTLA-4 therapy results in higher CD4+ICOS$^{hi}$ T cell frequency and IFN-γ levels in both nonmalignant and malignant prostate tissues," PNAS: vol. 106, No. 8, pp. 2729-2734 (Feb. 24, 2009).

Chen et al., "CD4 T Cells Require ICOS-Mediated PI3K Signaling to Increase T-Bet Expression in the Setting of Anti-CTLA-4 Therapy," Cancer Immunol Res; 2(2), pp. 167-176 (Feb. 2013).

Chevalier et al., "CXCR5 expressing human central memory CD4 T cells and their relevance for humoral immune responses," J Immunol 186:5556-68 (2011).

Chowdhury et al., "Ex vivo assays of dendritic cell activation and cytokine profiles as predictors of in vivo effects in an anti-human CD40 monoclonal antibody ChiLob 7/4 phase I trial," Cancer immunol Res 2:229-40 (2014).

Conrad, C., et al., "Plasmacytoid dendritic cells promote immunosuppression in ovarian cancer via ICOS costimulation of Foxp3(+) T-regulatory cells," Cancer Res., 72(20): 5240-5249 (2012).

Conrad and Gilliet "Plasmacytoid dendritic cells and regulatory T cells in the tumor microenvironment: A dangerous liaison," Oncoimmunology 2:e23887 (2013).

Das et al., "Combination therapy with anti-CTLA-4 and anti-PD-1 leads to distinct immunologic changes in vivo" J Immunol 194:950-9 (2015).

De Jong et al., "Blocking inducible co-stimulator in the absence of CD28 impairs $T_h1$ and CD25+regulatory T cells in murine colitis," International Immunology, vol. 16, No. 2, pp. 205-213 (2004).

Deng et al., "An Agonist Human ICOS Monoclonal Antibody that Induces T Cell Activation and Inhibits Proliferation of a Myeloma Cell Line," Hybridoma and Hybridomics, vol. 23, No. 3 pp. 176-182 (2004).

Di Giacomo, A.M., et al., "Long-Term Survival and Immunogical Parameters in Metastatic Melanoma Patients Who Responded to Ipilimumab 10 mg/kg Within an Expanded Access Programme," Cancer Immunol. Immunother., 62(6): 1021-1028 (2013).

Dianzani, C., et al., "B7h Triggering Inhibits the Migration of Tumor Cell Lines," J. Immuno., 192(10): 4921-4931 (2014).

Dong et al. "Tumor-associated B7-H1 promotes T-cell apoptosis: A potential mechanism of immune evasion," 8 Nature Medicine 793 (Aug. 2002) (published online Jun. 24, 2002).

Driessens et al., "Costimulatory and coinhibitory receptors in anti-tumor immunity," Immunological Reviews, vol. 229(1): pp. 126-144 (2009).

EP 10821297.8 Supplementary European Search Report dated Jul. 9, 2013.

Faget et al., "ICOS is associated with poor prognosis in breast cancer as it promotes the amplification of immunosuppressive CD4+ T cells by plasmacytoid dendritic cells," OncoImmunology 2:3, p. e23185; (Mar. 2013).

Faget et al., "ICOS-ligand expression on plasmacytoid dendritic cells supports breast cancer progression by promoting the accumulation of immunosuppressive CD4+ T cells," Cancer Research, vol. 72, No. 23, pp. 6130-5141 (Dec. 1, 2012).

Fan et al., "Engagement of the ICOS pathway markedly enhances efficacy of CTLA-4 blockade in cancer immunotherapy," J. Exp Med. 11 pgs. (2014), vol. 211, No. 4, pp. 715-725.

(56) References Cited

OTHER PUBLICATIONS

Freeman et al., "Engagement of the PD-1 Immunoinhibitory Receptor by a Novel B7 Family Member Leads to Negative Regulation of Lymphocyte Activation," 192 J. Exp. Med. 1027 (Oct. 2, 2000).
Fu, T., et al., "The ICOS/ICOSL Pathway is Required for Optimal Antitumor Responses Mediated by Anti-CTLA-4 Therapy," Cancer Res., 71, 5445-5454 (2011).
Garon et al., "Pembrolizumab for the treatment of non-small-cell lung cancer," N Engl J Med 372:2018-28 (2015).
Gillis et al., "Contribution of Human FcγRs to Disease with Evidence from Human Polymorphisms and Transgenic Animal Studies," Front Immunol 5:254 (2014).
Greenwald, R.J. et al. "The B7 Family Revisited," Ann. Rev. Immunol., 23:515-48 (2005).
Guedan et al., "ICOS-based chimeric antigen receptors program bipolar TH17/TH1 cells," Blood 124:1070-80 (2014).
Gustafson et al., "Immune monitoring using the predictive power of immune profiles" J Immunother Cancer 1:7 (2013).
Guo et al., "Prolonged Survival in Rat Liver Transplantation with Mouse Monoclonal Antibody Against an Inducible Costimulator (ICOS)," Transplantation, vol. 73: 7, pp. 1027-1032 (Apr. 15, 2002).
Harada et al., "A Single Amino Acid Alteration in Cytoplasmic Domain Determines IL-2 Promoter Activation by Ligation of CD28 but Not Inducible Costimulator (ICOS)," J. Exp. Med., vol. 197, No. 2, pp. 257-262 (Jan. 20, 2003).
Harada et al., "The role of the ICOS-B7h T cell costimulatory pathway in transplantation immunity," The Journal of Clinical Investigation, vol. 112, No. 2, pp. 234-243 (Jul. 2003).
Heissmeyer et al., "Molecular control of Tfh-cell differentiation by Roquin family Proteins," Immunological Reviews vol. 253: pp. 273-289 (2013).
Hirsch et al., "Molecular characterization of mouse syngeneic tumor models in response totreatment with anti-PD-1 immunotherapy" Cancer Res 75:1328 (2015).
Hu et al., "Noncanonical NF-κB regulates inducible costimulatory (ICOS) ligand expression and T follicular helper cell development," PNAS, vol. 8, No. 31, pp. 12827-12832 (Aug. 2, 2011).
Huang, Z., "Structural chemistry and therapeutic intervention of protein-protein interactions in immune response, human immunodeficiency virus entry, and apoptosis," Pharmacol. Ther., 86(3): 201-215 (2000).
Hutloff et al., "ICOS is an inducible T-cell co-stimulator structurally and functionally related to CD28," Nature 397, pp. 263-266 (1999).
Inman, B.A., et al., "Costimulation, Coinhibition and Cancer," Curr. Can. Drug. Targets, 7(1): 15-30 (2007).
International Search Report and Written Opinion of International Application No. PCT/US2016/023524 dated Dec. 15, 2016 (17 pages).
International Search Report and Written Opinion of International Application No. PCT/US2016/058032 dated Feb. 13, 2017 (20 pages).
Iwai, Y. et al., "Involvement of PD-L1 on tumor cells in the escape from host immune system and tumor immunotherapy by PD-L1 blockade", PNAS, 99 (19):12293-12297 (2002).
Kawamoto et al., "Expression and function of inducible co-stimulator in patients with systemic lupus erythematosus: possible involvement in excessive interferon-gamma and anti-double-stranded DNA antibody production," Arthristis Res Ther. 8:R62 (2006).
Keler et al., "Activity and safety of CTLA-4 blockade combined with vaccines in cynomolgus macaques," J Immunol 171:6251-9 (2003).
Khalil et al., "The future of cancer treatment: immunomodulation, CARs and combination immunotherapy" Nat Rev Clin Oncol 13: (2016), pp. 273-290.
Khayyamian et al. "ICOS-ligand, expressed on human endothelial cells, costimulates Th1 and Th2 cytokine secretion by memory CD4+ T cells," PNAS; vol. 99, No. 9 pp. 6198-6203 (Apr. 30, 2002).

Kosuge et al., "Induction Of Immunologic Tolerance To Cardiac Allograft By Simultaneous Blockade Of Inducible Co-Stimulator And Cytotoxic T-Lymphocyte Antigen 4 Pathway," Transplantation, vol. 75, pp. 374-1379, No. 8 (Apr. 27, 2003).
Lambert et al., "Immunomodulatory effects of OX40 agonists in a defined antigen challenge incynomolgus macaques," J Clin Oncol 33, (2015) (suppl; abstr 3086).
Latchman et al., "PD-L2 is a second ligand for PD-1 and inhibits T cell activation," 2 Nature Immunology 261 (Mar. 2001), vol. 2, No. 3.
Lee, K.H., et al., "Increased vaccine-specific T cell frequency after peptide-based vaccination correlates with increased susceptibility to in vitro stimulation but does not lead to tumor regression," J. Immunol., 163(11): 6292-6300 (1999).
Leavenworth et al., "A p85a-osteopontin axis couples the receptor ICOS to sustained Bcl-6 expression by follicular helper and regulatory T cells," Nat Immunol. 16:96-106 (2015).
Liakou et al., "CTLA-4 blockade increases IFNγ-producing CD4+ ICOS$^{hi}$ cells to shift the ratio of effector to regulatory T cells in cancer patients," PNAS, vol. 105, No. 39, pp. 14987-14992 (Sep. 30, 2008).
Ling et al., "Differential Expression of Inducible Costimulator-Ligand Splice Variants: Lymphoid Regulation of Mouse GL50-B and Human GL50 Molecules," J Immunol; 166, pp. 7300-7308 (2001).
Lischke, T., et al., "Comprehensive Analysis of CD4+ T Cells in the Decision Between Tolerance and Immunity In Vivo Reveals a Pivotal Rolse for ICOS," J. Immunol., 1-11 (2012).
Liu et al., "T-B-cell entanglement and ICOSL-drivenfeed-forward regulation of germinal centre reaction," Nature 517:214-218 (2015).
Liu et al., "B7H Costimulates Clonal Expansion of, and Cognate Destruction of Tumor Cells by, CD8+ T Lymphocytes In Vivo," J. Exp. Med., vol. 194, No. 9, pp. 1339-1349 (Nov. 5, 2001).
Lo et al., "A pilot trial targeting the ICOS-ICOS-L pathway in nonhuman primate kidney transplantation," Am J Transplant. 15:984-92 (2015).
Mages et al., "Molecular cloning and characterization of murine ICOS and identification of B7h as ICOS ligand," Eur. J. Immunol. 2000. 30: 1040-1047.
McArthur et al., "A Pilot Study of Preoperative Single-Dose Ipilimumab and/or Cryoablation in Women with Early-Stage Breast Cancer with Comprehensive Immune Profiling," Clin Cancer Res. 22:5729-5737 (2016).
Mandl et al., "Elucidating immunologic mechanisms of PROSTVAC cancer immunotherapy," J Immunother Cancer 2:34 (2014).
Martin-Orozco, N., et al., "Melanoma Cells Express ICOS Ligand to Promote the Activation and Expansion of T-Regulatory Cells," Cancer Res., 70(23): 9581-9590 (2010).
Matthews et al., "Clinical Trials of Transplant Tolerance: Slow But Steady Progress," American Journal of Transplantation 2003; 3: 794-803.
Mcadam et al., "Mouse Inducible Costimulatory Molecule (ICOS) Expression Is Enhanced by CD28 Costimulation and Regulates Differentiation of CD4 + T Cells," J Immunol 2000; 165: pp. 5035-5040 (2000).
Michot et al., "Immune-related adverse events with immune checkpoint blockade: a comprehensive review," Eur J Cancer 54:139-48 (2016).
Murphy et al., "Anaphylaxis caused by repetitive doses of a GITR agonist monoclonal antibody in mice," Blood 123:2172-80 (2014).
Nabeyama et al., "Beneficial Effects of Costimulatory Blockade with Anti-Inducible Costimulator Antibody in Conjunction with CTLA4Ig on Prevention of Islet Xenograft Rejection from Rat to Mouse," Transplantation, vol. 78, No. 11, pp. 1590-1596 (Dec. 15, 2004).
Nakamura et al., "Acceptance of Islet Allografts in the Liver of Mice by Blockade of an Inducible Costimulator," Transplantation, vol. 75, No. 8, pp. 1115-1118 (Apr. 27, 2003).
Nanji, S.A., "Multiple Combination Therapies Involving Blockade of ICOS/B7RP-1 Costimulation Facilitate Long-Term Islet Allograft Survival," Am J of Transplantation, 4:526-536 (2004).

(56) References Cited

OTHER PUBLICATIONS

Nelson et al., "The Inducible Costimulator Augments Tc17 Cell Responses to Self and Tumor Tissue," J Immunol. 194:1737-47 (2015).
Newman et al., "Robust enumeration of cell subsets from tissue expression profiles," Nat Methods 12:453-7 (2015).
Nielsen, M.B. and Marincola, F.M., "Melanoma vaccines: the paradox of T cell activation without clinical response," Cancer Chemother. Pharmacol., 46 (Suppl.): S62-S66 (2000).
Nurieva et al., "B7h is required for T cell activation, differentiation, and effector function," PNAS, vol. 100, No. 24, pp. 14163-14168 (Nov. 25, 2003).
Ogasawara et al., "Inducible costimulator costimulates cytotoxic activity and IFN-gamma production in activated murine NK cells," J Immunol. 169:3676-85 (2002).
Okano, K. et al. "Effects of double blockade of CD28 and inducible costimulator signaling on anti-glomerular basement membrane glomerulonephritis," J Lab Clin Med, 144:183-192 (2004).
Opdivo Prescribing Information, Food and Drug Administration Sep. 2015.
Ozkaynak et al., "Importance of ICOS-B7RP-I costimulation in acute and chronic allograft rejection," vol. 2, No. 7, pp. 591-596 (Jul. 2001).
Pasero et al., "The HVEM network: new directions in targeting novel costimulatory/co-inhibitory molecules for cancer therapy," Pharmacology, 12 pp. 478-485 (2012).
PCT/US2010/051008 International Preliminary Report on Patentability, dated Apr. 3, 2012.
PCT/US2010/051008 Transmittal of the International Search Report and the Written Opinion of the International Searching Authority, dated Jun. 16, 2011.
Peggs, K.S., et al., "Principles and Use of Anti-CTLA4 Antibody in Human Cancer Immunotherapy," Curr. Op. Immun., 18(2): 206-213 (2006).
Pimenta and Barnes "Role of Tertiary Lymphoid Structures (TLS) in Anti-Tumor Immunity: Potential Tumor-Induced Cytokines/ Chemokinesthat Regulate TLS Formation in Epithelial-Derived Cancers," Cancers 6:969-997 (2014).
Pot et al., "Cutting edge: IL-27 induces the transcription factor c-Maf, cytokine IL-21, and the costimulatory receptor ICOS that coordinately act together to promote differentiation of IL-10-producing Tr1 cells," J Immunol. 183:797-801 (2009).
Redmond et al., "Combined targeting of costimulatory (OX40) and coinhibitory (CTLA-4) pathways elicits potent effector T cells capable of driving robust antitumor immunity" Cancer Immunol Res 2:142-53 (2014).
Ribas et al., Association of response to programmed death receptor 1 (PD-1) blockade with pembrolizumab (MK-34 75) with an interferon-inflammatory immune gene signature, J Clin Oncol 33 (2015) Suppl: abstr 2001.
Riley et al., "Modulation of TCR-induced transcriptional profiles by ligation of CD28, ICOS, and CTLA-4 receptors," PNAS, vol. 99, No. 18, pp. 11790-11795 (Sep. 3, 2002).
Riley et al., "The CD28 family: a T-cell rheostat for therapeutic control of T-cell activation," Blood, vol. 105, No. 1, pp. 13-21 (Jan. 1, 2005).
Rooney et al., "Molecular and genetic properties of tumors associated with local immune cytolytic activity" Cell 160:48-61 (2015).
Roy et al., "NK cells lyse T regulatory cells that expand in response to an intracellular pathogen" J Immunol 180:1729-36 (2008).
Rottman, J.B., et al., "The costimulatory molecule ICOS plays an important role in the immunopathogenesis of EAE," Nat. Immunol., 2(7): 605-611 (2001).
Sakthivel et al., "Attenuation of Immune-Mediated Influenza Pneumonia by Targeting the Inducible Co-Stimulator (ICOS) Molecule on T Cells," PLOS One, vol. 9, Issue 7, 11 pages (Jul. 2014).
Sanmamed et al., "Agonists of Co-stimulation in Cancer Immunotherapy Directed Against CD137, OX40, GITR, CD27, CD28, and ICOS" Semin Oncol 42:640-55 (2015).

Schadendorf, D., et al., "Immunotherapy of distant metastatic disease," Ann. Oncol., 20 Supp. 6, vi41-vi50 (2009).
Schreiner et al., "Expression of the B7-Related Molecule ICOSL by Human Glioma Cells in Vitro and in Vivo," GLIA, 44, pp. 296-301 (2003).
Sim, G.C., et al., "IL-2 Therapy Promotes Suppressive ICOS+ Treg Expansion in Melanoma Patients," J. Clin. Invest., 124(1): 1-12 (2014), downloaded Dec. 9, 2013.
Simpson et al., "Regulation of CD4 T cell activation and effector function by inducible costimulator (ICOS)," Immunology 22 pp. 326-332 (2010).
Smigiel et al., "CCR7 provides localized access to IL-2 and defines homeostatically distinct regulatory T cell subsets," J. Exp. Med., vol. 211 No. 1 pp. 121-136. (2014).
Strauss et al., "Expression of ICOS on human melanoma-infiltrating CD4+CD25highFoxp3+ T regulatory cells: implications and impact on tumor-mediated immune suppression," J Immunol 180:2967-80 (2008).
Suntharalingam et al., "Cytokine Storm in a Phase 1 Trial of the Anti-CD28 Monoclonal Antibody TGN1412," New England Journal of Medicine, 355;10 pp. 1018-1028 (Sep. 7, 2006).
Swallow et al., "B7h, a Novel Costimulatory Homolog of B7.1 and B7.2, Is Induced by TNF α," Immunity, vol. 11, pp. 423-432, (Oct. 1999).
Tajima et al, "JTA-009, a fully human antibody against human AILIM/ICOS, ameliorates graft-vs-host reaction in SCID mice grafted with human PBMCs," Experimental Hematology; 36: pp. 1514-1523 (2008).
Tajima et al., "Critical role of activation-inducible lymphocyte immunomediatory molecule/inducible costimulatory in the effector function of human T cells: A comparative in vitro study of effects of its blockade and CD28 blockade in human beings and monkeys," Human Immunology 69, pp. 399-408 (2008).
Tamura, H., et al., "B7-H1 costimulation preferentially enhances CD28-independent T-helper cell function," Blood, 97(6): 1809-1816 (2001).
Tang, D.N., et al., "Increased Frequency of ICOS+ CD4 T-Cells as a Pharmacodynamic Biomarker for Anti-CTLA-4 Therapy," Cancer Immunol. Res., 2013, vol. 1, No. 4, pp. 229-234.
Tiriveedhi et al., "Mammaglobin-A cDNA vaccination of breast cancer patients induces antigen-specific cytotoxic CD4+ICOShi T cells" Breast cancer Res Treat, 138:109 (2013).
Topalian et al., "Safety, activity, and immune correlates of anti-PD-1 antibody in cancer," N Engl J Med 366:2443-54 (2012).
Van Berkel et al., "ICOS Contributes to T Cell Expansion in CTLA-4 Deficient Mice," J Immunol 2005; 175: pp. 182-188 (2005).
Vesosky, B., et al., "Modulation of Costimulation to Enhance Tumor Immunity," Cancer Immuno. Immunother., 52(11): 663-669 (2003).
Villadolid and Amin "Immune checkpoint inhibitors in clinical practice: update on management of immune-related toxicities" Trans! Lung Cancer Res 4:560-75 (2015).
Wahl et al., "Interaction of B7RP-1 with ICOS Negatively Regulates Antigen Presentation by B Cells," Inflammation, vol. 27, No. 4, pp. 191-201 (Aug. 2003).
Waibler et al., "Signaling signatures and functional properties of anti-human CD28 superagonistic antibodies," PLoS One 3:e1708 (2008).
Wallin et al., "Enhancement of CD8+ T Cell Responses by ICOS/ B7h Costimulation," J Immunol, 167:132-139 (2001).
Wang et al., "Biomarkers on melanoma patient T Cells associated with ipilimumab treatment," Journal of Translational Medicine: 10:146 (2012).
Wang et al., "Ligand Binding Sites of Inducible Costimulator and High Avidity Mutants with Improved Function," J. Exp. Med, vol. 195, No. 8, pp. 1033-1041 (Apr. 15, 2002).
Wang, S., et al., "Costimulation of T cells by B7-H2, a B7-like molecule that binds ICOS," Blood, 96(8): 2808-2813 (2000).
Ward, R.C. and Kaufman, H.L. "Targeting Costimulatory Pathways for Tumor Immunotherapy," International Reviews of Immunol., 26:161-196 (2007).

(56) References Cited

OTHER PUBLICATIONS

Watanabe et al., "A distinct role for ICOS-mediated co-stimulatory signaling in CD41 and CD81 T cell subsets," international Immunology, vol. 17, No. 3, pp. 269-278 (2005).
Watanabe et al., "Grb2 and Gads exhibit different interations with CD28 and play distinct roles in CD28-mediated costimulation," J. Immunol., 177:1085-1091 (2006).
Weber et al., "Management of immune-related adverse events and kinetics of response with ipilimumab" J Clin Oncol 30:2691-7 (2012).
Weber et al., "Toxicities of Immunotherapy for the Practitioner" J Clin Oncol 33:2092-9 (2015).
Weber et al., "Randomized phase I pharmacokinetic study of ipilimumab with or without one of two different chemotherapy regimens in patients with untreated advanced melanoma" Cancer Immunity 13:7-16 (2013).
Weng et al., "Costimulation of T cells by B7-H2, a B7-like molecule that binds ICOS," Blood, vol. 96, No. 8, pp. 2808-2813 (2000).
Wiendl et al., "Human muscle cells express a B7-related molecule, B7-H1, with strong negative immune regulatory potential: a novel mechanism of counterbalancing the immune attack in idiopathic inflammatory myopathies," The FASEB Journal express article 10.1096/fj.03-0039fje, (Aug. 15, 2003).
Winoto, A., and Littman, D.R., "Nuclear hormone receptors in T lymphocytes," Cell, 109 Suppl:S57-66 (2002).
Xu et al., "Follicular T-helper cell recruitment governed by bystander B cells and ICOS-driven motility," Nature, vol. 496, pp. 523-529 (Apr. 25, 2013).
Yagi et al., "Regulatory Roles of IL-2 and IL-4 in H4/Inducible Costimulator Expression on Activated CD4+ T Cells During Th Cell Development," J Immunol; 171, pp. 783-794 (2003).
Yao et al., "B7-H2 is a costimulatory ligand for CD28 in human," Immunity: 34(5): pp. 729-740 (May 27, 2011).
Yoshinaga et al., "Characterization of a new human B7-related protein: B7RP-1 is the ligand to co-stimulatory protein ICOS," International Immunology, vol. 12, No. 10, pp. 1439-1447 (2000).
Yoshinaga et al., "T-cell co-stimulation through B7RP-1 and ICOS," Nature, vol. 402, pp. 827-832 (Dec. 16, 1999).
Zang, X. and Allison, J.P., "The B7 Family and Cancer Therapy: Costimulation and Coinhibition," Clin. Can. Res., 13(18): 5271-5279 (2007).
Zhang et al., "The clinical impact of ICOS signal in colorectal cancer patients," Oncoimmunology 5:e1141857 (2016).
Zheng et al., "ICOS Regulates the Generation and Function of Human CD4+ Treg in a CTLA-4 Dependent Manner," PLOS One, vol. 8, Issue. 12 (Dec. 2013).
Zuberek et al., "Comparable in vivo efficacy of CD28/B7, ICOS/GL50, and ICOS/GL50B costimulatory pathways in murine tumor models: IFNc-dependent enhancement of CTL priming, effector functions, and tumor specific memory CTL," Cellular Immunology 225, pp. 53-63 (2003).
Extended European Search Report issued in European Application No. EP16769535 dated Apr. 4, 2018 (10 pages).
LEAF™ Purified anti-mouse CD278 (ICOS) Antibody, 7E.17G9, Nov. 30, 2012 (4 pages).
Michaelson J., Preclinical Assessment of JTX-2011, An Agonist Antibody Targeting ICOS, Supports Evaluation in ICONIC Clinical Trial, ACCR Annual Meeting, Apr. 2, 2017 (28 pages).
Clinicaltrials.Gov, "NCTO2904226: Dose Escalation and Expansion of JTX-2011 Alone or in Combination with Anti-PD-1 in Subjects with Advanced Solid Tumors," Jan. 27, 2017 (10 pages).
Burris et al., "Phase 1 Safety of ICOS Agonist Antibody JTX-2011 Alone and with Nivolumab (NIVO) in Advanced Solid Tumors; Predicted vs. Observed Pharmacokinetics (PK) in Iconic," Abstract No. 192770, Jun. 5, 2017.
Search Results under Rule 164(2)(b) EPC issued in European Application No. 16791734.3 dated Jul. 10, 2019, 3 pages.
Deng et al., Structural interaction fingerprint (SIFt): a novel method for analyzing three-dimensional protein-ligand binding interactions, J. Med. Chem., Jan. 15, 2004: 47(2), pp. 337-344.

\* cited by examiner

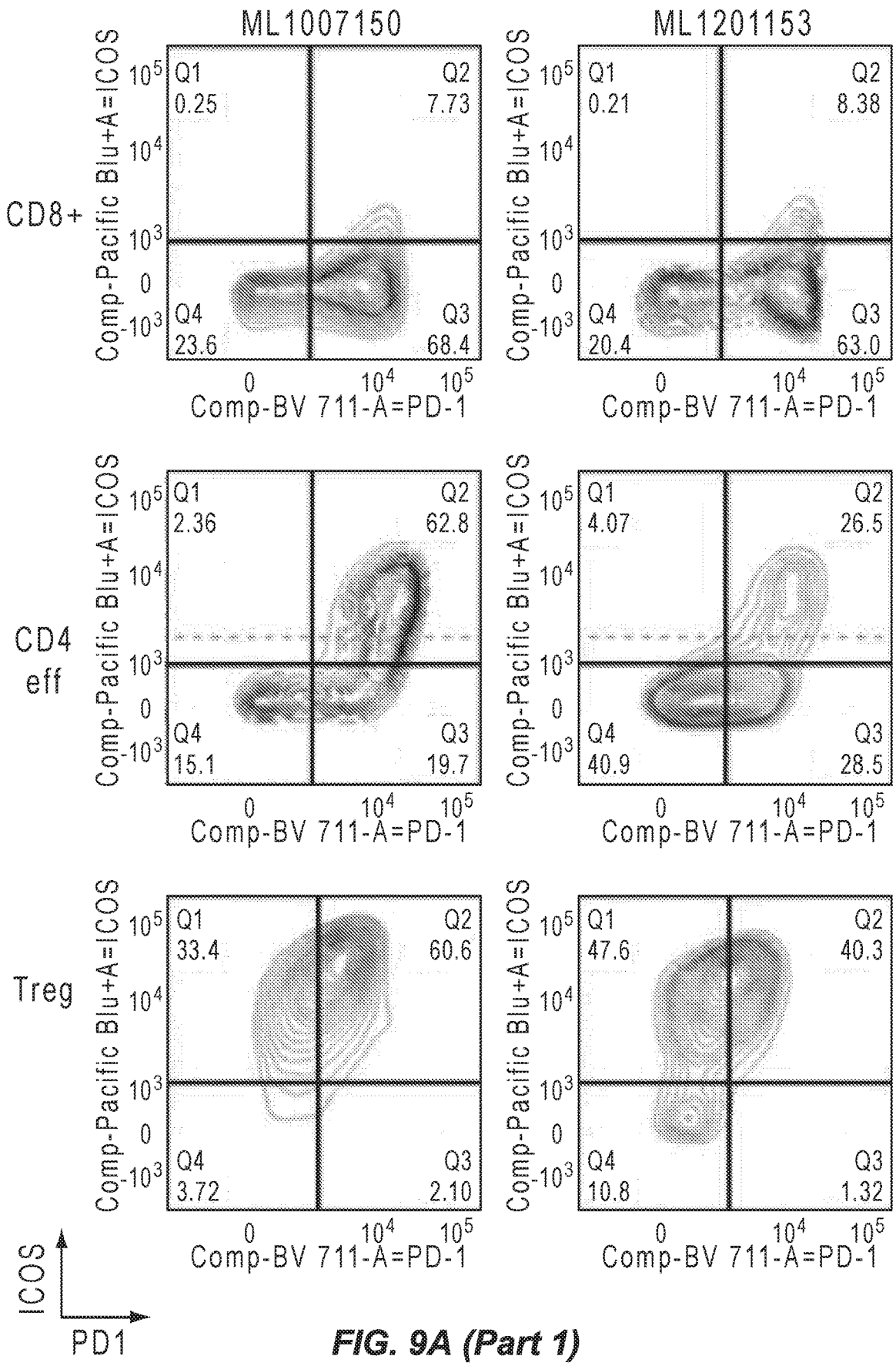
FIG. 9A (Part 1)

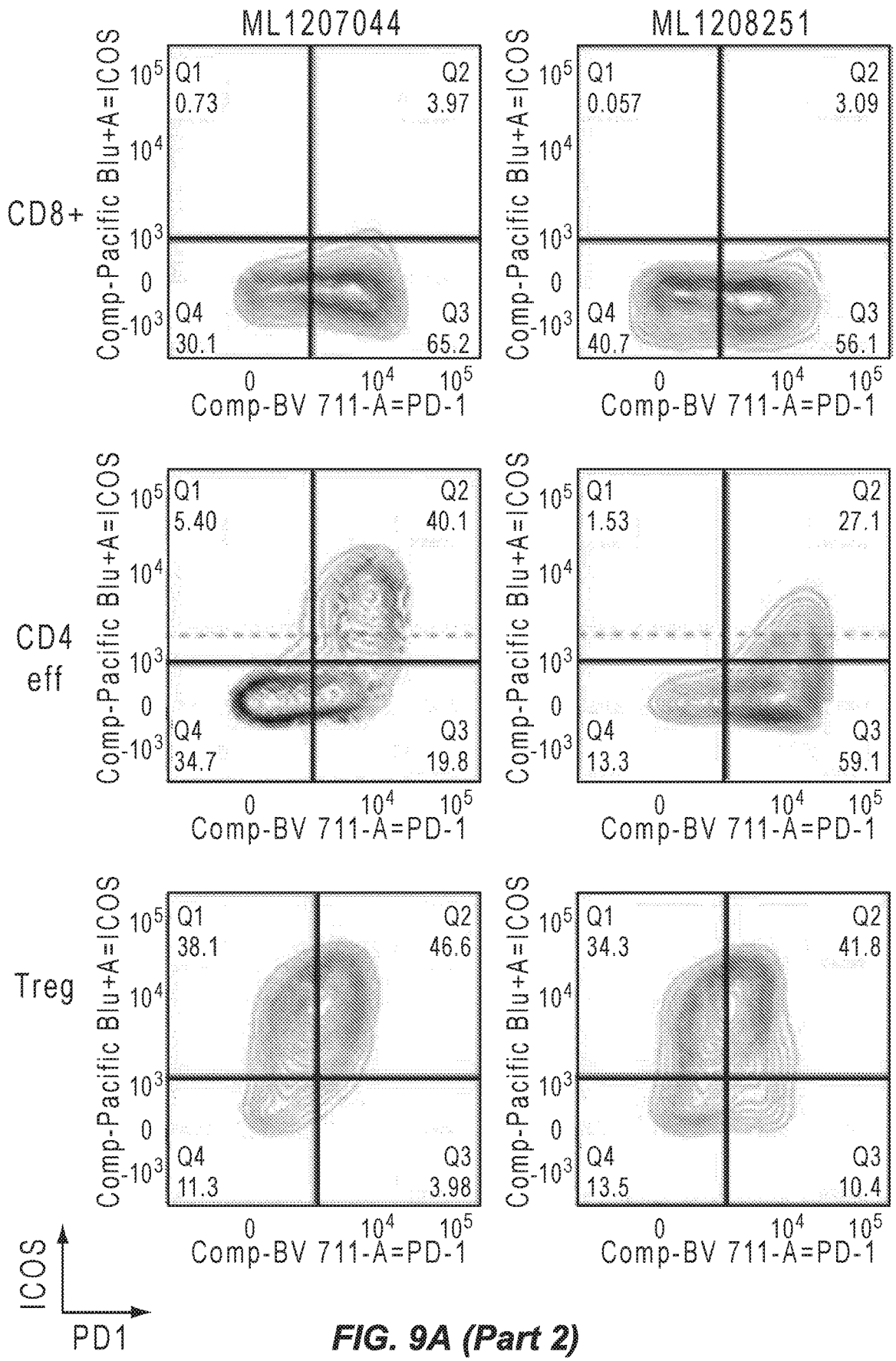
FIG. 9A (Part 2)

SEQUENCE LISTING

<160> NUMBER OF SEQ ID NOS: 215

<210> SEQ ID NO 1
<211> LENGTH: 199
<212> TYPE: PRT
<213> ORGANISM: Homo sapiens

<400> SEQUENCE: 1

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

-continued

Gln Gln Phe Lys Met Gln Leu Leu Lys Gly Gly Gln Ile Leu Cys Asp
       50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
              100                 105                 110

Ile Phe Asp Pro Pro Pro Phe Lys Val Thr Leu Thr Gly Gly Tyr Leu
              115                 120                 125

His Ile Tyr Glu Ser Gln Leu Cys Cys Gln Leu Lys Phe Trp Leu Pro
       130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Ser Val His Asp Pro
              165                 170                 175

Asn Gly Glu Tyr Met Phe Met Arg Ala Val Asn Thr Ala Lys Lys Ser
              180                 185                 190

Arg Leu Thr Asp Val Thr Leu
              195

<210> SEQ ID NO 2
<211> LENGTH: 179
<212> TYPE: PRT
<213> ORGANISM: Homo sapiens

<400> SEQUENCE: 2

Glu Ile Asn Gly Ser Ala Asn Tyr Glu Met Phe Ile Phe His Asn Gly
1               5                  10                  15

Gly Val Gln Ile Leu Cys Lys Tyr Pro Asp Ile Val Gln Gln Phe Lys
              20                  25                  30

Met Gln Leu Leu Lys Gly Gly Gln Ile Leu Cys Asp Leu Thr Lys Thr
          35                  40                  45

Lys Gly Ser Gly Asn Thr Val Ser Ile Lys Ser Leu Lys Phe Cys His
      50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
              100                 105                 110

Ser Gln Leu Cys Cys Gln Leu Lys Phe Trp Leu Pro Ile Gly Cys Ala
          115                 120                 125

Ala Phe Val Val Cys Ile Leu Gly Cys Ile Leu Ile Cys Trp Leu
      130                 135                 140

Thr Lys Lys Lys Tyr Ser Ser Ser Val His Asp Pro Asn Gly Glu Tyr
145                 150                 155                 160

Met Phe Met Arg Ala Val Asn Thr Ala Lys Lys Ser Arg Leu Thr Asp
              165                 170                 175

Val Thr Leu

<210> SEQ ID NO 3
<211> LENGTH: 200
<212> TYPE: PRT
<213> ORGANISM: Mus musculus

```
<400> SEQUENCE: 3

Met Lys Pro Tyr Phe Cys Arg Val Phe Val Phe Cys Phe Leu Ile Arg
1               5                   10                  15

Leu Leu Thr Gly Glu Ile Asn Gly Ser Ala Asp His Arg Met Phe Ser
            20                  25                  30

Phe His Asn Gly Gly Val Gln Ile Ser Cys Lys Tyr Pro Glu Thr Val
        35                  40                  45

Gln Gln Leu Lys Met Arg Leu Phe Arg Glu Arg Glu Val Leu Cys Glu
    50                  55                  60

Leu Thr Lys Thr Lys Gly Ser Gly Asn Ala Val Ser Ile Lys Asn Pro
65                  70                  75                  80

Met Leu Cys Leu Tyr His Leu Ser Asn Asn Ser Val Ser Phe Phe Leu
                85                  90                  95

Asn Asn Pro Asp Ser Ser Gln Gly Ser Tyr Tyr Phe Cys Ser Leu Ser
            100                 105                 110

Ile Phe Asp Pro Pro Pro Phe Gln Glu Arg Asn Leu Ser Gly Gly Tyr
        115                 120                 125

Leu His Ile Tyr Glu Ser Gln Leu Cys Cys Gln Leu Lys Leu Trp Leu
    130                 135                 140

Pro Val Gly Cys Ala Ala Phe Val Val Leu Leu Phe Gly Cys Ile
145                 150                 155                 160

Leu Ile Ile Trp Phe Ser Lys Lys Lys Tyr Gly Ser Ser Val His Asp
                165                 170                 175

Pro Asn Ser Glu Tyr Met Phe Met Ala Ala Val Asn Thr Asn Lys Lys
            180                 185                 190

Ser Arg Leu Ala Gly Val Thr Ser
        195                 200

<210> SEQ ID NO 4
<211> LENGTH: 180
<212> TYPE: PRT
<213> ORGANISM: Mus musculus

<400> SEQUENCE: 4

Glu Ile Asn Gly Ser Ala Asp His Arg Met Phe Ser Phe His Asn Gly
1               5                   10                  15

Gly Val Gln Ile Ser Cys Lys Tyr Pro Glu Thr Val Gln Gln Leu Lys
            20                  25                  30

Met Arg Leu Phe Arg Glu Arg Glu Val Leu Cys Glu Leu Thr Lys Thr
        35                  40                  45

Lys Gly Ser Gly Asn Ala Val Ser Ile Lys Asn Pro Met Leu Cys Leu
    50                  55                  60

Tyr His Leu Ser Asn Asn Ser Val Ser Phe Phe Leu Asn Asn Pro Asp
65                  70                  75                  80

Ser Ser Gln Gly Ser Tyr Tyr Phe Cys Ser Leu Ser Ile Phe Asp Pro
                85                  90                  95

Pro Pro Phe Gln Glu Arg Asn Leu Ser Gly Gly Tyr Leu His Ile Tyr
            100                 105                 110

Glu Ser Gln Leu Cys Cys Gln Leu Lys Leu Trp Leu Pro Val Gly Cys
        115                 120                 125

Ala Ala Phe Val Val Leu Leu Phe Gly Cys Ile Leu Ile Ile Trp
    130                 135                 140

Phe Ser Lys Lys Lys Tyr Gly Ser Ser Val His Asp Pro Asn Ser Glu
145                 150                 155                 160
```

Tyr Met Phe Met Ala Ala Val Asn Thr Asn Lys Lys Ser Arg Leu Ala
                165                 170                 175

Gly Val Thr Ser
            180

<210> SEQ ID NO 5
<211> LENGTH: 199
<212> TYPE: PRT
<213> ORGANISM: Macaca fascicularis

<400> SEQUENCE: 5

Met Lys Ser Gly Leu Trp Tyr Phe Phe Leu Phe Cys Leu His Met Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Lys Val Ser Ile Lys Ser Leu
65                  70                  75                  80

Lys Phe Cys His Ser Gln Leu Ser Asn Ser Val Ser Phe Phe Leu
                85                  90                  95

Tyr Asn Leu Asp Arg Ser His Ala Asn Tyr Tyr Phe Cys Asn Leu Ser
                100                 105                 110

Ile Phe Asp Pro Pro Phe Lys Val Thr Leu Thr Gly Gly Tyr Leu
            115                 120                 125

His Ile Tyr Glu Ser Gln Leu Cys Cys Gln Leu Lys Phe Trp Leu Pro
        130                 135                 140

Ile Gly Cys Ala Thr Phe Val Val Cys Ile Phe Gly Cys Ile Leu
145                 150                 155                 160

Ile Cys Trp Leu Thr Lys Lys Lys Tyr Ser Ser Thr Val His Asp Pro
                165                 170                 175

Asn Gly Glu Tyr Met Phe Met Arg Ala Val Asn Thr Ala Lys Lys Ser
            180                 185                 190

Arg Leu Thr Gly Thr Thr Pro
        195

<210> SEQ ID NO 6
<211> LENGTH: 179
<212> TYPE: PRT
<213> ORGANISM: Macaca fascicularis

<400> SEQUENCE: 6

Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Lys Val Ser Ile Lys Ser Leu Lys Phe Cys His
    50                  55                  60

Ser Gln Leu Ser Asn Asn Ser Val Ser Phe Phe Leu Tyr Asn Leu Asp
65                  70                  75                  80

Arg Ser His Ala Asn Tyr Tyr Phe Cys Asn Leu Ser Ile Phe Asp Pro
                85                  90                  95

```
Pro Pro Phe Lys Val Thr Leu Thr Gly Gly Tyr Leu His Ile Tyr Glu
            100                 105                 110

Ser Gln Leu Cys Cys Gln Leu Lys Phe Trp Leu Pro Ile Gly Cys Ala
        115                 120                 125

Thr Phe Val Val Cys Ile Phe Gly Cys Ile Leu Ile Cys Trp Leu
    130                 135                 140

Thr Lys Lys Lys Tyr Ser Ser Thr Val His Asp Pro Asn Gly Glu Tyr
145                 150                 155                 160

Met Phe Met Arg Ala Val Asn Thr Ala Lys Lys Ser Arg Leu Thr Gly
                165                 170                 175

Thr Thr Pro
```

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
<211> LENGTH: 117
<212> TYPE: PRT
<213> ORGANISM: Mesocricetus auratus

<400> SEQUENCE: 10

```
Glu Val Gln Leu Val Glu Ser Gly Gly Gly Leu Val Lys Pro Gly Gly
1               5                   10                  15

Ser Leu Thr Leu Ser Cys Ala Ala Ser Gly Phe Thr Phe Ser Asp Tyr
            20                  25                  30

Trp Met Asp Trp Val Arg Gln Gly Pro Gly Lys Gly Leu Glu Trp Val
        35                  40                  45

Gly Asn Ile Asp Glu Asp Gly Ser Thr Thr Tyr Ala Pro Phe Val
    50                  55                  60

Lys Gly Arg Phe Thr Ile Ser Arg Asp Asn Ala Lys Lys Thr Leu Tyr
65                  70                  75                  80

Leu Gln Met Asn Ser Val Lys Ser Glu Asp Thr Ala Thr Tyr Tyr Cys
                85                  90                  95

Thr Arg Trp Gly Arg Tyr Ala Phe Asp Ser Trp Gly Gln Gly Thr Leu
            100                 105                 110

Val Thr Val Ser Ser
        115
```

<210> SEQ ID NO 11
<211> LENGTH: 111
<212> TYPE: PRT
<213> ORGANISM: Mesocricetus auratus

<400> SEQUENCE: 11

```
Asp Ile Val Met Thr Gln Ser Pro Ser Ser Leu Ala Val Ser Pro Gly
1               5                   10                  15

Asp Lys Val Thr Ile Asn Cys Lys Ser Ser Gln Ser Leu Leu Ser Gly
            20                  25                  30

Asn Tyr Asn Tyr Leu Ala Trp Tyr Gln Gln Lys Thr Gly Gln Ala Pro
        35                  40                  45

Lys Leu Leu Ile Phe Tyr Ala Ser Thr Arg His Thr Gly Val Pro Asp
    50                  55                  60

Arg Phe Met Gly Ser Gly Ser Gly Thr Asp Phe Ser Leu Thr Ile Asn
65                  70                  75                  80

Ser Phe Gln Thr Glu Asp Leu Gly Asp Tyr Tyr Cys Gln His His Tyr
        85                  90                  95

Ser Thr Pro Pro Thr Phe Gly Pro Gly Thr Lys Leu Glu Ile Lys
            100                 105                 110
```

<210> SEQ ID NO 12
<211> LENGTH: 10
<212> TYPE: PRT
<213> ORGANISM: Mesocricetus auratus

<400> SEQUENCE: 12

```
Gly Phe Thr Phe Ser Asp Tyr Trp Met Asp
1               5                   10
```

<210> SEQ ID NO 13
<211> LENGTH: 17
<212> TYPE: PRT
<213> ORGANISM: Mesocricetus auratus

<400> SEQUENCE: 13

```
Asn Ile Asp Glu Asp Gly Ser Thr Thr Tyr Tyr Ala Pro Phe Val Lys
1               5                   10                  15

Gly
```

<210> SEQ ID NO 14
<211> LENGTH: 8
<212> TYPE: PRT
<213> ORGANISM: Mesocricetus auratus

<400> SEQUENCE: 14

```
Trp Gly Arg Tyr Ala Phe Asp Ser
1               5
```

<210> SEQ ID NO 15
<211> LENGTH: 15
<212> TYPE: PRT
<213> ORGANISM: Mesocricetus auratus

<400> SEQUENCE: 15

```
Lys Ser Ser Gln Ser Leu Leu Ser Gly Asn Tyr Asn Tyr Leu Ala
1               5                   10                  15
```

<210> SEQ ID NO 16
<211> LENGTH: 7
<212> TYPE: PRT
<213> ORGANISM: Mesocricetus auratus

<400> SEQUENCE: 16

```
Tyr Ala Ser Thr Arg His Thr
1               5
```

```
<210> SEQ ID NO 17
<211> LENGTH: 9
<212> TYPE: PRT
<213> ORGANISM: Mesocricetus auratus

<400> SEQUENCE: 17

Gln His His Tyr Ser Thr Pro Pro Thr
1               5

<210> SEQ ID NO 18

<400> SEQUENCE: 18

000

<210> SEQ ID NO 19

<400> SEQUENCE: 19

000

<210> SEQ ID NO 20
<211> LENGTH: 117
<212> TYPE: PRT
<213> ORGANISM: Mesocricetus auratus

<400> SEQUENCE: 20

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Trp Met Asp Trp Val Arg Gln Ala Pro Gly Lys Gly Leu Glu Trp Val
        35                  40                  45

Gly Asn Ile Asp Glu Asp Gly Ser Ile Thr Glu Tyr Ser Pro Phe Val
    50                  55                  60

Lys Gly Arg Phe Thr Ile Ser Arg Asp Asn Val Lys Asn Thr Leu Tyr
65                  70                  75                  80

Leu Gln Met Asn Ser Val Lys Ser Glu Asp Thr Ala Thr Tyr Tyr Cys
                85                  90                  95

Thr Arg Trp Gly Arg Phe Gly Phe Asp Ser Trp Gly Gln Gly Thr Leu
            100                 105                 110

Val Thr Val Ser Ser
        115

<210> SEQ ID NO 21
<211> LENGTH: 111
<212> TYPE: PRT
<213> ORGANISM: Mesocricetus auratus

<400> SEQUENCE: 21

Asp Ile Val Met Thr Gln Ser Pro Ser Ser Leu Ala Val Ser Ala Gly
1               5                   10                  15

Asp Arg Val Thr Ile Asn Cys Lys Ser Ser Gln Ser Leu Leu Ser Gly
            20                  25                  30

Ser Phe Asn Tyr Leu Thr Trp Tyr Gln Gln Lys Thr Gly Gln Ala Pro
        35                  40                  45

Lys Leu Leu Ile Phe Tyr Ala Ser Thr Arg His Thr Gly Val Pro Asp
    50                  55                  60

Arg Phe Met Gly Ser Gly Ser Gly Thr Asp Phe Thr Leu Thr Ile Asn
65                  70                  75                  80
```

Ser Phe Gln Thr Glu Asp Leu Gly Asp Tyr Tyr Cys His His Tyr
                85                  90                  95

Asn Ala Pro Pro Thr Phe Gly Pro Gly Thr Lys Leu Glu Leu Arg
            100                 105                 110

<210> SEQ ID NO 22
<211> LENGTH: 10
<212> TYPE: PRT
<213> ORGANISM: Mesocricetus auratus

<400> SEQUENCE: 22

Gly Phe Thr Phe Ser Asp Tyr Trp Met Asp
1               5                   10

<210> SEQ ID NO 23
<211> LENGTH: 17
<212> TYPE: PRT
<213> ORGANISM: Mesocricetus auratus

<400> SEQUENCE: 23

Asn Ile Asp Glu Asp Gly Ser Ile Thr Glu Tyr Ser Pro Phe Val Lys
1               5                   10                  15

Gly

<210> SEQ ID NO 24
<211> LENGTH: 8
<212> TYPE: PRT
<213> ORGANISM: Mesocricetus auratus

<400> SEQUENCE: 24

Trp Gly Arg Phe Gly Phe Asp Ser
1               5

<210> SEQ ID NO 25
<211> LENGTH: 15
<212> TYPE: PRT
<213> ORGANISM: Mesocricetus auratus

<400> SEQUENCE: 25

Lys Ser Ser Gln Ser Leu Leu Ser Gly Ser Phe Asn Tyr Leu Thr
1               5                   10                  15

<210> SEQ ID NO 26
<211> LENGTH: 7
<212> TYPE: PRT
<213> ORGANISM: Mesocricetus auratus

<400> SEQUENCE: 26

Tyr Ala Ser Thr Arg His Thr
1               5

<210> SEQ ID NO 27
<211> LENGTH: 9
<212> TYPE: PRT
<213> ORGANISM: Mesocricetus auratus

<400> SEQUENCE: 27

His His His Tyr Asn Ala Pro Pro Thr
1               5

<210> SEQ ID NO 28

<400> SEQUENCE: 28

<210> SEQ ID NO 29

<400> SEQUENCE: 29

000

<210> SEQ ID NO 30
<211> LENGTH: 117
<212> TYPE: PRT
<213> ORGANISM: Mesocricetus auratus

<400> SEQUENCE: 30

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Trp Met Asp Trp Val Arg Gln Ala Pro Gly Lys Gly Leu Glu Trp Val
        35                  40                  45

Gly Asn Ile Asp Glu Asp Gly Ser Ile Ala Glu Tyr Ser Pro Phe Val
    50                  55                  60

Lys Gly Arg Phe Thr Ile Ser Arg Asp Asn Val Lys Asn Thr Leu Tyr
65                  70                  75                  80

Leu Gln Met Asn Ser Val Lys Ser Glu Asp Thr Ala Thr Tyr Tyr Cys
                85                  90                  95

Ser Arg Trp Gly Arg Phe Ala Phe Asp Ser Trp Gly Gln Gly Thr Leu
            100                 105                 110

Val Thr Val Ser Ser
        115
```

<210> SEQ ID NO 31
<211> LENGTH: 111
<212> TYPE: PRT
<213> ORGANISM: Mesocricetus auratus

<400> SEQUENCE: 31

```
Asp Ile Val Met Thr Gln Ser Pro Ser Ser Leu Ala Val Ser Ala Gly
1               5                   10                  15

Asp Arg Val Thr Ile Asn Cys Lys Ser Ser Gln Ser Leu Leu Ser Gly
            20                  25                  30

Ser Phe Asn Tyr Leu Thr Trp Tyr Gln Gln Lys Thr Gly Gln Ala Pro
        35                  40                  45

Lys Leu Leu Ile Phe Tyr Ala Ser Thr Arg His Thr Gly Val Pro Asp
    50                  55                  60

Arg Phe Met Gly Ser Gly Ser Gly Thr Asp Phe Thr Leu Thr Ile Asn
65                  70                  75                  80

Ser Phe Gln Thr Glu Asp Leu Gly Asp Tyr Tyr Cys His His His Tyr
                85                  90                  95

Asn Ala Pro Pro Thr Phe Gly Pro Gly Thr Lys Leu Glu Leu Arg
            100                 105                 110
```

<210> SEQ ID NO 32
<211> LENGTH: 10
<212> TYPE: PRT
<213> ORGANISM: Mesocricetus auratus

<400> SEQUENCE: 32

Gly Phe Thr Phe Ser Asp Tyr Trp Met Asp

```
1               5                    10
```

<210> SEQ ID NO 33
<211> LENGTH: 17
<212> TYPE: PRT
<213> ORGANISM: Mesocricetus auratus

<400> SEQUENCE: 33

```
Asn Ile Asp Glu Asp Gly Ser Ile Ala Glu Tyr Ser Pro Phe Val Lys
1               5                   10                  15

Gly
```

<210> SEQ ID NO 34
<211> LENGTH: 8
<212> TYPE: PRT
<213> ORGANISM: Mesocricetus auratus

<400> SEQUENCE: 34

```
Trp Gly Arg Phe Ala Phe Asp Ser
1               5
```

<210> SEQ ID NO 35
<211> LENGTH: 15
<212> TYPE: PRT
<213> ORGANISM: Mesocricetus auratus

<400> SEQUENCE: 35

```
Lys Ser Ser Gln Ser Leu Leu Ser Gly Ser Phe Asn Tyr Leu Thr
1               5                   10                  15
```

<210> SEQ ID NO 36
<211> LENGTH: 7
<212> TYPE: PRT
<213> ORGANISM: Mesocricetus auratus

<400> SEQUENCE: 36

```
Tyr Ala Ser Thr Arg His Thr
1               5
```

<210> SEQ ID NO 37
<211> LENGTH: 9
<212> TYPE: PRT
<213> ORGANISM: Mesocricetus auratus

<400> SEQUENCE: 37

```
His His His Tyr Asn Ala Pro Pro Thr
1               5
```

<210> SEQ ID NO 38

<400> SEQUENCE: 38

000

<210> SEQ ID NO 39

<400> SEQUENCE: 39

000

<210> SEQ ID NO 40
<211> LENGTH: 117
<212> TYPE: PRT
<213> ORGANISM: Mesocricetus auratus -continued

<400> SEQUENCE: 40

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Trp Met Asp Trp Val Arg Gln Ala Pro Gly Lys Gly Leu Glu Trp Val
        35                  40                  45

Gly Asn Ile Asp Glu Asp Gly Ser Ile Thr Glu Tyr Ser Pro Phe Val
    50                  55                  60

Lys Gly Arg Phe Thr Ile Ser Arg Asp Asn Val Lys Asn Ile Leu Tyr
65                  70                  75                  80

Leu Gln Met Asn Ser Val Lys Ser Glu Asp Thr Ala Thr Tyr Tyr Cys
                85                  90                  95

Thr Arg Trp Gly Arg Phe Ala Phe Asp Ser Trp Gly Gln Gly Thr Leu
            100                 105                 110

Val Thr Val Ser Ser
        115

<210> SEQ ID NO 41
<211> LENGTH: 111
<212> TYPE: PRT
<213> ORGANISM: Mesocricetus auratus

<400> SEQUENCE: 41

Asp Ile Val Met Thr Gln Ser Pro Ser Ser Leu Ala Val Ser Pro Gly
1               5                   10                  15

Asp Arg Val Thr Ile Asn Cys Lys Ser Ser Gln Ser Leu Leu Ser Gly
            20                  25                  30

Ser Phe His Tyr Leu Thr Trp Tyr Gln Gln Lys Thr Gly Gln Ala Pro
        35                  40                  45

Lys Leu Leu Ile Phe Tyr Ala Ser Thr Arg His Thr Gly Val Pro Asp
    50                  55                  60

Arg Phe Met Gly Ser Gly Ser Gly Thr Asp Phe Thr Leu Thr Ile Asn
65                  70                  75                  80

Ser Phe Gln Thr Glu Asp Leu Gly Asp Tyr Tyr Cys His His His Tyr
                85                  90                  95

Asn Ala Pro Pro Thr Phe Gly Pro Gly Thr Lys Leu Glu Leu Arg
            100                 105                 110

<210> SEQ ID NO 42
<211> LENGTH: 10
<212> TYPE: PRT
<213> ORGANISM: Mesocricetus auratus

<400> SEQUENCE: 42

Gly Phe Thr Phe Ser Asp Tyr Trp Met Asp
1               5                   10

<210> SEQ ID NO 43
<211> LENGTH: 17
<212> TYPE: PRT
<213> ORGANISM: Mesocricetus auratus

<400> SEQUENCE: 43

Asn Ile Asp Glu Asp Gly Ser Ile Thr Glu Tyr Ser Pro Phe Val Lys
1               5                   10                  15

Gly

```
<210> SEQ ID NO 44
<211> LENGTH: 8
<212> TYPE: PRT
<213> ORGANISM: Mesocricetus auratus

<400> SEQUENCE: 44

Trp Gly Arg Phe Ala Phe Asp Ser
1               5

<210> SEQ ID NO 45
<211> LENGTH: 15
<212> TYPE: PRT
<213> ORGANISM: Mesocricetus auratus

<400> SEQUENCE: 45

Lys Ser Ser Gln Ser Leu Leu Ser Gly Ser Phe His Tyr Leu Thr
1               5                   10                  15

<210> SEQ ID NO 46
<211> LENGTH: 7
<212> TYPE: PRT
<213> ORGANISM: Mesocricetus auratus

<400> SEQUENCE: 46

Tyr Ala Ser Thr Arg His Thr
1               5

<210> SEQ ID NO 47
<211> LENGTH: 9
<212> TYPE: PRT
<213> ORGANISM: Mesocricetus auratus

<400> SEQUENCE: 47

His His His Tyr Asn Ala Pro Pro Thr
1               5

<210> SEQ ID NO 48

<400> SEQUENCE: 48

000

<210> SEQ ID NO 49

<400> SEQUENCE: 49

000

<210> SEQ ID NO 50
<211> LENGTH: 117
<212> TYPE: PRT
<213> ORGANISM: Mesocricetus auratus

<400> SEQUENCE: 50

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Trp Met Asp Trp Val Arg Gln Ala Pro Gly Lys Gly Leu Glu Trp Val
        35                  40                  45

Gly Asn Ile Asp His Asp Gly Asn Ile Asn Phe Ala Pro Ser Val
    50                  55                  60

Lys Gly Arg Phe Thr Ile Ser Arg Asp Asn Ala Lys Asn Thr Leu Tyr
```

```
                65                  70                  75                  80
Leu Gln Met Asn Ser Val Lys Ser Glu Asp Thr Ala Thr Tyr Tyr Cys
                    85                  90                  95
Ala Arg Trp Gly His Tyr Ala Phe Asp Ser Trp Gly Gln Gly Thr Leu
                    100                 105                 110
Val Thr Val Ser Ser
            115

<210> SEQ ID NO 51
<211> LENGTH: 111
<212> TYPE: PRT
<213> ORGANISM: Mesocricetus auratus

<400> SEQUENCE: 51

Asp Ile Val Met Thr Gln Ser Pro Ser Ser Leu Ala Val Ser Ala Gly
1               5                   10                  15

Asp Lys Val Thr Ile Asn Cys Lys Ser Ser Gln Ser Leu Leu Ser Ser
                20                  25                  30

Gly Tyr Asn Tyr Leu Ile Trp Tyr Gln Gln Lys Thr Gly Gln Ala Pro
            35                  40                  45

Lys Leu Leu Ile Phe Tyr Ala Ser Thr Arg His Thr Gly Val Pro Asp
    50                  55                  60

Arg Phe Ile Gly Ser Gly Ser Gly Thr Asp Phe Thr Leu Thr Ile Thr
65                  70                  75                  80

Ser Phe Gln Thr Glu Asp Leu Gly Asp Tyr Tyr Cys Gln His His Tyr
                85                  90                  95

Ser Ser Pro Pro Thr Phe Gly Pro Gly Thr Lys Leu Glu Ile Lys
                100                 105                 110

<210> SEQ ID NO 52
<211> LENGTH: 10
<212> TYPE: PRT
<213> ORGANISM: Mesocricetus auratus

<400> SEQUENCE: 52

Gly Phe Thr Phe Ser Asp Tyr Trp Met Asp
1               5                   10

<210> SEQ ID NO 53
<211> LENGTH: 17
<212> TYPE: PRT
<213> ORGANISM: Mesocricetus auratus

<400> SEQUENCE: 53

Asn Ile Asp His Asp Gly Asn Ile Ile Asn Phe Ala Pro Ser Val Lys
1               5                   10                  15

Gly

<210> SEQ ID NO 54
<211> LENGTH: 8
<212> TYPE: PRT
<213> ORGANISM: Mesocricetus auratus

<400> SEQUENCE: 54

Trp Gly His Tyr Ala Phe Asp Ser
1               5

<210> SEQ ID NO 55
<211> LENGTH: 15
<212> TYPE: PRT
```

```
<213> ORGANISM: Mesocricetus auratus

<400> SEQUENCE: 55

Lys Ser Ser Gln Ser Leu Leu Ser Ser Gly Tyr Asn Tyr Leu Ile
1               5                   10                  15

<210> SEQ ID NO 56
<211> LENGTH: 7
<212> TYPE: PRT
<213> ORGANISM: Mesocricetus auratus

<400> SEQUENCE: 56

Tyr Ala Ser Thr Arg His Thr
1               5

<210> SEQ ID NO 57
<211> LENGTH: 9
<212> TYPE: PRT
<213> ORGANISM: Mesocricetus auratus

<400> SEQUENCE: 57

Gln His His Tyr Ser Ser Pro Pro Thr
1               5

<210> SEQ ID NO 58

<400> SEQUENCE: 58

000

<210> SEQ ID NO 59

<400> SEQUENCE: 59

000

<210> SEQ ID NO 60
<211> LENGTH: 117
<212> TYPE: PRT
<213> ORGANISM: Artificial Sequence
<220> FEATURE:
<223> OTHER INFORMATION: 37A10S713 heavy chain variable region

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Asp Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Gly Arg Phe Gly Phe Gly Asp Ser Trp Gly Gln Gly Thr Leu
            100                 105                 110

Val Thr Val Ser Ser
        115

<210> SEQ ID NO 61
```

<211> LENGTH: 111
<212> TYPE: PRT
<213> ORGANISM: Artificial Sequence
<220> FEATURE:
<223> OTHER INFORMATION: 37A10S713 light chain variable region

<400> SEQUENCE: 61

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Leu Ser Gly
            20                  25                  30
Ser Phe Asn Tyr Leu Thr Trp Tyr Gln Gln Lys Pro Gly Gln Pro Pro
        35                  40                  45
Lys Leu Leu Ile Phe Tyr Ala Ser Thr Arg His Thr Gly Val Pro Asp
    50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Val Tyr Tyr Cys His His His Tyr
                85                  90                  95
Asn Ala Pro Pro Thr Phe Gly Pro Gly Thr Lys Val Asp Ile Lys
            100                 105                 110

<210> SEQ ID NO 62
<211> LENGTH: 10
<212> TYPE: PRT
<213> ORGANISM: Artificial Sequence
<220> FEATURE:
<223> OTHER INFORMATION: 37A10S713 VH CDR1

<400> SEQUENCE: 62

Gly Phe Thr Phe Ser Asp Tyr Trp Met Asp
1               5                   10

<210> SEQ ID NO 63
<211> LENGTH: 17
<212> TYPE: PRT
<213> ORGANISM: Artificial Sequence
<220> FEATURE:
<223> OTHER INFORMATION: 37A10S713 VH CDR2

<400> SEQUENCE: 63

Asn Ile Asp Glu Asp Gly Ser Ile Thr Glu Tyr Ser Pro Phe Val Lys
1               5                   10                  15
Gly

<210> SEQ ID NO 64
<211> LENGTH: 8
<212> TYPE: PRT
<213> ORGANISM: Artificial Sequence
<220> FEATURE:
<223> OTHER INFORMATION: 37A10S713 VH CDR3

<400> SEQUENCE: 64

Trp Gly Arg Phe Gly Phe Asp Ser
1               5

<210> SEQ ID NO 65
<211> LENGTH: 15
<212> TYPE: PRT
<213> ORGANISM: Artificial Sequence
<220> FEATURE:
<223> OTHER INFORMATION: 37A10S713 VL CDR1

<400> SEQUENCE: 65

```
Lys Ser Ser Gln Ser Leu Leu Ser Gly Ser Phe Asn Tyr Leu Thr
1               5                   10                  15
```

<210> SEQ ID NO 66
<211> LENGTH: 7
<212> TYPE: PRT
<213> ORGANISM: Artificial Sequence
<220> FEATURE:
<223> OTHER INFORMATION: 37A10S713 VL CDR2

<400> SEQUENCE: 66

```
Tyr Ala Ser Thr Arg His Thr
1               5
```

<210> SEQ ID NO 67
<211> LENGTH: 9
<212> TYPE: PRT
<213> ORGANISM: Artificial Sequence
<220> FEATURE:
<223> OTHER INFORMATION: 37A10S713 VL CDR3

<400> SEQUENCE: 67

```
His His His Tyr Asn Ala Pro Pro Thr
1               5
```

<210> SEQ ID NO 68

<400> SEQUENCE: 68

000

<210> SEQ ID NO 69

<400> SEQUENCE: 69

000

<210> SEQ ID NO 70
<211> LENGTH: 117
<212> TYPE: PRT
<213> ORGANISM: Artificial Sequence
<220> FEATURE:
<223> OTHER INFORMATION: 37A10S714 heavy chain variable region

<400> SEQUENCE: 70

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Asp Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Gly Arg Phe Gly Phe Asp Ser Trp Gly Gln Gly Thr Leu
            100                 105                 110

Val Thr Val Ser Ser
        115
```

<210> SEQ ID NO 71
<211> LENGTH: 111
<212> TYPE: PRT
<213> ORGANISM: Artificial Sequence
<220> FEATURE:
<223> OTHER INFORMATION: 37A10S714 light chain variable region

<400> SEQUENCE: 71

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg Glu Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His Tyr
                85                  90                  95

Asn Ala Pro Pro Thr Phe Gly Pro Gly Thr Lys Val Asp Ile Lys
            100                 105                 110

<210> SEQ ID NO 72
<211> LENGTH: 10
<212> TYPE: PRT
<213> ORGANISM: Artificial Sequence
<220> FEATURE:
<223> OTHER INFORMATION: 37A10S714 VH CDR1

<400> SEQUENCE: 72

Gly Phe Thr Phe Ser Asp Tyr Trp Met Asp
1               5                   10

<210> SEQ ID NO 73
<211> LENGTH: 17
<212> TYPE: PRT
<213> ORGANISM: Artificial Sequence
<220> FEATURE:
<223> OTHER INFORMATION: 37A10S714 VH CDR2

<400> SEQUENCE: 73

Asn Ile Asp Glu Asp Gly Ser Ile Thr Glu Tyr Ser Pro Phe Val Lys
1               5                   10                  15

Gly

<210> SEQ ID NO 74
<211> LENGTH: 8
<212> TYPE: PRT
<213> ORGANISM: Artificial Sequence
<220> FEATURE:
<223> OTHER INFORMATION: 37A10S714 VH CDR3

<400> SEQUENCE: 74

Trp Gly Arg Phe Gly Phe Asp Ser
1               5

<210> SEQ ID NO 75
<211> LENGTH: 15
<212> TYPE: PRT
<213> ORGANISM: Artificial Sequence
<220> FEATURE:
<223> OTHER INFORMATION: 37A10S714 VL CDR1

```
<400> SEQUENCE: 75

Lys Ser Ser Gln Ser Leu Leu Ser Gly Ser Phe Asn Tyr Leu Thr
1               5                   10                  15

<210> SEQ ID NO 76
<211> LENGTH: 7
<212> TYPE: PRT
<213> ORGANISM: Artificial Sequence
<220> FEATURE:
<223> OTHER INFORMATION: 37A10S714 VL CDR2

<400> SEQUENCE: 76

Tyr Ala Ser Thr Arg Glu Thr
1               5

<210> SEQ ID NO 77
<211> LENGTH: 9
<212> TYPE: PRT
<213> ORGANISM: Artificial Sequence
<220> FEATURE:
<223> OTHER INFORMATION: 37A10S714 VL CDR3

<400> SEQUENCE: 77

His His His Tyr Asn Ala Pro Pro Thr
1               5

<210> SEQ ID NO 78

<400> SEQUENCE: 78

000

<210> SEQ ID NO 79

<400> SEQUENCE: 79

000

<210> SEQ ID NO 80
<211> LENGTH: 117
<212> TYPE: PRT
<213> ORGANISM: Artificial Sequence
<220> FEATURE:
<223> OTHER INFORMATION: 37A10S715 heavy chain variable region

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Asp Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Gly Arg Phe Gly Phe Asp Ser Trp Gly Gln Gly Thr Leu
            100                 105                 110

Val Thr Val Ser Ser
        115
```

<210> SEQ ID NO 81
<211> LENGTH: 111
<212> TYPE: PRT
<213> ORGANISM: Artificial Sequence
<220> FEATURE:
<223> OTHER INFORMATION: 37A10S715 light chain variable region

<400> SEQUENCE: 81

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg Gln Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His Tyr
                85                  90                  95

Asn Ala Pro Pro Thr Phe Gly Pro Gly Thr Lys Val Asp Ile Lys
            100                 105                 110

<210> SEQ ID NO 82
<211> LENGTH: 10
<212> TYPE: PRT
<213> ORGANISM: Artificial Sequence
<220> FEATURE:
<223> OTHER INFORMATION: 37A10S715 VH CDR1

<400> SEQUENCE: 82

Gly Phe Thr Phe Ser Asp Tyr Trp Met Asp
1               5                   10

<210> SEQ ID NO 83
<211> LENGTH: 17
<212> TYPE: PRT
<213> ORGANISM: Artificial Sequence
<220> FEATURE:
<223> OTHER INFORMATION: 37A10S715 VH CDR2

<400> SEQUENCE: 83

Asn Ile Asp Glu Asp Gly Ser Ile Thr Glu Tyr Ser Pro Phe Val Lys
1               5                   10                  15

Gly

<210> SEQ ID NO 84
<211> LENGTH: 8
<212> TYPE: PRT
<213> ORGANISM: Artificial Sequence
<220> FEATURE:
<223> OTHER INFORMATION: 37A10S715 VH CDR3

<400> SEQUENCE: 84

Trp Gly Arg Phe Gly Phe Asp Ser
1               5

<210> SEQ ID NO 85
<211> LENGTH: 15
<212> TYPE: PRT
<213> ORGANISM: Artificial Sequence
<220> FEATURE:
<223> OTHER INFORMATION: 37A10S715 VL CDR1

```
<400> SEQUENCE: 85

Lys Ser Ser Gln Ser Leu Leu Ser Gly Ser Phe Asn Tyr Leu Thr
1               5                   10                  15

<210> SEQ ID NO 86
<211> LENGTH: 7
<212> TYPE: PRT
<213> ORGANISM: Artificial Sequence
<220> FEATURE:
<223> OTHER INFORMATION: 37A10S715 VL CDR2

<400> SEQUENCE: 86

Tyr Ala Ser Thr Arg Gln Thr
1               5

<210> SEQ ID NO 87
<211> LENGTH: 9
<212> TYPE: PRT
<213> ORGANISM: Artificial Sequence
<220> FEATURE:
<223> OTHER INFORMATION: 37A10S715 VL CDR3

<400> SEQUENCE: 87

His His His Tyr Asn Ala Pro Pro Thr
1               5

<210> SEQ ID NO 88

<400> SEQUENCE: 88

000

<210> SEQ ID NO 89

<400> SEQUENCE: 89

000

<210> SEQ ID NO 90
<211> LENGTH: 117
<212> TYPE: PRT
<213> ORGANISM: Artificial Sequence
<220> FEATURE:
<223> OTHER INFORMATION: 37A10S716 heavy chain variable region

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Ser Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Gly Arg Phe Gly Phe Asp Ser Trp Gly Gln Gly Thr Leu
            100                 105                 110

Val Thr Val Ser Ser
            115
```

<210> SEQ ID NO 91
<211> LENGTH: 111
<212> TYPE: PRT
<213> ORGANISM: Artificial Sequence
<220> FEATURE:
<223> OTHER INFORMATION: 37A10S716 light chain variable region

<400> SEQUENCE: 91

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg His Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His His Tyr
                85                  90                  95

Asn Ala Pro Pro Thr Phe Gly Pro Gly Thr Lys Val Asp Ile Lys
            100                 105                 110

<210> SEQ ID NO 92
<211> LENGTH: 10
<212> TYPE: PRT
<213> ORGANISM: Artificial Sequence
<220> FEATURE:
<223> OTHER INFORMATION: 37A10S716 VH CDR1

<400> SEQUENCE: 92

Gly Phe Thr Phe Ser Asp Tyr Trp Met Asp
1               5                   10

<210> SEQ ID NO 93
<211> LENGTH: 17
<212> TYPE: PRT
<213> ORGANISM: Artificial Sequence
<220> FEATURE:
<223> OTHER INFORMATION: 37A10S716 VH CDR2

<400> SEQUENCE: 93

Asn Ile Asp Glu Ser Gly Ser Ile Thr Glu Tyr Ser Pro Phe Val Lys
1               5                   10                  15

Gly

<210> SEQ ID NO 94
<211> LENGTH: 8
<212> TYPE: PRT
<213> ORGANISM: Artificial Sequence
<220> FEATURE:
<223> OTHER INFORMATION: 37A10S716 VH CDR3

<400> SEQUENCE: 94

Trp Gly Arg Phe Gly Phe Asp Ser
1               5

<210> SEQ ID NO 95
<211> LENGTH: 15
<212> TYPE: PRT
<213> ORGANISM: Artificial Sequence
<220> FEATURE:

<223> OTHER INFORMATION: 37A10S716 VL CDR1

<400> SEQUENCE: 95

Lys Ser Ser Gln Ser Leu Leu Ser Gly Ser Phe Asn Tyr Leu Thr
1               5                   10                  15

<210> SEQ ID NO 96
<211> LENGTH: 7
<212> TYPE: PRT
<213> ORGANISM: Artificial Sequence
<220> FEATURE:
<223> OTHER INFORMATION: 37A10S716 VL CDR2

<400> SEQUENCE: 96

Tyr Ala Ser Thr Arg His Thr
1               5

<210> SEQ ID NO 97
<211> LENGTH: 9
<212> TYPE: PRT
<213> ORGANISM: Artificial Sequence
<220> FEATURE:
<223> OTHER INFORMATION: 37A10S716 VL CDR3

<400> SEQUENCE: 97

His His His Tyr Asn Ala Pro Pro Thr
1               5

<210> SEQ ID NO 98

<400> SEQUENCE: 98

000

<210> SEQ ID NO 99

<400> SEQUENCE: 99

000

<210> SEQ ID NO 100
<211> LENGTH: 117
<212> TYPE: PRT
<213> ORGANISM: Artificial Sequence
<220> FEATURE:
<223> OTHER INFORMATION: 37A10S717 heavy chain variable region

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Ser Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Gly Arg Phe Gly Phe Asp Ser Trp Gly Gln Gly Thr Leu
            100                 105                 110

Val Thr Val Ser Ser

<210> SEQ ID NO 101
<211> LENGTH: 111
<212> TYPE: PRT
<213> ORGANISM: Artificial Sequence
<220> FEATURE:
<223> OTHER INFORMATION: 37A10S717 light chain variable region

<400> SEQUENCE: 101

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg Glu Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His His Tyr
                85                  90                  95

Asn Ala Pro Pro Thr Phe Gly Pro Gly Thr Lys Val Asp Ile Lys
            100                 105                 110

<210> SEQ ID NO 102
<211> LENGTH: 10
<212> TYPE: PRT
<213> ORGANISM: Artificial Sequence
<220> FEATURE:
<223> OTHER INFORMATION: 37A10S717 VH CDR1

<400> SEQUENCE: 102

Gly Phe Thr Phe Ser Asp Tyr Trp Met Asp
1               5                   10

<210> SEQ ID NO 103
<211> LENGTH: 17
<212> TYPE: PRT
<213> ORGANISM: Artificial Sequence
<220> FEATURE:
<223> OTHER INFORMATION: 37A10S717 VH CDR2

<400> SEQUENCE: 103

Asn Ile Asp Glu Ser Gly Ser Ile Thr Glu Tyr Ser Pro Phe Val Lys
1               5                   10                  15

Gly

<210> SEQ ID NO 104
<211> LENGTH: 8
<212> TYPE: PRT
<213> ORGANISM: Artificial Sequence
<220> FEATURE:
<223> OTHER INFORMATION: 37A10S717 VH CDR3

<400> SEQUENCE: 104

Trp Gly Arg Phe Gly Phe Asp Ser
1               5

<210> SEQ ID NO 105
<211> LENGTH: 15
<212> TYPE: PRT
<213> ORGANISM: Artificial Sequence

<220> FEATURE:
<223> OTHER INFORMATION: 37A10S717 VL CDR1

<400> SEQUENCE: 105

Lys Ser Ser Gln Ser Leu Leu Ser Gly Ser Phe Asn Tyr Leu Thr
1               5                   10                  15

<210> SEQ ID NO 106
<211> LENGTH: 7
<212> TYPE: PRT
<213> ORGANISM: Artificial Sequence
<220> FEATURE:
<223> OTHER INFORMATION: 37A10S717 VL CDR2

<400> SEQUENCE: 106

Tyr Ala Ser Thr Arg Glu Thr
1               5

<210> SEQ ID NO 107
<211> LENGTH: 9
<212> TYPE: PRT
<213> ORGANISM: Artificial Sequence
<220> FEATURE:
<223> OTHER INFORMATION: 37A10S717 VL CDR3

<400> SEQUENCE: 107

His His His Tyr Asn Ala Pro Pro Thr
1               5

<210> SEQ ID NO 108

<400> SEQUENCE: 108

000

<210> SEQ ID NO 109

<400> SEQUENCE: 109

000

<210> SEQ ID NO 110
<211> LENGTH: 117
<212> TYPE: PRT
<213> ORGANISM: Artificial Sequence
<220> FEATURE:
<223> OTHER INFORMATION: 37A10S718 heavy chain variable region

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Ser Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Gly Arg Phe Gly Asp Ser Trp Gly Gln Gly Thr Leu
            100                 105                 110

Val Thr Val Ser Ser
            115

<210> SEQ ID NO 111
<211> LENGTH: 111
<212> TYPE: PRT
<213> ORGANISM: Artificial Sequence
<220> FEATURE:
<223> OTHER INFORMATION: 37A10S718 light chain variable region

<400> SEQUENCE: 111

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg Gln Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His His Tyr
                85                  90                  95

Asn Ala Pro Pro Thr Phe Gly Pro Gly Thr Lys Val Asp Ile Lys
            100                 105                 110

<210> SEQ ID NO 112
<211> LENGTH: 10
<212> TYPE: PRT
<213> ORGANISM: Artificial Sequence
<220> FEATURE:
<223> OTHER INFORMATION: 37A10S718 VH CDR1

<400> SEQUENCE: 112

Gly Phe Thr Phe Ser Asp Tyr Trp Met Asp
1               5                   10

<210> SEQ ID NO 113
<211> LENGTH: 17
<212> TYPE: PRT
<213> ORGANISM: Artificial Sequence
<220> FEATURE:
<223> OTHER INFORMATION: 37A10S718 VH CDR2

<400> SEQUENCE: 113

Asn Ile Asp Glu Ser Gly Ser Ile Thr Glu Tyr Ser Pro Phe Val Lys
1               5                   10                  15

Gly

<210> SEQ ID NO 114
<211> LENGTH: 8
<212> TYPE: PRT
<213> ORGANISM: Artificial Sequence
<220> FEATURE:
<223> OTHER INFORMATION: 37A10S718 VH CDR3

<400> SEQUENCE: 114

Trp Gly Arg Phe Gly Phe Asp Ser
1               5

<210> SEQ ID NO 115
<211> LENGTH: 15
<212> TYPE: PRT

<213> ORGANISM: Artificial Sequence
<220> FEATURE:
<223> OTHER INFORMATION: 37A10S718 VL CDR1

<400> SEQUENCE: 115

Lys Ser Ser Gln Ser Leu Leu Ser Gly Ser Phe Asn Tyr Leu Thr
1               5                   10                  15

<210> SEQ ID NO 116
<211> LENGTH: 7
<212> TYPE: PRT
<213> ORGANISM: Artificial Sequence
<220> FEATURE:
<223> OTHER INFORMATION: 37A10S718 VL CDR2

<400> SEQUENCE: 116

Tyr Ala Ser Thr Arg Gln Thr
1               5

<210> SEQ ID NO 117
<211> LENGTH: 9
<212> TYPE: PRT
<213> ORGANISM: Artificial Sequence
<220> FEATURE:
<223> OTHER INFORMATION: 37A10S718 VL CDR3

<400> SEQUENCE: 117

His His His Tyr Asn Ala Pro Pro Thr
1               5

<210> SEQ ID NO 118

<400> SEQUENCE: 118

000

<210> SEQ ID NO 119

<400> SEQUENCE: 119

000

<210> SEQ ID NO 120
<211> LENGTH: 117
<212> TYPE: PRT
<213> ORGANISM: Artificial Sequence
<220> FEATURE:
<223> OTHER INFORMATION: 16G10S71 heavy chain variable region

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp His Asp Gly Asn Ile Ile Asn Phe Ala Pro Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly His Tyr Ala Phe Asp Ser Trp Gly Gln Gly Thr Leu
            100                 105                 110

Val Thr Val Ser Ser
        115

<210> SEQ ID NO 121
<211> LENGTH: 111
<212> TYPE: PRT
<213> ORGANISM: Artificial Sequence
<220> FEATURE:
<223> OTHER INFORMATION: 16G10S71 light chain variable region

<400> SEQUENCE: 121

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Ser
            20                  25                  30

Gly Tyr Asn Tyr Leu Ile Trp Tyr Gln Gln Lys Pro Gly Gln Pro Pro
        35                  40                  45

Lys Leu Leu Ile Phe Tyr Ala Ser Thr Arg His Thr Gly Val Pro Asp
 50                 55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His His Tyr
                85                  90                  95

Ser Ser Pro Pro Thr Phe Gly Pro Gly Thr Lys Val Asp Ile Lys
            100                 105                 110

<210> SEQ ID NO 122
<211> LENGTH: 10
<212> TYPE: PRT
<213> ORGANISM: Artificial Sequence
<220> FEATURE:
<223> OTHER INFORMATION: 16G10S71 VH CDR1

<400> SEQUENCE: 122

Gly Phe Thr Phe Ser Asp Tyr Trp Met Asp
1               5                   10

<210> SEQ ID NO 123
<211> LENGTH: 17
<212> TYPE: PRT
<213> ORGANISM: Artificial Sequence
<220> FEATURE:
<223> OTHER INFORMATION: 16G10S71 VH CDR2

<400> SEQUENCE: 123

Asn Ile Asp His Asp Gly Asn Ile Ile Asn Phe Ala Pro Ser Val Lys
1               5                   10                  15

Gly

<210> SEQ ID NO 124
<211> LENGTH: 8
<212> TYPE: PRT
<213> ORGANISM: Artificial Sequence
<220> FEATURE:
<223> OTHER INFORMATION: 16G10S71 VH CDR3

<400> SEQUENCE: 124

Trp Gly His Tyr Ala Phe Asp Ser
1               5

<210> SEQ ID NO 125
<211> LENGTH: 15

```
<212> TYPE: PRT
<213> ORGANISM: Artificial Sequence
<220> FEATURE:
<223> OTHER INFORMATION: 16G10S71 VL CDR1

<400> SEQUENCE: 125

Lys Ser Ser Gln Ser Leu Leu Ser Ser Gly Tyr Asn Tyr Leu Ile
1               5                   10                  15

<210> SEQ ID NO 126
<211> LENGTH: 7
<212> TYPE: PRT
<213> ORGANISM: Artificial Sequence
<220> FEATURE:
<223> OTHER INFORMATION: 16G10S71 VL CDR2

<400> SEQUENCE: 126

Tyr Ala Ser Thr Arg His Thr
1               5

<210> SEQ ID NO 127
<211> LENGTH: 9
<212> TYPE: PRT
<213> ORGANISM: Artificial Sequence
<220> FEATURE:
<223> OTHER INFORMATION: 16G10S71 VL CDR3

<400> SEQUENCE: 127

Gln His His Tyr Ser Ser Pro Pro Thr
1               5

<210> SEQ ID NO 128

<400> SEQUENCE: 128

000

<210> SEQ ID NO 129

<400> SEQUENCE: 129

000

<210> SEQ ID NO 130
<211> LENGTH: 117
<212> TYPE: PRT
<213> ORGANISM: Artificial Sequence
<220> FEATURE:
<223> OTHER INFORMATION: 16G10S72 heavy chain variable region

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Trp Met Asp Trp Val Arg Gln Ala Pro Gly Lys Gly Leu Val Trp Val
            35                  40                  45

Ser Asn Ile Asp His Asp Gly Asn Ile Ile Asn Phe Ala Pro Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly His Tyr Ala Phe Asp Ser Trp Gly Gln Gly Thr Leu
```

-continued

```
                100                 105                 110
Val Thr Val Ser Ser
            115

<210> SEQ ID NO 131
<211> LENGTH: 111
<212> TYPE: PRT
<213> ORGANISM: Artificial Sequence
<220> FEATURE:
<223> OTHER INFORMATION: 16G10S72 light chain variable region

<400> SEQUENCE: 131

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Ser
            20                  25                  30

Gly Tyr Asn Tyr Leu Ile Trp Tyr Gln Gln Lys Pro Gly Gln Pro Pro
        35                  40                  45

Lys Leu Leu Ile Phe Tyr Ala Ser Thr Arg Glu Thr Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His His Tyr
                85                  90                  95

Ser Ser Pro Pro Thr Phe Gly Pro Gly Thr Lys Val Asp Ile Lys
            100                 105                 110

<210> SEQ ID NO 132
<211> LENGTH: 10
<212> TYPE: PRT
<213> ORGANISM: Artificial Sequence
<220> FEATURE:
<223> OTHER INFORMATION: 16G10S72 VH CDR1

<400> SEQUENCE: 132

Gly Phe Thr Phe Ser Asp Tyr Trp Met Asp
1               5                   10

<210> SEQ ID NO 133
<211> LENGTH: 17
<212> TYPE: PRT
<213> ORGANISM: Artificial Sequence
<220> FEATURE:
<223> OTHER INFORMATION: 16G10S72 VH CDR2

<400> SEQUENCE: 133

Asn Ile Asp His Asp Gly Asn Ile Ile Asn Phe Ala Pro Ser Val Lys
1               5                   10                  15

Gly

<210> SEQ ID NO 134
<211> LENGTH: 8
<212> TYPE: PRT
<213> ORGANISM: Artificial Sequence
<220> FEATURE:
<223> OTHER INFORMATION: 16G10S72 VH CDR3

<400> SEQUENCE: 134

Trp Gly His Tyr Ala Phe Asp Ser
1               5

<210> SEQ ID NO 135
```

```
<211> LENGTH: 15
<212> TYPE: PRT
<213> ORGANISM: Artificial Sequence
<220> FEATURE:
<223> OTHER INFORMATION: 16G10S72 VL CDR1

<400> SEQUENCE: 135

Lys Ser Ser Gln Ser Leu Leu Ser Ser Gly Tyr Asn Tyr Leu Ile
1               5                   10                  15

<210> SEQ ID NO 136
<211> LENGTH: 7
<212> TYPE: PRT
<213> ORGANISM: Artificial Sequence
<220> FEATURE:
<223> OTHER INFORMATION: 16G10S72 VL CDR2

<400> SEQUENCE: 136

Tyr Ala Ser Thr Arg Glu Thr
1               5

<210> SEQ ID NO 137
<211> LENGTH: 9
<212> TYPE: PRT
<213> ORGANISM: Artificial Sequence
<220> FEATURE:
<223> OTHER INFORMATION: 16G10S72 VL CDR3

<400> SEQUENCE: 137

Gln His His Tyr Ser Ser Pro Pro Thr
1               5

<210> SEQ ID NO 138

<400> SEQUENCE: 138

000

<210> SEQ ID NO 139

<400> SEQUENCE: 139

000

<210> SEQ ID NO 140
<211> LENGTH: 117
<212> TYPE: PRT
<213> ORGANISM: Artificial Sequence
<220> FEATURE:
<223> OTHER INFORMATION: 16G10S73 heavy chain variable region

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp His Asp Gly Asn Ile Ile Asn Phe Ala Pro Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Trp Gly His Tyr Ala Phe Asp Ser Trp Gly Gln Gly Thr Leu
            100                 105                 110

Val Thr Val Ser Ser
        115

<210> SEQ ID NO 141
<211> LENGTH: 111
<212> TYPE: PRT
<213> ORGANISM: Artificial Sequence
<220> FEATURE:
<223> OTHER INFORMATION: 16G10S73 light chain variable region

<400> SEQUENCE: 141

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Ser
            20                  25                  30

Gly Tyr Asn Tyr Leu Ile Trp Tyr Gln Gln Lys Pro Gly Gln Pro Pro
        35                  40                  45

Lys Leu Leu Ile Phe Tyr Ala Ser Thr Arg Gln Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His His Tyr
                85                  90                  95

Ser Ser Pro Pro Thr Phe Gly Pro Gly Thr Lys Val Asp Ile Lys
            100                 105                 110

<210> SEQ ID NO 142
<211> LENGTH: 10
<212> TYPE: PRT
<213> ORGANISM: Artificial Sequence
<220> FEATURE:
<223> OTHER INFORMATION: 16G10S73 VH CDR1

<400> SEQUENCE: 142

Gly Phe Thr Phe Ser Asp Tyr Trp Met Asp
1               5                   10

<210> SEQ ID NO 143
<211> LENGTH: 17
<212> TYPE: PRT
<213> ORGANISM: Artificial Sequence
<220> FEATURE:
<223> OTHER INFORMATION: 16G10S73 VH CDR2

<400> SEQUENCE: 143

Asn Ile Asp His Asp Gly Asn Ile Ile Asn Phe Ala Pro Ser Val Lys
1               5                   10                  15

Gly

<210> SEQ ID NO 144
<211> LENGTH: 8
<212> TYPE: PRT
<213> ORGANISM: Artificial Sequence
<220> FEATURE:
<223> OTHER INFORMATION: 16G10S73 VH CDR3

<400> SEQUENCE: 144

Trp Gly His Tyr Ala Phe Asp Ser
1               5

```
<210> SEQ ID NO 145
<211> LENGTH: 15
<212> TYPE: PRT
<213> ORGANISM: Artificial Sequence
<220> FEATURE:
<223> OTHER INFORMATION: 16G10S73 VL CDR1

<400> SEQUENCE: 145

Lys Ser Ser Gln Ser Leu Leu Ser Ser Gly Tyr Asn Tyr Leu Ile
1               5                   10                  15

<210> SEQ ID NO 146
<211> LENGTH: 7
<212> TYPE: PRT
<213> ORGANISM: Artificial Sequence
<220> FEATURE:
<223> OTHER INFORMATION: 16G10S73 VL CDR2

<400> SEQUENCE: 146

Tyr Ala Ser Thr Arg Gln Thr
1               5

<210> SEQ ID NO 147
<211> LENGTH: 9
<212> TYPE: PRT
<213> ORGANISM: Artificial Sequence
<220> FEATURE:
<223> OTHER INFORMATION: 16G10S73 VL CDR3

<400> SEQUENCE: 147

Gln His His Tyr Ser Ser Pro Pro Thr
1               5

<210> SEQ ID NO 148

<400> SEQUENCE: 148

000

<210> SEQ ID NO 149

<400> SEQUENCE: 149

000

<210> SEQ ID NO 150
<211> LENGTH: 117
<212> TYPE: PRT
<213> ORGANISM: Artificial Sequence
<220> FEATURE:
<223> OTHER INFORMATION: 16G10S83 heavy chain variable region

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Glu Trp Val
        35                  40                  45

Ser Asn Ile Asp His Asp Gly Asn Ile Ile Asn Phe Ala Pro Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Val Arg Ala Glu Asp Thr Ala Val Tyr Tyr Cys
                85                  90                  95
```

```
Ala Arg Trp Gly His Tyr Ala Phe Asp Ser Trp Gly Gln Gly Thr Leu
            100                 105                 110

Val Thr Val Ser Ser
        115

<210> SEQ ID NO 151
<211> LENGTH: 111
<212> TYPE: PRT
<213> ORGANISM: Artificial Sequence
<220> FEATURE:
<223> OTHER INFORMATION: 16G10S83 light chain variable region

<400> SEQUENCE: 151

Asp Ile Val Met Thr Gln Ser Pro Asp Ser Leu Ala Val Ser Ala Gly
1               5                   10                  15

Glu Arg Val Thr Ile Asn Cys Lys Ser Ser Gln Ser Leu Leu Ser Ser
            20                  25                  30

Gly Tyr Asn Tyr Leu Ile Trp Tyr Gln Gln Lys Pro Gly Gln Pro Pro
        35                  40                  45

Lys Leu Leu Ile Phe Tyr Ala Ser Thr Arg Gln Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His His Tyr
                85                  90                  95

Ser Ser Pro Pro Thr Phe Gly Gln Gly Thr Lys Leu Glu Ile Lys
            100                 105                 110

<210> SEQ ID NO 152
<211> LENGTH: 10
<212> TYPE: PRT
<213> ORGANISM: Artificial Sequence
<220> FEATURE:
<223> OTHER INFORMATION: 16G10S83 VH CDR1

<400> SEQUENCE: 152

Gly Phe Thr Phe Ser Asp Tyr Trp Met Asp
1               5                   10

<210> SEQ ID NO 153
<211> LENGTH: 17
<212> TYPE: PRT
<213> ORGANISM: Artificial Sequence
<220> FEATURE:
<223> OTHER INFORMATION: 16G10S83 VH CDR2

<400> SEQUENCE: 153

Asn Ile Asp His Asp Gly Asn Ile Ile Asn Phe Ala Pro Ser Val Lys
1               5                   10                  15

Gly

<210> SEQ ID NO 154
<211> LENGTH: 8
<212> TYPE: PRT
<213> ORGANISM: Artificial Sequence
<220> FEATURE:
<223> OTHER INFORMATION: 16G10S83 VH CDR3

<400> SEQUENCE: 154

Trp Gly His Tyr Ala Phe Asp Ser
1               5
```

<210> SEQ ID NO 155
<211> LENGTH: 15
<212> TYPE: PRT
<213> ORGANISM: Artificial Sequence
<220> FEATURE:
<223> OTHER INFORMATION: 16G10S83 VL CDR1

<400> SEQUENCE: 155

Lys Ser Ser Gln Ser Leu Leu Ser Ser Gly Tyr Asn Tyr Leu Ile
1               5                   10                  15

<210> SEQ ID NO 156
<211> LENGTH: 7
<212> TYPE: PRT
<213> ORGANISM: Artificial Sequence
<220> FEATURE:
<223> OTHER INFORMATION: 16G10S83 VL CDR2

<400> SEQUENCE: 156

Tyr Ala Ser Thr Arg Gln Thr
1               5

<210> SEQ ID NO 157
<211> LENGTH: 9
<212> TYPE: PRT
<213> ORGANISM: Artificial Sequence
<220> FEATURE:
<223> OTHER INFORMATION: 16G10S83 VL CDR3

<400> SEQUENCE: 157

Gln His His Tyr Ser Ser Pro Pro Thr
1               5

<210> SEQ ID NO 158

<400> SEQUENCE: 158

000

<210> SEQ ID NO 159

<400> SEQUENCE: 159

000

<210> SEQ ID NO 160
<211> LENGTH: 117
<212> TYPE: PRT
<213> ORGANISM: Artificial Sequence
<220> FEATURE:
<223> OTHER INFORMATION: 35A9S79 heavy chain variable region

<400> SEQUENCE: 160

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Asp Gly Ser Ile Ala Glu Tyr Ser Pro Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys

```
                    85                  90                  95
Ser Arg Trp Gly Arg Phe Ala Phe Asp Ser Trp Gly Gln Gly Thr Leu
            100                 105                 110

Val Thr Val Ser Ser
            115

<210> SEQ ID NO 161
<211> LENGTH: 111
<212> TYPE: PRT
<213> ORGANISM: Artificial Sequence
<220> FEATURE:
<223> OTHER INFORMATION: 35A9S79 light chain variable region

<400> SEQUENCE: 161

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg Gln Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His His Tyr
                85                  90                  95

Asn Ala Pro Pro Thr Phe Gly Pro Gly Thr Lys Val Asp Ile Lys
            100                 105                 110

<210> SEQ ID NO 162
<211> LENGTH: 10
<212> TYPE: PRT
<213> ORGANISM: Artificial Sequence
<220> FEATURE:
<223> OTHER INFORMATION: 35A9S79 VH CDR1

<400> SEQUENCE: 162

Gly Phe Thr Phe Ser Asp Tyr Trp Met Asp
1               5                   10

<210> SEQ ID NO 163
<211> LENGTH: 17
<212> TYPE: PRT
<213> ORGANISM: Artificial Sequence
<220> FEATURE:
<223> OTHER INFORMATION: 35A9S79 VH CDR2

<400> SEQUENCE: 163

Asn Ile Asp Glu Asp Gly Ser Ile Ala Glu Tyr Ser Pro Phe Val Lys
1               5                   10                  15

Gly

<210> SEQ ID NO 164
<211> LENGTH: 8
<212> TYPE: PRT
<213> ORGANISM: Artificial Sequence
<220> FEATURE:
<223> OTHER INFORMATION: 35A9S79 VH CDR3

<400> SEQUENCE: 164

Trp Gly Arg Phe Ala Phe Asp Ser
1               5
```

<210> SEQ ID NO 165
<211> LENGTH: 15
<212> TYPE: PRT
<213> ORGANISM: Artificial Sequence
<220> FEATURE:
<223> OTHER INFORMATION: 35A9S79 VL CDR1

<400> SEQUENCE: 165

Lys Ser Ser Gln Ser Leu Leu Ser Gly Ser Phe Asn Tyr Leu Thr
1               5                   10                  15

<210> SEQ ID NO 166
<211> LENGTH: 7
<212> TYPE: PRT
<213> ORGANISM: Artificial Sequence
<220> FEATURE:
<223> OTHER INFORMATION: 35A9S79 VL CDR2

<400> SEQUENCE: 166

Tyr Ala Ser Thr Arg Gln Thr
1               5

<210> SEQ ID NO 167
<211> LENGTH: 9
<212> TYPE: PRT
<213> ORGANISM: Artificial Sequence
<220> FEATURE:
<223> OTHER INFORMATION: 35A9S79 VL CDR3

<400> SEQUENCE: 167

His His His Tyr Asn Ala Pro Pro Thr
1               5

<210> SEQ ID NO 168

<400> SEQUENCE: 168

000

<210> SEQ ID NO 169

<400> SEQUENCE: 169

000

<210> SEQ ID NO 170
<211> LENGTH: 117
<212> TYPE: PRT
<213> ORGANISM: Artificial Sequence
<220> FEATURE:
<223> OTHER INFORMATION: 35A9S710 heavy chain variable region

<400> SEQUENCE: 170

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Ser Gly Ser Ile Ala Glu Tyr Ser Pro Phe Val
    50                  55                  60

Lys Gly Arg Phe Thr Ile Ser Arg Asp Asn Ala Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ser Arg Trp Gly Arg Phe Ala Phe Asp Ser Trp Gly Gln Gly Thr Leu
            100                 105                 110

Val Thr Val Ser Ser
        115

<210> SEQ ID NO 171
<211> LENGTH: 111
<212> TYPE: PRT
<213> ORGANISM: Artificial Sequence
<220> FEATURE:
<223> OTHER INFORMATION: 35A9S710 light chain variable region

<400> SEQUENCE: 171

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg His Thr Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His Tyr
                85                  90                  95

Asn Ala Pro Pro Thr Phe Gly Pro Gly Thr Lys Val Asp Ile Lys
            100                 105                 110

<210> SEQ ID NO 172
<211> LENGTH: 10
<212> TYPE: PRT
<213> ORGANISM: Artificial Sequence
<220> FEATURE:
<223> OTHER INFORMATION: 35A9S710 VH CDR1

<400> SEQUENCE: 172

Gly Phe Thr Phe Ser Asp Tyr Trp Met Asp
1               5                   10

<210> SEQ ID NO 173
<211> LENGTH: 17
<212> TYPE: PRT
<213> ORGANISM: Artificial Sequence
<220> FEATURE:
<223> OTHER INFORMATION: 35A9S710 VH CDR2

<400> SEQUENCE: 173

Asn Ile Asp Glu Ser Gly Ser Ile Ala Glu Tyr Ser Pro Phe Val Lys
1               5                   10                  15

Gly

<210> SEQ ID NO 174
<211> LENGTH: 8
<212> TYPE: PRT
<213> ORGANISM: Artificial Sequence
<220> FEATURE:
<223> OTHER INFORMATION: 35A9S710 VH CDR3

<400> SEQUENCE: 174

Trp Gly Arg Phe Ala Phe Asp Ser
```

<210> SEQ ID NO 175
<211> LENGTH: 15
<212> TYPE: PRT
<213> ORGANISM: Artificial Sequence
<220> FEATURE:
<223> OTHER INFORMATION: 35A9S710 VL CDR1

<400> SEQUENCE: 175

Lys Ser Ser Gln Ser Leu Leu Ser Gly Ser Phe Asn Tyr Leu Thr
1               5                   10                  15

<210> SEQ ID NO 176
<211> LENGTH: 7
<212> TYPE: PRT
<213> ORGANISM: Artificial Sequence
<220> FEATURE:
<223> OTHER INFORMATION: 35A9S710 VL CDR2

<400> SEQUENCE: 176

Tyr Ala Ser Thr Arg His Thr
1               5

<210> SEQ ID NO 177
<211> LENGTH: 9
<212> TYPE: PRT
<213> ORGANISM: Artificial Sequence
<220> FEATURE:
<223> OTHER INFORMATION: 35A9S710 VL CDR3

<400> SEQUENCE: 177

His His His Tyr Asn Ala Pro Pro Thr
1               5

<210> SEQ ID NO 178

<400> SEQUENCE: 178

000

<210> SEQ ID NO 179

<400> SEQUENCE: 179

000

<210> SEQ ID NO 180
<211> LENGTH: 117
<212> TYPE: PRT
<213> ORGANISM: Artificial Sequence
<220> FEATURE:
<223> OTHER INFORMATION: 35A9S89 heavy chain variable region

<400> SEQUENCE: 180

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Glu Trp Val
        35                  40                  45

Ser Asn Ile Asp Glu Asp Gly Ser Ile Ala Glu Tyr Ser Pro Phe Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
            85                  90                  95

Ser Arg Trp Gly Arg Phe Ala Phe Asp Ser Trp Gly Gln Gly Thr Leu
            100                 105                 110

Val Thr Val Ser Ser
        115

<210> SEQ ID NO 181
<211> LENGTH: 111
<212> TYPE: PRT
<213> ORGANISM: Artificial Sequence
<220> FEATURE:
<223> OTHER INFORMATION: 35A9S89 light chain variable region

<400> SEQUENCE: 181

Asp Ile Val Met Thr Gln Ser Pro Asp Ser Leu Ala Val Ser Ala Gly
1               5                   10                  15

Glu Arg Val Thr Ile Asn Cys Lys Ser Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg Gln Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His His Tyr
                85                  90                  95

Asn Ala Pro Pro Thr Phe Gly Gln Gly Thr Lys Leu Glu Ile Lys
            100                 105                 110

<210> SEQ ID NO 182
<211> LENGTH: 10
<212> TYPE: PRT
<213> ORGANISM: Artificial Sequence
<220> FEATURE:
<223> OTHER INFORMATION: 35A9S89 VH CDR1

<400> SEQUENCE: 182

Gly Phe Thr Phe Ser Asp Tyr Trp Met Asp
1               5                   10

<210> SEQ ID NO 183
<211> LENGTH: 17
<212> TYPE: PRT
<213> ORGANISM: Artificial Sequence
<220> FEATURE:
<223> OTHER INFORMATION: 35A9S89 VH CDR2

<400> SEQUENCE: 183

Asn Ile Asp Glu Asp Gly Ser Ile Ala Glu Tyr Ser Pro Phe Val Lys
1               5                   10                  15

Gly

<210> SEQ ID NO 184
<211> LENGTH: 8
<212> TYPE: PRT
<213> ORGANISM: Artificial Sequence
<220> FEATURE:
<223> OTHER INFORMATION: 35A9S89 VH CDR3

<400> SEQUENCE: 184
```

Trp Gly Arg Phe Ala Phe Asp Ser
1               5

<210> SEQ ID NO 185
<211> LENGTH: 15
<212> TYPE: PRT
<213> ORGANISM: Artificial Sequence
<220> FEATURE:
<223> OTHER INFORMATION: 35A9S89 VL CDR1

<400> SEQUENCE: 185

Lys Ser Ser Gln Ser Leu Leu Ser Gly Ser Phe Asn Tyr Leu Thr
1               5                   10                  15

<210> SEQ ID NO 186
<211> LENGTH: 7
<212> TYPE: PRT
<213> ORGANISM: Artificial Sequence
<220> FEATURE:
<223> OTHER INFORMATION: 35A9S89 VL CDR2

<400> SEQUENCE: 186

Tyr Ala Ser Thr Arg Gln Thr
1               5

<210> SEQ ID NO 187
<211> LENGTH: 9
<212> TYPE: PRT
<213> ORGANISM: Artificial Sequence
<220> FEATURE:
<223> OTHER INFORMATION: 35A9S89 VL CDR3

<400> SEQUENCE: 187

His His His Tyr Asn Ala Pro Pro Thr
1               5

<210> SEQ ID NO 188
<211> LENGTH: 447
<212> TYPE: PRT
<213> ORGANISM: Artificial Sequence
<220> FEATURE:
<223> OTHER INFORMATION: 37A10S713 human IgG1 heavy chain

<400> SEQUENCE: 188

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Asp Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Gly Arg Phe Gly Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

-continued

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
    195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 189
<211> LENGTH: 218
<212> TYPE: PRT
<213> ORGANISM: Artificial Sequence
<220> FEATURE:
<223> OTHER INFORMATION: 37A10S713 human kappa light chain

<400> SEQUENCE: 189

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg His Thr Gly Val Pro Asp
    50                  55                  60

```
Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys His His His Tyr
                 85                  90                  95

Asn Ala Pro Pro Thr Phe Gly Pro Gly Thr Lys Val Asp Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 190
<211> LENGTH: 200
<212> TYPE: PRT
<213> ORGANISM: Rattus norvegicus

<400> SEQUENCE: 190

Met Lys Pro Tyr Phe Ser Cys Val Phe Val Phe Cys Phe Leu Ile Lys
 1               5                  10                  15

Leu Leu Thr Gly Glu Leu Asn Asp Leu Ala Asn His Arg Met Phe Ser
                20                  25                  30

Phe His Asp Gly Gly Val Gln Ile Ser Cys Asn Tyr Pro Glu Thr Val
            35                  40                  45

Gln Gln Leu Lys Met Gln Leu Phe Lys Asp Arg Glu Val Leu Cys Asp
        50                  55                  60

Leu Thr Lys Thr Lys Gly Ser Gly Asn Thr Val Ser Ile Lys Asn Pro
 65                  70                  75                  80

Met Ser Cys Pro Tyr Gln Leu Ser Asn Asn Ser Val Ser Phe Phe Leu
                 85                  90                  95

Asp Asn Ala Asp Ser Ser Gln Gly Ser Tyr Phe Leu Cys Ser Leu Ser
            100                 105                 110

Ile Phe Asp Pro Pro Pro Phe Gln Glu Lys Asn Leu Ser Gly Gly Tyr
        115                 120                 125

Leu Leu Ile Tyr Glu Ser Gln Leu Cys Cys Gln Leu Lys Leu Trp Leu
    130                 135                 140

Pro Val Gly Cys Ala Ala Phe Val Ala Ala Leu Leu Phe Gly Cys Ile
145                 150                 155                 160

Phe Ile Val Trp Phe Ala Lys Lys Lys Tyr Arg Ser Ser Val His Asp
                165                 170                 175

Pro Asn Ser Glu Tyr Met Phe Met Ala Ala Val Asn Thr Asn Lys Lys
            180                 185                 190

Ser Arg Leu Ala Gly Met Thr Ser
        195                 200

<210> SEQ ID NO 191
```

```
<211> LENGTH: 180
<212> TYPE: PRT
<213> ORGANISM: Rattus norvegicus

<400> SEQUENCE: 191

Glu Leu Asn Asp Leu Ala Asn His Arg Met Phe Ser Phe His Asp Gly
1               5                   10                  15

Gly Val Gln Ile Ser Cys Asn Tyr Pro Glu Thr Val Gln Gln Leu Lys
            20                  25                  30

Met Gln Leu Phe Lys Asp Arg Glu Val Leu Cys Asp Leu Thr Lys Thr
        35                  40                  45

Lys Gly Ser Gly Asn Thr Val Ser Ile Lys Asn Pro Met Ser Cys Pro
50                  55                  60

Tyr Gln Leu Ser Asn Asn Ser Val Ser Phe Phe Leu Asp Asn Ala Asp
65                  70                  75                  80

Ser Ser Gln Gly Ser Tyr Phe Leu Cys Ser Leu Ser Ile Phe Asp Pro
                85                  90                  95

Pro Pro Phe Gln Glu Lys Asn Leu Ser Gly Gly Tyr Leu Leu Ile Tyr
            100                 105                 110

Glu Ser Gln Leu Cys Cys Gln Leu Lys Leu Trp Leu Pro Val Gly Cys
        115                 120                 125

Ala Ala Phe Val Ala Ala Leu Leu Phe Gly Cys Ile Phe Ile Val Trp
    130                 135                 140

Phe Ala Lys Lys Lys Tyr Arg Ser Ser Val His Asp Pro Asn Ser Glu
145                 150                 155                 160

Tyr Met Phe Met Ala Ala Val Asn Thr Asn Lys Lys Ser Arg Leu Ala
                165                 170                 175

Gly Met Thr Ser
            180

<210> SEQ ID NO 192
<211> LENGTH: 120
<212> TYPE: PRT
<213> ORGANISM: Mus musculus

<400> SEQUENCE: 192

Glu Val Gln Leu Gln Gln Ser Gly Ala Glu Leu Val Arg Pro Gly Ala
1               5                   10                  15

Val Val Lys Leu Ser Cys Lys Ala Ser Gly Phe Asp Ile Lys Asp Tyr
            20                  25                  30

Tyr Met His Trp Val Gln Gln Arg Pro Glu Gln Gly Leu Glu Trp Ile
        35                  40                  45

Gly Trp Ile Asp Pro Glu Asn Gly Asn Ala Val Tyr Asp Pro Gln Phe
50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Asp Tyr Tyr Gly Ser Lys Gly Tyr Leu Asp Val Trp Gly Ala
            100                 105                 110

Gly Thr Thr Val Thr Val Ser Ser
        115                 120

<210> SEQ ID NO 193
<211> LENGTH: 106
<212> TYPE: PRT
<213> ORGANISM: Mus musculus
```

<400> SEQUENCE: 193

Gln Ile Val Leu Thr Gln Ser Pro Thr Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Gly Gly Ser
    50                  55                  60

Arg Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys
            100                 105

<210> SEQ ID NO 194
<211> LENGTH: 5
<212> TYPE: PRT
<213> ORGANISM: Mus musculus

<400> SEQUENCE: 194

Asp Tyr Tyr Met His
1               5

<210> SEQ ID NO 195
<211> LENGTH: 17
<212> TYPE: PRT
<213> ORGANISM: Mus musculus

<400> SEQUENCE: 195

Trp Ile Asp Pro Glu Asn Gly Asn Ala Val Tyr Asp Pro Gln Phe Gln
1               5                   10                  15

Gly

<210> SEQ ID NO 196
<211> LENGTH: 11
<212> TYPE: PRT
<213> ORGANISM: Mus musculus

<400> SEQUENCE: 196

Asp Tyr Tyr Gly Ser Lys Gly Tyr Leu Asp Val
1               5                   10

<210> SEQ ID NO 197
<211> LENGTH: 10
<212> TYPE: PRT
<213> ORGANISM: Mus musculus

<400> SEQUENCE: 197

Ser Ala Ser Ser Ser Val Ser Tyr Met His
1               5                   10

<210> SEQ ID NO 198
<211> LENGTH: 7
<212> TYPE: PRT
<213> ORGANISM: Mus musculus

<400> SEQUENCE: 198

Ser Thr Ser Asn Leu Ala Ser

```
<210> SEQ ID NO 199
<211> LENGTH: 9
<212> TYPE: PRT
<213> ORGANISM: Mus musculus

<400> SEQUENCE: 199

Gln Gln Arg Ser Ser Tyr Pro Phe Thr
1               5

<210> SEQ ID NO 200
<211> LENGTH: 115
<212> TYPE: PRT
<213> ORGANISM: Mus musculus

<400> SEQUENCE: 200

Glu Val Gln Leu Gln Gln Ser Gly Ala Glu Leu Val Arg Ser Gly Ala
1               5                   10                  15

Ser Val Lys Leu Ser Cys Thr Thr Ser Ala Phe Asn Ile Ile Asp Tyr
            20                  25                  30

Tyr Met His Trp Val Ile Gln Arg Pro Glu Gln Gly Leu Glu Trp Ile
        35                  40                  45

Ala Trp Ile Asp Pro Glu Asn Gly Asp Pro Glu Tyr Ala Pro Lys Phe
    50                  55                  60

Gln Asp Lys Ala Thr Met Thr Thr Asp Thr Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Ala Trp Arg Gly Phe Ala Tyr Trp Gly Gln Gly Thr Leu Val Thr
            100                 105                 110

Val Ser Ala
        115

<210> SEQ ID NO 201
<211> LENGTH: 112
<212> TYPE: PRT
<213> ORGANISM: Mus musculus

<400> SEQUENCE: 201

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Ile His Val Pro Pro Thr Phe Gly Gly Gly Thr Lys Leu Glu Ile Lys
            100                 105                 110

<210> SEQ ID NO 202
<211> LENGTH: 5
<212> TYPE: PRT
<213> ORGANISM: Mus musculus
```

<400> SEQUENCE: 202

Asp Tyr Tyr Met His
1               5

<210> SEQ ID NO 203
<211> LENGTH: 17
<212> TYPE: PRT
<213> ORGANISM: Mus musculus

<400> SEQUENCE: 203

Trp Ile Asp Pro Glu Asn Gly Asp Pro Glu Tyr Ala Pro Lys Phe Gln
1               5                   10                  15

Asp

<210> SEQ ID NO 204
<211> LENGTH: 6
<212> TYPE: PRT
<213> ORGANISM: Mus musculus

<400> SEQUENCE: 204

Trp Arg Gly Phe Ala Tyr
1               5

<210> SEQ ID NO 205
<211> LENGTH: 16
<212> TYPE: PRT
<213> ORGANISM: Mus musculus

<400> SEQUENCE: 205

Arg Ser Ser Gln Ser Leu Val His Ser Asn Gly Asn Thr Tyr Leu His
1               5                   10                  15

<210> SEQ ID NO 206
<211> LENGTH: 7
<212> TYPE: PRT
<213> ORGANISM: Mus musculus

<400> SEQUENCE: 206

Lys Val Ser Asn Arg Phe Ser
1               5

<210> SEQ ID NO 207
<211> LENGTH: 9
<212> TYPE: PRT
<213> ORGANISM: Mus musculus

<400> SEQUENCE: 207

Ser Gln Ser Ile His Val Pro Pro Thr
1               5

<210> SEQ ID NO 208
<211> LENGTH: 115
<212> TYPE: PRT
<213> ORGANISM: Mus musculus

<400> SEQUENCE: 208

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Arg Asp Tyr
                20                  25                  30

Tyr Met His Trp Val Arg Gln Arg Pro Glu Gln Gly Leu Glu Trp Ile
            35                  40                  45

Gly Trp Ile Asp Pro Glu Asn Gly Asp Ile Asp Tyr Ala Pro Lys Phe
        50                  55                  60

Gln Asp Lys Ala Thr Met Thr Ala Asp Thr Ser Asn Thr Ala Tyr
65                  70                  75                  80

Leu Gln Leu Ser Ser Leu Thr Ser Glu Asp Ser Ala Val Tyr Tyr Phe
                85                  90                  95

Thr Ala Trp Lys Gly Leu Ala Tyr Trp Gly Gln Gly Thr Leu Val Thr
                100                 105                 110

Val Ser Ala
        115

<210> SEQ ID NO 209
<211> LENGTH: 112
<212> TYPE: PRT
<213> ORGANISM: Mus musculus

<400> SEQUENCE: 209

Asp Val Val Met Thr Gln Thr Pro Leu Ser Leu Pro Val Ser Leu Gly
1               5                   10                  15

Asp Gln Ala Ser Met Ser Cys Arg Ser Ser Gln Ser Leu Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Phe Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
                100                 105                 110

<210> SEQ ID NO 210
<211> LENGTH: 5
<212> TYPE: PRT
<213> ORGANISM: Mus musculus

<400> SEQUENCE: 210

Asp Tyr Tyr Met His
1               5

<210> SEQ ID NO 211
<211> LENGTH: 17
<212> TYPE: PRT
<213> ORGANISM: Mus musculus

<400> SEQUENCE: 211

Trp Ile Asp Pro Glu Asn Gly Asp Ile Asp Tyr Ala Pro Lys Phe Gln
1               5                   10                  15

Asp

<210> SEQ ID NO 212
<211> LENGTH: 6
<212> TYPE: PRT
<213> ORGANISM: Mus musculus

<400> SEQUENCE: 212

Trp Lys Gly Leu Ala Tyr
1               5

```
<210> SEQ ID NO 213
<211> LENGTH: 16
<212> TYPE: PRT
<213> ORGANISM: Mus musculus

<400> SEQUENCE: 213

Arg Ser Ser Gln Ser Leu Val His Ser Asn Gly Asn Thr Tyr Leu Gln
1               5                   10                  15

<210> SEQ ID NO 214
<211> LENGTH: 7
<212> TYPE: PRT
<213> ORGANISM: Mus musculus

<400> SEQUENCE: 214

Lys Val Phe Asn Arg Phe Ser
1               5

<210> SEQ ID NO 215
<211> LENGTH: 9
<212> TYPE: PRT
<213> ORGANISM: Mus musculus

<400> SEQUENCE: 215

Ser Gln Ser Thr His Val Pro Pro Thr
1               5
```

GENE SIGNATURES FOR DETERMINING ICOS EXPRESSION

CROSS-REFERENCE TO RELATED APPLICATIONS

This application is a national phase entry pursuant to 35 U.S.C. § 371 of International Application No. PCT/US2016/058032, filed Oct. 21, 2016, which claims the benefit of priority of U.S. Provisional Application Nos. 62/245,180, filed Oct. 22, 2015; 62/311,486, filed Mar. 22, 2016; 62/359,069, filed Jul. 6, 2016; and 62/395,970, filed Sep. 16, 2016; each of which is incorporated by reference in its entirety for any purpose.

FIELD OF THE INVENTION

Gene expression signatures correlating to ICOS expression levels are provided. Methods of treatment comprising determining ICOS expression levels using gene signatures in patients and administering anti-ICOS antibodies are also provided.

BACKGROUND

ICOS is a member of the B7/CD28/CTLA-4 immunoglobulin superfamily and is specifically expressed on T cells. Unlike CD28, which is constitutively expressed on T cells and provides co-stimulatory signals necessary for full activation of resting T cells, ICOS is expressed only after initial T cell activation.

ICOS has been implicated in diverse aspects of T cell responses (reviewed in Simpson et al., 2010, *Curr. Opin. Immunol.*, 22: 326-332). It plays a role in the formation of germinal centers, TB cell collaboration, and immunoglobulin class switching. ICOS-deficient mice show impaired germinal center formation and have decreased production of interleukin IL-10. These defects have been specifically linked to deficiencies in T follicular helper cells.

ICOS also plays a role in the development and function of other T cell subsets, including Th1, Th2, and Th17. Notably, ICOS co-stimulates T cell proliferation and cytokine secretion associated with both Th1 and Th2 cells. Accordingly, ICOS KO mice demonstrate impaired development of autoimmune phenotypes in a variety of disease models, including diabetes (Th1), airway inflammation (Th2) and EAE neuro-inflammatory models (Th17).

In addition to its role in modulating T effector (Teff) cell function, ICOS also modulates T regulatory cells (Tregs). ICOS is expressed at high levels on Tregs, and has been implicated in Treg homeostasis and function.

Upon activation, ICOS, a disulfide-linked homodimer, induces a signal through the PI3K and AKT pathways. Subsequent signaling events result in expression of lineage specific transcription factors (e.g., T-bet, GATA-3) and, in turn, effects on T cell proliferation and survival.

ICOS ligand (ICOSL; B7-H2; B7RP1; CD275; GL50), also a member of the B7 superfamily, is the only ligand for ICOS and is expressed on the cell surface of B cells, macrophages and dendritic cells. ICOSL functions as a non-covalently linked homodimer on the cell surface in its interaction with ICOS. Human ICOSL, although not mouse ICOSL, has been reported to bind to human CD28 and CTLA-4 (Yao et al., 2011, *Immunity*, 34: 729-740).

SUMMARY

In some embodiments, a method of determining the level of ICOS expression in a sample is provided, comprising detecting the levels of at least two, at least three, at least four, at least five, at least six, at least seven, at least eight, at least nine, or at least ten mRNAs selected from the mRNAs in Table 6. In some embodiments, detection of at least two, at least three, at least four, at least five, at least six, at least seven, at least eight, at least nine, or at least ten mRNAs selected from the mRNAs in Table 6 provides a more robust assay for determining ICOS expression than detecting ICOS alone.

In some embodiments, a method of determining the level of ICOS expression in a sample is provided, comprising determining whether the cancer is microsatellite insability (MSI) positive. In some embodiments, if the cancer is MSI positive, ICOS expression is determined to be elevated. In some embodiments, if the cancer is MSI high, ICOS expression is determined to be elevated.

In some embodiments, a method of predicting whether a cancer will respond to anti-ICOS antibody therapy is provided, comprising detecting the levels of at least two, at least three, at least four, at least five, at least six, at least seven, at least eight, at least nine, or at least ten mRNAs selected from the mRNAs in Table 6 in a sample from a subject with cancer. In some embodiments, if the level of at least one, at least two, at least three, at least four, at least five, at least six, at least seven, at least eight, at least nine, or at least ten of the mRNAs is above a threshold level, the cancer is predicted to respond to anti-ICOS antibody therapy.

In some embodiments, a method of predicting whether a cancer will respond to anti-ICOS antibody therapy is provided, comprising determining whether the cancer is microsatellite insability (MSI) positive. In some embodiments, if the cancer is MSI positive, the cancer is predicted to respond to anti-ICOS antibody therapy. In some embodiments, if the cancer is MSI high, the cancer is predicted to respond to anti-ICOS antibody therapy. As shown in FIG. 36, MSI high (MSI-H) cancers express higher levels of ICOS. Accordingly, in some embodiments, methods of treating MSI-H cancers are provided, comprising administering anti-ICOS antibody therapy. In some embodiments, the MSI-H cancer is selected from colon adenocarcinoma (COAD), stomach adenocarcinoma (STAD; also known as gastric cancer), and uterine corpus endometrial carcinoma (UCEC).

In some embodiments, a method of identifying a subject with cancer who is likely to benefit from treatment with an anti-ICOS antibody is provided, comprising detecting the levels of at least two, at least three, at least four, at least five, at least six, at least seven, at least eight, at least nine, or at least ten mRNAs selected from the mRNAs in Table 6 in a sample from the subject. In some embodiments, if the level of at least one, at least two, at least three, at least four, at least five, at least six, at least seven, at least eight, at least nine, or at least ten of the mRNAs is above a threshold level, the subject is identified as likely to benefit from treatment with an anti-ICOS antibody.

In some embodiments, a method of identifying a subject with cancer who is likely to benefit from treatment with an anti-ICOS antibody is provided, comprising determining whether the cancer is microsatellite insability (MSI) positive. In some embodiments, if the cancer is MSI positive, the subject is likely to benefit from treatment with an anti-ICOS antibody therapy. In some embodiments, if the cancer is MSI high, the subject is likely to benefit from treatment with an anti-ICOS antibody therapy.

In some embodiments, a method of selecting a cancer therapy for a subject with cancer is provided, comprising detecting the levels of at least two, at least three, at least four, at least five, at least six, at least seven, at least eight, at least nine, or at least ten mRNAs selected from the mRNAs in Table 6 in a sample from the subject, and if the level of at least one, at least two, at least three, at least four, at least five, at least six, at least seven, at least eight, at least nine, or at least ten of the mRNAs is above a threshold level, selecting an anti-ICOS antibody for the therapy.

In some embodiments, a method of selecting a cancer therapy for a subject with cancer is provided, comprising determining whether the cancer is microsatellite insability (MSI) positive. In some embodiments, if the cancer is MSI positive, an anti-ICOS antibody therapy is selected. In some embodiments, if the cancer is MSI high, an anti-ICOS antibody therapy is selected.

In some embodiments, a method according to this disclosure further comprises administering an effective amount of an anti-ICOS antibody to the subject.

In some embodiments, a method of treating cancer in a subject is provided, comprising detecting the levels of at least two, at least three, at least four, at least five, at least six, at least seven, at least eight, at least nine, or at least ten mRNAs selected from the mRNAs in Table 6 in a sample from a subject; and if the level of at least one, at least two, at least three, at least four, at least five, at least six, at least seven, at least eight, at least nine, or at least ten of the mRNAs is above a threshold level, then treating the subject with an effective amount of anti-ICOS antibody.

In some embodiments of a method according to this disclosure, the threshold level is determined relative to a reference mRNA. In some embodiments, the reference mRNA is a housekeeping mRNA.

In some embodiments of a method according to this disclosure, the method comprises detecting the levels of at least two, at least three, at least four, at least five, at least six, at least seven, at least eight, at least nine, or at least ten mRNAs selected from CCR5, CD2, CD96, CTLA4, CXCR6, FOXP3, ICOS, ITK, P2RY10, SIRPG, and TIGIT.

In some embodiments of a method according to this disclosure, the detecting comprises at least one method selected from amplification and hybridization. In some embodiments, the method comprises quantitative PCR. In some embodiments, the method comprises hybridization on an array.

In some embodiments of a method according to this disclosure, determining if a cancer is MSI positive comprises detecting markers of microsatellite instability by PCR. In some such embodiments, the method comprises detecting genetic instability at markers (loci) BAT25, BAT26, D5S346, D2S123, and D17S250 by PCR. In some embodiments, if genetic instability is detected at 2 or more of the markers, a cancer is MSI-high. In some embodiments, if genetic instability is detected at 1 marker, the cancer is MSI-low. In some embodiments, if genetic instability is detected at 0 markers, the cancer is MSS. In some embodiments, if genentic instability is detected at at least 30% of the markers (loci) tested by PCR, then the cancer is MSI-high. In some embodiments, if genentic instability is detected at more than 0% but less than 30% of the markers (loci) tested by PCR, then the cancer is MSI-low. In some embodiments, if genentic instability is detected at 0% of the markers (loci) tested by PCR, then the cancer is MSS. In some embodiments of a method according to this disclosure, determining if a cancer is MSI positive comprises detecting one or more mismatch repair proteins by IHC. In some embodiments, the method comprises detecting one, two, three, or four mismatch repair proteins selected from MLH1, MSH2, PMS2, and MSH6. In some embodiments, if one or more of the mismatch repair proteins is not detected by IHC, the cancer is MSI-positive.

In some embodiments of a method according to this disclosure, the sample is a cancer sample.

In some embodiments of a method according to this disclosure, the subject has a cancer is selected from melanoma, non-small cell lung cancer (NSCLC), renal cell carcinoma (RCC), gastric cancer, bladder cancer, endometrial cancer (including uterine corpus endometrial carcinoma (UCEC)), diffuse large B-cell lymphoma (DLBCL), Hodgkin's lymphoma, ovarian cancer, head & neck squamous cell cancer (HNSCC), and triple negative breast cancer (TNBC). In some embodiments, the subject has a cancer selected from melanoma, gastric cancer, endometrial cancer (including uterine corpus endometrial carcinoma (UCEC)), head & neck squamous cell cancer (HNSCC), non-small cell lung cancer (NSCLC), and triple negative breast cancer (TNBC). In some embodiments, the subject has a lung adenocarcinoma subtype selected from terminal respiratory unit (TRU) and prox-inflammatory. In some embodiments, the subject has the secretory subtype of lung squamous cell carcinoma. In some embodiments, the subject has a head and neck squamous cell carcinoma subtype selected from HPV+, HPV−, basal, atypical, and mesenchymal. In some embodiments, the subject has a breast invasive carcinoma subtype selected from HER2+ and triple negative. In some embodiments, the subject has the POLE mutation subtype of uterine corpus endometrial carcinoma. In some embodiments, the subject has MSI-H uterine corpus endometrial carcinoma (UCEC). In some embodiments, the subject has HPV+ cervical squamous cell carcinoma and endocervical adenocarcinoma. In some embodiments, the subject has a stomach adenocarcinoma subtype selected from MSI-H, CN stable, and EV+. In some embodiments, the subject has the basal III (squamous) or basal IV (mesenchymal) subtype of bladder urothelial carcinoma. In some embodiments, the subject has the immunogenic subtype of pancreatic adenocarcinoma. In some embodiments, the subject has the S1 subtype of liver hepatocellular carcinoma.

In some embodiments, a method of selecting a patient for treatment with a therapeutic agonist anti-ICOS antibody is provided, comprising contacting T cells from the patient with a test agonist anti-ICOS antibody and determining whether NKp46 ligand (NKp46-L) is induced on the T cells. In some embodiments, a method of determining whether a patient will respond to treatment with a therapeutic agonist anti-ICOS antibody is provided, comprising contacting T cells from the patient with a test agonist anti-ICOS antibody and determining whether NKp46 ligand (NKp46-L) is induced on the T cells. In some embodiments, if NKp46-L is induced on the T cells, the patient is selected for treatment with the therapeutic anti-ICOS agonist antibody. In some embodiments, the T cells are Treg cells. In some embodiments, if NKp46-L is induced on Treg cells to a greater extent than on Teff cells, the patient is selected for treatment with the therapeutic anti-ICOS agonist antibody. In some embodiments, the induction of NKp46-L on T cells is determined using a soluble NKp46 extracellular domain in a flow cytometry assay. In some embodiments, the T cells are comprised in a blood sample from the patient. In some embodiments, the T cells are comprised in a peripheral blood mononucleocyte (PBMC) sample from the patient. In some embodiments, the therapeutic agonist anti-ICOS antibody and the test agonist anti-ICOS antibody are the same. In some embodiments, the therapeutic agonist anti-ICOS antibody and the test agonist anti-ICOS antibody are different.

In some embodiments of a method according to this disclosure, the anti-ICOS antibody binds to human ICOS, and the antibody also binds to mouse ICOS and/or rat ICOS. In some embodiments, the antibody binds to human ICOS with an affinity ($K_D$) of less than 5 nM. In some embodiments, the antibody binds to rat ICOS with an affinity ($K_D$) of less than 10 nM. In some embodiments, affinity is determined using biolayer interferometry. In some embodiments, the antibody binds to human ICOS, mouse ICOS, and rat ICOS. In some embodiments, the antibody binds to cynomolgus monkey ICOS.

In some embodiments of a method according to this disclosure, the anti-ICOS antibody comprises:

i) (a) HCDR1 comprising the amino acid sequence of SEQ ID NO: 12; (b) HCDR2 comprising the amino acid sequence of SEQ ID NO: 13; (c) HCDR3 comprising the amino acid sequence of SEQ ID NO: 14; (d) LCDR1 comprising the amino acid sequence of SEQ ID NO: 15; (e) LCDR2 comprising the amino acid sequence of SEQ ID NO: 16; and (f) LCDR3 comprising the amino acid sequence of SEQ ID NO: 17; or ii) (a) HCDR1 comprising the amino acid sequence of SEQ ID NO: 42; (b) HCDR2 comprising the amino acid sequence of SEQ ID NO: 43; (c) HCDR3 comprising the amino acid sequence of SEQ ID NO: 44; (d) LCDR1 comprising the amino acid sequence of SEQ ID NO: 45; (e) LCDR2 comprising the amino acid sequence of SEQ ID NO: 46; and (f) LCDR3 comprising the amino acid sequence of SEQ ID NO: 47; or iii) (a) HCDR1 comprising the amino acid sequence of SEQ ID NO: 62; (b) HCDR2 comprising the amino acid sequence of SEQ ID NO: 63; (c) HCDR3 comprising the amino acid sequence of SEQ ID NO: 64; (d) LCDR1 comprising the amino acid sequence of SEQ ID NO: 65; (e) LCDR2 comprising the amino acid sequence of SEQ ID NO: 66; and (f) LCDR3 comprising the amino acid sequence of SEQ ID NO: 67; or iv) (a) HCDR1 comprising an amino acid sequence selected from SEQ ID NOs: 22, 62, 72, 82, 92, 102, and 112; (b) HCDR2 comprising an amino acid sequence selected from SEQ ID NOs: 23, 63, 73, 83, 93, 103, and 113; (c) HCDR3 comprising an amino acid sequence selected from SEQ ID NOs: 24, 64, 74, 84, 94, 104, and 114; (d) LCDR1 comprising an amino acid sequence selected from SEQ ID NOs: 25, 65, 75, 85, 95, 105, and 115; (e) LCDR2 comprising an amino acid sequence selected from SEQ ID NOs: 26, 66, 76, 86, 96, 106, and 116; and (f) LCDR3 comprising an amino acid sequence selected from SEQ ID NOs: 27, 67, 77, 87, 97, 107, and 117; or v) (a) HCDR1 comprising an amino acid sequence selected from SEQ ID NOs: 32, 162, 172, and 182; (b) HCDR2 comprising an amino acid sequence selected from SEQ ID NOs: 33, 163, 173, and 183; (c) HCDR3 comprising an amino acid sequence selected from SEQ ID NOs: 34, 164, 174, and 184; (d) LCDR1 comprising an amino acid sequence selected from SEQ ID NOs: 35, 165, 175, and 185; (e) LCDR2 comprising an amino acid sequence selected from SEQ ID NOs: 36, 166, 176, and 186; and (f) LCDR3 comprising an amino acid sequence selected from SEQ ID NOs: 37, 167, 177, and 187; or vi) (a) HCDR1 comprising an amino acid sequence selected from SEQ ID NOs: 52, 122, 132, 142, and 152; (b) HCDR2 comprising an amino acid sequence selected from SEQ ID NOs: 53, 123, 133, 143, and 153; (c) HCDR3 comprising an amino acid sequence selected from SEQ ID NOs: 54, 124, 134, 144, and 154; (d) LCDR1 comprising an amino acid sequence selected from SEQ ID NOs: 55, 125, 135, 145, and 155; (e) LCDR2 comprising an amino acid sequence selected from SEQ ID NOs: 56, 126, 136, 146, and 156; and (f) LCDR3 comprising an amino acid sequence selected from SEQ ID NOs: 57, 127, 137, 147, and 157; or vii) (a) HCDR1 comprising the amino acid sequence of SEQ ID NO: 22; (b) HCDR2 comprising the amino acid sequence of SEQ ID NO: 23; (c) HCDR3 comprising the amino acid sequence of SEQ ID NO: 24; (d) LCDR1 comprising the amino acid sequence of SEQ ID NO: 25; (e) LCDR2 comprising the amino acid sequence of SEQ ID NO: 26; and (f) LCDR3 comprising the amino acid sequence of SEQ ID NO: 27; or viii) (a) HCDR1 comprising the amino acid sequence of SEQ ID NO: 32; (b) HCDR2 comprising the amino acid sequence of SEQ ID NO: 33; (c) HCDR3 comprising the amino acid sequence of SEQ ID NO: 34; (d) LCDR1 comprising the amino acid sequence of SEQ ID NO: 35; (e) LCDR2 comprising the amino acid sequence of SEQ ID NO: 36; and (f) LCDR3 comprising the amino acid sequence of SEQ ID NO: 37; or ix) (a) HCDR1 comprising the amino acid sequence of SEQ ID NO: 52; (b) HCDR2 comprising the amino acid sequence of SEQ ID NO: 53; (c) HCDR3 comprising the amino acid sequence of SEQ ID NO: 54; (d) LCDR1 comprising the amino acid sequence of SEQ ID NO: 55; (e) LCDR2 comprising the amino acid sequence of SEQ ID NO: 56; and (f) LCDR3 comprising the amino acid sequence of SEQ ID NO: 57; or x) (a) HCDR1 comprising the amino acid sequence of SEQ ID NO: 72; (b) HCDR2 comprising the amino acid sequence of SEQ ID NO: 73; (c) HCDR3 comprising the amino acid sequence of SEQ ID NO: 74; (d) LCDR1 comprising the amino acid sequence of SEQ ID NO: 75; (e) LCDR2 comprising the amino acid sequence of SEQ ID NO: 76; and (f) LCDR3 comprising the amino acid sequence of SEQ ID NO: 77; or xi) (a) HCDR1 comprising the amino acid sequence of SEQ ID NO: 82; (b) HCDR2 comprising the amino acid sequence of SEQ ID NO: 83; (c) HCDR3 comprising the amino acid sequence of SEQ ID NO: 84; (d) LCDR1 comprising the amino acid sequence of SEQ ID NO: 85; (e) LCDR2 comprising the amino acid sequence of SEQ ID NO: 86; and (f) LCDR3 comprising the amino acid sequence of SEQ ID NO: 87; or xii) (a) HCDR1 comprising the amino acid sequence of SEQ ID NO: 92; (b) HCDR2 comprising the amino acid sequence of SEQ ID NO: 93; (c) HCDR3 comprising the amino acid sequence of SEQ ID NO: 94; (d) LCDR1 comprising the amino acid sequence of SEQ ID NO: 95; (e) LCDR2 comprising the amino acid sequence of SEQ ID NO: 96; and (f) LCDR3 comprising the amino acid sequence of SEQ ID NO: 97; or xiii) (a) HCDR1 comprising the amino acid sequence of SEQ ID NO: 102; (b) HCDR2 comprising the amino acid sequence of SEQ ID NO: 103; (c) HCDR3 comprising the amino acid sequence of SEQ ID NO: 104; (d) LCDR1 comprising the amino acid sequence of SEQ ID NO: 105; (e) LCDR2 comprising the amino acid sequence of SEQ ID NO: 106; and (f) LCDR3 comprising the amino acid sequence of SEQ ID NO: 107; or xiv) (a) HCDR1 comprising the amino acid sequence of SEQ ID NO: 112; (b) HCDR2 comprising the amino acid sequence of SEQ ID NO: 113; (c) HCDR3 comprising the amino acid sequence of SEQ ID NO: 114; (d) LCDR1 comprising the amino acid sequence of SEQ ID NO: 115; (e) LCDR2 comprising the amino acid sequence of SEQ ID NO: 116; and (f) LCDR3 comprising the amino acid sequence of SEQ ID NO: 117; or xv) (a) HCDR1 comprising the amino acid sequence of SEQ ID NO: 122; (b) HCDR2 comprising the amino acid sequence of SEQ ID NO: 123; (c) HCDR3 comprising the amino acid sequence of SEQ ID NO: 124; (d) LCDR1 comprising the amino acid sequence of SEQ ID NO: 125; (e) LCDR2 comprising the amino acid sequence of SEQ ID NO: 126; and (f) LCDR3 comprising the amino acid sequence of SEQ ID NO: 127; or xvi) (a) HCDR1 comprising the amino acid sequence of SEQ ID NO: 132; (b) HCDR2 comprising the amino acid sequence of SEQ ID NO: 133; (c) HCDR3 comprising the amino acid sequence of SEQ ID NO: 134; (d) LCDR1 comprising the amino acid sequence of SEQ ID NO: 135; (e) LCDR2 comprising the amino acid sequence of SEQ ID NO: 136; and (f) LCDR3 comprising the amino acid sequence of SEQ ID NO: 137; or (a) HCDR1 comprising the amino acid sequence of SEQ ID NO: 142; (b) HCDR2 comprising the amino acid sequence of SEQ ID NO: 143; (c) HCDR3 comprising the amino acid sequence of SEQ ID NO: 144; (d) LCDR1 comprising the amino acid sequence of SEQ ID NO: 145; (e) LCDR2 comprising the amino acid sequence of SEQ ID NO: 146; and (f) LCDR3 comprising the amino acid sequence of SEQ ID NO: 147; or xvii) (a) HCDR1 comprising the amino acid sequence of SEQ ID NO: 152; (b) HCDR2 comprising the amino acid sequence of SEQ ID NO: 153; (c) HCDR3 comprising the amino acid sequence of SEQ ID NO: 154; (d) LCDR1 comprising the amino acid sequence of SEQ ID NO: 155; (e) LCDR2 comprising the amino acid sequence of SEQ ID NO: 156; and (f) LCDR3 comprising the amino acid sequence of SEQ ID NO: 157; or xviii) (a) HCDR1 comprising the amino acid sequence of SEQ ID NO: 162; (b) HCDR2 comprising the amino acid sequence of SEQ ID NO: 163; (c) HCDR3 comprising the amino acid sequence of SEQ ID NO: 164; (d) LCDR1 comprising the amino acid sequence of SEQ ID NO: 165; (e) LCDR2 comprising the amino acid sequence of SEQ ID NO: 166; and (f) LCDR3 comprising the amino acid sequence of SEQ ID NO: 167; or xix) (a) HCDR1 comprising the amino acid sequence of SEQ ID NO: 172; (b) HCDR2 comprising the amino acid sequence of SEQ ID NO: 173; (c) HCDR3 comprising the amino acid sequence of SEQ ID NO: 174; (d) LCDR1 comprising the amino acid sequence of SEQ ID NO: 175; (e) LCDR2 comprising the amino acid sequence of SEQ ID NO: 176; and (f) LCDR3 comprising the amino acid sequence of SEQ ID NO: 177; or xx) (a) HCDR1 comprising the amino acid sequence of SEQ ID NO: 182; (b) HCDR2 comprising the amino acid sequence of SEQ ID NO: 183; (c) HCDR3 comprising the amino acid sequence of SEQ ID NO: 184; (d) LCDR1 comprising the amino acid sequence of SEQ ID NO: 185; (e) LCDR2 comprising the amino acid sequence of SEQ ID NO: 186; and (f) LCDR3 comprising the amino acid sequence of SEQ ID NO: 187.

In some embodiments of a method according to this disclosure, the anti-ICOS antibody comprises:

i) (a) HCDR1 comprising the amino acid sequence of SEQ ID NO: 194; (b) HCDR2 comprising the amino acid sequence of SEQ ID NO: 195; (c) HCDR3 comprising the amino acid sequence of SEQ ID NO: 196; (d) LCDR1 comprising the amino acid sequence of SEQ ID NO: 197; (e) LCDR2 comprising the amino acid sequence of SEQ ID NO: 198; and (f) LCDR3 comprising the amino acid sequence of SEQ ID NO: 199; or ii) (a) HCDR1 comprising the amino acid sequence of SEQ ID NO: 202; (b) HCDR2 comprising the amino acid sequence of SEQ ID NO: 203; (c) HCDR3 comprising the amino acid sequence of SEQ ID NO: 204; (d) LCDR1 comprising the amino acid sequence of SEQ ID NO: 205; (e) LCDR2 comprising the amino acid sequence of SEQ ID NO: 206; and (f) LCDR3 comprising the amino acid sequence of SEQ ID NO: 207; or iii) (a) HCDR1 comprising the amino acid sequence of SEQ ID NO: 210; (b) HCDR2 comprising the amino acid sequence of SEQ ID NO: 211; (c) HCDR3 comprising the amino acid sequence of SEQ ID NO: 212; (d) LCDR1 comprising the amino acid sequence of SEQ ID NO: 213; (e) LCDR2 comprising the amino acid sequence of SEQ ID NO: 214; and (f) LCDR3 comprising the amino acid sequence of SEQ ID NO: 215.

In some embodiments of a method according to this disclosure, the anti-ICOS antibody comprises a heavy chain variable region ($V_H$) and a light chain variable region ($V_L$), wherein:

i) the $V_H$ is at least 90%, 91%, 92%, 93%, 94%, 95%, 96%, 97%, 98%, 99%, or 100% identical to the amino acid sequence of SEQ ID NO: 192 and the $V_L$ is at least 90%, 91%, 92%, 93%, 94%, 95%, 96%, 97%, 98%, 99%, or 100% identical to the amino acid sequence of SEQ ID NO: 193; or ii) the $V_H$ is at least 90%, 91%, 92%, 93%, 94%, 95%, 96%, 97%, 98%, 99%, or 100% identical to the amino acid sequence of SEQ ID NO: 200 and the $V_L$ is at least 90%, 91%, 92%, 93%, 94%, 95%, 96%, 97%, 98%, 99%, or 100% identical to the amino acid sequence of SEQ ID NO: 201; or iii) the $V_H$ is at least 90%, 91%, 92%, 93%, 94%, 95%, 96%, 97%, 98%, 99%, or 100% identical to the amino acid sequence of SEQ ID NO: 208 and the $V_L$ is at least 90%, 91%, 92%, 93%, 94%, 95%, 96%, 97%, 98%, 99%, or 100% identical to the amino acid sequence of SEQ ID NO: 209.

In some embodiments of a method according to this disclosure, the anti-ICOS antibody comprises a heavy chain variable region ($V_H$) and a light chain variable region ($V_L$), wherein:

iv) the $V_H$ comprises the amino acid sequence of SEQ ID NO: 192 and the $V_L$ comprises the amino acid sequence of SEQ ID NO: 193; or v) the $V_H$ comprises the amino acid sequence of SEQ ID NO: 200 and the $V_L$ comprises the amino acid sequence of SEQ ID NO: 201; or vi) the $V_H$ comprises the amino acid sequence of SEQ ID NO: 208 and the $V_L$ comprises the amino acid sequence of SEQ ID NO: 209.

In some embodiments of a method according to this disclosure, the anti-ICOS antibody comprises a heavy chain variable region ($V_H$) and a light chain variable region ($V_L$), wherein:
- i) the $V_H$ is at least 90%, 91%, 92%, 93%, 94%, 95%, 96%, 97%, 98%, 99%, or 100% identical to the amino acid sequence of SEQ ID NO: 10 and the $V_L$ is at least 90%, 91%, 92%, 93%, 94%, 95%, 96%, 97%, 98%, 99%, or 100% identical to the amino acid sequence of SEQ ID NO: 11; or
- ii) the $V_H$ is at least 90%, 91%, 92%, 93%, 94%, 95%, 96%, 97%, 98%, 99%, or 100% identical to the amino acid sequence of SEQ ID NO: 20 and the $V_L$ is at least 90%, 91%, 92%, 93%, 94%, 95%, 96%, 97%, 98%, 99%, or 100% identical to the amino acid sequence of SEQ ID NO: 21; or
- iii) the $V_H$ is at least 90%, 91%, 92%, 93%, 94%, 95%, 96%, 97%, 98%, 99%, or 100% identical to the amino acid sequence of SEQ ID NO: 30 and the $V_L$ is at least 90%, 91%, 92%, 93%, 94%, 95%, 96%, 97%, 98%, 99%, or 100% identical to the amino acid sequence of SEQ ID NO: 31; or
- iv) the $V_H$ is at least 90%, 91%, 92%, 93%, 94%, 95%, 96%, 97%, 98%, 99%, or 100% identical to the amino acid sequence of SEQ ID NO: 40 and the $V_L$ is at least 90%, 91%, 92%, 93%, 94%, 95%, 96%, 97%, 98%, 99%, or 100% identical to the amino acid sequence of SEQ ID NO: 41; or
- v) the $V_H$ is at least 90%, 91%, 92%, 93%, 94%, 95%, 96%, 97%, 98%, 99%, or 100% identical to the amino acid sequence of SEQ ID NO: 50 and the $V_L$ is at least 90%, 91%, 92%, 93%, 94%, 95%, 96%, 97%, 98%, 99%, or 100% identical to the amino acid sequence of SEQ ID NO: 51; or
- vi) the $V_H$ is at least 90%, 91%, 92%, 93%, 94%, 95%, 96%, 97%, 98%, 99%, or 100% identical to the amino acid sequence of SEQ ID NO: 60 and the $V_L$ is at least 90%, 91%, 92%, 93%, 94%, 95%, 96%, 97%, 98%, 99%, or 100% identical to the amino acid sequence of SEQ ID NO: 61; or
- vii) the $V_H$ is at least 90%, 91%, 92%, 93%, 94%, 95%, 96%, 97%, 98%, 99%, or 100% identical to the amino acid sequence of SEQ ID NO: 70 and the $V_L$ is at least 90%, 91%, 92%, 93%, 94%, 95%, 96%, 97%, 98%, 99%, or 100% identical to the amino acid sequence of SEQ ID NO: 71; or
- viii) the $V_H$ is at least 90%, 91%, 92%, 93%, 94%, 95%, 96%, 97%, 98%, 99%, or 100% identical to the amino acid sequence of SEQ ID NO: 80 and the $V_L$ is at least 90%, 91%, 92%, 93%, 94%, 95%, 96%, 97%, 98%, 99%, or 100% identical to the amino acid sequence of SEQ ID NO: 81; or
- ix) the $V_H$ is at least 90%, 91%, 92%, 93%, 94%, 95%, 96%, 97%, 98%, 99%, or 100% identical to the amino acid sequence of SEQ ID NO: 90 and the $V_L$ is at least 90%, 91%, 92%, 93%, 94%, 95%, 96%, 97%, 98%, 99%, or 100% identical to the amino acid sequence of SEQ ID NO: 91; or
- x) the $V_H$ is at least 90%, 91%, 92%, 93%, 94%, 95%, 96%, 97%, 98%, 99%, or 100% identical to the amino acid sequence of SEQ ID NO: 100 and the $V_L$ is at least 90%, 91%, 92%, 93%, 94%, 95%, 96%, 97%, 98%, 99%, or 100% identical to the amino acid sequence of SEQ ID NO: 101; or
- xi) the $V_H$ is at least 90%, 91%, 92%, 93%, 94%, 95%, 96%, 97%, 98%, 99%, or 100% identical to the amino acid sequence of SEQ ID NO: 110 and the $V_L$ is at least 90%, 91%, 92%, 93%, 94%, 95%, 96%, 97%, 98%, 99%, or 100% identical to the amino acid sequence of SEQ ID NO: 111; or
- xii) the $V_H$ is at least 90%, 91%, 92%, 93%, 94%, 95%, 96%, 97%, 98%, 99%, or 100% identical to the amino acid sequence of SEQ ID NO: 120 and the $V_L$ is at least 90%, 91%, 92%, 93%, 94%, 95%, 96%, 97%, 98%, 99%, or 100% identical to the amino acid sequence of SEQ ID NO: 121; or
- xiii) the $V_H$ is at least 90%, 91%, 92%, 93%, 94%, 95%, 96%, 97%, 98%, 99%, or 100% identical to the amino acid sequence of SEQ ID NO: 130 and the $V_L$ is at least 90%, 91%, 92%, 93%, 94%, 95%, 96%, 97%, 98%, 99%, or 100% identical to the amino acid sequence of SEQ ID NO: 131; or
- xiv) the $V_H$ is at least 90%, 91%, 92%, 93%, 94%, 95%, 96%, 97%, 98%, 99%, or 100% identical to the amino acid sequence of SEQ ID NO: 140 and the $V_L$ is at least 90%, 91%, 92%, 93%, 94%, 95%, 96%, 97%, 98%, 99%, or 100% identical to the amino acid sequence of SEQ ID NO: 141; or
- xv) the $V_H$ is at least 90%, 91%, 92%, 93%, 94%, 95%, 96%, 97%, 98%, 99%, or 100% identical to the amino acid sequence of SEQ ID NO: 150 and the $V_L$ is at least 90%, 91%, 92%, 93%, 94%, 95%, 96%, 97%, 98%, 99%, or 100% identical to the amino acid sequence of SEQ ID NO: 151; or
- xvi) the $V_H$ is at least 90%, 91%, 92%, 93%, 94%, 95%, 96%, 97%, 98%, 99%, or 100% identical to the amino acid sequence of SEQ ID NO: 160 and the $V_L$ is at least 90%, 91%, 92%, 93%, 94%, 95%, 96%, 97%, 98%, 99%, or 100% identical to the amino acid sequence of SEQ ID NO: 161; or
- xvii) the $V_H$ is at least 90%, 91%, 92%, 93%, 94%, 95%, 96%, 97%, 98%, 99%, or 100% identical to the amino acid sequence of SEQ ID NO: 170 and the $V_L$ is at least 90%, 91%, 92%, 93%, 94%, 95%, 96%, 97%, 98%, 99%, or 100% identical to the amino acid sequence of SEQ ID NO: 171; or
- xviii) the $V_H$ is at least 90%, 91%, 92%, 93%, 94%, 95%, 96%, 97%, 98%, 99%, or 100% identical to the amino acid sequence of SEQ ID NO: 180 and the $V_L$ is at least 90%, 91%, 92%, 93%, 94%, 95%, 96%, 97%, 98%, 99%, or 100% identical to the amino acid sequence of SEQ ID NO: 181.

In some embodiments of a method according to this disclosure, the anti-ICOS antibody comprises a heavy chain variable region ($V_H$) and a light chain variable region ($V_L$), wherein:
- i) the $V_H$ comprises the amino acid sequence of SEQ ID NO: 10 and the $V_L$ comprises the amino acid sequence of SEQ ID NO: 11; or
- ii) the $V_H$ comprises the amino acid sequence of SEQ ID NO: 20 and the $V_L$ comprises the amino acid sequence of SEQ ID NO: 21; or
- iii) the $V_H$ comprises the amino acid sequence of SEQ ID NO: 30 and the $V_L$ comprises the amino acid sequence of SEQ ID NO: 31; or
- iv) the $V_H$ comprises the amino acid sequence of SEQ ID NO: 40 and the $V_L$ comprises the amino acid sequence of SEQ ID NO: 41; or
- v) the $V_H$ comprises the amino acid sequence of SEQ ID NO: 50 and the $V_L$ comprises the amino acid sequence of SEQ ID NO: 51; or
- vi) the $V_H$ comprises the amino acid sequence of SEQ ID NO: 60 and the $V_L$ comprises the amino acid sequence of SEQ ID NO: 61; or vii) the $V_H$ comprises the amino acid sequence of SEQ ID NO: 70 and the $V_L$ comprises the amino acid sequence of SEQ ID NO: 71; or
viii) the $V_H$ comprises the amino acid sequence of SEQ ID NO: 80 and the $V_L$ comprises the amino acid sequence of SEQ ID NO: 81; or
ix) the $V_H$ comprises the amino acid sequence of SEQ ID NO: 90 and the $V_L$ comprises the amino acid sequence of SEQ ID NO: 91; or
x) the $V_H$ comprises the amino acid sequence of SEQ ID NO: 100 and the $V_L$ comprises the amino acid sequence of SEQ ID NO: 101; or
xi) the $V_H$ comprises the amino acid sequence of SEQ ID NO: 110 and the $V_L$ comprises the amino acid sequence of SEQ ID NO: 111; or
xii) the $V_H$ comprises the amino acid sequence of SEQ ID NO: 120 and the $V_L$ comprises the amino acid sequence of SEQ ID NO: 121; or
xiii) the $V_H$ comprises the amino acid sequence of SEQ ID NO: 130 and the $V_L$ comprises the amino acid sequence of SEQ ID NO: 131; or
xiv) the $V_H$ comprises the amino acid sequence of SEQ ID NO: 140 and the $V_L$ comprises the amino acid sequence of SEQ ID NO: 141; or
xv) the $V_H$ comprises the amino acid sequence of SEQ ID NO: 150 and the $V_L$ comprises the amino acid sequence of SEQ ID NO: 151; or
xvi) the $V_H$ comprises the amino acid sequence of SEQ ID NO: 160 and the $V_L$ comprises the amino acid sequence of SEQ ID NO: 161; or
xvii) the $V_H$ comprises the amino acid sequence of SEQ ID NO: 170 and the $V_L$ comprises the amino acid sequence of SEQ ID NO: 171; or
xviii) the $V_H$ comprises the amino acid sequence of SEQ ID NO: 180 and the $V_L$ comprises the amino acid sequence of SEQ ID NO: 181.

In some embodiments, the anti-ICOS antibody is a monoclonal antibody. In some embodiments, the anti-ICOS antibody is a chimeric antibody or a humanized antibody. In some embodiments, the anti-ICOS antibody is an antibody fragment selected from a Fab, Fab', Fv, scFv or (Fab')$_2$ fragment. In some embodiments, the anti-ICOS antibody is a full length antibody.

In some embodiments, the anti-ICOS antibody comprises a heavy chain comprising the amino acid sequence of SEQ ID NO: 188 and a light chain comprising the amino acid sequence of SEQ ID NO: 189.

In some embodiments of a method according to this disclosure, administration of the anti-ICOS antibody to a mammal results in an increase in T effector (Teff) cells in the mammal. In some embodiments, administration of the antibody to a mammal results in activation of T effector (Teff) cells in the mammal. In some embodiments, administration of the antibody to a mammal increases the ratio of Teff cells to Treg cells. In some embodiments, the Teff cells are CD4+ FoxP3− T cells. In some embodiments, the Teff cells are CD4+ FoxP3− T cells and CD8+ T cells. In some embodiments, the Teff cells are CD8+ T cells.

In some embodiments of a method according to this disclosure, administration of the antibody to a mammal results in a decrease in T regulatory (Treg) cells in the mammal. In some embodiments, the Treg cells are CD4+ FoxP3+ T cells.

In some embodiments of a method according to this disclosure, administration of the antibody to a mammal results in an increase of the level of the ligand for NKp46 (NKp46-L) on T cells. In some embodiments, the increased level of NKp46-L on T cells is determined using a soluble NKp46 extracellular domain in a flow cytometry assay. In some embodiments, the antibody increases the level of NKp46-L on Treg cells more than the antibody increases the level of NKp46-L on Teff cells. In some embodiments, the antibody increases CD16 shedding on NK cells.

In some embodiments of a method according to this disclosure, the subject is a human.

In some embodiments of a method according to this disclosure, the method comprises administering an anti-ICOS antibody and at least one additional therapeutic agent. In some embodiments, the additional therapeutic agent is administered concurrently or sequentially with the anti-ICOS antibody. In some embodiments, the additional therapeutic agent is a PD-1 therapy. In some embodiments, the additional therapeutic agent is selected from an anti-PD-1 antibody and an anti-PD-L1 antibody. In some embodiments, an anti-ICOS antibody provided herein is administered with nivolumab. In some embodiments, an anti-ICOS antibody provided herein is administered with pembrolizumab. In some embodiments, an anti-ICOS antibody provided herein is administered with atezolizumab. In some embodiments, an anti-ICOS antibody provided herein is administered with avelumab. In some embodiments, an anti-ICOS antibody provided herein is administered with durvalumab.

In some embodiments, the additional therapeutic agent is a cancer vaccine. In some embodiments, the cancer vaccine is selected from a DNA vaccine, an engineered virus vaccine, an engineered tumor cell vaccine, and a cancer vaccine developed using neoantigens.

In some embodiments, the anti-ICOS antibody provided herein is administered with an agonist anti-OX40 antibody. In some embodiments, the anti-ICOS antibody provided herein is administered with an anti-CTLA4 antibody. In some embodiments, the anti-ICOS antibody provided herein is administered with ipilimumab.

In some embodiments, the additional therapeutic is a chemotherapeutic agent. Nonlimiting exemplary chemotherapeutic agents include capectiabine, cyclophosphamide, dacarbazine, temozolomide, cyclophosphamide, docetaxel, doxorubicin, daunorubicin, cisplatin, carboplatin, epirubicin, eribulin, 5-FU, gemcitabine, irinotecan, ixabepilone, methotrexate, mitoxantrone, oxaliplatin, paclitaxel, nab-paclitaxel, ABRAXANE® (protein-bound paclitaxel), pemetrexed, vinorelbine, and vincristine. In some embodiments, the anti-ICOS antibody provided herein is administered with ABRAXANE® (Celgene). In some embodiments, an anti-ICOS antibody provided herein is administered with at least one kinase inhibitor. Nonlimiting exemplary kinase inhibitors include erlotinib, afatinib, gefitinib, crizotinib, dabrafenib, trametinib, vemurafenib, and cobimetanib.

In some embodiments, the additional therapeutic agent is an IDO inhibitor. Nonlimiting exemplary IDO inhibitors include Indoximod (New Link Genetics), INCB024360 (Incyte Corp), 1-methyl-D-tryptophan (New Link Genetics), and GDC-0919 (Genentech). In some embodiments, the additional therapeutic agent is an immune-modifying drug (IMiD). Nonlimiting exemplary IMiDs include thalidomide, lenalidomide, and pomalidomide.

In some embodiments, the mammal receives CAR-T therapy in addition to administration of anti-ICOS an antibody described herein.

In some embodiments, the mammal undergoes surgery and/or radiation therapy in addition to administration of an anti-ICOS antibody described herein, with or without an additional therapeutic agent. In some embodiments, the mammal undergoes radiation therapy in addition to administration of anti-ICOS an antibody described herein, with or without an additional therapeutic agent.

In some embodiments, use of at least two, at least three, at least four, at least five, at least six, at least seven, at least eight, at least nine, or at least ten mRNAs selected from the mRNAs in Table 6 for determining the level of ICOS expression in a sample is provided. In some embodiments, the sample is a cancer sample.

In some embodiments, use of at least two, at least three, at least four, at least five, at least six, at least seven, at least eight, at least nine, or at least ten mRNAs selected from the mRNAs in Table 6 for predicting whether a cancer will respond to anti-ICOS antibody therapy is provided.

In some embodiments, use of at least two, at least three, at least four, at least five, at least six, at least seven, at least eight, at least nine, or at least ten mRNAs selected from the mRNAs in Table 6 for identifying a subject with cancer who is likely to benefit from treatment with an anti-ICOS antibody.

In some embodiments, use of at least two, at least three, at least four, at least five, at least six, at least seven, at least eight, at least nine, or at least ten mRNAs selected from the mRNAs in Table 6 for selecting a cancer therapy for a subject with cancer, wherein the cancer therapy comprises an anti-ICOS antibody.

In some embodiments of a use according to this disclosure, the cancer is selected from melanoma, non-small cell lung cancer (NSCLC), renal cell carcinoma (RCC), gastric cancer, bladder cancer, diffuse large B-cell lymphoma (DLBCL), Hodgkin's lymphoma, ovarian cancer, head & neck squamous cell cancer (HNSCC), and triple negative breast cancer (TNBC). In some embodiments, the cancer is selected from melanoma, gastric cancer, head & neck squamous cell cancer (HNSCC), non-small cell lung cancer (NSCLC), and triple negative breast cancer (TNBC).

In some embodiments, the disclosure provides an isolated antibody comprising:
(a) HCDR1 comprising the amino acid sequence of SEQ ID NO: 194; (b) HCDR2 comprising the amino acid sequence of SEQ ID NO: 195; (c) HCDR3 comprising the amino acid sequence of SEQ ID NO: 196; (d) LCDR1 comprising the amino acid sequence of SEQ ID NO: 197; (e) LCDR2 comprising the amino acid sequence of SEQ ID NO: 198; and (f) LCDR3 comprising the amino acid sequence of SEQ ID NO: 199; or
(a) HCDR1 comprising the amino acid sequence of SEQ ID NO: 202; (b) HCDR2 comprising the amino acid sequence of SEQ ID NO: 203; (c) HCDR3 comprising the amino acid sequence of SEQ ID NO: 204; (d) LCDR1 comprising the amino acid sequence of SEQ ID NO: 205; (e) LCDR2 comprising the amino acid sequence of SEQ ID NO: 206; and (f) LCDR3 comprising the amino acid sequence of SEQ ID NO: 207; or
(a) HCDR1 comprising the amino acid sequence of SEQ ID NO: 210; (b) HCDR2 comprising the amino acid sequence of SEQ ID NO: 211; (c) HCDR3 comprising the amino acid sequence of SEQ ID NO: 212; (d) LCDR1 comprising the amino acid sequence of SEQ ID NO: 213; (e) LCDR2 comprising the amino acid sequence of SEQ ID NO: 214; and (f) LCDR3 comprising the amino acid sequence of SEQ ID NO: 215.

In some embodiments, the antibody comprises a heavy chain variable region ($V_H$) and a light chain variable region ($V_L$), wherein:
the $V_H$ is at least 90%, 91%, 92%, 93%, 94%, 95%, 96%, 97%, 98%, 99%, or 100% identical to the amino acid sequence of SEQ ID NO: 192 and the $V_L$ is at least 90%, 91%, 92%, 93%, 94%, 95%, 96%, 97%, 98%, 99%, or 100% identical to the amino acid sequence of SEQ ID NO: 193; or
the $V_H$ is at least 90%, 91%, 92%, 93%, 94%, 95%, 96%, 97%, 98%, 99%, or 100% identical to the amino acid sequence of SEQ ID NO: 200 and the $V_L$ is at least 90%, 91%, 92%, 93%, 94%, 95%, 96%, 97%, 98%, 99%, or 100% identical to the amino acid sequence of SEQ ID NO: 201; or
the $V_H$ is at least 90%, 91%, 92%, 93%, 94%, 95%, 96%, 97%, 98%, 99%, or 100% identical to the amino acid sequence of SEQ ID NO: 208 and the $V_L$ is at least 90%, 91%, 92%, 93%, 94%, 95%, 96%, 97%, 98%, 99%, or 100% identical to the amino acid sequence of SEQ ID NO: 209.

In some embodiments, the antibody comprises a heavy chain variable region ($V_H$) and a light chain variable region ($V_L$), wherein:
the $V_H$ comprises the amino acid sequence of SEQ ID NO: 192 and the $V_L$ comprises the amino acid sequence of SEQ ID NO: 193; or
the $V_H$ comprises the amino acid sequence of SEQ ID NO: 200 and the $V_L$ comprises the amino acid sequence of SEQ ID NO: 201; or
the $V_H$ comprises the amino acid sequence of SEQ ID NO: 208 and the $V_L$ comprises the amino acid sequence of SEQ ID NO: 209.

In some embodiments, the antibody is a monoclonal antibody. In some embodiments, the antibody is a chimeric antibody or a humanized antibody. In some embodiments, the antibody is an antibody fragment selected from a Fab, Fab', Fv, scFv or (Fab')$_2$ fragment. In some embodiments, the antibody is a full length antibody.

In some embodiments, the disclosure provides a composition comprising an antibody disclosed herein and a pharmaceutically acceptable carrier.

In some embodiments, the disclosure provides a use of an antibody disclosed herein to detect ICOS, inhibit ICOS, determine a level of expression of ICOS, predict whether a cancer will respond to anti-ICOS therapy, identify a subject with cancer who is likely to benefit from treatment with an anti-ICOS antibody, select a cancer therapy for a subject with cancer, or treat cancer.

In some embodiments, the disclosure provides a use of an antibody disclosed herein in the preparation of a medicament for inhibiting ICOS or treating cancer.

In some embodiments, the disclosure provides a use of an antibody disclosed herein in the preparation of a composition for detecting ICOS, determining a level of expression of ICOS, predicting whether a cancer will respond to anti-ICOS therapy, identifying a subject with cancer who is likely to benefit from treatment with an anti-ICOS antibody, or selecting a cancer therapy for a subject with cancer.

In some embodiments, the disclosure provides a nucleic acid encoding an antibody disclosed herein.

In some embodiments, the disclosure provides a host cell comprising a nucleic acid encoding an antibody disclosed herein.

In some embodiments, the disclosure provides a method of producing an antibody disclosed herein comprising culturing host cell comprising a nucleic acid encoding an antibody disclosed herein, the host cell being cultured under conditions wherein the antibody is expressed. In some embodiments, the method further comprises purifying the antibody.

BRIEF DESCRIPTION OF THE DRAWINGS

FIG. 9A-C. Human tumor TIL analysis show ICOS expression in the Treg cells and CD4 effectors. A) Representative contour plots of PD-1 and ICOS expression in different T-cells subsets from HNSCC patients (N=4). B) The frequency of ICOS alone positive cells or the ICOS PD-1 double positive cells in the T-cell compartment is shown (HNSCC N=4; NSCLC N=3; Ovarian N=4). C) Comparison of ICOS levels in CD4 Treg cells and CD4 Teff. The staining intensity of ICOS as measured by Mean Fluorescent Intensity (MFI; or ICOS geometric mean) in the CD4 T-cell subsets from patient tumor samples is plotted.

DETAILED DESCRIPTION OF SOME EMBODIMENTS

Figure 1A:
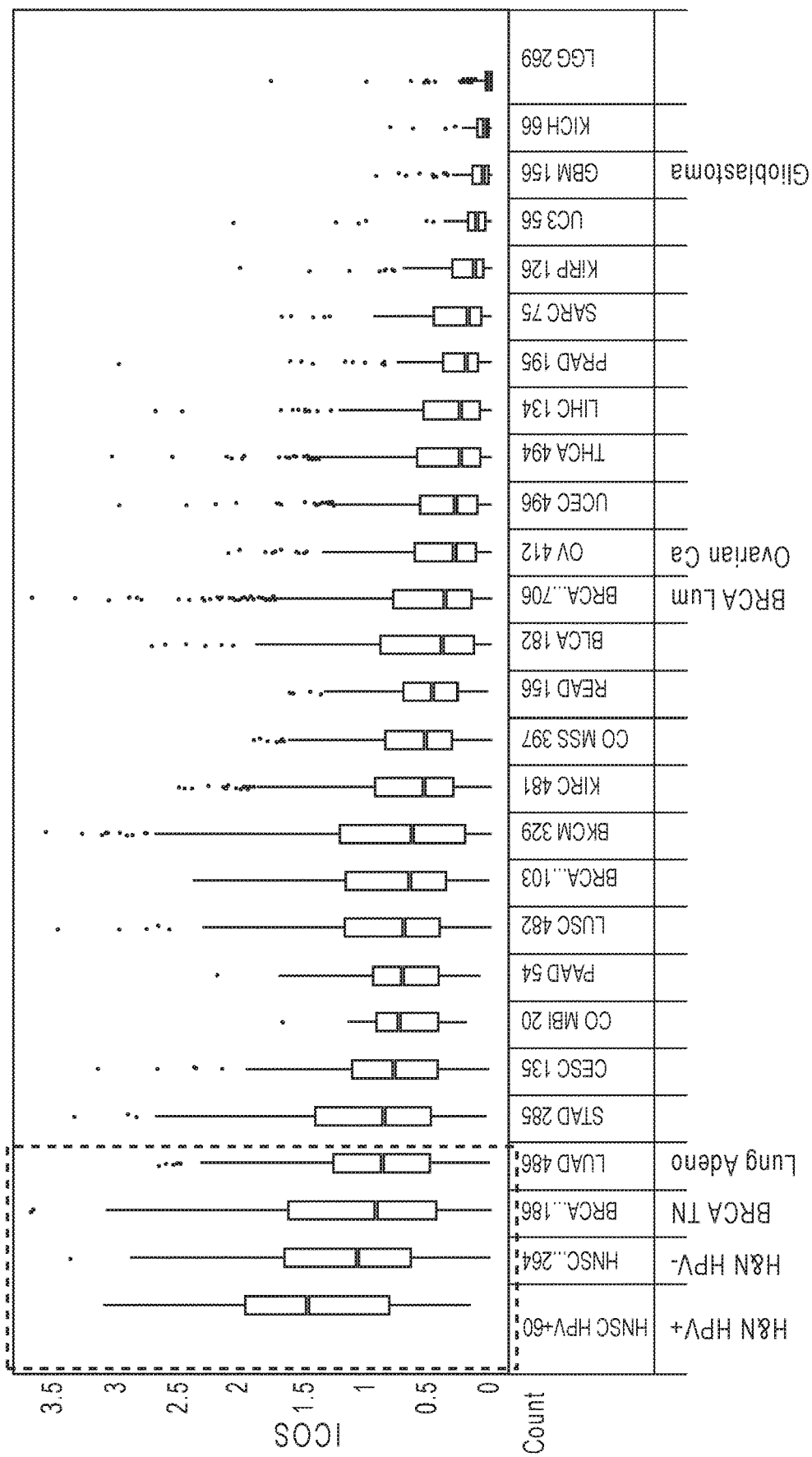
FIG. 1A-B. Levels of ICOS mRNA across multiple human tumors. A) Mean intensity and 75% confidence intervals of normalized ICOS mRNA levels across various indications are plotted. Samples with intensities outside of the 75% confidence range are indicated (dot). B) The percentage of each indicated tumor type showing 0, 1+, 2+ or 3+ ICOS staining by immunohistochemistry (IHC).

Gene expression signatures for predicting or determining ICOS expression, e.g., in a tumor environment, are provided. In some embodiments, the gene expression signatures may be used to identify patients who are likely to respond to anti-ICOS antibody therapy. In some embodiments, a gene expression signature comprising two or more genes in place of, or in addition to, ICOS may provide a more robust assay for ICOS expression than detecting ICOS alone. In some embodiments, methods of treatment are provided, comprising identifying a patient who is likely to respond to anti-ICOS antibody therapy using a gene expression signature described herein, and administering an anti-ICOS antibody.

The section headings used herein are for organizational purposes only and are not to be construed as limiting the subject matter described.

All references cited herein, including patent applications, patent publications, and Genbank Accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J.B. Lippincott Company, 1993); and updated versions thereof.

I. Definitions

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

It is understood that embodiments of the invention described herein include "consisting" and/or "consisting essentially of" embodiments. As used herein, the singular form "a", "an", and "the" includes plural references unless indicated otherwise. Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

As is understood by one skilled in the art, reference to "about" a value or parameter herein includes (and describes) embodiments that are directed to that value or parameter per se. For example, description referring to "about X" includes description of "X".

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

"ICOS" and "inducible T-cell costimulatory" as used herein refer to any native ICOS that results from expression and processing of ICOS in a cell. The term includes ICOS from any vertebrate source, including mammals such as primates (e.g., humans and cynomolgus monkeys) and rodents (e.g., mice and rats), unless otherwise indicated. The term also includes naturally occurring variants of ICOS, e.g., splice variants or allelic variants. The amino acid sequence of an exemplary human ICOS precursor protein, with signal sequence (with signal sequence, amino acids 1-20) is shown in SEQ ID NO: 1. The amino acid sequence of an exemplary mature human ICOS is shown in SEQ ID NO: 2. The amino acid sequence of an exemplary mouse ICOS precursor protein, with signal sequence (with signal sequence, amino acids 1-20) is shown in SEQ ID NO: 3. The amino acid sequence of an exemplary mature mouse ICOS is shown in SEQ ID NO: 4. The amino acid sequence of an exemplary rat ICOS precursor protein, with signal sequence (with signal sequence, amino acids 1-20) is shown in SEQ ID NO: 190. The amino acid sequence of an exemplary mature rat ICOS is shown in SEQ ID NO: 191. The amino acid sequence of an exemplary cynomolgus monkey ICOS precursor protein, with signal sequence (with signal sequence, amino acids 1-20) is shown in SEQ ID NO: 5. The amino acid sequence of an exemplary mature cynomolgus monkey ICOS is shown in SEQ ID NO: 6.

The term "specifically binds" to an antigen or epitope is a term that is well understood in the art, and methods to determine such specific binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an ICOS epitope is an antibody that binds this epitope with greater affinity, avidity, more readily, and/or with greater duration than it binds to other ICOS epitopes or non-ICOS epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specificity" refers to the ability of a binding protein to selectively bind an antigen.

As used herein, "substantially pure" refers to material which is at least 50% pure (that is, free from contaminants), more preferably, at least 90% pure, more preferably, at least 95% pure, yet more preferably, at least 98% pure, and most preferably, at least 99% pure.

As used herein, the term "epitope" refers to a site on a target molecule (for example, an antigen, such as a protein, nucleic acid, carbohydrate or lipid) to which an antigen-binding molecule (for example, an antibody, antibody fragment, or scaffold protein containing antibody binding regions) binds. Epitopes often include a chemically active surface grouping of molecules such as amino acids, polypeptides or sugar side chains and have specific three-dimensional structural characteristics as well as specific charge characteristics. Epitopes can be formed both from contiguous and/or juxtaposed noncontiguous residues (for example, amino acids, nucleotides, sugars, lipid moiety) of the target molecule. Epitopes formed from contiguous residues (for example, amino acids, nucleotides, sugars, lipid moiety) typically are retained on exposure to denaturing solvents whereas epitopes formed by tertiary folding typically are lost on treatment with denaturing solvents. An epitope may include but is not limited to at least 3, at least 5 or 8-10 residues (for example, amino acids or nucleotides). In some examples an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between an antibody residue and an antigen residue. An epitope can be identified by various scans as well, for example an alanine or arginine scan can indicate one or more residues that the antigen-binding molecule can interact with. Unless explicitly denoted, a set of residues as an epitope does not exclude other residues from being part of the epitope for a particular antibody. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

A "nonlinear epitope" or "conformational epitope" comprises noncontiguous polypeptides, amino acids and/or sugars within the antigenic protein to which an antibody specific to the epitope binds. In some embodiments, at least one of the residues will be noncontiguous with the other noted residues of the epitope; however, one or more of the residues can also be contiguous with the other residues.

A "linear epitope" comprises contiguous polypeptides, amino acids and/or sugars within the antigenic protein to which an antibody specific to the epitope binds. It is noted that, in some embodiments, not every one of the residues within the linear epitope need be directly bound (or involved in a bond) with the antibody. In some embodiments, linear epitopes can be from immunizations with a peptide that effectively consisted of the sequence of the linear epitope, or from structural sections of a protein that are relatively isolated from the remainder of the protein (such that the antibody can interact, at least primarily), just with that sequence section.

The term "antibody" herein is used in the broadest sense and encompasses various antibody structures, including but not limited to monoclonal antibodies, polyclonal antibodies, multispecific antibodies (for example, bispecific (such as Bi-specific T-cell engagers) and trispecific antibodies), and antibody fragments so long as they exhibit the desired antigen-binding activity.

The term antibody includes, but is not limited to, fragments that are capable of binding to an antigen, such as Fv, single-chain Fv (scFv), Fab, Fab', di-scFv, sdAb (single domain antibody) and (Fab')$_2$ (including a chemically linked F(ab')$_2$). Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen. The term antibody also includes, but is not limited to, chimeric antibodies, humanized antibodies, and antibodies of various species such as mouse, human, cynomolgus monkey, etc. Furthermore, for all antibody constructs provided herein, variants having the sequences from other organisms are also contemplated. Thus, if a human version of an antibody is disclosed, one of skill in the art will appreciate how to transform the human sequence based antibody into a mouse, rat, cat, dog, horse, etc. sequence. Antibody fragments also include either orientation of single chain scFvs, tandem di-scFv, diabodies, tandem tri-sdcFv, minibodies, etc. Antibody fragments also include nanobodies (sdAb, an antibody having a single, monomeric domain, such as a pair of variable domains of heavy chains, without a light chain). An antibody fragment can be referred to as being a specific species in some embodiments (for example, human scFv or a mouse scFv). This denotes the sequences of at least part of the non-CDR regions, rather than the source of the construct.

The term "monoclonal antibody" refers to an antibody of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

The term "CDR" denotes a complementarity determining region as defined by at least one manner of identification to one of skill in the art. In some embodiments, CDRs can be defined in accordance with any of the Chothia numbering schemes, the Kabat numbering scheme, a combination of Kabat and Chothia, the AbM definition, the contact definition, and/or a combination of the Kabat, Chothia, AbM, and/or contact definitions. Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991)). The AbM definition can include, for example, CDRs (CDR-L1, CDR-L2, CDR-L3, CDR-H1, CDR-H2, and CDR-H3) at amino acid residues 24-34 of L1, 50-56 of L2, 89-97 of L3, H26-H35B of H1, 50-58 of H2, and 95-102 of H3. The Contact definition can include, for example, CDRs (CDR-L1, CDR-L2, CDR-L3, CDR-H1, CDR-H2, and CDR-H3) at amino acid residues 30-36 of L1, 46-55 of L2, 89-96 of L3, 30-35 of H1, 47-58 of H2, and 93-101 of H3. The Chothia definition can include, for example, CDRs (CDR-L1, CDR-L2, CDR-L3, CDR-H1, CDR-H2, and CDR-H3) at amino acid residues 24-34 of L1, 50-56 of L2, 89-97 of L3, 26-32 . . . 34 of H1, 52-56 of H2, and 95-102 of H3. CDRs can also be provided as shown in any one or more of the accompanying figures. With the exception of CDR1 in $V_H$, CDRs generally comprise the amino acid residues that form the hypervariable loops. The various CDRs within an antibody can be designated by their appropriate number and chain type, including, without limitation as: a) CDR-L1, CDR-L2, CDR-L3, CDR-H1, CDR-H2, and CDR-H3; b) CDRL1, CDRL2, CDRL3, CDRH1, CDRH2, and CDRH3; c) LCDR-1, LCDR-2, LCDR-3, HCDR-1, HCDR-2, and HCDR-3; or d) LCDR1, LCDR2, LCDR3, HCDR1, HCDR2, and HCDR3; etc. The term "CDR" is used herein to also encompass HVR or a "hyper variable region", including hypervariable loops. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).)

The term "heavy chain variable region" as used herein refers to a region comprising at least three heavy chain CDRs. In some embodiments, the heavy chain variable region includes the three CDRs and at least FR2 and FR3. In some embodiments, the heavy chain variable region includes at least heavy chain HCDR1, framework (FR) 2, HCDR2, FR3, and HCDR3. In some embodiments, a heavy chain variable region also comprises at least a portion of an FR1 and/or at least a portion of an FR4.

The term "heavy chain constant region" as used herein refers to a region comprising at least three heavy chain constant domains, $C_H1$, $C_H2$, and $C_H3$. Of course, non-function-altering deletions and alterations within the domains are encompassed within the scope of the term "heavy chain constant region," unless designated otherwise. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

The term "heavy chain" as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence.

The term "light chain variable region" as used herein refers to a region comprising at least three light chain CDRs. In some embodiments, the light chain variable region includes the three CDRs and at least FR2 and FR3. In some embodiments, the light chain variable region includes at least light chain LCR1, framework (FR) 2, LCD2, FR3, and LCD3. For example, a light chain variable region may comprise light chain CDR1, framework (FR) 2, CDR2, FR3, and CDR3. In some embodiments, a light chain variable region also comprises at least a portion of an FR1 and/or at least a portion of an FR4.

The term "light chain constant region" as used herein refers to a region comprising a light chain constant domain, $C_L$. Nonlimiting exemplary light chain constant regions include λ and κ. Of course, non-function-altering deletions and alterations within the domains are encompassed within the scope of the term "light chain constant region," unless designated otherwise.

The term "light chain" as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

An "acceptor human framework" for the purposes herein is a framework comprising the amino acid sequence of a light chain variable domain ($V_L$) framework or a heavy chain variable domain ($V_H$) framework derived from a human immunoglobulin framework or a human consensus framework, as defined below. An acceptor human framework derived from a human immunoglobulin framework or a human consensus framework can comprise the same amino acid sequence thereof, or it can contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the $V_L$ acceptor human framework is identical in sequence to the $V_L$ human immunoglobulin framework sequence or human consensus framework sequence.

"Affinity" refers to the strength of the sum total of noncovalent interactions between a single binding site of a molecule (for example, an antibody) and its binding partner (for example, an antigen). The affinity of a molecule X for its partner Y can generally be represented by the dissociation constant ($K_D$). Affinity can be measured by common methods known in the art (such as, for example, ELISA $K_D$, KinExA, bio-layer interferometry (BLI), and/or surface plasmon resonance devices (such as a BIAcore® device), including those described herein).

The term "$K_D$", as used herein, refers to the equilibrium dissociation constant of an antibody-antigen interaction.

In some embodiments, the "$K_D$," "$K_d$," "Kd" or "Kd value" of the antibody is measured by using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µL/minute to achieve approximately 10 response units (RU) of coupled protein. Following the injection of antigen, 1 M ethanolamine is injected to block unreacted groups. For kinetics measurements, serial dilutions of polypeptide, for example, full length antibody, are injected in PBS with 0.05% TWEEN-20™ surfactant (PBST) at 25° C. at a flow rate of approximately 25 µL/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_d$) is calculated as the ratio $k_{off}/k_{on}$. See, for example, Chen et al., *J. Mol. Biol.* 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

In some embodiments, the difference between said two values (for example, Ct values) is substantially the same, for example, less than about 50%, less than about 40%, less than about 30%, less than about 20%, and/or less than about 10% as a function of the reference/comparator value.

In some embodiments, the difference between said two values (for example, Ct values) is substantially different, for example, greater than about 10%, greater than about 20%, greater than about 30%, greater than about 40%, and/or greater than about 50% as a function of the value for the reference/comparator molecule.

"Surface plasmon resonance" denotes an optical phenomenon that allows for the analysis of real-time biospecific interactions by detection of alterations in protein concentrations within a biosensor matrix, for example using the BIAcore™ system (BIAcore International AB, a GE Healthcare company, Uppsala, Sweden and Piscataway, N.J.). For further descriptions, see Jonsson et al. (1993) *Ann. Biol. Clin.* 51:19-26.

"Biolayer interferometry" refers to an optical analytical technique that analyzes the interference pattern of light reflected from a layer of immobilized protein on a biosensor tip and an internal reference layer. Changes in the number of molecules bound to the biosensor tip cause shifts in the interference pattern that can be measured in real-time. A nonlimiting exemplary device for biolayer interferometry is ForteBio Octet® RED96 system (Pall Corporation). See, e.g., Abdiche et al., 2008, *Anal. Biochem.* 377: 209-277.

The term "$k_{on}$", as used herein, refers to the rate constant for association of an antibody to an antigen. Specifically, the rate constants ($k_{on}$ and $k_{off}$) and equilibrium dissociation constants are measured using IgGs (bivalent) with monovalent ICOS antigen. "$K_{on}$", "$k_{on}$", "association rate constant", or "ka", are used interchangeably herein. The value indicates the binding rate of a binding protein to its target antigen or the rate of complex formation between an antibody and antigen, shown by the equation:

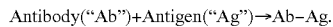

The term "$k_{off}$", as used herein, refers to the rate constant for dissociation of an antibody from the antibody/antigen complex. $k_{off}$ is also denoted as "$K_{off}$" or the "dissociation rate constant". This value indicates the dissociation rate of an antibody from its target antigen or separation of Ab–Ag complex over time into free antibody and antigen as shown by the equation:

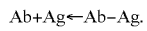

The term "biological activity" refers to any one or more biological properties of a molecule (whether present naturally as found in vivo, or provided or enabled by recombinant means). Biological properties include, but are not limited to, binding a receptor, inducing cell proliferation, inhibiting cell growth, inducing other cytokines, inducing apoptosis, and enzymatic activity. In some embodiments, biological activity of an ICOS protein includes, for example, costimulation of T cell proliferation and cytokine secretion associated with Th1 and Th2 cells; modulation of Treg cells; effects on T cell differentiation including modulation of transcription factor gene expression; induction of signaling through PI3K and AKT pathways; and mediating ADCC.

An "affinity matured" antibody refers to an antibody with one or more alterations in one or more CDRs compared to a parent antibody which does not possess such alterations, such alterations resulting in an improvement in the affinity of the antibody for antigen.

A "chimeric antibody" as used herein refers to an antibody in which a portion of the heavy and/or light chain is derived from a particular source or species, while at least a part of the remainder of the heavy and/or light chain is derived from a different source or species. In some embodiments, a chimeric antibody refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, all of the variable regions of a chimeric antibody are from a first species and all of the constant regions of the chimeric antibody are from a second species. The chimeric construct can also be a functional fragment, as noted above.

A "humanized antibody" as used herein refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is an antibody fragment, such as Fab, an scFv, a (Fab)$_2$, etc. The term humanized also denotes forms of non-human (for example, murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence of non-human immunoglobulin. Humanized antibodies can include human immunoglobulins (recipient antibody) in which residues from a complementary determining region (CDR) of the recipient are substituted by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody can comprise residues that are found neither in the recipient antibody nor in the imported CDR or framework sequences, but are included to further refine and optimize antibody performance. In general, the humanized antibody can comprise substantially all of at least one, and typically two, variable domains, in which all or substantially all of the CDR regions correspond to those of a non-human immunoglobulin and all or substantially all of the FR regions are those of a human immunoglobulin consensus sequence. In some embodiments, the humanized antibody can also comprise at least a portion of an immunoglobulin constant region or domain (Fc), typically that of a human immunoglobulin. Other forms of humanized antibodies have one or more CDRs (CDR L1, CDR L2, CDR L3, CDR H1, CDR H2, and/or CDR H3) which are altered with respect to the original antibody, which are also termed one or more CDRs "derived from" one or more CDRs from the original antibody. As will be appreciated, a humanized sequence can be identified by its primary sequence and does not necessarily denote the process by which the antibody was created.

A "CDR-grafted antibody" as used herein refers to a humanized antibody in which one or more complementarity determining regions (CDRs) of a first (non-human) species have been grafted onto the framework regions (FRs) of a second (human) species.

A "human antibody" as used herein encompasses antibodies produced in humans, antibodies produced in non-human animals that comprise human immunoglobulin genes, such as XenoMouse® mice, and antibodies selected using in vitro methods, such as phage display (Vaughan et al., 1996, Nature Biotechnology, 14:309-314; Sheets et al., 1998, Proc. Natl. Acad. Sci. (USA) 95:6157-6162; Hoogenboom and Winter, 1991, J. Mol. Biol., 227:381; Marks et al., 1991, J. Mol. Biol., 222:581), wherein the antibody repertoire is based on a human immunoglobulin sequence. The term "human antibody" denotes the genus of sequences that are human sequences. Thus, the term is not designating the process by which the antibody was created, but the genus of sequences that are relevant.

A "functional Fc region" possesses an "effector function" of a native sequence Fc region. Exemplary "effector functions" include Fc receptor binding; C1q binding; CDC; ADCC; phagocytosis; down regulation of cell surface receptors (for example B cell receptor; BCR), etc. Such effector functions generally require the Fc region to be combined with a binding domain (for example, an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In some embodiments, a "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, for example, from about one to about ten amino acid substitutions, and preferably, from about one to about five amino acid substitutions in a native sequence Fc region or in the Fc region of the parent polypeptide. In some embodiments, the variant Fc region herein will possess at least about 80% sequence identity with a native sequence Fc region and/or with an Fc region of a parent polypeptide, at least about 90% sequence identity therewith, at least about 95%, at least about 96%, at least about 97%, at least about 98%, or at least about 99% sequence identity therewith.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, for example, Daeron, Annu. Rev. Immunol. 15:203-234 (1997)). FcRs are reviewed, for example, in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, for example, Ghetie and Ward., Immunol. Today 18(12):592-598 (1997); Ghetie et al., Nature Biotechnology, 15(7):637-640 (1997); Hinton et al., J. Biol. Chem. 279(8):6213-6216 (2004); WO 2004/92219 (Hinton et al.).

"Effector functions" refer to biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (for example B cell receptor); and B cell activation.

"Human effector cells" are leukocytes which express one or more FcRs and perform effector functions. In some embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, for example, from blood.

"Antibody-dependent cell-mediated cytotoxicity" or "ADCC" refers to a form of cytotoxicity in which secreted Ig bound onto Fc receptors (FcRs) present on certain cytotoxic cells (for example NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, for example, in an animal model such as that disclosed in Clynes et al. Proc. Natl. Acad. Sci. (USA) 95:652-656 (1998). Additional polypeptide variants with altered Fc region amino acid sequences (polypeptides with a variant Fc region) and increased or decreased ADCC activity are described, for example, in U.S. Pat. Nos. 7,923,538, and 7,994,290.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, for example, as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, for example, in U.S. Pat. No. 6,194,551 B1, U.S. Pat. Nos. 7,923,538, 7,994,290 and WO 1999/51642. See also, for example, Idusogie et al., *J. Immunol.* 164: 4178-4184 (2000).

A polypeptide variant with "altered" FcR binding affinity or ADCC activity is one which has either enhanced or diminished FcR binding activity and/or ADCC activity compared to a parent polypeptide or to a polypeptide comprising a native sequence Fc region. The polypeptide variant which "displays increased binding" to an FcR binds at least one FcR with better affinity than the parent polypeptide. The polypeptide variant which "displays decreased binding" to an FcR, binds at least one FcR with lower affinity than a parent polypeptide. Such variants which display decreased binding to an FcR may possess little or no appreciable binding to an FcR, for example, 0-20% binding to the FcR compared to a native sequence IgG Fc region.

The polypeptide variant which "mediates antibody-dependent cell-mediated cytotoxicity (ADCC) in the presence of human effector cells more effectively" than a parent antibody is one which in vitro or in vivo is more effective at mediating ADCC, when the amounts of polypeptide variant and parent antibody used in the assay are essentially the same. Generally, such variants will be identified using the in vitro ADCC assay as herein disclosed, but other assays or methods for determining ADCC activity, for example in an animal model etc., are contemplated.

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

The phrase "substantially different," as used herein, denotes a sufficiently high degree of difference between two numeric values such that one of skill in the art would consider the difference between the two values to be of statistical significance within the context of the biological characteristic measured by said values. In some embodiments, the two substantially different numeric values differ by greater than about any one of 10%, 20%, 25%, 30%, 35%, 40%, 45%, 50%, 60%, 70%, 80%, 90%, or 100%.

The phrase "substantially reduced," as used herein, denotes a sufficiently high degree of reduction between a numeric value and a reference numeric value such that one of skill in the art would consider the difference between the two values to be of statistical significance within the context of the biological characteristic measured by said values. In some embodiments, the substantially reduced numeric values is reduced by greater than about any one of 10%, 20%, 25%, 30%, 35%, 40%, 45%, 50%, 60%, 70%, 80%, 90%, or 100% compared to the reference value.

The term "leader sequence" refers to a sequence of amino acid residues located at the N-terminus of a polypeptide that facilitates secretion of a polypeptide from a mammalian cell. A leader sequence can be cleaved upon export of the polypeptide from the mammalian cell, forming a mature protein. Leader sequences can be natural or synthetic, and they can be heterologous or homologous to the protein to which they are attached.

A "native sequence" polypeptide comprises a polypeptide having the same amino acid sequence as a polypeptide found in nature. Thus, a native sequence polypeptide can have the amino acid sequence of naturally occurring polypeptide from any mammal. Such native sequence polypeptide can be isolated from nature or can be produced by recombinant or synthetic means. The term "native sequence" polypeptide specifically encompasses naturally occurring truncated or secreted forms of the polypeptide (for example, an extracellular domain sequence), naturally occurring variant forms (for example, alternatively spliced forms) and naturally occurring allelic variants of the polypeptide.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide.

As used herein, "Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 1. Amino acid substitutions may be introduced into an antibody of interest and the products screened for a desired activity, for example, retained/improved antigen binding, decreased immunogenicity, or improved ADCC or CDC.

TABLE 1

| Original Residue | Exemplary Substitutions |
| --- | --- |
| Ala (A) | Val; Leu; Ile |
| Arg (R) | Lys; Gln; Asn |

TABLE 1-continued

| Original Residue | Exemplary Substitutions |
| --- | --- |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E and DG44 cells, respectively. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) a provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The terms "individual" or "subject" are used interchangeably herein to refer to an animal; for example a mammal. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some examples, an "individual" or "subject" refers to an individual or subject in need of treatment for a disease or disorder. In some embodiments, the subject to receive the treatment can be a patient, designating the fact that the subject has been identified as having a disorder of relevance to the treatment, or being at adequate risk of contracting the disorder.

The term "sample" or "patient sample" as used herein, refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

A "reference sample", "reference cell", or "reference tissue", as used herein, refers to a sample, cell or tissue obtained from a source known, or believed, not to be afflicted with the disease or condition for which a method or composition of the invention is being used to identify. In some embodiments, a reference sample, reference cell or reference tissue is obtained from a healthy part of the body of the same subject or patient in whom a disease or condition is being identified using a composition or method of the invention. In some embodiments, a reference sample, reference cell or reference tissue is obtained from a healthy part of the body of one or more individuals who are not the subject or patient in whom a disease or condition is being identified using a composition or method of the invention.

A "disease" or "disorder" as used herein refers to a condition where treatment is needed and/or desired.

"Cancer" and "tumor," as used herein, are interchangeable terms that refer to any abnormal cell or tissue growth or proliferation in an animal. As used herein, the terms "cancer" and "tumor" encompass solid and hematological/lymphatic cancers and also encompass malignant, pre-malignant, and benign growth, such as dysplasia. Examples of cancer include but are not limited to, carcinoma, lymphoma, blastoma, sarcoma, and leukemia. More particular non-limiting examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma (including uterine corpus endometrial carcinoma), salivary gland carcinoma, kidney cancer, renal cancer, liver cancer, prostate cancer, vulval cancer, thyroid cancer, hepatic carcinoma, brain cancer, testis cancer, cholangiocarcinoma, gallbladder carcinoma, gastric cancer, melanoma, and various types of head and neck cancer.

As used herein, "treatment" is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

"Ameliorating" means a lessening or improvement of one or more symptoms as compared to not administering an anti-ICOS antibody. "Ameliorating" also includes shortening or reduction in duration of a symptom.

In the context of cancer, the term "treating" includes any or all of: inhibiting growth of cancer cells, inhibiting replication of cancer cells, lessening of overall tumor burden and ameliorating one or more symptoms associated with the disease.

The term "biological sample" means a quantity of a substance from a living thing or formerly living thing. Such substances include, but are not limited to, blood, (for example, whole blood), plasma, serum, urine, amniotic fluid, synovial fluid, endothelial cells, leukocytes, monocytes, other cells, organs, tissues, bone marrow, lymph nodes and spleen.

A sample that has an "elevated level of ICOS" or "expresses ICOS at an elevated level" or is "ICOS$^{HIGH}$" means, in some embodiments, that the level of ICOS that is such that one of skill in the art would conclude that the cancer may be treatable with an anti-ICOS therapy, such as an antibody provided herein. In some embodiments, an "elevated level of ICOS" is one in which 1% of the cells within a tumor sample show staining for ICOS. In some embodiments a "high level" in regard to ICOS is 1% or more staining, for example, 1, 5, 10, 20, 30, 40, 50, 60, 70, 80, 90, or 100% of the cells within the tumor sample show staining. In some embodiments, the ICOS levels can be measured by chromogenic IHC or immunofluorescence IHC (Aqua scoring).

A sample that "expresses ICOS" or has "positive staining for ICOS" or is "ICOS positive" means, in some embodiments, that 1% or more of the cells in a sample show staining for ICOS. In some embodiments, a sample that is ICOS positive displays at least weak, moderate, and/or strong cell staining (based on membrane expression of ICOS). A sample with moderate or strong cell staining for ICOS is also considered to be "ICOS$^{HIGH}$."

A sample that has a "low level of PD-L1" or expresses "PD-L1 at a low level" or is "PD-L1$^{LOW}$" means that the level of PD-L1 is below the threshold level of expression for a cancer that is normally indicated for treatment with a PD-1 therapy. In some embodiments, a "low level of PD-L1" is one in which less than 5% of the cells in the tumor show membrane staining for PD-L1. In some embodiments a "low level" in regard to PD-L1 is less than 5% staining, for example, 4%, 3%, 2%, 1%, or 0% of the cells of the tumor show staining. In some embodiments, the PD-L1 levels can be measured by chromogenic IHC or immunofluorescence IHC (Aqua scoring). A sample that expresses no detectable PD-L1 can also be said to "express a low level of PD-L1." Thus, no detectable PD-L1 is encompassed within the term "low."

A sample that has an "elevated level of PD-L1" or "expresses PD-L1 at an elevated level" or is "PD-L1$^{HIGH}$" means that the level of PD-L1 that is such that one of skill in the art would conclude that the cancer may be treatable with a PD-1 therapy. In some embodiments, an "elevated level of PD-L1" is one in which 5% of the cells in the tumor or more have membrane staining of PD-L1. In some embodiments a "high level" in regard to PD-L1 is 5% or more staining, for example, 5, 10, 20, 30, 40, 50, 60, 70, 80, 90, or 100% of the cells of the tumor show staining. In some embodiments, the PD-L1 levels can be measured by chromogenic IHC or immunofluorescence IHC (Aqua scoring).

A sample that "expresses PD-L1" or has "positive staining for PD-L1" or is "PD-L1 positive" means that 1% or more of the cells have membrane staining for PD-L1. In some embodiments, a sample that is PD-L1 positive displays at least weak, moderate, and/or strong cell staining (based on membrane expression of PD-L1). A sample with moderate or strong cell staining for PD-L1 is also considered to be "PD-L1$^{HIGH}$."

A sample that "lacks PD-L1 expression" or has "negative staining for PD-L1" or is "PD-L1 negative" means that PD-L1 expression on the surface of cells of the sample is undetectable by IHC, such as chromogenic IHC or immunofluorescence IHC (Aqua scoring). A PD-L1 negative sample is also be considered to be "PD-L1$^{LOW}$."

In some embodiments, any method for measuring the level of PD-L1 can be employed. In some embodiments, this can include using the PD-L1 IHC 22C3 pharmDx test (Dako Inc., Carpinteria, Calif.), which is a clinically validated and FDA approved test for evaluation of PD-L1 expression in NSCLC. PD-L1 IHC 22C3 pharmDx is a qualitative immunohistochemical assay using monoclonal mouse anti-PD-L1 antibody, (clone 22C3), that can be used in the detection of PD-L1 protein in formalin-fixed paraffin-embedded (FFPE) Non-Small Cell Lung Cancer (NSCLC) tissues. The assay can be performed on Autostainer Link 48 system and visualized using the EnVision FLEX system. PD-L1 protein expression is qualified using Tumor Proportion Score (TPS), which is the percentage of viable tumor cells showing partial or complete membrane staining. In some embodiments, the specimen is considered PD-L1 positive if TPS≥50% of the viable tumor cells exhibit membrane staining at any intensity. PD-L1 IHC 22C3 pharmDx is indicated as an aid in identifying NSCLC patients for treatment with KEYTRUDA® (pembrolizumab). Additional details on the scoring system and response to pembrolizumab are described in the article by Garon et al. (N Engl J Med 2015; 372:2018-28). In some embodiments, NSCLC patient specimens can be considered positive for PD-L1 expression if Tumor Proportion Score is ≥50% of the of viable tumor cells exhibit membrane staining (partial or complete) at any intensity (i.e. ≥1+). In some embodiments, this can be in specific regard to antibody clone 22C3. In some embodiments, if TPS=5% to 50% of the viable tumor cells exhibit membrane staining at any intensity, the sample and/or patient is considered to be PD-L1 positive. In some embodiments, if TPS≥50% of the viable tumor cells exhibit membrane staining at any intensity, the sample and/or patient is considered to be PD-L1$^{HIGH}$.

The terms "microsatellite instability high" and "MSI-high" refer to cancer comprising genetic instability (e.g., an expansion or reduction in the length of the microsatellites) in 2 or more of the 5 markers (loci): BAT25, BAT26, D5S346, D2S123, and D17S250, as determined by PCR analysis. See, e.g., Boland et al., 1998, *Cancer Res.* 58: 5248-5257.

The terms "microsatellite instability low" and "MSI-low" refer to cancer comprising genetic instability (e.g., an expansion or reduction in the length of the microsatellites) in 1 of the 5 markers (loci): BAT25, BAT26, D5S346, D2S123, and D17S250, as determined by PCR analysis. See, e.g., Boland et al., 1998, *Cancer Res.* 58: 5248-5257.

The terms "microsatellite instability positive" and "MSI-positive" refer to tumors that are MSI-high or MSI-low. A cancer is also considered to be MSI-positive if one or more mismatch repair proteins selected from MLH1, MSH2, PMS2, and MSH6 are absent by immunohistochemistry (IHC).

The terms "microsatellite stable" and "MSS" refer to cancer comprising genetic instability (e.g., an expansion or reduction in the length of the microsatellites) in none of the 5 markers (loci): BAT25, BAT26, D5S346, D2S123, and D17S250, as determined by PCR analysis. See, e.g., Boland et al., 1998, *Cancer Res.* 58: 5248-5257.

The term "control" refers to a composition known to not contain an analyte ("negative control") or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (for example, analytes).

"Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (for example, severity of disease, progression/nonprogression/improvement, etc.). While the present disclosure may provide exemplary predetermined levels, it is well-known that cutoff values may vary depending on the nature of the immunoassay (for example, antibodies employed, etc.). It further is well within the skill of one of ordinary skill in the art to adapt the disclosure herein for other immunoassays to obtain immunoassay-specific cutoff values for those other immunoassays based on this disclosure. Whereas the precise value of the predetermined cutoff/level may vary between assays, correlations as described herein (if any) may be generally applicable.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In some embodiments, by "reduce" or "inhibit" is meant the ability to cause an overall decrease of 20% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control dose (such as a placebo) over the same period of time. A "reference" as used herein, refers to any sample, standard, or level that is used for comparison purposes. A reference may be obtained from a healthy and/or non-diseased sample. In some examples, a reference may be obtained from an untreated sample. In some examples, a reference is obtained from a non-diseased on non-treated sample of a subject individual. In some examples, a reference is obtained from one or more healthy individuals who are not the subject or patient.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. Unless otherwise specified, the terms "reduce", "inhibit", or "prevent" do not denote or require complete prevention over all time.

As used herein, to "suppress" a function or activity is to reduce the function or activity when compared to otherwise same conditions except for a condition or parameter of interest, or alternatively, as compared to another condition. For example, an antibody which suppresses tumor growth reduces the rate of growth of the tumor compared to the rate of growth of the tumor in the absence of the antibody.

A "therapeutically effective amount" of a substance/molecule, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed.

A "sterile" formulation is aseptic or essentially free from living microorganisms and their spores.

A "PD-1 therapy" encompasses any therapy that modulates PD-1 binding to PD-L1 and/or PD-L2. PD-1 therapies may, for example, directly interact with PD-1 and/or PD-L1. In some embodiments, a PD-1 therapy includes a molecule that directly binds to and/or influences the activity of PD-1. In some embodiments, a PD-1 therapy includes a molecule that directly binds to and/or influences the activity of PD-L1. Thus, an antibody that binds to PD-1 or PD-L1 and blocks the interaction of PD-1 to PD-L1 is a PD-1 therapeutic. When a desired subtype of PD-1 therapy is intended, it will be designated by the phrase "PD-1 specific" for a therapy involving a molecule that interacts directly with PD-1, or "PD-L1 specific" for a molecule that interacts directly with PD-L1, as appropriate. Unless designated otherwise, all disclosure contained herein regarding PD-1 therapy applies to PD-1 therapy generally, as well as PD-1 specific and/or PD-L1 specific therapies. Nonlimiting exemplary PD-1 therapies include nivolumab (anti-PD-1 antibody; BMS-936558, MDX-1106, ONO-4538; OPDIVO®; Bristol-Myers Squibb); pidilizumab (anti-PD-1 antibody, CureTech); pembrolizumab (anti-PD-1 antibody; KEYTRUDA®, MK-3475, lambrolizumab); durvalumab (anti-PD-L1 antibody, MEDI-4736; AstraZeneca/MedImmune); RG-7446; MSB-0010718C; AMP-224; BMS-936559 (an anti-PD-L1 antibody; Bristol-Myers Squibb); AMP-514; MDX-1105; ANB-011; anti-LAG-3/PD-1; anti-PD-1 Ab (CoStim); anti-PD-1 Ab (Kadmon Pharm.); anti-PD-1 Ab (Immunovo); anti-TIM-3/PD-1 Ab (AnaptysBio); anti-PD-L1 Ab (CoStim/Novartis); atezolizumab (an anti-PD-L1 antibody, Genentech/Roche); avelumab (an anti-PD-L1 antibody, MSB0010718C, Pfizer); KD-033, PD-1 antagonist (Agenus); STI-A1010; STI-A1110; TSR-042; and other antibodies that are directed against programmed death-1 (PD-1) or programmed death ligand 1 (PD-L1).

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. A "reversible IDO inhibitor" is a compound that reversibly inhibits IDO enzyme activity either at the catalytic site or at a non-catalytic site and an "irreversible IDO inhibitor" is a compound that irreversibly inhibits IDO enzyme activity by forming a covalent bond with the enzyme. Nonlimiting exemplary IDO inhibitors include Indoximod (New Link Genetics), INCB024360 (Incyte Corp.), 1-methyl-D-tryptophan (New Link Genetics), and GDC-0919 (Genentech).

A "chimeric antigen receptor T cell therapy" or "CAR-T therapy" refers to a therapeutic agent comprising a T cell genetically modified to express a receptor that recognizes an antigen expressed by tumor cell. The antigen may be an antigen specifically expressed by the tumor or an antigen expressed by both cancerous cells and healthy tissue. In some embodiments CAR-T therapy is adoptive CAR-T therapy, in which a patients T cells are removed and modified to express the chimeric antigen receptor, and then returned to the patient. See, e.g., Dai et al., 2016, *J Natl Cancer Inst*, 108 (7): djv439, doi: 10.1093/jnci/djv439; Gill et al., 2015, *Blood Rev*, pii: S0268-960X(15)00080-6, doi: 10.1016/j.blre.2015.10.003; Gill et al., 2015, *Immunol Rev*, 263(1):68-89. doi: 10.1111/imr.12243.

Administration "in combination with" one or more further therapeutic agents includes simultaneous (concurrent) and consecutive or sequential administration in any order.

The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about a specified number of minutes.

The term "sequentially" is used herein to refer to administration of two or more therapeutic agents where the administration of one or more agent(s) continues after discontinuing the administration of one or more other agent(s), or wherein administration of one or more agent(s) begins before the administration of one or more other agent(s). For example, administration of the two or more therapeutic agents are administered with a time separation of more than about a specified number of minutes.

As used herein, "in conjunction with" refers to administration of one treatment modality in addition to another treatment modality. As such, "in conjunction with" refers to administration of one treatment modality before, during or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (for example, a package or container) or kit comprising at least one reagent, for example, a medicament for treatment of a disease or disorder (for example, cancer), or a probe for specifically detecting a biomarker described herein. In some embodiments, the manufacture or kit is promoted, distributed, or sold as a unit for performing the methods described herein.

The terms "label" and "detectable label" mean a moiety attached to a polynucleotide or polypeptide to render a reaction (for example, polynucleotide amplification or antibody binding) detectable. The polynucleotide or polypeptide comprising the label may be referred to as "detectably labeled." Thus, the term "labeled binding protein" refers to a protein with a label incorporated that provides for the identification of the binding protein. The term "labeled oligonucleotide," "labeled primer," "labeled probe," etc. refers to a polynucleotide with a label incorporated that provides for the identification of nucleic acids that comprise or are hybridized to the labeled oligonucleotide, primer, or probe. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels include, but are not limited to, the following: radioisotopes or radionuclides (for example, $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In some embodiments, the moiety itself may not be detectably labeled but may become detectable upon reaction with yet another moiety.

The term "conjugate" refers to an antibody that is chemically linked to a second chemical moiety, such as a therapeutic or cytotoxic agent. The term "agent" includes a chemical compound, a mixture of chemical compounds, a biological macromolecule, or an extract made from biological materials. In some embodiments, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, the conjugate antibody may be a detectably labeled antibody used as the detection antibody.

The term "amplification" refers to the process of producing one or more copies of a nucleic acid sequence or its complement. Amplification may be linear or exponential (e.g., PCR).

The technique of "polymerase chain reaction" or "PCR" as used herein generally refers to a procedure wherein a specific region of nucleic acid, such as RNA and/or DNA, is amplified as described, for example, in U.S. Pat. No. 4,683,195. Generally, oligonucleotide primers are designed the hybridize to opposite strands of the template to be amplified, a desired distance apart. PCR can be used to amplify specific RNA sequences, specific DNA sequences from total genomic DNA, and cDNA transcribed from total cellular RNA, bacteriophage or plasmid sequences, etc.

"Quantitative real time PCR" or "qRT-PCR" refers to a form of PCR wherein the PCR is performed such that the amounts, or relative amounts of the amplified product can be quantified. This technique has been described in various publications including Cronin et al., Am. J. Pathol. 164(1): 35-42 (2004); and Ma et al., Cancer Cell 5:607-616 (2004).

The term "target sequence," "target nucleic acid," or "target nucleic acid sequence" refers generally to a poly- nucleotide sequence of interest, e.g., a polynucleotide sequence that is targeted for amplification using, for example, qRT-PCR.

The term "detection" includes any means of detecting, including direct and indirect detection.

The term "prediction" is used herein to refer to the likelihood that a subject will respond either favorably or unfavorably to a therapeutic agent or combination of therapeutic agents. In some embodiments, the prediction relates to the extent of those responses. In some embodiments, the methods of prediction described herein can be used to make treatment decisions by choosing the most appropriate treatment modalities for a particular subject.

II. Anti-ICOS Antibodies

Antibodies directed against ICOS are provided. Anti-ICOS antibodies include, but are not limited to, humanized antibodies, chimeric antibodies, mouse antibodies, human antibodies, and antibodies comprising the heavy chain and/or light chain CDRs discussed herein. In some embodiments, an isolated antibody that binds to ICOS is provided. In some embodiments, a monoclonal antibody that binds to ICOS is provided. In some embodiments, an anti-ICOS antibody is an agonist anti-ICOS antibody. In some embodiments, administration of the anti-ICOS antibodies described herein increases the number of Teff cells; activates Teff cells; depletes Treg cells in a subject; and/or increases the ratio of Teff cells to Treg cells. In some embodiments, the Treg cells are CD4+ FoxP3+ T cells. In some embodiments, the Teff cells are CD8+ T cells. In some embodiments, the Teff cells are CD4+ FoxP3− T cells and CD8+ T cells.

In some embodiments, an anti-ICOS antibody comprises at least one, two, three, four, five, or six CDRs selected from (a) HCDR1 comprising the amino acid sequence of SEQ ID NO: 12; (b) HCDR2 comprising the amino acid sequence of SEQ ID NO: 13; (c) HCDR3 comprising the amino acid sequence of SEQ ID NO: 14; (d) LCDR1 comprising the amino acid sequence of SEQ ID NO: 15; (e) LCDR2 comprising the amino acid sequence of SEQ ID NO: 16; and (f) LCDR3 comprising the amino acid sequence of SEQ ID NO: 17.

In some embodiments, an anti-ICOS antibody comprises at least one, two, three, four, five, or six CDRs selected from (a) HCDR1 comprising the amino acid sequence of SEQ ID NO: 42; (b) HCDR2 comprising the amino acid sequence of SEQ ID NO: 43; (c) HCDR3 comprising the amino acid sequence of SEQ ID NO: 44; (d) LCDR1 comprising the amino acid sequence of SEQ ID NO: 45; (e) LCDR2 comprising the amino acid sequence of SEQ ID NO: 46; and (f) LCDR3 comprising the amino acid sequence of SEQ ID NO: 47.

In some embodiments, the anti-ICOS antibody comprises six CDRs including (a) HCDR1 comprising the amino acid sequence of SEQ ID NO: 62; (b) HCDR2 comprising the amino acid sequence of SEQ ID NO: 63; (c) HCDR3 comprising the amino acid sequence of SEQ ID NO: 64; (d) LCDR1 comprising the amino acid sequence of SEQ ID NO: 65; (e) LCDR2 comprising the amino acid sequence of SEQ ID NO: 66; and (f) LCDR3 comprising the amino acid sequence of SEQ ID NO: 67.

In some embodiments, an anti-ICOS antibody comprises at least one, two, three, four, five, or six CDRs selected from (a) HCDR1 comprising an amino acid sequence selected from SEQ ID NOs: 22, 62, 72, 82, 92, 102, and 112; (b) HCDR2 comprising an amino acid sequence selected from SEQ ID NOs: 23, 63, 73, 83, 93, 103, and 113; (c) HCDR3 comprising an amino acid sequence selected from SEQ ID NOs: 24, 64, 74, 84, 94, 104, and 114; (d) LCDR1 comprising an amino acid sequence selected from SEQ ID NOs: 25, 65, 75, 85, 95, 105, and 115; (e) LCDR2 comprising an amino acid sequence selected from SEQ ID NOs: 26, 66, 76, 86, 96, 106, and 116; and (f) LCDR3 comprising an amino acid sequence selected from SEQ ID NOs: 27, 67, 77, 87, 97, 107, and 117.

In some embodiments, an anti-ICOS antibody comprises at least one, two, three, four, five, or six CDRs selected from (a) HCDR1 comprising an amino acid sequence selected from SEQ ID NOs: 32, 162, 172, and 182; (b) HCDR2 comprising an amino acid sequence selected from SEQ ID NOs: 33, 163, 173, and 183; (c) HCDR3 comprising an amino acid sequence selected from SEQ ID NOs: 34, 164, 174, and 184; (d) LCDR1 comprising an amino acid sequence selected from SEQ ID NOs: 35, 165, 175, and 185; (e) LCDR2 comprising an amino acid sequence selected from SEQ ID NOs: 36, 166, 176, and 186; and (f) LCDR3 comprising an amino acid sequence selected from SEQ ID NOs: 37, 167, 177, and 187.

In some embodiments, an anti-ICOS antibody comprises at least one, two, three, four, five, or six CDRs selected from (a) HCDR1 comprising an amino acid sequence selected from SEQ ID NOs: 52, 122, 132, 142, and 152; (b) HCDR2 comprising an amino acid sequence selected from SEQ ID NOs: 53, 123, 133, 143, and 153; (c) HCDR3 comprising an amino acid sequence selected from SEQ ID NOs: 54, 124, 134, 144, and 154; (d) LCDR1 comprising an amino acid sequence selected from SEQ ID NOs: 55, 125, 135, 145, and 155; (e) LCDR2 comprising an amino acid sequence selected from SEQ ID NOs: 56, 126, 136, 146, and 156; and (f) LCDR3 comprising an amino acid sequence selected from SEQ ID NOs: 57, 127, 137, 147, and 157.

In some embodiments, an anti-ICOS antibody comprises a heavy chain variable region and a light chain variable region. In some embodiments, an anti-ICOS antibody comprises at least one heavy chain comprising a heavy chain variable region and at least a portion of a heavy chain constant region, and at least one light chain comprising a light chain variable region and at least a portion of a light chain constant region. In some embodiments, an anti-ICOS antibody comprises two heavy chains, wherein each heavy chain comprises a heavy chain variable region and at least a portion of a heavy chain constant region, and two light chains, wherein each light chain comprises a light chain variable region and at least a portion of a light chain constant region. As used herein, a single-chain Fv (scFv), or any other antibody that comprises, for example, a single polypeptide chain comprising all six CDRs (three heavy chain CDRs and three light chain CDRs) is considered to have a heavy chain and a light chain. In some embodiments, the heavy chain is the region of the anti-ICOS antibody that comprises the three heavy chain CDRs. In some embodiments, the light chain is the region of the anti-ICOS antibody that comprises the three light chain CDRs.

In some embodiments, the anti-ICOS antibody comprises six CDRs including (a) HCDR1 comprising the amino acid sequence of SEQ ID NO: 12; (b) HCDR2 comprising the amino acid sequence of SEQ ID NO: 13; (c) HCDR3 comprising the amino acid sequence of SEQ ID NO: 14; (d) LCDR1 comprising the amino acid sequence of SEQ ID NO: 15; (e) LCDR2 comprising the amino acid sequence of SEQ ID NO: 16; and (f) LCDR3 comprising the amino acid sequence of SEQ ID NO: 17.

In some embodiments, the anti-ICOS antibody comprises six CDRs including (a) HCDR1 comprising the amino acid sequence of SEQ ID NO: 22; (b) HCDR2 comprising the amino acid sequence of SEQ ID NO: 23; (c) HCDR3 comprising the amino acid sequence of SEQ ID NO: 24; (d) LCDR1 comprising the amino acid sequence of SEQ ID NO: 25; (e) LCDR2 comprising the amino acid sequence of SEQ ID NO: 26; and (f) LCDR3 comprising the amino acid sequence of SEQ ID NO: 27.

In some embodiments, the anti-ICOS antibody comprises six CDRs including (a) HCDR1 comprising the amino acid sequence of SEQ ID NO: 32; (b) HCDR2 comprising the amino acid sequence of SEQ ID NO: 33; (c) HCDR3 comprising the amino acid sequence of SEQ ID NO: 34; (d) LCDR1 comprising the amino acid sequence of SEQ ID NO: 35; (e) LCDR2 comprising the amino acid sequence of SEQ ID NO: 36; and (f) LCDR3 comprising the amino acid sequence of SEQ ID NO: 37.

In some embodiments, the anti-ICOS antibody comprises six CDRs including (a) HCDR1 comprising the amino acid sequence of SEQ ID NO: 42; (b) HCDR2 comprising the amino acid sequence of SEQ ID NO: 43; (c) HCDR3 comprising the amino acid sequence of SEQ ID NO: 44; (d) LCDR1 comprising the amino acid sequence of SEQ ID NO: 45; (e) LCDR2 comprising the amino acid sequence of SEQ ID NO: 46; and (f) LCDR3 comprising the amino acid sequence of SEQ ID NO: 47.

In some embodiments, the anti-ICOS antibody comprises six CDRs including (a) HCDR1 comprising the amino acid sequence of SEQ ID NO: 52; (b) HCDR2 comprising the amino acid sequence of SEQ ID NO: 53; (c) HCDR3 comprising the amino acid sequence of SEQ ID NO: 54; (d) LCDR1 comprising the amino acid sequence of SEQ ID NO: 55; (e) LCDR2 comprising the amino acid sequence of SEQ ID NO: 56; and (f) LCDR3 comprising the amino acid sequence of SEQ ID NO: 57.

In some embodiments, the anti-ICOS antibody comprises six CDRs including (a) HCDR1 comprising the amino acid sequence of SEQ ID NO: 72; (b) HCDR2 comprising the amino acid sequence of SEQ ID NO: 73; (c) HCDR3 comprising the amino acid sequence of SEQ ID NO: 74; (d) LCDR1 comprising the amino acid sequence of SEQ ID NO: 75; (e) LCDR2 comprising the amino acid sequence of SEQ ID NO: 76; and (f) LCDR3 comprising the amino acid sequence of SEQ ID NO: 77.

In some embodiments, the anti-ICOS antibody comprises six CDRs including (a) HCDR1 comprising the amino acid sequence of SEQ ID NO: 82; (b) HCDR2 comprising the amino acid sequence of SEQ ID NO: 83; (c) HCDR3 comprising the amino acid sequence of SEQ ID NO: 84; (d) LCDR1 comprising the amino acid sequence of SEQ ID NO: 85; (e) LCDR2 comprising the amino acid sequence of SEQ ID NO: 86; and (f) LCDR3 comprising the amino acid sequence of SEQ ID NO: 87.

In some embodiments, the anti-ICOS antibody comprises six CDRs including (a) HCDR1 comprising the amino acid sequence of SEQ ID NO: 92; (b) HCDR2 comprising the amino acid sequence of SEQ ID NO: 93; (c) HCDR3 comprising the amino acid sequence of SEQ ID NO: 94; (d) LCDR1 comprising the amino acid sequence of SEQ ID NO: 95; (e) LCDR2 comprising the amino acid sequence of SEQ ID NO: 96; and (f) LCDR3 comprising the amino acid sequence of SEQ ID NO: 97.

In some embodiments, the anti-ICOS antibody comprises six CDRs including (a) HCDR1 comprising the amino acid sequence of SEQ ID NO: 102; (b) HCDR2 comprising the amino acid sequence of SEQ ID NO: 103; (c) HCDR3 comprising the amino acid sequence of SEQ ID NO: 104; (d) LCDR1 comprising the amino acid sequence of SEQ ID NO: 105; (e) LCDR2 comprising the amino acid sequence of SEQ ID NO: 106; and (f) LCDR3 comprising the amino acid sequence of SEQ ID NO: 107.

In some embodiments, the anti-ICOS antibody comprises six CDRs including (a) HCDR1 comprising the amino acid sequence of SEQ ID NO: 112; (b) HCDR2 comprising the amino acid sequence of SEQ ID NO: 113; (c) HCDR3 comprising the amino acid sequence of SEQ ID NO: 114; (d) LCDR1 comprising the amino acid sequence of SEQ ID NO: 115; (e) LCDR2 comprising the amino acid sequence of SEQ ID NO: 116; and (f) LCDR3 comprising the amino acid sequence of SEQ ID NO: 117.

In some embodiments, the anti-ICOS antibody comprises six CDRs including (a) HCDR1 comprising the amino acid sequence of SEQ ID NO: 122; (b) HCDR2 comprising the amino acid sequence of SEQ ID NO: 123; (c) HCDR3 comprising the amino acid sequence of SEQ ID NO: 124; (d) LCDR1 comprising the amino acid sequence of SEQ ID NO: 125; (e) LCDR2 comprising the amino acid sequence of SEQ ID NO: 126; and (f) LCDR3 comprising the amino acid sequence of SEQ ID NO: 127.

In some embodiments, the anti-ICOS antibody comprises six CDRs including (a) HCDR1 comprising the amino acid sequence of SEQ ID NO: 132; (b) HCDR2 comprising the amino acid sequence of SEQ ID NO: 133; (c) HCDR3 comprising the amino acid sequence of SEQ ID NO: 134; (d) LCDR1 comprising the amino acid sequence of SEQ ID NO: 135; (e) LCDR2 comprising the amino acid sequence of SEQ ID NO: 136; and (f) LCDR3 comprising the amino acid sequence of SEQ ID NO: 137.

In some embodiments, the anti-ICOS antibody comprises six CDRs including (a) HCDR1 comprising the amino acid sequence of SEQ ID NO: 142; (b) HCDR2 comprising the amino acid sequence of SEQ ID NO: 143; (c) HCDR3 comprising the amino acid sequence of SEQ ID NO: 144; (d) LCDR1 comprising the amino acid sequence of SEQ ID NO: 145; (e) LCDR2 comprising the amino acid sequence of SEQ ID NO: 146; and (f) LCDR3 comprising the amino acid sequence of SEQ ID NO: 147.

In some embodiments, the anti-ICOS antibody comprises six CDRs including (a) HCDR1 comprising the amino acid sequence of SEQ ID NO: 152; (b) HCDR2 comprising the amino acid sequence of SEQ ID NO: 153; (c) HCDR3 comprising the amino acid sequence of SEQ ID NO: 154; (d) LCDR1 comprising the amino acid sequence of SEQ ID NO: 155; (e) LCDR2 comprising the amino acid sequence of SEQ ID NO: 156; and (f) LCDR3 comprising the amino acid sequence of SEQ ID NO: 157.

In some embodiments, the anti-ICOS antibody comprises six CDRs including (a) HCDR1 comprising the amino acid sequence of SEQ ID NO: 162; (b) HCDR2 comprising the amino acid sequence of SEQ ID NO: 163; (c) HCDR3 comprising the amino acid sequence of SEQ ID NO: 164; (d) LCDR1 comprising the amino acid sequence of SEQ ID NO: 165; (e) LCDR2 comprising the amino acid sequence of SEQ ID NO: 166; and (f) LCDR3 comprising the amino acid sequence of SEQ ID NO: 167.

In some embodiments, the anti-ICOS antibody comprises six CDRs including (a) HCDR1 comprising the amino acid sequence of SEQ ID NO: 172; (b) HCDR2 comprising the amino acid sequence of SEQ ID NO: 173; (c) HCDR3 comprising the amino acid sequence of SEQ ID NO: 174; (d) LCDR1 comprising the amino acid sequence of SEQ ID NO: 175; (e) LCDR2 comprising the amino acid sequence of SEQ ID NO: 176; and (f) LCDR3 comprising the amino acid sequence of SEQ ID NO: 177.

In some embodiments, the anti-ICOS antibody comprises six CDRs including (a) HCDR1 comprising the amino acid sequence of SEQ ID NO: 182; (b) HCDR2 comprising the amino acid sequence of SEQ ID NO: 183; (c) HCDR3 comprising the amino acid sequence of SEQ ID NO: 184; (d) LCDR1 comprising the amino acid sequence of SEQ ID NO: 185; (e) LCDR2 comprising the amino acid sequence of SEQ ID NO: 186; and (f) LCDR3 comprising the amino acid sequence of SEQ ID NO: 187.

In some embodiments, the anti-ICOS antibody comprises the six CDRs as described above and binds to ICOS. In some embodiments, the anti-ICOS antibody comprises the six CDRs as described above, binds to ICOS and increases the number of Teff cells and/or activates Teff cells and/or decreases the number of Treg cells and/or increases the ratio of Teff cells to Treg cells in a mammal, such as a human. In some embodiments, the Treg cells are CD4+ FoxP3+ T cells. In some embodiments, the Teff cells are CD8+ T cells. In some embodiments, the Teff cells are CD4+ FoxP3− T cells and/or CD8+ T cells.

In some embodiments, an anti-ICOS antibody is provided that competes with an anti-ICOS antibody described herein for binding to ICOS. In some embodiments, an antibody that competes for binding with any of the antibodies provided herein can be made and/or used.

In some embodiments, the anti-ICOS antibody comprises at least one, at least two, or all three VH CDR sequences selected from (a) HCDR1 comprising the amino acid sequence of SEQ ID NO: 12; (b) HCDR2 comprising the amino acid sequence of SEQ ID NO: 13; and (c) HCDR3 comprising the amino acid sequence of SEQ ID NO: 14.

In some embodiments, the anti-ICOS antibody comprises at least one, at least two, or all three VH CDR sequences selected from (a) HCDR1 comprising the amino acid sequence of SEQ ID NO: 22; (b) HCDR2 comprising the amino acid sequence of SEQ ID NO: 23; and (c) HCDR3 comprising the amino acid sequence of SEQ ID NO: 24.

In some embodiments, the anti-ICOS antibody comprises at least one, at least two, or all three VH CDR sequences selected from (a) HCDR1 comprising the amino acid sequence of SEQ ID NO: 32; (b) HCDR2 comprising the amino acid sequence of SEQ ID NO: 33; and (c) HCDR3 comprising the amino acid sequence of SEQ ID NO: 34.

In some embodiments, the anti-ICOS antibody comprises at least one, at least two, or all three VH CDR sequences selected from (a) HCDR1 comprising the amino acid sequence of SEQ ID NO: 42; (b) HCDR2 comprising the amino acid sequence of SEQ ID NO: 43; and (c) HCDR3 comprising the amino acid sequence of SEQ ID NO: 44.

In some embodiments, the anti-ICOS antibody comprises at least one, at least two, or all three VH CDR sequences selected from (a) HCDR1 comprising the amino acid sequence of SEQ ID NO: 52; (b) HCDR2 comprising the amino acid sequence of SEQ ID NO: 53; and (c) HCDR3 comprising the amino acid sequence of SEQ ID NO: 54.

In some embodiments, the anti-ICOS antibody comprises at least one, at least two, or all three VH CDR sequences selected from (a) HCDR1 comprising the amino acid sequence of SEQ ID NO: 62; (b) HCDR2 comprising the amino acid sequence of SEQ ID NO: 63; and (c) HCDR3 comprising the amino acid sequence of SEQ ID NO: 64.

In some embodiments, the anti-ICOS antibody comprises at least one, at least two, or all three VH CDR sequences selected from (a) HCDR1 comprising the amino acid sequence of SEQ ID NO: 72; (b) HCDR2 comprising the amino acid sequence of SEQ ID NO: 73; and (c) HCDR3 comprising the amino acid sequence of SEQ ID NO: 74.

In some embodiments, the anti-ICOS antibody comprises at least one, at least two, or all three VH CDR sequences selected from (a) HCDR1 comprising the amino acid sequence of SEQ ID NO: 82; (b) HCDR2 comprising the amino acid sequence of SEQ ID NO: 83; and (c) HCDR3 comprising the amino acid sequence of SEQ ID NO: 84.

In some embodiments, the anti-ICOS antibody comprises at least one, at least two, or all three VH CDR sequences selected from (a) HCDR1 comprising the amino acid sequence of SEQ ID NO: 92; (b) HCDR2 comprising the amino acid sequence of SEQ ID NO: 93; and (c) HCDR3 comprising the amino acid sequence of SEQ ID NO: 94.

In some embodiments, the anti-ICOS antibody comprises at least one, at least two, or all three VH CDR sequences selected from (a) HCDR1 comprising the amino acid sequence of SEQ ID NO: 102; (b) HCDR2 comprising the amino acid sequence of SEQ ID NO: 103; and (c) HCDR3 comprising the amino acid sequence of SEQ ID NO: 104.

In some embodiments, the anti-ICOS antibody comprises at least one, at least two, or all three VH CDR sequences selected from (a) HCDR1 comprising the amino acid sequence of SEQ ID NO: 112; (b) HCDR2 comprising the amino acid sequence of SEQ ID NO: 113; and (c) HCDR3 comprising the amino acid sequence of SEQ ID NO: 114.

In some embodiments, the anti-ICOS antibody comprises at least one, at least two, or all three VH CDR sequences selected from (a) HCDR1 comprising the amino acid sequence of SEQ ID NO: 122; (b) HCDR2 comprising the amino acid sequence of SEQ ID NO: 123; and (c) HCDR3 comprising the amino acid sequence of SEQ ID NO: 124.

In some embodiments, the anti-ICOS antibody comprises at least one, at least two, or all three VH CDR sequences selected from (a) HCDR1 comprising the amino acid sequence of SEQ ID NO: 132; (b) HCDR2 comprising the amino acid sequence of SEQ ID NO: 133; and (c) HCDR3 comprising the amino acid sequence of SEQ ID NO: 134.

In some embodiments, the anti-ICOS antibody comprises at least one, at least two, or all three VH CDR sequences selected from (a) HCDR1 comprising the amino acid sequence of SEQ ID NO: 142; (b) HCDR2 comprising the amino acid sequence of SEQ ID NO: 143; and (c) HCDR3 comprising the amino acid sequence of SEQ ID NO: 144.

In some embodiments, the anti-ICOS antibody comprises at least one, at least two, or all three VH CDR sequences selected from (a) HCDR1 comprising the amino acid sequence of SEQ ID NO: 152; (b) HCDR2 comprising the amino acid sequence of SEQ ID NO: 153; and (c) HCDR3 comprising the amino acid sequence of SEQ ID NO: 154.

In some embodiments, the anti-ICOS antibody comprises at least one, at least two, or all three VH CDR sequences selected from (a) HCDR1 comprising the amino acid sequence of SEQ ID NO: 162; (b) HCDR2 comprising the amino acid sequence of SEQ ID NO: 163; and (c) HCDR3 comprising the amino acid sequence of SEQ ID NO: 164.

In some embodiments, the anti-ICOS antibody comprises at least one, at least two, or all three VH CDR sequences selected from (a) HCDR1 comprising the amino acid sequence of SEQ ID NO: 172; (b) HCDR2 comprising the amino acid sequence of SEQ ID NO: 173; and (c) HCDR3 comprising the amino acid sequence of SEQ ID NO: 174.

In some embodiments, the anti-ICOS antibody comprises at least one, at least two, or all three VH CDR sequences selected from (a) HCDR1 comprising the amino acid sequence of SEQ ID NO: 182; (b) HCDR2 comprising the amino acid sequence of SEQ ID NO: 183; and (c) HCDR3 comprising the amino acid sequence of SEQ ID NO: 184.

In some embodiments, the antibody comprises at least one, at least two, or all three VL CDR sequences selected from (a) LCDR1 comprising the amino acid sequence of SEQ ID NO: 15; (b) LCDR2 comprising the amino acid sequence of SEQ ID NO: 16; and (c) LCDR3 comprising the amino acid sequence of SEQ ID NO: 17.

In some embodiments, the antibody comprises at least one, at least two, or all three VL CDR sequences selected from (a) LCDR1 comprising the amino acid sequence of SEQ ID NO: 25; (b) LCDR2 comprising the amino acid sequence of SEQ ID NO: 26; and (c) LCDR3 comprising the amino acid sequence of SEQ ID NO: 27.

In some embodiments, the antibody comprises at least one, at least two, or all three VL CDR sequences selected from (a) LCDR1 comprising the amino acid sequence of SEQ ID NO: 35; (b) LCDR2 comprising the amino acid sequence of SEQ ID NO: 36; and (c) LCDR3 comprising the amino acid sequence of SEQ ID NO: 37.

In some embodiments, the antibody comprises at least one, at least two, or all three VL CDR sequences selected from (a) LCDR1 comprising the amino acid sequence of SEQ ID NO: 45; (b) LCDR2 comprising the amino acid sequence of SEQ ID NO: 46; and (c) LCDR3 comprising the amino acid sequence of SEQ ID NO: 47.

In some embodiments, the antibody comprises at least one, at least two, or all three VL CDR sequences selected from (a) LCDR1 comprising the amino acid sequence of SEQ ID NO: 55; (b) LCDR2 comprising the amino acid sequence of SEQ ID NO: 56; and (c) LCDR3 comprising the amino acid sequence of SEQ ID NO: 57.

In some embodiments, the antibody comprises at least one, at least two, or all three VL CDR sequences selected from (a) LCDR1 comprising the amino acid sequence of SEQ ID NO: 65; (b) LCDR2 comprising the amino acid sequence of SEQ ID NO: 66; and (c) LCDR3 comprising the amino acid sequence of SEQ ID NO: 67.

In some embodiments, the antibody comprises at least one, at least two, or all three VL CDR sequences selected from (a) LCDR1 comprising the amino acid sequence of SEQ ID NO: 75; (b) LCDR2 comprising the amino acid sequence of SEQ ID NO: 76; and (c) LCDR3 comprising the amino acid sequence of SEQ ID NO: 77.

In some embodiments, the antibody comprises at least one, at least two, or all three VL CDR sequences selected from (a) LCDR1 comprising the amino acid sequence of SEQ ID NO: 85; (b) LCDR2 comprising the amino acid sequence of SEQ ID NO: 86; and (c) LCDR3 comprising the amino acid sequence of SEQ ID NO: 87.

In some embodiments, the antibody comprises at least one, at least two, or all three VL CDR sequences selected from (a) LCDR1 comprising the amino acid sequence of SEQ ID NO: 95; (b) LCDR2 comprising the amino acid sequence of SEQ ID NO: 96; and (c) LCDR3 comprising the amino acid sequence of SEQ ID NO: 97.

In some embodiments, the antibody comprises at least one, at least two, or all three VL CDR sequences selected from (a) LCDR1 comprising the amino acid sequence of SEQ ID NO: 105; (b) LCDR2 comprising the amino acid sequence of SEQ ID NO: 106; and (c) LCDR3 comprising the amino acid sequence of SEQ ID NO: 107.

In some embodiments, the antibody comprises at least one, at least two, or all three VL CDR sequences selected from (a) LCDR1 comprising the amino acid sequence of SEQ ID NO: 115; (b) LCDR2 comprising the amino acid sequence of SEQ ID NO: 116; and (c) LCDR3 comprising the amino acid sequence of SEQ ID NO: 117.

In some embodiments, the antibody comprises at least one, at least two, or all three VL CDR sequences selected from (a) LCDR1 comprising the amino acid sequence of SEQ ID NO: 125; (b) LCDR2 comprising the amino acid sequence of SEQ ID NO: 126; and (c) LCDR3 comprising the amino acid sequence of SEQ ID NO: 127.

In some embodiments, the antibody comprises at least one, at least two, or all three VL CDR sequences selected from (a) LCDR1 comprising the amino acid sequence of SEQ ID NO: 135; (b) LCDR2 comprising the amino acid sequence of SEQ ID NO: 136; and (c) LCDR3 comprising the amino acid sequence of SEQ ID NO: 137.

In some embodiments, the antibody comprises at least one, at least two, or all three VL CDR sequences selected from (a) LCDR1 comprising the amino acid sequence of SEQ ID NO: 145; (b) LCDR2 comprising the amino acid sequence of SEQ ID NO: 146; and (c) LCDR3 comprising the amino acid sequence of SEQ ID NO: 147.

In some embodiments, the antibody comprises at least one, at least two, or all three VL CDR sequences selected from (a) LCDR1 comprising the amino acid sequence of SEQ ID NO: 155; (b) LCDR2 comprising the amino acid sequence of SEQ ID NO: 156; and (c) LCDR3 comprising the amino acid sequence of SEQ ID NO: 157.

In some embodiments, the antibody comprises at least one, at least two, or all three VL CDR sequences selected from (a) LCDR1 comprising the amino acid sequence of SEQ ID NO: 165; (b) LCDR2 comprising the amino acid sequence of SEQ ID NO: 166; and (c) LCDR3 comprising the amino acid sequence of SEQ ID NO: 167.

In some embodiments, the antibody comprises at least one, at least two, or all three VL CDR sequences selected from (a) LCDR1 comprising the amino acid sequence of SEQ ID NO: 175; (b) LCDR2 comprising the amino acid sequence of SEQ ID NO: 176; and (c) LCDR3 comprising the amino acid sequence of SEQ ID NO: 177.

In some embodiments, the antibody comprises at least one, at least two, or all three VL CDR sequences selected from (a) LCDR1 comprising the amino acid sequence of SEQ ID NO: 185; (b) LCDR2 comprising the amino acid sequence of SEQ ID NO: 186; and (c) LCDR3 comprising the amino acid sequence of SEQ ID NO: 187.

In some embodiments, any of the six CDRs provided herein can be combined as subparts with any of the other CDRs provided herein, for a total of six CDRs in a construct. Thus, in some embodiments, two CDRs from a first antibody (for example, HCDR1 and HCDR2) can be combined with four CDRs from a second antibody (HCDR3, LCDR1, LCDR2, and LCDR3). In some embodiments, two or fewer residues in one or more of the CDRs can be replaced to obtain a variant thereof. In some embodiments, two or fewer residues can be replaced in 1, 2, 3, 4, 5, or 6 of the CDRs.

In some embodiments, the anti-ICOS antibody comprises (I) a VH domain comprising at least one, at least two, or all three VH CDR sequences selected from (a) HCDR1 comprising the amino acid sequence of SEQ ID NO: 12; (b) HCDR2 comprising the amino acid sequence of SEQ ID NO: 13; and (c) HCDR3 comprising the amino acid sequence of SEQ ID NO: 14; and (II) a VL domain comprising at least one, at least two, or all three VL CDR sequences selected from (d) LCDR1 comprising the amino acid sequence of SEQ ID NO: 15; (e) LCDR2 comprising the amino acid sequence of SEQ ID NO: 16; and (f) LCDR3 comprising the amino acid sequence of SEQ ID NO: 17.

In some embodiments, the anti-ICOS antibody comprises (I) a VH domain comprising at least one, at least two, or all three VH CDR sequences selected from (a) HCDR1 comprising the amino acid sequence of SEQ ID NO: 22; (b) HCDR2 comprising the amino acid sequence of SEQ ID NO: 23; and (c) HCDR3 comprising the amino acid sequence of SEQ ID NO: 24; and (II) a VL domain comprising at least one, at least two, or all three VL CDR sequences selected from (d) LCDR1 comprising the amino acid sequence of SEQ ID NO: 25; (e) LCDR2 comprising the amino acid sequence of SEQ ID NO: 26; and (f) LCDR3 comprising the amino acid sequence of SEQ ID NO: 27.

In some embodiments, the anti-ICOS antibody comprises (I) a VH domain comprising at least one, at least two, or all three VH CDR sequences selected from (a) HCDR1 comprising the amino acid sequence of SEQ ID NO: 32; (b) HCDR2 comprising the amino acid sequence of SEQ ID NO: 33; and (c) HCDR3 comprising the amino acid sequence of SEQ ID NO: 34; and (II) a VL domain comprising at least one, at least two, or all three VL CDR sequences selected from (d) LCDR1 comprising the amino acid sequence of SEQ ID NO: 35; (e) LCDR2 comprising the amino acid sequence of SEQ ID NO: 36; and (f) LCDR3 comprising the amino acid sequence of SEQ ID NO: 37.

In some embodiments, the anti-ICOS antibody comprises (I) a VH domain comprising at least one, at least two, or all three VH CDR sequences selected from (a) HCDR1 comprising the amino acid sequence of SEQ ID NO: 42; (b) HCDR2 comprising the amino acid sequence of SEQ ID NO: 43; and (c) HCDR3 comprising the amino acid sequence of SEQ ID NO: 44; and (II) a VL domain comprising at least one, at least two, or all three VL CDR sequences selected from (d) LCDR1 comprising the amino acid sequence of SEQ ID NO: 45; (e) LCDR2 comprising the amino acid sequence of SEQ ID NO: 46; and (f) LCDR3 comprising the amino acid sequence of SEQ ID NO: 47.

In some embodiments, the anti-ICOS antibody comprises (I) a VH domain comprising at least one, at least two, or all three VH CDR sequences selected from (a) HCDR1 comprising the amino acid sequence of SEQ ID NO: 52; (b) HCDR2 comprising the amino acid sequence of SEQ ID NO: 53; and (c) HCDR3 comprising the amino acid sequence of SEQ ID NO: 54; and (II) a VL domain comprising at least one, at least two, or all three VL CDR sequences selected from (d) LCDR1 comprising the amino acid sequence of SEQ ID NO: 55; (e) LCDR2 comprising the amino acid sequence of SEQ ID NO: 56; and (f) LCDR3 comprising the amino acid sequence of SEQ ID NO: 57.

In some embodiments, the anti-ICOS antibody comprises (I) a VH domain comprising at least one, at least two, or all three VH CDR sequences selected from (a) HCDR1 comprising the amino acid sequence of SEQ ID NO: 62; (b) HCDR2 comprising the amino acid sequence of SEQ ID NO: 63; and (c) HCDR3 comprising the amino acid sequence of SEQ ID NO: 64; and (II) a VL domain comprising at least one, at least two, or all three VL CDR sequences selected from (d) LCDR1 comprising the amino acid sequence of SEQ ID NO: 65; (e) LCDR2 comprising the amino acid sequence of SEQ ID NO: 66; and (f) LCDR3 comprising the amino acid sequence of SEQ ID NO: 67.

In some embodiments, the anti-ICOS antibody comprises (I) a VH domain comprising at least one, at least two, or all three VH CDR sequences selected from (a) HCDR1 comprising the amino acid sequence of SEQ ID NO: 72; (b) HCDR2 comprising the amino acid sequence of SEQ ID NO: 73; and (c) HCDR3 comprising the amino acid sequence of SEQ ID NO: 74; and (II) a VL domain comprising at least one, at least two, or all three VL CDR sequences selected from (d) LCDR1 comprising the amino acid sequence of SEQ ID NO: 75; (e) LCDR2 comprising the amino acid sequence of SEQ ID NO: 76; and (f) LCDR3 comprising the amino acid sequence of SEQ ID NO: 77.

In some embodiments, the anti-ICOS antibody comprises (I) a VH domain comprising at least one, at least two, or all three VH CDR sequences selected from (a) HCDR1 comprising the amino acid sequence of SEQ ID NO: 82; (b) HCDR2 comprising the amino acid sequence of SEQ ID NO: 83; and (c) HCDR3 comprising the amino acid sequence of SEQ ID NO: 84; and (II) a VL domain comprising at least one, at least two, or all three VL CDR sequences selected from (d) LCDR1 comprising the amino acid sequence of SEQ ID NO: 85; (e) LCDR2 comprising the amino acid sequence of SEQ ID NO: 86; and (f) LCDR3 comprising the amino acid sequence of SEQ ID NO: 87.

In some embodiments, the anti-ICOS antibody comprises (I) a VH domain comprising at least one, at least two, or all three VH CDR sequences selected from (a) HCDR1 comprising the amino acid sequence of SEQ ID NO: 92; (b) HCDR2 comprising the amino acid sequence of SEQ ID NO: 93; and (c) HCDR3 comprising the amino acid sequence of SEQ ID NO: 94; and (II) a VL domain comprising at least one, at least two, or all three VL CDR sequences selected from (d) LCDR1 comprising the amino acid sequence of SEQ ID NO: 95; (e) LCDR2 comprising the amino acid sequence of SEQ ID NO: 96; and (f) LCDR3 comprising the amino acid sequence of SEQ ID NO: 97.

In some embodiments, the anti-ICOS antibody comprises (I) a VH domain comprising at least one, at least two, or all three VH CDR sequences selected from (a) HCDR1 comprising the amino acid sequence of SEQ ID NO: 102; (b) HCDR2 comprising the amino acid sequence of SEQ ID NO: 103; and (c) HCDR3 comprising the amino acid sequence of SEQ ID NO: 104; and (II) a VL domain comprising at least one, at least two, or all three VL CDR sequences selected from (d) LCDR1 comprising the amino acid sequence of SEQ ID NO: 105; (e) LCDR2 comprising the amino acid sequence of SEQ ID NO: 106; and (f) LCDR3 comprising the amino acid sequence of SEQ ID NO: 107.

In some embodiments, the anti-ICOS antibody comprises (I) a VH domain comprising at least one, at least two, or all three VH CDR sequences selected from (a) HCDR1 comprising the amino acid sequence of SEQ ID NO: 112; (b) HCDR2 comprising the amino acid sequence of SEQ ID NO: 113; and (c) HCDR3 comprising the amino acid sequence of SEQ ID NO: 114; and (II) a VL domain comprising at least one, at least two, or all three VL CDR sequences selected from (d) LCDR1 comprising the amino acid sequence of SEQ ID NO: 115; (e) LCDR2 comprising the amino acid sequence of SEQ ID NO: 116; and (f) LCDR3 comprising the amino acid sequence of SEQ ID NO: 117.

In some embodiments, the anti-ICOS antibody comprises (I) a VH domain comprising at least one, at least two, or all three VH CDR sequences selected from (a) HCDR1 comprising the amino acid sequence of SEQ ID NO: 122; (b) HCDR2 comprising the amino acid sequence of SEQ ID NO: 123; and (c) HCDR3 comprising the amino acid sequence of SEQ ID NO: 124; and (II) a VL domain comprising at least one, at least two, or all three VL CDR sequences selected from (d) LCDR1 comprising the amino acid sequence of SEQ ID NO: 125; (e) LCDR2 comprising the amino acid sequence of SEQ ID NO: 126; and (f) LCDR3 comprising the amino acid sequence of SEQ ID NO: 127.

In some embodiments, the anti-ICOS antibody comprises (I) a VH domain comprising at least one, at least two, or all three VH CDR sequences selected from (a) HCDR1 comprising the amino acid sequence of SEQ ID NO: 132; (b) HCDR2 comprising the amino acid sequence of SEQ ID NO: 133; and (c) HCDR3 comprising the amino acid sequence of SEQ ID NO: 134; and (II) a VL domain comprising at least one, at least two, or all three VL CDR sequences selected from (d) LCDR1 comprising the amino acid sequence of SEQ ID NO: 135; (e) LCDR2 comprising the amino acid sequence of SEQ ID NO: 136; and (f) LCDR3 comprising the amino acid sequence of SEQ ID NO: 137.

In some embodiments, the anti-ICOS antibody comprises (I) a VH domain comprising at least one, at least two, or all three VH CDR sequences selected from (a) HCDR1 comprising the amino acid sequence of SEQ ID NO: 142; (b) HCDR2 comprising the amino acid sequence of SEQ ID NO: 143; and (c) HCDR3 comprising the amino acid sequence of SEQ ID NO: 144; and (II) a VL domain comprising at least one, at least two, or all three VL CDR sequences selected from (d) LCDR1 comprising the amino acid sequence of SEQ ID NO: 145; (e) LCDR2 comprising the amino acid sequence of SEQ ID NO: 146; and (f) LCDR3 comprising the amino acid sequence of SEQ ID NO: 147.

In some embodiments, the anti-ICOS antibody comprises (I) a VH domain comprising at least one, at least two, or all three VH CDR sequences selected from (a) HCDR1 comprising the amino acid sequence of SEQ ID NO: 152; (b) HCDR2 comprising the amino acid sequence of SEQ ID NO: 153; and (c) HCDR3 comprising the amino acid sequence of SEQ ID NO: 154; and (II) a VL domain comprising at least one, at least two, or all three VL CDR sequences selected from (d) LCDR1 comprising the amino acid sequence of SEQ ID NO: 155; (e) LCDR2 comprising the amino acid sequence of SEQ ID NO: 156; and (f) LCDR3 comprising the amino acid sequence of SEQ ID NO: 157.

In some embodiments, the anti-ICOS antibody comprises (I) a VH domain comprising at least one, at least two, or all three VH CDR sequences selected from (a) HCDR1 comprising the amino acid sequence of SEQ ID NO: 162; (b) HCDR2 comprising the amino acid sequence of SEQ ID NO: 163; and (c) HCDR3 comprising the amino acid sequence of SEQ ID NO: 164; and (II) a VL domain comprising at least one, at least two, or all three VL CDR sequences selected from (d) LCDR1 comprising the amino acid sequence of SEQ ID NO: 165; (e) LCDR2 comprising the amino acid sequence of SEQ ID NO: 166; and (f) LCDR3 comprising the amino acid sequence of SEQ ID NO: 167.

In some embodiments, the anti-ICOS antibody comprises (I) a VH domain comprising at least one, at least two, or all three VH CDR sequences selected from (a) HCDR1 comprising the amino acid sequence of SEQ ID NO: 172; (b) HCDR2 comprising the amino acid sequence of SEQ ID NO: 173; and (c) HCDR3 comprising the amino acid sequence of SEQ ID NO: 174; and (II) a VL domain comprising at least one, at least two, or all three VL CDR sequences selected from (d) LCDR1 comprising the amino acid sequence of SEQ ID NO: 175; (e) LCDR2 comprising the amino acid sequence of SEQ ID NO: 176; and (f) LCDR3 comprising the amino acid sequence of SEQ ID NO: 177.

In some embodiments, the anti-ICOS antibody comprises (I) a VH domain comprising at least one, at least two, or all three VH CDR sequences selected from (a) HCDR1 comprising the amino acid sequence of SEQ ID NO: 182; (b)

HCDR2 comprising the amino acid sequence of SEQ ID NO: 183; and (c) HCDR3 comprising the amino acid sequence of SEQ ID NO: 184; and (II) a VL domain comprising at least one, at least two, or all three VL CDR sequences selected from (d) LCDR1 comprising the amino acid sequence of SEQ ID NO: 185; (e) LCDR2 comprising the amino acid sequence of SEQ ID NO: 186; and (f) LCDR3 comprising the amino acid sequence of SEQ ID NO: 187.

In some embodiments, the anti-ICOS antibody comprises (I) a VH domain comprising at least one, at least two, or all three VH CDR sequences selected from (a) HCDR1 comprising the amino acid sequence of SEQ ID NO: 194; (b) HCDR2 comprising the amino acid sequence of SEQ ID NO: 195; and (c) HCDR3 comprising the amino acid sequence of SEQ ID NO: 196; and (II) a VL domain comprising at least one, at least two, or all three VL CDR sequences selected from (d) LCDR1 comprising the amino acid sequence of SEQ ID NO: 197; (e) LCDR2 comprising the amino acid sequence of SEQ ID NO: 198; and (f) LCDR3 comprising the amino acid sequence of SEQ ID NO: 199.

In some embodiments, the anti-ICOS antibody comprises (I) a VH domain comprising at least one, at least two, or all three VH CDR sequences selected from (a) HCDR1 comprising the amino acid sequence of SEQ ID NO: 202; (b) HCDR2 comprising the amino acid sequence of SEQ ID NO: 203; and (c) HCDR3 comprising the amino acid sequence of SEQ ID NO: 204; and (II) a VL domain comprising at least one, at least two, or all three VL CDR sequences selected from (d) LCDR1 comprising the amino acid sequence of SEQ ID NO: 205; (e) LCDR2 comprising the amino acid sequence of SEQ ID NO: 206; and (f) LCDR3 comprising the amino acid sequence of SEQ ID NO: 207.

In some embodiments, the anti-ICOS antibody comprises (I) a VH domain comprising at least one, at least two, or all three VH CDR sequences selected from (a) HCDR1 comprising the amino acid sequence of SEQ ID NO: 210; (b) HCDR2 comprising the amino acid sequence of SEQ ID NO: 211; and (c) HCDR3 comprising the amino acid sequence of SEQ ID NO: 212; and (II) a VL domain comprising at least one, at least two, or all three VL CDR sequences selected from (d) LCDR1 comprising the amino acid sequence of SEQ ID NO: 213; (e) LCDR2 comprising the amino acid sequence of SEQ ID NO: 214; and (f) LCDR3 comprising the amino acid sequence of SEQ ID NO: 215.

In some embodiments, an anti-ICOS antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 10, 20, 30, 40, 50, 60, 70, 80, 90, 100, 110, 120, 130, 140, 150, 160, 170, or 180. In some embodiments, an anti-ICOS antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 192, 200, or 208. In some embodiments, a VH sequence having at least 90%, 91%, 92%, 93%, 94%, 95%, 96%, 97%, 98%, or 99% identity contains substitutions (for example, conservative substitutions), insertions, or deletions relative to the reference sequence, but an anti-ICOS antibody comprising that sequence retains the ability to bind to ICOS. In some embodiments, a total of 1 to 10 amino acids have been substituted, inserted and/or deleted in SEQ ID NO: 10, 20, 30, 40, 50, 60, 70, 80, 90, 100, 110, 120, 130, 140, 150, 160, 170, or 180. In some embodiments, a total of 1 to 10 amino acids have been substituted, inserted and/or deleted in SEQ ID NO: 192, 200, or 208. In some embodiments, substitutions, insertions, or deletions occur in regions outside the CDRs (that is, in the FRs). Optionally, the anti-ICOS antibody comprises the VH sequence in SEQ ID NO: 10, 20, 30, 40, 50, 60, 70, 80, 90, 100, 110, 120, 130, 140, 150, 160, 170, or 180, including post-translational modifications of that sequence. Optionally, the anti-ICOS antibody comprises the VH sequence in SEQ ID NO: 192, 200, or 208, including post-translational modifications of that sequence.

In some embodiments, the VH comprises: (a) HCDR1 comprising the amino acid sequence of SEQ ID NO: 12; (b) HCDR2 comprising the amino acid sequence of SEQ ID NO: 13; and (c) HCDR3 comprising the amino acid sequence of SEQ ID NO: 14.

In some embodiments, the VH comprises: (a) HCDR1 comprising the amino acid sequence of SEQ ID NO: 22; (b) HCDR2 comprising the amino acid sequence of SEQ ID NO: 23; and (c) HCDR3 comprising the amino acid sequence of SEQ ID NO: 24.

In some embodiments, the VH comprises: (a) HCDR1 comprising the amino acid sequence of SEQ ID NO: 32; (b) HCDR2 comprising the amino acid sequence of SEQ ID NO: 33; and (c) HCDR3 comprising the amino acid sequence of SEQ ID NO: 34.

In some embodiments, the VH comprises: (a) HCDR1 comprising the amino acid sequence of SEQ ID NO: 42; (b) HCDR2 comprising the amino acid sequence of SEQ ID NO: 43; and (c) HCDR3 comprising the amino acid sequence of SEQ ID NO: 44.

In some embodiments, the VH comprises: (a) HCDR1 comprising the amino acid sequence of SEQ ID NO: 52; (b) HCDR2 comprising the amino acid sequence of SEQ ID NO: 53; and (c) HCDR3 comprising the amino acid sequence of SEQ ID NO: 54.

In some embodiments, the VH comprises: (a) HCDR1 comprising the amino acid sequence of SEQ ID NO: 62; (b) HCDR2 comprising the amino acid sequence of SEQ ID NO: 63; and (c) HCDR3 comprising the amino acid sequence of SEQ ID NO: 64.

In some embodiments, the VH comprises: (a) HCDR1 comprising the amino acid sequence of SEQ ID NO: 72; (b) HCDR2 comprising the amino acid sequence of SEQ ID NO: 73; and (c) HCDR3 comprising the amino acid sequence of SEQ ID NO: 74.

In some embodiments, the VH comprises: (a) HCDR1 comprising the amino acid sequence of SEQ ID NO: 82; (b) HCDR2 comprising the amino acid sequence of SEQ ID NO: 83; and (c) HCDR3 comprising the amino acid sequence of SEQ ID NO: 84.

In some embodiments, the VH comprises: (a) HCDR1 comprising the amino acid sequence of SEQ ID NO: 92; (b) HCDR2 comprising the amino acid sequence of SEQ ID NO: 93; and (c) HCDR3 comprising the amino acid sequence of SEQ ID NO: 94.

In some embodiments, the VH comprises: (a) HCDR1 comprising the amino acid sequence of SEQ ID NO: 102; (b) HCDR2 comprising the amino acid sequence of SEQ ID NO: 103; and (c) HCDR3 comprising the amino acid sequence of SEQ ID NO: 104.

In some embodiments, the VH comprises: (a) HCDR1 comprising the amino acid sequence of SEQ ID NO: 112; (b) HCDR2 comprising the amino acid sequence of SEQ ID NO: 113; and (c) HCDR3 comprising the amino acid sequence of SEQ ID NO: 114.

In some embodiments, the VH comprises: (a) HCDR1 comprising the amino acid sequence of SEQ ID NO: 122; (b) HCDR2 comprising the amino acid sequence of SEQ ID NO: 123; and (c) HCDR3 comprising the amino acid sequence of SEQ ID NO: 124.

In some embodiments, the VH comprises: (a) HCDR1 comprising the amino acid sequence of SEQ ID NO: 132; (b) HCDR2 comprising the amino acid sequence of SEQ ID NO: 133; and (c) HCDR3 comprising the amino acid sequence of SEQ ID NO: 134.

In some embodiments, the VH comprises: (a) HCDR1 comprising the amino acid sequence of SEQ ID NO: 142; (b) HCDR2 comprising the amino acid sequence of SEQ ID NO: 143; and (c) HCDR3 comprising the amino acid sequence of SEQ ID NO: 144.

In some embodiments, the VH comprises: (a) HCDR1 comprising the amino acid sequence of SEQ ID NO: 152; (b) HCDR2 comprising the amino acid sequence of SEQ ID NO: 153; and (c) HCDR3 comprising the amino acid sequence of SEQ ID NO: 154.

In some embodiments, the VH comprises: (a) HCDR1 comprising the amino acid sequence of SEQ ID NO: 162; (b) HCDR2 comprising the amino acid sequence of SEQ ID NO: 163; and (c) HCDR3 comprising the amino acid sequence of SEQ ID NO: 164.

In some embodiments, the VH comprises: (a) HCDR1 comprising the amino acid sequence of SEQ ID NO: 172; (b) HCDR2 comprising the amino acid sequence of SEQ ID NO: 173; and (c) HCDR3 comprising the amino acid sequence of SEQ ID NO: 174.

In some embodiments, the VH comprises: (a) HCDR1 comprising the amino acid sequence of SEQ ID NO: 182; (b) HCDR2 comprising the amino acid sequence of SEQ ID NO: 183; and (c) HCDR3 comprising the amino acid sequence of SEQ ID NO: 184.

In some embodiments, the VH comprises: (a) HCDR1 comprising the amino acid sequence of SEQ ID NO: 194; (b) HCDR2 comprising the amino acid sequence of SEQ ID NO: 195; and (c) HCDR3 comprising the amino acid sequence of SEQ ID NO: 196.

In some embodiments, the VH comprises: (a) HCDR1 comprising the amino acid sequence of SEQ ID NO: 202; (b) HCDR2 comprising the amino acid sequence of SEQ ID NO: 203; and (c) HCDR3 comprising the amino acid sequence of SEQ ID NO: 204.

In some embodiments, the VH comprises: (a) HCDR1 comprising the amino acid sequence of SEQ ID NO: 210; (b) HCDR2 comprising the amino acid sequence of SEQ ID NO: 211; and (c) HCDR3 comprising the amino acid sequence of SEQ ID NO: 212.

In some embodiments, an anti-ICOS antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 11, 21, 31, 41, 51, 61, 71, 81, 91, 101, 111, 121, 131, 141, 151, 161, 171, or 181. In some embodiments, an anti-ICOS antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 193, 201, or 209. In some embodiments, a VL sequence having at least 90%, 91%, 92%, 93%, 94%, 95%, 96%, 97%, 98%, or 99% identity contains substitutions (for example, conservative substitutions), insertions, or deletions relative to the reference sequence, but an anti-ICOS antibody comprising that sequence retains the ability to bind to ICOS. In some embodiments, a total of 1 to 10 amino acids have been substituted, inserted and/or deleted in SEQ ID NO: 11, 21, 31, 41, 51, 61, 71, 81, 91, 101, 111, 121, 131, 141, 151, 161, 171, or 181. In some embodiments, a total of 1 to 10 amino acids have been substituted, inserted and/or deleted in SEQ ID NO: 193, 201, or 209. In some embodiments, the substitutions, insertions, or deletions occur in regions outside the CDRs (that is, in the FRs). Optionally, the anti-ICOS antibody comprises the VL sequence in SEQ ID NO: 11, 21, 31, 41, 51, 61, 71, 81, 91, 101, 111, 121, 131, 141, 151, 161, 171, or 181, including post-translational modifications of that sequence. Optionally, the anti-ICOS antibody comprises the VL sequence in SEQ ID NO: 193, 201, or 209, including post-translational modifications of that sequence.

In some embodiments, the VL comprises: (a) LCDR1 comprising the amino acid sequence of SEQ ID NO: 15; (b) LCDR2 comprising the amino acid sequence of SEQ ID NO: 16; and (c) LCDR3 comprising the amino acid sequence of SEQ ID NO: 17.

In some embodiments, the VL comprises: (a) LCDR1 comprising the amino acid sequence of SEQ ID NO: 25; (b) LCDR2 comprising the amino acid sequence of SEQ ID NO: 26; and (c) LCDR3 comprising the amino acid sequence of SEQ ID NO: 27.

In some embodiments, the VL comprises: (a) LCDR1 comprising the amino acid sequence of SEQ ID NO: 35; (b) LCDR2 comprising the amino acid sequence of SEQ ID NO: 36; and (c) LCDR3 comprising the amino acid sequence of SEQ ID NO: 37.

In some embodiments, the VL comprises: (a) LCDR1 comprising the amino acid sequence of SEQ ID NO: 45; (b) LCDR2 comprising the amino acid sequence of SEQ ID NO: 46; and (c) LCDR3 comprising the amino acid sequence of SEQ ID NO: 47.

In some embodiments, the VL comprises: (a) LCDR1 comprising the amino acid sequence of SEQ ID NO: 55; (b) LCDR2 comprising the amino acid sequence of SEQ ID NO: 56; and (c) LCDR3 comprising the amino acid sequence of SEQ ID NO: 57.

In some embodiments, the VL comprises: (a) LCDR1 comprising the amino acid sequence of SEQ ID NO: 65; (b) LCDR2 comprising the amino acid sequence of SEQ ID NO: 66; and (c) LCDR3 comprising the amino acid sequence of SEQ ID NO: 67.

In some embodiments, the VL comprises: (a) LCDR1 comprising the amino acid sequence of SEQ ID NO: 75; (b) LCDR2 comprising the amino acid sequence of SEQ ID NO: 76; and (c) LCDR3 comprising the amino acid sequence of SEQ ID NO: 77.

In some embodiments, the VL comprises: (a) LCDR1 comprising the amino acid sequence of SEQ ID NO: 85; (b) LCDR2 comprising the amino acid sequence of SEQ ID NO: 86; and (c) LCDR3 comprising the amino acid sequence of SEQ ID NO: 87.

In some embodiments, the VL comprises: (a) LCDR1 comprising the amino acid sequence of SEQ ID NO: 95; (b) LCDR2 comprising the amino acid sequence of SEQ ID NO: 96; and (c) LCDR3 comprising the amino acid sequence of SEQ ID NO: 97.

In some embodiments, the VL comprises: (a) LCDR1 comprising the amino acid sequence of SEQ ID NO: 105; (b) LCDR2 comprising the amino acid sequence of SEQ ID NO: 106; and (c) LCDR3 comprising the amino acid sequence of SEQ ID NO: 107.

In some embodiments, the VL comprises: (a) LCDR1 comprising the amino acid sequence of SEQ ID NO: 115; (b) LCDR2 comprising the amino acid sequence of SEQ ID NO: 116; and (c) LCDR3 comprising the amino acid sequence of SEQ ID NO: 117.

In some embodiments, the VL comprises: (a) LCDR1 comprising the amino acid sequence of SEQ ID NO: 125; (b) LCDR2 comprising the amino acid sequence of SEQ ID NO: 126; and (c) LCDR3 comprising the amino acid sequence of SEQ ID NO: 127.

In some embodiments, the VL comprises: (a) LCDR1 comprising the amino acid sequence of SEQ ID NO: 135; (b) LCDR2 comprising the amino acid sequence of SEQ ID NO: 136; and (c) LCDR3 comprising the amino acid sequence of SEQ ID NO: 137.

In some embodiments, the VL comprises: (a) LCDR1 comprising the amino acid sequence of SEQ ID NO: 145; (b) LCDR2 comprising the amino acid sequence of SEQ ID NO: 146; and (c) LCDR3 comprising the amino acid sequence of SEQ ID NO: 147.

In some embodiments, the VL comprises: (a) LCDR1 comprising the amino acid sequence of SEQ ID NO: 155; (b) LCDR2 comprising the amino acid sequence of SEQ ID NO: 156; and (c) LCDR3 comprising the amino acid sequence of SEQ ID NO: 157.

In some embodiments, the VL comprises: (a) LCDR1 comprising the amino acid sequence of SEQ ID NO: 165; (b) LCDR2 comprising the amino acid sequence of SEQ ID NO: 166; and (c) LCDR3 comprising the amino acid sequence of SEQ ID NO: 167.

In some embodiments, the VL comprises: (a) LCDR1 comprising the amino acid sequence of SEQ ID NO: 175; (b) LCDR2 comprising the amino acid sequence of SEQ ID NO: 176; and (c) LCDR3 comprising the amino acid sequence of SEQ ID NO: 177.

In some embodiments, the VL comprises: (a) LCDR1 comprising the amino acid sequence of SEQ ID NO: 185; (b) LCDR2 comprising the amino acid sequence of SEQ ID NO: 186; and (c) LCDR3 comprising the amino acid sequence of SEQ ID NO: 187.

In some embodiments, the VL comprises: (a) LCDR1 comprising the amino acid sequence of SEQ ID NO: 197; (b) LCDR2 comprising the amino acid sequence of SEQ ID NO: 198; and (c) LCDR3 comprising the amino acid sequence of SEQ ID NO: 199.

In some embodiments, the VL comprises: (a) LCDR1 comprising the amino acid sequence of SEQ ID NO: 205; (b) LCDR2 comprising the amino acid sequence of SEQ ID NO: 206; and (c) LCDR3 comprising the amino acid sequence of SEQ ID NO: 207.

In some embodiments, the VL comprises: (a) LCDR1 comprising the amino acid sequence of SEQ ID NO: 213; (b) LCDR2 comprising the amino acid sequence of SEQ ID NO: 214; and (c) LCDR3 comprising the amino acid sequence of SEQ ID NO: 215.

In some embodiments, an anti-ICOS antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 10, 20, 30, 40, 50, 60, 70, 80, 90, 100, 110, 120, 130, 140, 150, 160, 170, or 180 and a light chain variable domain (VL) having at least 90%, 91%, 92%, 93%, 94%, 95%, 96%, 97%, 98%, 99%, or 100% sequence identity to the amino acid sequence of SEQ ID NO: 11, 21, 31, 41, 51, 61, 71, 81, 91, 101, 111, 121, 131, 141, 151, 161, 171, or 181. In some embodiments, an anti-ICOS antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 192, 200, or 208 and a light chain variable domain (VL) having at least 90%, 91%, 92%, 93%, 94%, 95%, 96%, 97%, 98%, 99%, or 100% sequence identity to the amino acid sequence of SEQ ID NO: 193, 201, or 209. In some embodiments, an anti-ICOS antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 10, 20, 30, 40, 50, 60, 70, 80, 90, 100, 110, 120, 130, 140, 150, 160, 170, 180, 192, 200, or 208 and a light chain variable domain (VL) having at least 90%, 91%, 92%, 93%, 94%, 95%, 96%, 97%, 98%, 99%, or 100% sequence identity to the amino acid sequence of SEQ ID NO: 11, 21, 31, 41, 51, 61, 71, 81, 91, 101, 111, 121, 131, 141, 151, 161, 171, 181, 193, 201, or 209. In some embodiments, a VH sequence having at least 90%, 91%, 92%, 93%, 94%, 95%, 96%, 97%, 98%, or 99% identity contains substitutions (for example, conservative substitutions), insertions, or deletions relative to the reference sequence, and a VL sequence having at least 90%, 91%, 92%, 93%, 94%, 95%, 96%, 97%, 98%, or 99% identity contains substitutions (for example, conservative substitutions), insertions, or deletions relative to the reference sequence, but an anti-ICOS antibody comprising that sequence retains the ability to bind to ICOS. In some embodiments, a total of 1 to 10 amino acids have been substituted, inserted and/or deleted in SEQ ID NO: 10, 20, 30, 40, 50, 60, 70, 80, 90, 100, 110, 120, 130, 140, 150, 160, 170, or 180. In some embodiments, a total of 1 to 10 amino acids have been substituted, inserted and/or deleted in SEQ ID NO: 11, 21, 31, 41, 51, 61, 71, 81, 91, 101, 111, 121, 131, 141, 151, 161, 171, or 181. In some embodiments, a total of 1 to 10 amino acids have been substituted, inserted and/or deleted in SEQ ID NO: 192, 200, or 208. In some embodiments, a total of 1 to 10 amino acids have been substituted, inserted and/or deleted in SEQ ID NO: 193, 201, or 209. In some embodiments, a total of 1 to 10 amino acids have been substituted, inserted and/or deleted in SEQ ID NO: 10, 20, 30, 40, 50, 60, 70, 80, 90, 100, 110, 120, 130, 140, 150, 160, 170, 180, 192, 200, or 208. In some embodiments, a total of 1 to 10 amino acids have been substituted, inserted and/or deleted in SEQ ID NO: 11, 21, 31, 41, 51, 61, 71, 81, 91, 101, 111, 121, 131, 141, 151, 161, 171, 181, 193, 201, or 209. In some embodiments, substitutions, insertions, or deletions occur in regions outside the CDRs (that is, in the FRs). Optionally, the anti-ICOS antibody comprises the VH sequence in SEQ ID NO: 10, 20, 30, 40, 50, 60, 70, 80, 90, 100, 110, 120, 130, 140, 150, 160, 170, or 180 and the VL sequence of SEQ ID NO: 11, 21, 31, 41, 51, 61, 71, 81, 91, 101, 111, 121, 131, 141, 151, 161, 171, or 181, including post-translational modifications of one or both sequence. Optionally, the anti-ICOS antibody comprises the VH sequence in SEQ ID NO: 192, 200, or 208, and the VL sequence of SEQ ID NO: 193, 201, or 209, including post-translational modifications of one or both sequence. Optionally, the anti-ICOS antibody comprises the VH sequence in SEQ ID NO: 10, 20, 30, 40, 50, 60, 70, 80, 90, 100, 110, 120, 130, 140, 150, 160, 170, 180, 192, 200, or 208 and the VL sequence of SEQ ID NO: 11, 21, 31, 41, 51, 61, 71, 81, 91, 101, 111, 121, 131, 141, 151, 161, 171, 181, 193, 201, or 209, including post-translational modifications of one or both sequence.

In some embodiments, the anti-ICOS antibody comprises (I) a VH domain comprising: (a) HCDR1 comprising the amino acid sequence of SEQ ID NO: 12; (b) HCDR2 comprising the amino acid sequence of SEQ ID NO: 13; and (c) HCDR3 comprising the amino acid sequence of SEQ ID NO: 14; and (II) a VL domain comprising: (d) LCDR1 comprising the amino acid sequence of SEQ ID NO: 15; (e)

LCDR2 comprising the amino acid sequence of SEQ ID NO: 16; and (f) LCDR3 comprising the amino acid sequence of SEQ ID NO: 17.

In some embodiments, the anti-ICOS antibody comprises (I) a VH domain comprising: (a) HCDR1 comprising the amino acid sequence of SEQ ID NO: 22; (b) HCDR2 comprising the amino acid sequence of SEQ ID NO: 23; and (c) HCDR3 comprising the amino acid sequence of SEQ ID NO: 24; and (II) a VL domain comprising: (d) LCDR1 comprising the amino acid sequence of SEQ ID NO: 25; (e) LCDR2 comprising the amino acid sequence of SEQ ID NO: 26; and (f) LCDR3 comprising the amino acid sequence of SEQ ID NO: 27.

In some embodiments, the anti-ICOS antibody comprises (I) a VH domain comprising: (a) HCDR1 comprising the amino acid sequence of SEQ ID NO: 32; (b) HCDR2 comprising the amino acid sequence of SEQ ID NO: 33; and (c) HCDR3 comprising the amino acid sequence of SEQ ID NO: 34; and (II) a VL domain comprising: (d) LCDR1 comprising the amino acid sequence of SEQ ID NO: 35; (e) LCDR2 comprising the amino acid sequence of SEQ ID NO: 36; and (f) LCDR3 comprising the amino acid sequence of SEQ ID NO: 37.

In some embodiments, the anti-ICOS antibody comprises (I) a VH domain comprising: (a) HCDR1 comprising the amino acid sequence of SEQ ID NO: 42; (b) HCDR2 comprising the amino acid sequence of SEQ ID NO: 43; and (c) HCDR3 comprising the amino acid sequence of SEQ ID NO: 44; and (II) a VL domain comprising: (d) LCDR1 comprising the amino acid sequence of SEQ ID NO: 45; (e) LCDR2 comprising the amino acid sequence of SEQ ID NO: 46; and (f) LCDR3 comprising the amino acid sequence of SEQ ID NO: 47.

In some embodiments, the anti-ICOS antibody comprises (I) a VH domain comprising: (a) HCDR1 comprising the amino acid sequence of SEQ ID NO: 52; (b) HCDR2 comprising the amino acid sequence of SEQ ID NO: 53; and (c) HCDR3 comprising the amino acid sequence of SEQ ID NO: 54; and (II) a VL domain comprising: (d) LCDR1 comprising the amino acid sequence of SEQ ID NO: 55; (e) LCDR2 comprising the amino acid sequence of SEQ ID NO: 56; and (f) LCDR3 comprising the amino acid sequence of SEQ ID NO: 57.

In some embodiments, the anti-ICOS antibody comprises (I) a VH domain comprising: (a) HCDR1 comprising the amino acid sequence of SEQ ID NO: 62; (b) HCDR2 comprising the amino acid sequence of SEQ ID NO: 63; and (c) HCDR3 comprising the amino acid sequence of SEQ ID NO: 64; and (II) a VL domain comprising: (d) LCDR1 comprising the amino acid sequence of SEQ ID NO: 65; (e) LCDR2 comprising the amino acid sequence of SEQ ID NO: 66; and (f) LCDR3 comprising the amino acid sequence of SEQ ID NO: 67.

In some embodiments, the anti-ICOS antibody comprises (I) a VH domain comprising: (a) HCDR1 comprising the amino acid sequence of SEQ ID NO: 72; (b) HCDR2 comprising the amino acid sequence of SEQ ID NO: 73; and (c) HCDR3 comprising the amino acid sequence of SEQ ID NO: 74; and (II) a VL domain comprising: (d) LCDR1 comprising the amino acid sequence of SEQ ID NO: 75; (e) LCDR2 comprising the amino acid sequence of SEQ ID NO: 76; and (f) LCDR3 comprising the amino acid sequence of SEQ ID NO: 77.

In some embodiments, the anti-ICOS antibody comprises (I) a VH domain comprising: (a) HCDR1 comprising the amino acid sequence of SEQ ID NO: 82; (b) HCDR2 comprising the amino acid sequence of SEQ ID NO: 83; and (c) HCDR3 comprising the amino acid sequence of SEQ ID NO: 84; and (II) a VL domain comprising: (d) LCDR1 comprising the amino acid sequence of SEQ ID NO: 85; (e) LCDR2 comprising the amino acid sequence of SEQ ID NO: 86; and (f) LCDR3 comprising the amino acid sequence of SEQ ID NO: 87.

In some embodiments, the anti-ICOS antibody comprises (I) a VH domain comprising: (a) HCDR1 comprising the amino acid sequence of SEQ ID NO: 92; (b) HCDR2 comprising the amino acid sequence of SEQ ID NO: 93; and (c) HCDR3 comprising the amino acid sequence of SEQ ID NO: 94; and (II) a VL domain comprising: (d) LCDR1 comprising the amino acid sequence of SEQ ID NO: 95; (e) LCDR2 comprising the amino acid sequence of SEQ ID NO: 96; and (f) LCDR3 comprising the amino acid sequence of SEQ ID NO: 97.

In some embodiments, the anti-ICOS antibody comprises (I) a VH domain comprising: (a) HCDR1 comprising the amino acid sequence of SEQ ID NO: 102; (b) HCDR2 comprising the amino acid sequence of SEQ ID NO: 103; and (c) HCDR3 comprising the amino acid sequence of SEQ ID NO: 104; and (II) a VL domain comprising: (d) LCDR1 comprising the amino acid sequence of SEQ ID NO: 105; (e) LCDR2 comprising the amino acid sequence of SEQ ID NO: 106; and (f) LCDR3 comprising the amino acid sequence of SEQ ID NO: 107.

In some embodiments, the anti-ICOS antibody comprises (I) a VH domain comprising: (a) HCDR1 comprising the amino acid sequence of SEQ ID NO: 112; (b) HCDR2 comprising the amino acid sequence of SEQ ID NO: 113; and (c) HCDR3 comprising the amino acid sequence of SEQ ID NO: 114; and (II) a VL domain comprising: (d) LCDR1 comprising the amino acid sequence of SEQ ID NO: 115; (e) LCDR2 comprising the amino acid sequence of SEQ ID NO: 116; and (f) LCDR3 comprising the amino acid sequence of SEQ ID NO: 117.

In some embodiments, the anti-ICOS antibody comprises (I) a VH domain comprising: (a) HCDR1 comprising the amino acid sequence of SEQ ID NO: 122; (b) HCDR2 comprising the amino acid sequence of SEQ ID NO: 123; and (c) HCDR3 comprising the amino acid sequence of SEQ ID NO: 124; and (II) a VL domain comprising: (d) LCDR1 comprising the amino acid sequence of SEQ ID NO: 125; (e) LCDR2 comprising the amino acid sequence of SEQ ID NO: 126; and (f) LCDR3 comprising the amino acid sequence of SEQ ID NO: 127.

In some embodiments, the anti-ICOS antibody comprises (I) a VH domain comprising: (a) HCDR1 comprising the amino acid sequence of SEQ ID NO: 132; (b) HCDR2 comprising the amino acid sequence of SEQ ID NO: 133; and (c) HCDR3 comprising the amino acid sequence of SEQ ID NO: 134; and (II) a VL domain comprising: (d) LCDR1 comprising the amino acid sequence of SEQ ID NO: 135; (e) LCDR2 comprising the amino acid sequence of SEQ ID NO: 136; and (f) LCDR3 comprising the amino acid sequence of SEQ ID NO: 137.

In some embodiments, the anti-ICOS antibody comprises (I) a VH domain comprising: (a) HCDR1 comprising the amino acid sequence of SEQ ID NO: 142; (b) HCDR2 comprising the amino acid sequence of SEQ ID NO: 143; and (c) HCDR3 comprising the amino acid sequence of SEQ ID NO: 144; and (II) a VL domain comprising: (d) LCDR1 comprising the amino acid sequence of SEQ ID NO: 145; (e) LCDR2 comprising the amino acid sequence of SEQ ID NO: 146; and (f) LCDR3 comprising the amino acid sequence of SEQ ID NO: 147.

In some embodiments, the anti-ICOS antibody comprises (I) a VH domain comprising: (a) HCDR1 comprising the amino acid sequence of SEQ ID NO: 152; (b) HCDR2 comprising the amino acid sequence of SEQ ID NO: 153; and (c) HCDR3 comprising the amino acid sequence of SEQ ID NO: 154; and (II) a VL domain comprising: (d) LCDR1 comprising the amino acid sequence of SEQ ID NO: 155; (e) LCDR2 comprising the amino acid sequence of SEQ ID NO: 156; and (f) LCDR3 comprising the amino acid sequence of SEQ ID NO: 157.

In some embodiments, the anti-ICOS antibody comprises (I) a VH domain comprising: (a) HCDR1 comprising the amino acid sequence of SEQ ID NO: 162; (b) HCDR2 comprising the amino acid sequence of SEQ ID NO: 163; and (c) HCDR3 comprising the amino acid sequence of SEQ ID NO: 164; and (II) a VL domain comprising: (d) LCDR1 comprising the amino acid sequence of SEQ ID NO: 165; (e) LCDR2 comprising the amino acid sequence of SEQ ID NO: 166; and (f) LCDR3 comprising the amino acid sequence of SEQ ID NO: 167.

In some embodiments, the anti-ICOS antibody comprises (I) a VH domain comprising: (a) HCDR1 comprising the amino acid sequence of SEQ ID NO: 172; (b) HCDR2 comprising the amino acid sequence of SEQ ID NO: 173; and (c) HCDR3 comprising the amino acid sequence of SEQ ID NO: 174; and (II) a VL domain comprising: (d) LCDR1 comprising the amino acid sequence of SEQ ID NO: 175; (e) LCDR2 comprising the amino acid sequence of SEQ ID NO: 176; and (f) LCDR3 comprising the amino acid sequence of SEQ ID NO: 177.

In some embodiments, the anti-ICOS antibody comprises (I) a VH domain comprising: (a) HCDR1 comprising the amino acid sequence of SEQ ID NO: 182; (b) HCDR2 comprising the amino acid sequence of SEQ ID NO: 183; and (c) HCDR3 comprising the amino acid sequence of SEQ ID NO: 184; and (II) a VL domain comprising: (d) LCDR1 comprising the amino acid sequence of SEQ ID NO: 185; (e) LCDR2 comprising the amino acid sequence of SEQ ID NO: 186; and (f) LCDR3 comprising the amino acid sequence of SEQ ID NO: 187.

In some embodiments, the anti-ICOS antibody comprises (I) a VH domain comprising: (a) HCDR1 comprising the amino acid sequence of SEQ ID NO: 194; (b) HCDR2 comprising the amino acid sequence of SEQ ID NO: 195; and (c) HCDR3 comprising the amino acid sequence of SEQ ID NO: 196; and (II) a VL domain comprising: (d) LCDR1 comprising the amino acid sequence of SEQ ID NO: 197; (e) LCDR2 comprising the amino acid sequence of SEQ ID NO: 198; and (f) LCDR3 comprising the amino acid sequence of SEQ ID NO: 199.

In some embodiments, the anti-ICOS antibody comprises (I) a VH domain comprising: (a) HCDR1 comprising the amino acid sequence of SEQ ID NO: 202; (b) HCDR2 comprising the amino acid sequence of SEQ ID NO: 203; and (c) HCDR3 comprising the amino acid sequence of SEQ ID NO: 204; and (II) a VL domain comprising: (d) LCDR1 comprising the amino acid sequence of SEQ ID NO: 205; (e) LCDR2 comprising the amino acid sequence of SEQ ID NO: 206; and (f) LCDR3 comprising the amino acid sequence of SEQ ID NO: 207.

In some embodiments, the anti-ICOS antibody comprises (I) a VH domain comprising: (a) HCDR1 comprising the amino acid sequence of SEQ ID NO: 210; (b) HCDR2 comprising the amino acid sequence of SEQ ID NO: 211; and (c) HCDR3 comprising the amino acid sequence of SEQ ID NO: 212; and (II) a VL domain comprising: (d) LCDR1 comprising the amino acid sequence of SEQ ID NO: 213; (e) LCDR2 comprising the amino acid sequence of SEQ ID NO: 214; and (f) LCDR3 comprising the amino acid sequence of SEQ ID NO: 215.

In some embodiments, an anti-ICOS antibody comprises a VH as in any of the embodiments provided herein, and a VL as in any of the embodiments provided herein. In some embodiments, the antibody comprises the VH and VL sequences in SEQ ID NO: 10 and SEQ ID NO: 11, respectively, including post-translational modifications of those sequences. In some embodiments, the antibody comprises the VH and VL sequences in SEQ ID NO: 20 and SEQ ID NO: 21, respectively, including post-translational modifications of those sequences. In some embodiments, the antibody comprises the VH and VL sequences in SEQ ID NO: 30 and SEQ ID NO: 31, respectively, including post-translational modifications of those sequences. In some embodiments, the antibody comprises the VH and VL sequences in SEQ ID NO: 40 and SEQ ID NO: 41, respectively, including post-translational modifications of those sequences. In some embodiments, the antibody comprises the VH and VL sequences in SEQ ID NO: 50 and SEQ ID NO: 51, respectively, including post-translational modifications of those sequences. In some embodiments, the antibody comprises the VH and VL sequences in SEQ ID NO: 60 and SEQ ID NO: 61, respectively, including post-translational modifications of those sequences. In some embodiments, the antibody comprises the VH and VL sequences in SEQ ID NO: 70 and SEQ ID NO: 71, respectively, including post-translational modifications of those sequences. In some embodiments, the antibody comprises the VH and VL sequences in SEQ ID NO: 80 and SEQ ID NO: 81, respectively, including post-translational modifications of those sequences. In some embodiments, the antibody comprises the VH and VL sequences in SEQ ID NO: 90 and SEQ ID NO: 91, respectively, including post-translational modifications of those sequences. In some embodiments, the antibody comprises the VH and VL sequences in SEQ ID NO: 100 and SEQ ID NO: 101, respectively, including post-translational modifications of those sequences. In some embodiments, the antibody comprises the VH and VL sequences in SEQ ID NO: 110 and SEQ ID NO: 111, respectively, including post-translational modifications of those sequences. In some embodiments, the antibody comprises the VH and VL sequences in SEQ ID NO: 120 and SEQ ID NO: 121, respectively, including post-translational modifications of those sequences. In some embodiments, the antibody comprises the VH and VL sequences in SEQ ID NO: 130 and SEQ ID NO: 131, respectively, including post-translational modifications of those sequences. In some embodiments, the antibody comprises the VH and VL sequences in SEQ ID NO: 140 and SEQ ID NO: 141, respectively, including post-translational modifications of those sequences. In some embodiments, the antibody comprises the VH and VL sequences in SEQ ID NO: 150 and SEQ ID NO: 151, respectively, including post-translational modifications of those sequences. In some embodiments, the antibody comprises the VH and VL sequences in SEQ ID NO: 160 and SEQ ID NO: 161, respectively, including post-translational modifications of those sequences. In some embodiments, the antibody comprises the VH and VL sequences in SEQ ID NO: 170 and SEQ ID NO: 171, respectively, including post-translational modifications of those sequences. In some embodiments, the antibody comprises the VH and VL sequences in SEQ ID NO: 180 and SEQ ID NO: 181, respectively, including post-translational modifications of those sequences. In some embodiments, the antibody comprises the VH and VL sequences in SEQ ID NO: 192 and SEQ ID NO: 193, respectively, including post-translational modifications of those sequences. In some embodiments, the antibody comprises the VH and VL sequences in SEQ ID NO: 200 and SEQ ID NO: 201, respectively, including post-translational modifications of those sequences. In some embodiments, the antibody comprises the VH and VL sequences in SEQ ID NO: 208 and SEQ ID NO: 209, respectively, including post-translational modifications of those sequences.

In some embodiments, antibodies which compete with the anti-ICOS antibodies provided herein for binding to ICOS are provided. In some embodiments, antibodies compete with the anti-ICOS antibodies provided herein for binding to an epitope on ICOS.

In some embodiments, competition assays may be used to identify a monoclonal antibody that competes with an anti-ICOS antibody described herein (such as 7F12, 37A10, 35A9, 36E10, 16G10, 37A10S713, 37A10S714, 37A10S715, 37A10S716, 37A10S717, 37A10S718, 16G10S71, 16G10S72, 16G10S73, 16G10S83, 35A9S79, 35A9S710, or 35A9S89; and/or 2M13, 2M19, or 2M24) for binding to ICOS. Competition assays can be used to determine whether two antibodies bind the same epitope by recognizing identical or sterically overlapping epitopes or one antibody competitively inhibits binding of another antibody to the antigen. In some embodiments, such a competing antibody binds to the same epitope that is bound by an antibody described herein. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). In some embodiments, two antibodies are said to bind to the same epitope if each blocks binding of the other by 50% or more. In some embodiments, the antibody that competes with an anti-ICOS antibody described herein is a chimeric, humanized or human antibody. In some embodiments, an antibody that competes with a chimeric, humanized, or human anti-ICOS antibody as described herein is provided.

In some embodiments, antibodies that bind to any one or more of the epitopes that the antibodies provided herein are provided. In some embodiments, antibodies that bind and overlap an epitope to which the present antibodies bind to are provided. In some embodiments, an antibody is provided that competes with at least one of the antibodies provided herein. In some embodiments, an antibody is provided that competes with at least two of the antibodies provided herein. In some embodiments, an antibody is provided that competes with at least three of the antibodies provided herein. In some embodiments, the antibody binds to an overlapping epitope as an antibody described in the examples herein. In some embodiments, the entire epitope is bound and/or obstructed by the competing antibody. In some embodiments, a part of the epitope is bound and/or obstructed by the competing antibody. In some embodiments, the competing antibody's paratope binds to at least a part of the epitope of an antibody provided herein. In some embodiments, the competing antibody's paratope binds the target, and a different section of the competing antibody's structure obstruct at least a part of the epitope of an antibody provided herein.

Exemplary Chimeric Antibodies

In some embodiments, an antibody provided herein is a chimeric antibody. Certain chimeric antibodies are described, for example, in U.S. Pat. No. 4,816,567; and Morrison et al., (1984) Proc. Natl. Acad. Sci. USA, 81:6851-6855 (1984)). In one example, a chimeric antibody comprises a non-human variable region (for example, a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

Nonlimiting exemplary chimeric antibodies include chimeric antibodies comprising the heavy and/or light chain variable regions of an antibody selected from 7F12, 37A10, 35A9, 36E10, 16G10, 37A10S713, 37A10S714, 37A10S715, 37A10S716, 37A10S717, 37A10S718, 16G10S71, 16G10S72, 16G10S73, 16G10S83, 35A9S79, 35A9S710, 35A9S89, 2M13, 2M19, or 2M24. Additional nonlimiting exemplary chimeric antibodies include chimeric antibodies comprising heavy chain CDR1, CDR2, and CDR3, and/or light chain CDR1, CDR2, and CDR3 of an antibody selected from 7F12, 37A10, 35A9, 36E10, 16G10, 37A10S713, 37A10S714, 37A10S715, 37A10S716, 37A10S717, 37A10S718, 16G10S71, 16G10S72, 16G10S73, 16G10S83, 35A9S79, 35A9S710, 35A9S89, 2M13, 2M19, or 2M24. Further nonlimiting exemplary chimeric antibodies include chimeric antibodies comprising heavy chain CDR1, CDR2, and CDR3, and/or light chain CDR1, CDR2, and CDR3 of an antibody selected from 7F12, 37A10, 35A9, 36E10, 16G10, 37A10S713, 37A10S714, 37A10S715, 37A10S716, 37A10S717, 37A10S718, 16G10S71, 16G10S72, 16G10S73, 16G10S83, 35A9S79, 35A9S710, 35A9S89, 2M13, 2M19, or 2M24. In some embodiments, the chimeric anti-ICOS antibody comprises the variable regions described above and binds to ICOS. In some embodiments, the chimeric anti-ICOS antibody comprises the variable regions described above, binds to ICOS, and increases the number of Teff cells and/or activates Teff cells and/or decreases the number of Treg cells and/or increases the ratio of Teff cells to Treg cells. In some embodiments, the Treg cells are CD4+ FoxP3+ T cells. In some embodiments, the Teff cells are CD4+ FoxP3− T cells. In some embodiments, the Teff cells are CD8+ T cells. In some embodiments, the Teff cells are CD4+ FoxP3− T cells and CD8+ T cells.

In some embodiments, a chimeric anti-ICOS antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 20, 30, 40, 50, 60, 70, 80, 90, 100, 110, 120, 130, 140, 150, 160, 170, 180, 192, 200, or 208, wherein the antibody binds ICOS. In some embodiments, a chimeric anti-ICOS antibody comprises a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 11, 21, 31, 41, 51, 61, 71, 81, 91, 101, 111, 121, 131, 141, 151, 161, 171, 181, 193, 201, or 209, wherein the antibody binds ICOS. In some embodiments, a chimeric anti-ICOS antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 20, 30, 40, 50, 60, 70, 80, 90, 100, 110, 120, 130, 140, 150, 160, 170, and 180; and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 11, 21, 31, 41, 51, 61, 71, 81, 91, 101, 111, 121, 131, 141, 151, 161, 171, and 181; wherein the antibody binds ICOS. In some embodiments, a chimeric anti-ICOS antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 192, 200, or 208; and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 193, 201, or 209; wherein the antibody binds ICOS. In some embodiments, a chimeric anti-ICOS antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 20, 30, 40, 50, 60, 70, 80, 90, 100, 110, 120, 130, 140, 150, 160, 170, 180, 192, 200, or 208; and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 11, 21, 31, 41, 51, 61, 71, 81, 91, 101, 111, 121, 131, 141, 151, 161, 171, 181, 193, 201, and 209; wherein the antibody binds ICOS.

Exemplary chimeric anti-ICOS antibodies also include chimeric antibodies that compete for binding to ICOS with an antibody or fragment thereof described herein. Thus, in some embodiments, a chimeric anti-ICOS antibody is provided that competes for binding to ICOS with an antibody selected from 7F12, 37A10, 35A9, 36E10, 16G10, 37A10S713, 37A10S714, 37A10S715, 37A10S716, 37A10S717, 37A10S718, 16G10S71, 16G10S72, 16G10S73, 16G10S83, 35A9S79, 35A9S710, 35A9S89, 2M13, 2M19, and 2M24, or fragment thereof. In some embodiments, the antibody competes for binding to ICOS and increases the number of Teff cells and/or activates Teff cells and/or decreases the number of Treg cells and/or increases the ratio of Teff cells to Treg cells. In some embodiments, the Treg cells are CD4+ FoxP3+ T cells. In some embodiments, the Teff cells are CD8+ T cells. In some embodiments, the Teff cells are CD4+ FoxP3– T cells and CD8+ T cells.

In some embodiments, a chimeric antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, a chimeric antibody described herein comprises a human IgG constant region. In some embodiments, a chimeric antibody described herein comprises a human IgG4 heavy chain constant region. In some embodiments, a chimeric antibody described herein comprises a human IgG4 constant region and a human κ light chain.

As noted above, whether or not effector function is desirable may depend on the particular method of treatment intended for an antibody. Thus, in some embodiments, when effector function is desirable, a chimeric anti-ICOS antibody comprising a human IgG1 heavy chain constant region or a human IgG3 heavy chain constant region is selected. In some embodiments, when effector function is not desirable, a chimeric anti-ICOS antibody comprising a human IgG4 or IgG2 heavy chain constant region is selected.

Exemplary Humanized Antibodies

In some embodiments, humanized antibodies that bind ICOS are provided. Humanized antibodies are useful as therapeutic molecules because humanized antibodies reduce or eliminate the human immune response as compared to non-human antibodies, which can result in an immune response to an antibody therapeutic (such as the human anti-mouse antibody (HAMA) response), and decreased effectiveness of the therapeutic.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (for example, the antibody from which the CDR residues are derived), for example, to restore or improve antibody specificity or affinity.

Humanized antibodies and methods of making them are reviewed, for example, in Almagro and Fransson, (2008) *Front. Biosci.* 13: 1619-1633, and are further described, for example, in Riechmann et al., (1988) *Nature* 332:323-329; Queen et al., (1989) *Proc. Natl Acad. Sci. USA* 86: 10029-10033; U.S. Pat. Nos. 5,821,337, 7,527,791, 6,982,321, and 7,087,409; Kashmiri et al., (2005) *Methods* 36:25-34; Padlan, (1991) *Mol. Immunol.* 28:489-498 (describing "resurfacing"); Dall'Acqua et al., (2005) *Methods* 36:43-60 (describing "FR shuffling"); and Osbourn et al., (2005) *Methods* 36:61-68 and Klimka et al., (2000) *Br. J. Cancer*, 83:252-260 (describing the "guided selection" approach to FR shuffling).

Human framework regions that can be used for humanization include but are not limited to: framework regions selected using the "best-fit" method (see, for example, Sims et al. (1993) *J. Immunol.* 151:2296); framework regions derived from the consensus sequence of human antibodies of a particular subgroup of light or heavy chain variable regions (see, for example, Carter et al. (1992) *Proc. Natl. Acad. Sci. USA,* 89:4285; and Presta et al. (1993) *J. Immunol,* 151:2623); human mature (somatically mutated) framework regions or human germline framework regions (see, for example, Almagro and Fransson, (2008) *Front. Biosci.* 13:1619-1633); and framework regions derived from screening FR libraries (see, for example, Baca et al., (1997) *J. Biol. Chem.* 272: 10678-10684 and Rosok et al., (1996) *J. Biol. Chem.* 271:22611-22618).

Nonlimiting exemplary humanized antibodies include 37A10S713, 37A10S714, 37A10S715, 37A10S716, 37A10S717, 37A10S718, 16G10S71, 16G10S72, 16G10S73, 16G10S83, 35A9S79, 35A9S710, and 35A9S89, described herein. Nonlimiting exemplary humanized antibodies also include antibodies comprising a heavy chain variable region of an antibody selected from 37A10S713, 37A10S714, 37A10S715, 37A10S716, 37A10S717, 37A10S718, 16G10S71, 16G10S72, 16G10S73, 16G10S83, 35A9S79, 35A9S710, and 35A9S89 and/or a light chain variable region of an antibody selected from 37A10S713, 37A10S714, 37A10S715, 37A10S716, 37A10S717, 37A10S718, 16G10S71, 16G10S72, 16G10S73, 16G10S83, 35A9S79, 35A9S710, and 35A9S89. Nonlimiting exemplary humanized antibodies include antibodies comprising a heavy chain variable region selected from SEQ ID NOs: 60, 70, 80, 90, 100, 110, 120, 130, 140, 150, 160, 170, and 180 and/or a light chain variable region selected from SEQ ID NOs: 61, 71, 81, 91, 101, 111, 121, 131, 141, 151, 161, 171, and 181. Exemplary humanized antibodies also include, but are not limited to, humanized antibodies comprising heavy chain CDR1, CDR2, and CDR3, and/or light chain CDR1, CDR2, and CDR3 of an antibody selected from 7F12, 37A10, 35A9, 36E10, 16G10, 37A10S713, 37A10S714, 37A10S715, 37A10S716, 37A10S717, 37A10S718, 16G10S71, 16G10S72, 16G10S73, 16G10S83, 35A9S79, 35A9S710, 35A9S89, 2M13, 2M19, and 2M24. In some embodiments, the humanized anti-ICOS antibody comprises the CDRs described above and binds to ICOS. In some embodiments, the humanized anti-ICOS antibody comprises the CDRs described above, binds to ICOS and increases the number of Teff cells and/or activates Teff cells and/or decreases the number of Treg cells and/or increases the ratio of Teff cells to Treg cells. In some embodiments, the Treg cells are CD4+ FoxP3+ T cells. In some embodiments, the Teff cells are CD8+ T cells. In some embodiments, the Teff cells are CD4+ FoxP3− T cells and CD8+ T cells.

In some embodiments, a humanized anti-ICOS antibody comprises a heavy chain CDR1, CDR2, and CDR3 and/or a light chain CDR1, CDR2, and CDR3 of an antibody selected from 7F12, 37A10, 35A9, 36E10, 16G10, 37A10S713, 37A10S714, 37A10S715, 37A10S716, 37A10S717, 37A10S718, 16G10S71, 16G10S72, 16G10S73, 16G10S83, 35A9S79, 35A9S710, 35A9S89, 2M13, 2M19, and 2M24.

In some embodiments, a humanized anti-ICOS antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 60, 70, 80, 90, 100, 110, 120, 130, 140, 150, 160, 170, and 180, and wherein the antibody binds ICOS. In some embodiments, a humanized anti-ICOS antibody comprises a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 61, 71, 81, 91, 101, 111, 121, 131, 141, 151, 161, 171, and 181, wherein the antibody binds ICOS. In some embodiments, a humanized anti-ICOS antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 60, 70, 80, 90, 100, 110, 120, 130, 140, 150, 160, 170, and 180; and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 61, 71, 81, 91, 101, 111, 121, 131, 141, 151, 161, 171, and 181; wherein the antibody binds ICOS.

In some embodiments, any one or more of the CDR sequences provided herein are maintained, while the remaining heavy, light, or heavy and light chain region (that is, FR1, FR2, FR3, and FR4) is at least 90%, at least 91%, at least 92%, at least 93%, at least 94%, at least 95%, at least 96%, at least 97%, at least 98%, or at least 99% identical to a sequence selected from SEQ ID NOs: 10, 20, 30, 40, 50, 60, 70, 80, 90, 100, 110, 120, 130, 140, 150, 160, 170, 180, 11, 21, 31, 41, 51, 61, 71, 81, 91, 101, 111, 121, 131, 141, 151, 161, 171, and 181. In some embodiments, any one or more of the CDR sequences provided herein are maintained, while the remaining heavy, light, or heavy and light chain region (that is, FR1, FR2, FR3, and FR4) is at least 90%, at least 91%, at least 92%, at least 93%, at least 94%, at least 95%, at least 96%, at least 97%, at least 98%, or at least 99% identical to a sequence selected from SEQ ID NOs: 192, 193, 200, 201, 208, and 209. In some embodiments, any one or more of the CDR sequences provided herein are maintained, while the remaining heavy, light, or heavy and light chain region (that is, FR1, FR2, FR3, and FR4) is at least 90%, at least 91%, at least 92%, at least 93%, at least 94%, at least 95%, at least 96%, at least 97%, at least 98%, or at least 99% identical to a sequence selected from SEQ ID NOs: 10, 20, 30, 40, 50, 60, 70, 80, 90, 100, 110, 120, 130, 140, 150, 160, 170, 180, 11, 21, 31, 41, 51, 61, 71, 81, 91, 101, 111, 121, 131, 141, 151, 161, 171, 181, 192, 193, 200, 201, 208, and 209.

In some embodiments, a humanized anti-ICOS antibody comprises at least one of the CDRs discussed herein. That is, in some embodiments, a humanized anti-ICOS antibody comprises at least one CDR selected from a heavy chain CDR1 discussed herein, a heavy chain CDR2 discussed herein, a heavy chain CDR3 discussed herein, a light chain CDR1 discussed herein, a light chain CDR2 discussed herein, and a light chain CDR3 discussed herein. Further, in some embodiments, a humanized anti-ICOS antibody comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the antibody comprising the mutated CDR.

Exemplary humanized anti-ICOS antibodies also include antibodies that compete for binding to ICOS with an antibody or fragment thereof described herein. Thus, in some embodiments, a humanized anti-ICOS antibody is provided that competes for binding to ICOS with an antibody or fragment thereof selected from 7F12, 37A10, 35A9, 36E10, 16G10, 37A10S713, 37A10S714, 37A10S715, 37A10S716, 37A10S717, 37A10S718, 16G10S71, 16G10S72, 16G10S73, 16G10S83, 35A9S79, 35A9S710, 35A9S89, 2M13, 2M19, and 2M24. In some embodiments, a humanized anti-ICOS antibody is provided that competes for binding to ICOS with an antibody or fragment thereof selected from 7F12, 37A10, 35A9, 36E10, 16G10, 37A10S713, 37A10S714, 37A10S715, 37A10S716, 37A10S717, 37A10S718, 16G10S71, 16G10S72, 16G10S73, 16G10S83, 35A9S79, 35A9S710, 35A9S89, 2M13, 2M19, and 2M24 and increases the number of Teff cells and/or activates Teff cells and/or decreases the number of Treg cells and/or increases the ratio of Teff cells to Treg cells. In some embodiments, the Treg cells are CD4+ FoxP3+ T cells. In some embodiments, the Teff cells are CD8+ T cells. In some embodiments, the Teff cells are CD4+ FoxP3− T cells and CD8+ T cells.

In some embodiments, a humanized anti-ICOS antibody comprises a heavy chain comprising the amino acid sequence of SEQ ID NO: 188 and a light chain comprising the amino acid sequence of SEQ ID NO: 189.

Exemplary Human Antibodies

In some embodiments, an anti-ICOS antibody provided herein is a human antibody. Human antibodies can be produced using various techniques known in the art. Human antibodies are described generally in van Dijk and van de Winkel, (2001) *Curr. Opin. Pharmacol.* 5:368-374 and Lonberg, (2008) *Curr. Opin. Immunol.* 20:450-459. In some embodiments, the human antibody is not a naturally occurring antibody. In some embodiments, the human antibody is a monoclonal antibody; thus, in some embodiments, each of the human antibodies in a set can bind to the same epitope on the antigen.

Human antibodies can be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, (2005) *Nat. Biotech.* 23: 1117-1125. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, for example, by combining with a different human constant region.

Human antibodies can also be made by hybridoma-based methods. Human myeloma and mouse-human heteromyeloma cell lines for the production of human monoclonal antibodies have been described. (See, for example, Kozbor (1984) *J. Immunol,* 133: 3001; Brodeur et al., *Monoclonal Antibody Production Techniques and Applications*, pp. 51-63 (Marcel Dekker, Inc., New York, 1987); and Boerner et al, (1991) *J. Immunol.*, 147:86). Human antibodies generated via human B-cell hybridoma technology are also described in Li et al., (2006) *Proc. Natl. Acad. Sci. USA*, 103:3557-3562. Additional methods include those described, for example, in U.S. Pat. No. 7,189,826 (describing production of monoclonal human IgM antibodies from hybridoma cell lines) and Ni, (2006) *Xiandai Mianyixue*, 26(4):265-268 (describing human-human hybridomas). Human hybridoma technology (Trioma technology) is also described in Vollmers and Brandlein, (2005) *Histology and Histopathology*, 20(3):927-937 (2005) and Vollmers and Brandlein, (2005) *Methods and Findings in Experimental and Clinical Pharmacology*, 27(3): 185-191.

Human antibodies can also be generated by isolating Fv clone variable domain sequences selected from human-derived phage display libraries. Such variable domain sequences may then be combined with a desired human constant domain. Techniques for selecting human antibodies from antibody libraries are described below.

Antibodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, for example, in Hoogenboom et al. in Methods in Molecular Biology 178: 1-37 (O'Brien et al., ed., Human Press, Totowa, N.J., 2001) and further described, for example, in the McCafferty et al, (1990) *Nature* 348:552-554; Clackson et al, (1991) *Nature* 352: 624-628; Marks et al, (1992) *J. Mol. Biol* 222: 581-597; Marks and Bradbury, in Methods in Molecular Biology 248: 161-175 (Lo, ed., Human Press, Totowa, N.J., 2003); Sidhu et al, (2004)*J. Mol. Biol.* 338(2): 299-310; Lee et al., (2004) *J. Mol. Biol.* 340(5): 1073-1093; Fellouse, (2004) *Proc. Natl. Acad. Sci. USA* 101(34): 12467-12472; and Lee et al, (2004) *J. Immunol. Methods* 284(1-2): 119-132 and PCT publication WO 99/10494.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., (1994) *Ann. Rev. Immunol.*, 12:433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (for example, from human) to provide a single source of antibodies to a wide range of non-self and also self-antigens without any immunization as described by Griffiths et al., (1993) *EMBO J* 12:725-734. Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter (1992), *J. Mol. Biol*, 227:381-388. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

In some embodiments, a human anti-ICOS antibody binds to a polypeptide having the sequence of SEQ ID NO: 1 or 2. In some embodiments, the human anti-ICOS antibody binds to ICOS and increases the number of Teff cells and/or activates Teff cells and/or decreases the number of Treg cells and/or increases the ratio of Teff cells to Treg cells. In some embodiments, the Treg cells are CD4+ FoxP3+ T cells. In some embodiments, the Teff cells are CD8+ T cells. In some embodiments, the Teff cells are CD4+ FoxP3− T cells and CD8+ T cells.

Exemplary human anti-ICOS antibodies also include antibodies that compete for binding to ICOS with a human antibody or fragment thereof described herein. Thus, in some embodiments, a human anti-ICOS antibody is provided that competes for binding to ICOS with an antibody or fragment thereof selected from 7F12, 37A10, 35A9, 36E10, 16G10, 37A105713, 37A10S714, 37A10S715, 37A10S716, 37A10S717, 37A10S718, 16G10S71, 16G10S72, 16G10S73, 16G10S83, 35A9S79, 35A9S710, 35A9S89, 2M13, 2M19, and 2M24. In some embodiments, a human anti-ICOS antibody is provided that competes for binding to ICOS with an antibody or fragment thereof selected from 7F12, 37A10, 35A9, 36E10, 16G10, 37A105713, 37A10S714, 37A10S715, 37A10S716, 37A10S717, 37A10S718, 16G10S71, 16G10S72, 16G10S73, 16G10S83, 35A9S79, 35A9S710, 35A9S89, 2M13, 2M19, and 2M24 and increases the number of Teff cells and/or activates Teff cells and/or decreases the number of Treg cells and/or increases the ratio of Teff cells to Treg cells. In some embodiments, the Treg cells are CD4+ FoxP3+ T cells. In some embodiments, the Teff cells are CD8+ T cells. In some embodiments, the Teff cells are CD4+ FoxP3− T cells and CD8+ T cells.

In some embodiments, a chimeric human anti-ICOS antibody is provided, where the antibody comprises the variable region from a human antibody that binds ICOS and the constant region from a different human antibody. In some embodiments, a chimeric human anti-ICOS antibody, where the antibody comprises the CDRs from a human antibody that binds ICOS and a framework from a different human antibody is provided. In some embodiments, the antibody is not a naturally occurring human antibody.

In some embodiments, a human anti-ICOS antibody comprises one or more human constant regions. In some embodiments, the human heavy chain constant region is of an isotype selected from IgA, IgG, and IgD. In some embodiments, the human light chain constant region is of an isotype selected from κ and λ. In some embodiments, a human antibody described herein comprises a human IgG constant region. In some embodiments, a human antibody described herein comprises a human IgG4 heavy chain constant region. In some embodiments, a human antibody described herein comprises a human IgG4 constant region and a human κ light chain.

In some embodiments, when effector function is desirable, a human anti-ICOS antibody comprising a human IgG1 heavy chain constant region or a human IgG3 heavy chain constant region is selected. In some embodiments, when effector function is not desirable, a human anti-ICOS antibody comprising a human IgG4 or IgG2 heavy chain constant region is selected.

As noted herein, the term "human antibody" denotes the genus of possible sequences for the antibody construct, rather than a source of the antibody.

Exemplary Antibody Constant Regions

In some embodiments, an antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, an antibody described herein comprises a human IgG constant region. In some embodiments, an antibody described herein comprises a human IgG4 heavy chain constant region. In some embodiments, an antibody described herein comprises a human IgG4 constant region and a human κ light chain.

Throughout the present specification and claims unless explicitly stated or known to one skilled in the art, the numbering of the residues in an immunoglobulin heavy chain is that of the EU index as in Kabat et al., *Sequences of Proteins of Immunological Interest,* 5th Ed. Public Health Service, National Institutes of Health, Bethesda, Md. (1991), expressly incorporated herein by reference. The "EU index as in Kabat" refers to the residue numbering of the human IgG1 EU antibody.

As noted above, whether or not effector function is desirable may depend on the particular method of treatment intended for an antibody. Thus, in some embodiments, when effector function is desirable, an anti-ICOS antibody comprising a human IgG1 heavy chain constant region or a human IgG3 heavy chain constant region is selected. In some embodiments, when effector function is not desirable, an anti-ICOS antibody comprising a human IgG4 or IgG2 heavy chain constant region is selected.

In some embodiments, an antibody comprises a variant Fc region has at least one amino acid substitution compared to the Fc region of a wild-type IgG or a wild-type antibody. In some embodiments, the variant Fc region has two or more amino acid substitutions in the Fc region of the wild-type antibody. In some embodiments, the variant Fc region has three or more amino acid substitutions in the Fc region of the wild-type antibody. In some embodiments, the variant Fc region has at least one, two or three or more Fc region amino acid substitutions described herein. In some embodiments, the variant Fc region herein will possess at least about 80% homology with a native sequence Fc region and/or with an Fc region of a parent polypeptide. In some embodiments, the variant Fc region herein will possess at least about 90% homology with a native sequence Fc region and/or with an Fc region of a parent polypeptide. In some embodiments, the variant Fc region herein will possess at least about 95% homology with a native sequence Fc region and/or with an Fc region of a parent polypeptide.

In some embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, for example, Wright et al. *TIBTECH* 15:26-32 (1997). The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (for example, complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, that is, between positions 294 and 300, due to minor sequence variations in antibodies. Such fucosylation variants may have improved ADCC function. See, for example, US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch.*

*Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, for example, Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibody variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, for example, in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, for example, in WO 1997/30087 (Patel et al.); WO 1998/58964 (Raju, S.); and WO 1999/22764 (Raju, S.).

Antibody variants are also provided with amino-terminal leader extensions. For example, one or more amino acid residues of the amino-terminal leader sequence are present at the amino-terminus of any one or more heavy or light chains of an antibody. An exemplary amino-terminal leader extension comprises or consists of three amino acid residues, VHS, present on one or both light chains of an antibody variant.

The in vivo or serum half-life of human FcRn high affinity binding polypeptides can be assayed, for example, in transgenic mice, in humans, or in non-human primates to which the polypeptides with a variant Fc region are administered. See also, for example, Petkova et al. *International Immunology* 18(12):1759-1769 (2006).

In some embodiments, the antibody variant mediates ADCC in the presence of human effector cells more effectively than a parent antibody. In some embodiments, the antibody variant is substantially more effective at mediating ADCC in vitro, when the amounts of polypeptide variant and parent antibody used in the assay are essentially the same. In some embodiments, the antibody variant is substantially more effective at mediating ADCC in vivo, when the amounts of polypeptide variant and parent antibody used in the assay are essentially the same. Generally, such variants will be identified using the in vitro ADCC assay as herein disclosed, but other assays or methods for determining ADCC activity, for example in an animal model etc., are contemplated.

Exemplary Antibody Conjugates

In some embodiments, an anti-ICOS antibody is conjugated to another molecule. In some embodiments, the additional molecule can be a detectable marker, such as a label. In some embodiments, the additional molecule can be a therapeutic molecule, such as a cytotoxic agent. In some embodiments, a label and/or a cytotoxic agent can be conjugated to the antibody. As used herein, a label is a moiety that facilitates detection of the antibody and/or facilitates detection of a molecule to which the antibody binds. Nonlimiting exemplary labels include, but are not limited to, radioisotopes, fluorescent groups, enzymatic groups, chemiluminescent groups, biotin, epitope tags, metal-binding tags, etc. One skilled in the art can select a suitable label according to the specific application.

As used herein, a cytotoxic agent is a moiety that reduces the proliferative capacity of one or more cells. A cell has reduced proliferative capacity when the cell becomes less able to proliferate, for example, because the cell undergoes apoptosis or otherwise dies, the cell fails to proceed through the cell cycle and/or fails to divide, the cell differentiates, etc. Nonlimiting exemplary cytotoxic agents include, but are not limited to, radioisotopes, toxins, and chemotherapeutic agents. One skilled in the art can select a suitable cytotoxic according to the intended application. In some embodiments, the cytotoxic agent is at least one of an antimetabolite, an alkylating agent, an antibiotic, a growth factor, a cytokine, an anti-angiogenic agent, an anti-mitotic agent, an anthracycline, toxin, or an apoptotic agent In some embodiments, a label and/or a cytotoxic agent is conjugated to an antibody using chemical methods in vitro. Nonlimiting exemplary chemical methods of conjugation are known in the art, and include services, methods and/or reagents commercially available from, for example, Thermo Scientific Life Science Research Produces (formerly Pierce; Rockford, Ill.), Prozyme (Hayward, Calif.), SACRI Antibody Services (Calgary, Canada), AbD Serotec (Raleigh, N.C.), etc. In some embodiments, when a label and/or cytotoxic agent is a polypeptide, the label and/or cytotoxic agent can be expressed from the same expression vector with at least one antibody chain to produce a polypeptide comprising the label and/or cytotoxic agent fused to an antibody chain. One skilled in the art can select a suitable method for conjugating a label and/or cytotoxic agent to an antibody according to the intended application.

In some embodiments, conjugation can be covalent. In some embodiments, conjugation can be non-covalent. In some embodiments, conjugation can be via a specific binding interaction, for example, through the binding of a secondary antibody.

Exemplary Leader Sequences

In order for some secreted proteins to express and secrete in large quantities, a leader sequence from a heterologous protein may be desirable. In some embodiments, employing heterologous leader sequences can be advantageous in that a resulting mature polypeptide can remain unaltered as the leader sequence is removed in the ER during the secretion process. The addition of a heterologous leader sequence can be useful to express and secrete some proteins.

Certain exemplary leader sequence sequences are described, for example, in the online Leader sequence Database maintained by the Department of Biochemistry, National University of Singapore. See Choo et al., *BMC Bioinformatics,* 6: 249 (2005); and PCT Publication No. WO 2006/081430.

III. Antibody Expression and Production

Nucleic Acid Molecules Encoding Anti-ICOS Antibodies

Nucleic acid molecules comprising polynucleotides that encode one or more chains of an anti-ICOS antibody are provided herein. In some embodiments, a nucleic acid molecule comprises a polynucleotide that encodes a heavy chain or a light chain of an anti-ICOS antibody. In some embodiments, a nucleic acid molecule comprises both a polynucleotide that encodes a heavy chain and a polynucleotide that encodes a light chain, of an anti-ICOS antibody. In some embodiments, a first nucleic acid molecule comprises a first polynucleotide that encodes a heavy chain and a second nucleic acid molecule comprises a second polynucleotide that encodes a light chain.

In some embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an anti-ICOS antibody comprises a nucleotide sequence that encodes at least one of the CDRs provided herein. In some embodiments, a polynucleotide encoding a heavy chain or light chain of an anti-ICOS antibody comprises a nucleotide sequence that encodes at least 3 of the CDRs provided herein. In some embodiments, a polynucleotide encoding a heavy chain or light chain of an anti-ICOS antibody comprises a nucleotide sequence that encodes at least 6 of the CDRs provided herein. In some embodiments, a polynucleotide encoding a heavy chain or light chain of an anti-ICOS antibody comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

In some embodiments, the nucleic acid is one that encodes for any of the amino acid sequences for the antibodies in the Sequence Table herein. In some embodiments, the nucleic acid is one that is at least 80% identical to a nucleic acid encoding any of the amino acid sequences for the antibodies in the Sequence Table herein, for example, at least 80, 85, 90, 91, 92, 93, 94, 95, 96, 97, 98, or 99% identical. In some embodiments, the nucleic acid is one that hybridizes to any one or more of the nucleic acid sequences provided herein. In some of the embodiments, the hybridization is under moderate conditions. In some embodiments, the hybridization is under highly stringent conditions, such as: at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C.

Nucleic acid molecules can be constructed using recombinant DNA techniques conventional in the art. In some embodiments, a nucleic acid molecule is an expression vector that is suitable for expression in a selected host cell.

Vectors

Vectors comprising polynucleotides that encode anti-ICOS heavy chains and/or anti-ICOS light chains are provided. Vectors comprising polynucleotides that encode anti-ICOS heavy chains and/or anti-ICOS light chains are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NSO cells. Exemplary such vectors are described, for example, in Running Deer et al., *Biotechnol. Prog.* 20:880-889 (2004).

Host Cells

In some embodiments, anti-ICOS antibody heavy chains and/or anti-ICOS antibody light chains may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, anti-ICOS antibody heavy chains and/or anti-ICOS antibody light chains may be expressed in yeast. See, for example, U.S. Publication No. US 2006/0270045 A1. In some embodiments, a particular eukaryotic host cell is selected based on its ability to make desired post-translational modifications to the anti-ICOS antibody heavy chains and/or anti-ICOS antibody light chains. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, for example, in Sambrook et al., Molecular Cloning, A Laboratory Manual, $3^{rd}$ ed. Cold Spring Harbor Laboratory Press (2001). Nucleic acids may be transiently or stably transfected in the desired host cells, according to any suitable method.

Host cells comprising any of the polynucleotides or vectors described herein are also provided. In some embodiments, a host cell comprising an anti-ICOS antibody is provided. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*).

Purification of Antibodies

Anti-ICOS antibodies can be purified by any suitable method. Such methods include, but are not limited to, the use of affinity matrices or hydrophobic interaction chromatography. Suitable affinity ligands include the ROR1 ECD and ligands that bind antibody constant regions. For example, a Protein A, Protein G, Protein A/G, or an antibody affinity column may be used to bind the constant region and to purify an anti-ICOS antibody. Hydrophobic interactive chromatography, for example, a butyl or phenyl column, may also suitable for purifying some polypeptides such as antibodies. Ion exchange chromatography (for example anion exchange chromatography and/or cation exchange chromatography) may also suitable for purifying some polypeptides such as antibodies. Mixed-mode chromatography (for example reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

Cell-Free Production of Antibodies

In some embodiments, an anti-ICOS antibody is produced in a cell-free system. Nonlimiting exemplary cell-free systems are described, for example, in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

Antibody Compositions

In some embodiments, antibodies prepared by the methods described above are provided. In some embodiments, the antibody is prepared in a host cell. In some embodiments, the antibody is prepared in a cell-free system. In some embodiments, the antibody is purified. In some embodiments, the antibody prepared in a host cell or a cell-free system is a chimeric antibody. In some embodiments, the antibody prepared in a host cell or a cell-free system is a humanized antibody. In some embodiments, the antibody prepared in a host cell or a cell-free system is a human antibody. In some embodiments, a cell culture media comprising an anti-ICOS antibody is provided. In some embodiments, a host cell culture fluid comprising an anti-ICOS antibody is provided.

In some embodiments, compositions comprising antibodies prepared by the methods described above are provided. In some embodiments, the composition comprises an antibody prepared in a host cell. In some embodiments, the composition comprises an antibody prepared in a cell-free system. In some embodiments, the composition comprises a purified antibody. In some embodiments, the composition comprises a chimeric antibody prepared in a host cell or a cell-free system. In some embodiments, the composition comprises a humanized antibody prepared in a host cell or a cell-free system. In some embodiments, the composition comprises a human antibody prepared in a host cell or a cell-free system.

In some embodiments, a composition comprising anti-ICOS antibody at a concentration of more than about any one of 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 125 mg/mL, 150 mg/mL, 175 mg/mL, 200 mg/mL, 225 mg/mL, or 250 mg/mL is provided. In some embodiments, the composition comprises a chimeric antibody prepared in a host cell or a cell-free system. In some embodiments, the composition comprises a humanized antibody prepared in a host cell or a cell-free system. In some embodiments, the composition comprises a human antibody prepared in a host cell or a cell-free system.

IV. Compositions and Methods

Methods, Polynucleotides, Compositions, and Kits Related to Gene Expression, RNA Signatures, Identifying Subjects, and/or Predicting Responsiveness Provided herein are methods of using the anti-ICOS antibodies, polypeptides and polynucleotides for detection, diagnosis and monitoring of a disease, disorder or condition associated with the anti-ICOS antibody epitope expression (either increased or decreased relative to a normal sample, and/or inappropriate expression, such as presence of expression in tissues(s) and/or cell(s) that normally lack the epitope expression). Provided herein are methods of determining whether a patient will respond to anti-ICOS antibody therapy. In some embodiments, methods of identifying a subject who may benefit from treatment with an anti-ICOS antibody are provided. In some embodiments, methods of predicting responsiveness of a subject with cancer to an anti-ICOS antibody are provided.

In some embodiments, the method comprises detecting whether the patient has cells that express ICOS using an anti-ICOS antibody. In some embodiments, the method of detection comprises contacting the sample with an antibody, polypeptide, or polynucleotide and determining whether the level of binding differs from that of a reference or comparison sample (such as a control). In some embodiments, the method may be useful to determine whether the antibodies or polypeptides described herein are an appropriate treatment for the subject.

In some embodiments, the cells or cell/tissue lysate are contacted with an anti-ICOS antibody and the binding between the antibody and the cell is determined. When the test cells are shown binding activity as compared to a reference cell of the same tissue type, it may indicate that the subject would benefit from treatment with an anti-ICOS antibody. In some embodiments, the test cells are from human tissues.

Various methods known in the art for detecting specific antibody-antigen binding can be used. Exemplary immunoassays which can be conducted include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (MA). An indicator moiety, or label group, can be attached to the subject antibodies and is selected so as to meet the needs of various uses of the method which are often dictated by the availability of assay equipment and compatible immunoassay procedures. Appropriate labels include, without limitation, radionuclides (for example $^{125}$I, $^{131}$I, $^{35}$S, $^{3}$H, or $^{32}$P), enzymes (for example, alkaline phosphatase, horseradish peroxidase, luciferase, or β-glactosidase), fluorescent moieties or proteins (for example, fluorescein, rhodamine, phycoerythrin, GFP, or BFP), or luminescent moieties (for example, Qdot™ nanoparticles supplied by the Quantum Dot Corporation, Palo Alto, Calif.). General techniques to be used in performing the various immunoassays noted above are known to those of ordinary skill in the art.

In some embodiments, an immunohistochemistry assay, such as an automated immunohistochemistry assay, is used to detect ICOS expressing cells, e.g., in tissue samples such as human tissue samples (e.g., tonsil tissue), which can be human normal tissue samples or human tumor tissue samples. In some embodiments, the tissue sample is an FFPE sample, such as a clinical FFPE sample.

For purposes of diagnosis, the polypeptide including antibodies can be labeled with a detectable moiety including but not limited to radioisotopes, fluorescent labels, and various enzyme-substrate labels know in the art. Methods of conjugating labels to an antibody are known in the art.

In some embodiments, the anti-ICOS antibodies need not be labeled, and the presence thereof can be detected using a second labeled antibody which binds to the first anti-ICOS antibody.

In some embodiments, the anti-ICOS antibody can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

The anti-ICOS antibodies and polypeptides can also be used for in vivo diagnostic assays, such as in vivo imaging. Generally, the antibody or the polypeptide is labeled with a radionuclide (such as $^{111}$In, $^{99}$Tc, $^{14}$C, $^{131}$I, $^{125}$I, $^{3}$H, or any other radionuclide label, including those outlined herein) so that the cells or tissue of interest can be localized using immunoscintiography.

The antibody may also be used as staining reagent in pathology using techniques well known in the art.

In some embodiments, a first antibody is used for a diagnostic and a second antibody is used as a therapeutic. In some embodiments, the first and second antibodies are different. In some embodiments, the first antibody is from a non-human, while the therapeutic is from a human. In some embodiments, the first and second antibodies can both bind to the antigen at the same time, by binding to separate epitopes.

In some embodiments, the methods provided herein comprise determining microsatellite instability (MSI) by PCR. In some embodiments, determining microsatellite instability comprises detecting genetic instability at one or more markers (loci): BAT25, BAT26, D5S346, D2S123, and D17S250. See, e.g., Boland et al., 1998, *Cancer Res.* 58: 5248-5257. In some embodiments, if genetic instability is detected at 2 or more of the 5 loci, the cancer is MSI-high. In some embodiments, if genetic instability is detected at 1 of the 5 loci, the cancer is MSI-low. In some embodiments, if genetic instability is detected at none of the 5 loci, the cancer is MSS.

In some embodiments, the methods provided herein comprise determining microsatellite instability (MSI) by IHC. See, e.g., AMA and NCHPEG Colorectal Cancer Fact Sheets: 11-0456:2/12:jt:Updated February 2012. In some embodiments, determining microsatellite instability comprises detecting one or more mismatch repair proteins selected from MLH1, MSH2, PMS2, and MSH6 by IHC. In some embodiments, if one or more of the mismatch repair proteins is not detected by IHC, the cancer is MSI-positive.

In some embodiments, the methods provided herein comprise measuring an mRNA level. In some embodiments, the methods provided herein comprise measuring an ICOS RNA signature, e.g., a plurality of mRNA levels that are predictive of or correlated to ICOS expression. In some embodiments, the ICOS RNA signature comprises at least two, at least three, at least four, at least five, at least six, at least seven, at least eight, at least nine, or at least ten mRNA levels, the mRNA levels being levels of mRNAs selected from Table 6.

Any suitable method of determining mRNA levels may be used. Methods for the evaluation of mRNAs include, for example, hybridization assays using complementary DNA probes (such as in situ hybridization using labeled riboprobes specific for target sequences, Northern blot and related techniques) and various nucleic acid amplification assays (such as RT-PCR using complementary primers specific for target sequences and other amplification type detection methods, such as, for example, branched DNA, SISBA, TMA and the like).

In some embodiments, the mRNA level is determined by quantitative RT-PCR. In some embodiments, the mRNA level is determined by digital PCR. In some embodiments, the mRNA level is determined by RNA-Seq. In some embodiments, the mRNA level is determined by RNase Protection Assay (RPA). In some embodiments, the mRNA level is determined by Northern blot. In some embodiments, the mRNA level is determined by in situ hybridization (ISH). In some embodiments, the mRNA level is determined by a method selected from quantitative RT-PCR, microarray, digital PCR, RNA-Seq, RNase Protection Assay (RPA), Northern blot, and in situ hybridization (ISH).

RNA-seq is a technique based on enumeration of RNA transcripts using next-generation sequencing methodologies. The level of an mRNA is determined using the frequency of observation of fragments of its sequence. For a review of RNA-Seq, see, e.g., Wang et al., Nat. Rev. Genet. (2009) 10:57-63.

A Northern blot involves the use of electrophoresis to separate RNA samples by size, and detection with a hybridization probe complementary to part of or the entire target sequence. For a discussion of Northern blotting see, e.g., Trayhurn, P. (1996) Northern Blotting. Pro. Nutrition Soc. 55:583-589.

Quantitative RT-PCR involves reverse-transcribing mRNA and then amplifying the cDNA with a polymerase chain reaction (PCR) which is monitored in real time, e.g., by measuring fluorescence, wherein dye signal is a readout of the amount of product. The dye can be, e.g., an intercalating dye, or a dye attached to a probe also comprising a quencher, wherein degradation of the probe releases the dye and results in fluorescence, the degradation being catalyzed by an exonuclease activity driven by product formation, as in the TaqMan® assay. In some embodiments of the invention, a method for detecting a target mRNA in a biological sample comprises producing cDNA from the sample by reverse transcription using at least one primer; amplifying the cDNA so produced using a target polynucleotide as sense and antisense primers to amplify target cDNAs therein; and detecting the presence of the amplified target cDNA. In addition, such methods can include one or more steps that allow one to determine the levels of target mRNA in a biological sample (e.g., by simultaneously examining the levels a reference mRNA sequence, e.g., a "housekeeping" gene such as an actin family member or the reference RNAs discussed below). Optionally, the sequence of the amplified target cDNA can be determined.

In Digital PCR, a sample is partitioned into a plurality of reaction areas and PCR is conducted in the areas. The number of areas that are positive, i.e., in which detectable product formation occurs, can be used to determine the level of the target sequence in the original sample.

In an RPA, a sample is contacted with a probe under hybridization conditions and then with a single-stranded RNA nuclease. Formation of double-stranded complexes of probe with target protect the probe from degradation, such that the amount of probe remaining can be used to determine the level of the target.

In ISH, a cell or tissue sample is contacted with a probe that hybridizes to a target RNA and hybridization is detected to determine the level of the target.

In some embodiments, methods include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment (see, e.g., WO 01/75166 published Oct. 11, 2001; U.S. Pat. Nos. 5,700,637; 5,445,934; and 5,807,522; Lockart, *Nature Biotechnology,* 14:1675-1680 (1996); Cheung, V. G. et al., *Nature Genetics* 21(Suppl):15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps: 1) preparation of fluorescently labeled target from RNA isolated from the sample, 2) hybridization of the labeled target to the microarray, 3) washing, staining, and scanning of the array, 4) analysis of the scanned image and 5) generation of gene expression profiles. Two types of DNA microarrays are oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ). In some embodiments, a DNA microarray is a single-nucleotide polymorphism (SNP) microarrays, e.g., Affymetrix® SNP Array 6.0.

The Affymetrix GeneChip® system is a commercially available microarray system which comprises arrays fabricated by direct synthesis of oligonucleotides on a glass surface. Probe/Gene Arrays: Oligonucleotides, usually 25 mers, are directly synthesized onto a glass wafer by a combination of semiconductor-based photolithography and solid phase chemical synthesis technologies. Each array contains up to 400,000 different oligos and each oligo is present in millions of copies. Since oligonucleotide probes are synthesized in known locations on the array, the hybridization patterns and signal intensities can be interpreted in terms of gene identity and relative levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligo. The Microarray Suite software subtracts the hybridization intensities of the mismatch probes from those of the perfect match probes to determine the absolute or specific intensity value for each probe set. Probes are chosen based on current information from Genbank and other nucleotide repositories. The sequences are believed to recognize unique regions of the 3' end of the gene. A GeneChip Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

In some embodiments, for example when quantitative RT-PCR is used, the threshold cycle number is compared between two mRNAs, and the lower threshold indicates a higher level of the respective mRNA. As a nonlimiting example, in some embodiments, if levels of ICOS mRNA and at least one reference mRNA are analyzed and the threshold cycle number (Ct) for ICOS is 28 and the Ct for the reference mRNA is 30, then ICOS is at a higher level compared to the reference. In various embodiments, similar comparisons may be carried out for any type of quantitative or semi-quantitative analytical method.

In some embodiments, the level of at least one mRNA is normalized. In some embodiments, the level of at least two mRNAs are normalized and compared to each other. In some embodiments, such normalization may allow comparison of mRNA levels when the levels are not determined simultaneously and/or in the same assay reaction. One skilled in the art can select a suitable basis for normalization, such as at least one reference mRNA or other factor, depending on the assay.

In some embodiments, the at least one reference mRNA comprises a housekeeping gene. In some embodiments, the at least one reference mRNA comprises one or more of RPLP0, PPIA, TUBB, ACTB, YMHAZ, B2M, UBC, TBP, GUSB, HPRT1, or GAPDH.

Provided herein are also polynucleotides, kits, medicines, compositions, and unit dosage forms suitable for use in any of the methods described herein.

In some embodiments, a polynucleotide provided herein is isolated. In some embodiments, a polynucleotide provided herein is detectably labeled, e.g., with a radioisotope, a fluorescent agent, or a chromogenic agent. In another embodiment, a polynucleotide is a primer. In another embodiment, a polynucleotide is an oligonucleotide, e.g., an mRNA-specific oligonucleotide. In another embodiment, an oligonucleotide may be, for example, from 7-60 nucleotides in length, 9-45 nucleotides in length, 15-30 nucleotides in length, or 18-25 nucleotides in length. In another embodiment, an oligonucleotide may be, e.g., PNA, morpholino-phosphoramidates, LNA, or 2'-alkoxyalkoxy. Polynucleotides as provided herein are useful, e.g., for the detection of target sequences, such as a sequence contained within the mRNAs in Table 6 or a reference mRNA, such as the reference mRNAs discussed above. Detection can involve hybridization, amplification, and/or sequencing, as discussed above.

In some embodiments, a composition is provided comprising a plurality of polynucleotides, the plurality comprising at least a first polynucleotide specific for a first mRNA and a second polynucleotide specific for a second mRNA, the first and second mRNAs being selected from the mRNAs in Table 6. In some embodiments, the plurality further comprises a third polynucleotide specific for a third mRNA, the third mRNA being selected from the mRNAs in Table 6. In some embodiments, the plurality further comprises a fourth polynucleotide specific for a fourth mRNA, the fourth mRNA being selected from the mRNAs in Table 6. In some embodiments, the plurality further comprises a fifth polynucleotide specific for a fifth mRNA, the fifth mRNA being selected from the mRNAs in Table 6. In some embodiments, the plurality further comprises a sixth polynucleotide specific for a sixth mRNA, the sixth mRNA being selected from the mRNAs in Table 6. In some embodiments, the plurality further comprises a seventh polynucleotide specific for a seventh mRNA, the seventh mRNA being selected from the mRNAs in Table 6. In some embodiments, the plurality further comprises an eighth polynucleotide specific for a eighth mRNA, the eighth mRNA being selected from the mRNAs in Table 6. In some embodiments, the plurality further comprises a ninth polynucleotide specific for a ninth mRNA, the ninth mRNA being selected from the mRNAs in Table 6. In some embodiments, the plurality further comprises a tenth polynucleotide specific for a tenth mRNA, the tenth mRNA being selected from the mRNAs in Table 6. It is understood that the use of ordinals ("first," "second," etc.) to designate polynucleotides or mRNAs indicates that the polynucleotides or mRNAs, as the case may be, are not identical to each other.

In some embodiments, a composition comprises cells or tissue obtained from a subject. In some embodiments, a composition comprises mRNA isolated from a subject. In some embodiments, a composition comprises cDNA synthesized from mRNA isolated from a subject.

In some embodiments, a composition comprises at least one polynucleotide or a plurality of polynucleotides suitable for use in detecting at least one reference mRNA. In some embodiments, a composition comprises reagents for performing hybridization and/or amplification, such as quantitative RT-PCR, microarray, digital PCR, RNA-Seq, RPA, Northern blot, or in situ hybridization ISH. Such reagents can include one or more of an enzyme with reverse transcriptase activity, a DNA polymerase (which may be thermophilic), an intercalating dye, dNTPs, buffer, a single-strand RNA nuclease, detergent, fixative (e.g., formaldehyde), cosolvent (e.g., formamide), etc.

In some embodiments, a kit is provided including one or more containers comprising at least one polynucleotide specific for an mRNA selected from the mRNAs in Table 6 or a plurality of polynucleotides, the plurality comprising at least a first polynucleotide specific for a first mRNA and a second polynucleotide specific for a second mRNA, the first and second mRNAs being selected from the mRNAs in Table 6. In some embodiments, the plurality further comprises a third polynucleotide specific for a third mRNA, the third mRNA being selected from the mRNAs in Table 6. In some embodiments, the plurality further comprises a fourth polynucleotide specific for a fourth mRNA, the fourth mRNA being selected from the mRNAs in Table 6. In some embodiments, the plurality further comprises a fifth polynucleotide specific for a fifth mRNA, the fifth mRNA being selected from the mRNAs in Table 6. In some embodiments, the plurality further comprises a sixth polynucleotide specific for a sixth mRNA, the sixth mRNA being selected from the mRNAs in Table 6. In some embodiments, the plurality further comprises a seventh polynucleotide specific for a seventh mRNA, the seventh mRNA being selected from the mRNAs in Table 6. In some embodiments, the plurality further comprises an eighth polynucleotide specific for an eighth mRNA, the eighth mRNA being selected from the mRNAs in Table 6. In some embodiments, the plurality further comprises a ninth polynucleotide specific for a ninth mRNA, the ninth mRNA being selected from the mRNAs in Table 6. In some embodiments, the plurality further comprises a tenth polynucleotide specific for a tenth mRNA, the tenth mRNA being selected from the mRNAs in Table 6. It is understood that the use of ordinals ("first," "second," etc.) to designate polynucleotides or mRNAs indicates that the polynucleotides or mRNAs, as the case may be, are not identical to each other. In some embodiments, the kit includes one or more containers comprising at least one polynucleotide or a plurality of polynucleotides suitable for use in detecting at least one reference mRNA. In some embodiments, the kit comprises one or more containers comprising reagents for performing hybridization and/or amplification, such as quantitative RT-PCR, microarray, digital PCR, RNA-Seq, RNase Protection Assay (RPA), Northern blot, and in situ hybridization (ISH). Such reagents can include one or more of an enzyme with reverse transcriptase activity, a DNA polymerase (which may be thermophilic), an intercalating dye, dNTPs, buffer, a single-strand RNA nuclease, detergent, fixative (e.g., formaldehyde), cosolvent (e.g., formamide), etc.

Kits can include one or more containers comprising an anti-ICOS antibody (or unit dosage forms and/or articles of manufacture). In some embodiments, a unit dosage is provided wherein the unit dosage contains a predetermined amount of a composition comprising an anti-ICOS antibody, with or without one or more additional agents. In some embodiments, such a unit dosage is supplied in single-use prefilled syringe for injection. In some embodiments, the composition contained in the unit dosage can comprise saline, sucrose, or the like; a buffer, such as phosphate, or the like; and/or be formulated within a stable and effective pH range. In some embodiments, the composition can be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition comprises heparin and/or a proteoglycan.

In some embodiments, the amount of the anti-ICOS antibody used in the unit dose can be any of the amounts provided herein for the various methods and/or compositions described.

In some embodiments, kits further comprise instructions for use in the treatment of cancer or for detection of at least one mRNA level or RNA signature in accordance with any of the methods described herein. The kit may further comprise a description of selection an individual suitable or treatment. Instructions supplied in the kits are typically written instructions on a label or package insert (for example, a paper sheet included in the kit), but machine-readable instructions (for example, instructions carried on a magnetic or optical storage disk) are also acceptable. In some embodiments, the kit further comprises two or more therapeutic agents.

The kits are in suitable packaging. Suitable packaging includes, but is not limited to, vials, bottles, jars, flexible packaging (for example, sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

Methods of Treating Diseases Using Anti-ICOS Antibodies

Antibodies and compositions comprising antibodies are provided for use in methods of treatment for humans or animals. Methods of treating disease comprising administering anti-ICOS antibodies are also provided. Nonlimiting exemplary diseases that can be treated with anti-ICOS antibodies include, but are not limited to cancer.

In some embodiments, a method of treating a tumor is provided, wherein cells within a sample of the tumor express ICOS. In some such embodiments, the tumor may be considered to be ICOS-positive, or to express ICOS. Expression of ICOS may be determined by IHC, e.g., as discussed herein. In some embodiments, a tumor is considered to express ICOS when a sample from the tumor shows 1+, 2+, or 3+ staining of ICOS by IHC. In some embodiments, the sample from the tumor shows 2+ or 3+ staining of ICOS by IHC. In some embodiments, a tumor sample from a subject is analyzed for ICOS expression and the subject is selected for treatment with an antibody described herein if the tumor sample shows ICOS expression. In some embodiments, the subject is selected if the tumor sample shows elevated expression of ICOS.

In some embodiments, a subject is selected for treatment with an anti-ICOS antibody provided herein if the subject's tumor is PD-L1$^{LOW}$. In some embodiments, a subject is selected for treatment with an anti-ICOS antibody provided herein if the subject's tumor is ICOS$^{HIGH}$/PD-L1$^{LOW}$. In some embodiments, a subject is selected for treatment with an anti-ICOS antibody provided herein if the subject's tumor is ICOS$^{HIGH}$/PD-L1$^{HIGH}$.

The anti-ICOS antibody can be administered as needed to subjects. Determination of the frequency of administration can be made by persons skilled in the art, such as an attending physician based on considerations of the condition being treated, age of the subject being treated, severity of the condition being treated, general state of health of the subject being treated and the like. In some embodiments, an effective dose of an anti-ICOS antibody is administered to a subject one or more times. In some embodiments, an effective dose of an anti-ICOS antibody is administered to the subject once a month, less than once a month, such as, for example, every two months or every three months. In some embodiments, an effective dose of an anti-ICOS antibody is administered less than once a month, such as, for example, once every three weeks, once every two weeks, or once every week. An effective dose of an anti-ICOS antibody is administered to the subject at least once. In some embodiments, the effective dose of an anti-ICOS antibody may be administered multiple times, including for periods of at least a month, at least six months, or at least a year.

In some embodiments, pharmaceutical compositions are administered in an amount effective for treatment of (including prophylaxis of) cancer. The therapeutically effective amount is typically dependent on the weight of the subject being treated, his or her physical or health condition, the extensiveness of the condition to be treated, or the age of the subject being treated. In general, anti-ICOS antibodies may be administered in an amount in the range of about 10 µg/kg body weight to about 100 mg/kg body weight per dose. In some embodiments, anti-ICOS antibodies may be administered in an amount in the range of about 50 µg/kg body weight to about 5 mg/kg body weight per dose. In some embodiments, anti-ICOS antibodies may be administered in an amount in the range of about 100 µg/kg body weight to about 10 mg/kg body weight per dose. In some embodiments, anti-ICOS antibodies may be administered in an amount in the range of about 100 µg/kg body weight to about 20 mg/kg body weight per dose. In some embodiments, anti-ICOS antibodies may be administered in an amount in the range of about 0.5 mg/kg body weight to about 20 mg/kg body weight per dose.

Pharmaceutical compositions are administered in an amount effective for increasing the number of Teff cells; activating Teff cells; depleting Treg cells; and/or increasing the ratio of Teff cells to Treg cells. In some embodiments, the Treg cells are CD4+ FoxP3+ T cells. In some embodiments, the Teff cells are CD8+ T cells. In some embodiments, the Teff cells are CD4+ FoxP3− T cells and CD8+ T cells.

In some embodiments, treatment with anti-ICOS antibody results in a pharmacodynamics readout, such as up-regulation of ICOS ligand (ICOSL). In some embodiments, up-regulation of ICOSL is observed on the surface of B cells. In some embodiments, up-regulation of ICOSL is observed on the surface of granulocytes. In some embodiments, up-regulation of ICOSL is observed on the surface of neutrophils. Up-regulation of ICOSL may be observed on cells in the tumor; on cells in the spleen; on cells in peripheral blood. Up-regulation of ICOSL on the cell surface can be detected, for example, by flow cytometry. In some embodiments, soluble ICOSL is increased in the serum following treatment with anti-ICOS antibody. Soluble ICOSL can be detected by methods including, but not limited to, ELISA, MSD, and mass spectrometry. In some embodiments, ICOS target engagement, as measured by availability of free-receptor, by anti-ICOS antibodies may also be used as a pharmacodynamics readout. In some such embodiments, upon treatment by an anti-ICOS antibody, the number of ICOS receptors on the surface of T lymphocytes that are free to bind additional antibodies may be quantified. Decrease in observed available receptors may serve as an indication that anti-ICOS antibodies are binding their target molecule.

The therapeutically effective amount is typically dependent on the weight of the subject being treated, his or her physical or health condition, the extensiveness of the condition to be treated, or the age of the subject being treated. In general, anti-ICOS antibodies may be administered in an amount in the range of about 10 µg/kg body weight to about 100 mg/kg body weight per dose. In some embodiments, anti-ICOS antibodies may be administered in an amount in the range of about 50 µg/kg body weight to about 5 mg/kg body weight per dose. In some embodiments, anti-ICOS antibodies may be administered in an amount in the range of about 100 µg/kg body weight to about 10 mg/kg body weight per dose. In some embodiments, anti-ICOS antibodies may be administered in an amount in the range of about 100 µg/kg body weight to about 20 mg/kg body weight per dose. In some embodiments, anti-ICOS antibodies may be administered in an amount in the range of about 0.5 mg/kg body weight to about 20 mg/kg body weight per dose.

Pharmaceutical Compositions

In some embodiments, compositions comprising anti-ICOS antibodies are provided in formulations with a wide variety of pharmaceutically acceptable carriers (see, for example, Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7$^{th}$ ed., Lippencott Williams and Wilkins (2004); Kibbe et al., Handbook of Pharmaceutical Excipients, 3$^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In some embodiments, a pharmaceutical composition comprising an anti-ICOS antibody is provided. In some embodiments, the pharmaceutical composition comprises a chimeric antibody. In some embodiments, the pharmaceutical composition comprises a humanized antibody. In some embodiments, the pharmaceutical composition comprises an antibody prepared in a host cell or cell-free system as described herein. In some embodiments, the pharmaceutical composition comprises pharmaceutically acceptable carrier.

In some embodiments, pharmaceutical compositions are administered in an amount effective for treatment of (including prophylaxis of) cancer. The therapeutically effective amount is typically dependent on the weight of the subject being treated, his or her physical or health condition, the extensiveness of the condition to be treated, or the age of the subject being treated. In general, anti-ICOS antibodies may be administered in an amount in the range of about 0.05 mg/kg body weight to about 100 mg/kg body weight per dose. In some embodiments, anti-ICOS antibodies may be administered in an amount in the range of about 10 µg/kg body weight to about 100 mg/kg body weight per dose. In some embodiments, anti-ICOS antibodies may be administered in an amount in the range of about 50 µg/kg body weight to about 5 mg/kg body weight per dose. In some embodiments, anti-ICOS antibodies may be administered in an amount in the range of about 100 µg/kg body weight to about 10 mg/kg body weight per dose. In some embodiments, anti-ICOS antibodies may be administered in an amount in the range of about 100 µg/kg body weight to about 20 mg/kg body weight per dose. In some embodiments, anti-ICOS antibodies may be administered in an amount in the range of about 0.5 mg/kg body weight to about 20 mg/kg body weight per dose. In some embodiments, anti-ICOS antibodies may be administered in an amount in the range of about 0.5 mg/kg body weight to about 10 mg/kg body weight per dose. In some embodiments, anti-ICOS antibodies may be administered in an amount in the range of about 0.05 mg/kg body weight to about 20 mg/kg body weight per dose. In some embodiments, anti-ICOS antibodies may be administered in an amount in the range of about 0.05 mg/kg body weight to about 10 mg/kg body weight per dose. In some embodiments, anti-ICOS antibodies may be administered in an amount in the range of about 5 mg/kg body weight or lower, for example less than 4, less than 3, less than 2, or less than 1 mg/kg of the antibody.

In some embodiments, anti-ICOS antibodies can be present in an amount in the range of about 50 µg/kg body weight to about 5 mg/kg body weight per dose. For example, in some embodiments, a dose for a 20 kg person can be within a range of about 1 mg to about 100 mg. In some embodiments, the dose can be within a range of 2 mg to 200 mg of the anti-ICOS antibody. In some embodiments, the dose can be within a range of 10 mg to 400 mg of the anti-ICOS antibody.

Routes of Administration

In some embodiments, anti-ICOS antibodies can be administered in vivo by various routes, including, but not limited to, intravenous, intra-arterial, parenteral, intratumoral, intraperitoneal or subcutaneous. The appropriate formulation and route of administration may be selected according to the intended application.

Combination Therapy

Anti-ICOS antibodies can be administered alone or with other modes of treatment. They can be provided before, substantially contemporaneous with, and/or after other modes of treatment, for example, surgery, chemotherapy, radiation therapy, or the administration of a biologic, such as another therapeutic antibody. In some embodiments, an anti-ICOS antibody is administered in conjunction with another anti-cancer agent.

In some embodiments, the anti-ICOS antibody is given concurrently with a second therapeutic agent. For example, the two or more therapeutic agents are administered with a time separation of no more than about 60 minutes, such as no more than about any of 30, 15, 10, 5, or 1 minutes. In some embodiments, the anti-ICOS antibody is administered sequentially with a second therapeutic agent. For example, administration of the two or more therapeutic agents are administered with a time separation of more than about 15 minutes, such as about any of 20, 30, 40, 50, or 60 minutes, 1 day, 2 days, 3 days, 1 week, 2 weeks, or 1 month, or longer.

In some embodiments, the anti-ICOS antibody is administered with a second therapeutic method for treatment. Thus, the administration of an antibody provided herein can be in combination with another system of treatment.

In some embodiments, an anti-ICOS antibody provided herein is administered with a PD-1 therapy. Exemplary PD-1 therapies include, but are not limited to, nivolumab (OPDIVO®, BMS-936558, MDX-1106, ONO-4538); pidilizumab, lambrolizumab/pembrolizumab (KEYTRUDA, MK-3475); durvalumab (anti-PD-L1 antibody, MEDI-4736; AstraZeneca/MedImmune); RG-7446; avelumab (anti-PD-L1 antibody; MSB-0010718C; Pfizer); AMP-224; BMS-936559 (anti-PD-L1 antibody); AMP-514; MDX-1105; ANB-011; anti-LAG-3/PD-1; anti-PD-1 antibody (CoStim); anti-PD-1 antibody (Kadmon Pharm.); anti-PD-1 antibody (Immunovo); anti-TIM-3/PD-1 antibody (AnaptysBio); anti-PD-L1 antibody (CoStim/Novartis); RG7446/ MPDL3280A (anti-PD-L1 antibody, Genentech/Roche); KD-033, PD-1 antagonist (Agenus); STI-A1010; STI-A1110; TSR-042; and other antibodies that are directed against programmed death-1 (PD-1) or programmed death ligand 1 (PD-L1).

In some embodiments, a subject is selected for treatment with an anti-ICOS antibody provided herein and a PD-1 therapy if the subject's tumor expresses PD-L1. In some embodiments, a subject is selected for treatment with an anti-ICOS antibody provided herein and a PD-1 therapy if the subject's tumor is PD-L1$^{HIGH}$. In some embodiments, a subject is selected for treatment with an anti-ICOS antibody provided herein and a PD-1 therapy if the subject's tumor expresses ICOS and PD-L1. In some embodiments, a subject is selected for treatment with an anti-ICOS antibody provided herein and a PD-1 therapy if the subject's tumor is ICOS$^{HIGH}$/PD-L1$^{HIGH}$. Determining the level of PD-L1 and/or ICOS may be determined, for example, using IHC. A patient's tumor is considered to express PD-L1, in some embodiments, when 1% or more, or 5% or more, of the tumor cells in a sample show PD-L1 membrane staining by IHC. In some embodiments, more than 50% of the tumor cells in a sample show PD-L1 membrane staining by IHC. In some such embodiments, the subject's tumor is considered to be PD-L1$^{HIGH}$. A patient's tumor is considered to express ICOS, in some embodiments, when 1% or more of the cells in a tumor sample show ICOS staining by IHC. In some embodiments, a subject is first treated with a PD-1 therapy, and is later treated with an anti-ICOS antibody provided herein, with or without continuing the PD-1 therapy. Thus, methods provided herein include treatment of a subject with an anti-ICOS antibody, wherein the subject has previously been treated with a PD-1 therapy.

In some embodiments, the anti-ICOS antibody provided herein is administered with an agonist anti-OX40 antibody (such as Medi6469, MedImmune; MOXR0916/RG7888, Roche). In some embodiments, the anti-ICOS antibody provided herein is administered with an anti-CTLA4 antibody (such as ipilimumab, YERVOY®, BMS).

In some embodiments, an additional therapeutic agent is a chemotherapeutic agent. Exemplary chemotherapeutic agents that may be combined with the anti-ICOS antibodies provided herein include, but are not limited to, capectiabine, cyclophosphamide, dacarbazine, temozolomide, cyclophosphamide, docetaxel, doxorubicin, daunorubicin, cisplatin, carboplatin, epirubicin, eribulin, 5-FU, gemcitabine, irinotecan, ixabepilone, methotrexate, mitoxantrone, oxaliplatin, paclitaxel, nab-paclitaxel, ABRAXANE® (protein-bound paclitaxel), pemetrexed, vinorelbine, and vincristine. In some embodiments, an anti-ICOS antibody provided herein is administered with at least one kinase inhibitor. Nonlimiting exemplary kinase inhibitors include erlotinib, afatinib, gefitinib, crizotinib, dabrafenib, trametinib, vemurafenib, and cobimetanib.

In some embodiments, the additional therapeutic agent is an IDO inhibitor. Nonlimiting exemplary IDO inhibitors are described, e.g., in US 2016/0060237; and US 2015/0352206. Nonlimiting exemplary IDO inhibitors include Indoximod (New Link Genetics), INCB024360 (Incyte Corp), 1-methyl-D-tryptophan (New Link Genetics), and GDC-0919 (Genentech).

In some embodiments, an anti-ICOS antibody provided herein is administered in combination with an immune-modifying drug (IMiD). Nonlimiting exemplary IMiDs include thalidomide, lenalidomide, and pomalidomide.

In some embodiments, an additional therapeutic agent is a cancer vaccine. Cancer vaccines have been investigated as a potential approach for antigen transfer and activation of dendritic cells. In particular, vaccination in combination with immunologic checkpoints or agonists for co-stimulatory pathways have shown evidence of overcoming tolerance and generating increased anti-tumor response. A range of cancer vaccines have been tested that employ different approaches to promoting an immune response against the tumor (see, e.g., Emens L A, Expert Opin Emerg Drugs 13(2): 295-308 (2008)). Approaches have been designed to enhance the response of B cells, T cells, or professional antigen-presenting cells against tumors. Exemplary types of cancer vaccines include, but are not limited to, peptide-based vaccines that employ targeting distinct tumor antigens, which may be delivered as peptides/proteins or as genetically-engineered DNA vectors, viruses, bacteria, or the like; and cell biology approaches, for example, for cancer vaccine development against less well-defined targets, including, but not limited to, vaccines developed from patient-derived dendritic cells, autologous tumor cells or tumor cell lysates, allogeneic tumor cells, and the like.

Thus, in certain embodiments, the anti-ICOS antibodies provided herein may be used in combination with a cancer vaccine. Exemplary cancer vaccines include, but are not limited to, dendritic cell vaccines, oncolytic viruses, tumor cell vaccines, etc. In some embodiments, such vaccines augment the anti-tumor response. Examples of cancer vaccines that can be used in combination with anti-ICOS antibodies provided herein include, but are not limited to, MAGE3 vaccine (e.g., for melanoma and bladder cancer), MUC1 vaccine (e.g., for breast cancer), EGFRv3 (such as Rindopepimut, e.g., for brain cancer, including glioblastoma multiforme), or ALVAC-CEA (e.g., for CEA+ cancers).

Nonlimiting exemplary cancer vaccines also include Sipuleucel-T, which is derived from autologous peripheral-blood mononuclear cells (PBMCs) that include antigen-presenting cells (see, e.g., Kantoff P W et al., N Engl J Med 363:411-22 (2010)). In Sipuleucel-T generation, the patient's PBMCs are activated ex vivo with PA2024, a recombinant fusion protein of prostatic acid phosphatase (a prostate antigen) and granulocyte-macrophage colony-stimulating factor (an immune-cell activator). Another approach to a candidate cancer vaccine is to generate an immune response against specific peptides mutated in tumor tissue, such as melanoma (see, e.g., Carreno B M et al., Science 348:6236 (2015)). Such mutated peptides may, in some embodiments, be referred to as neoantigens. As a nonlimiting example of the use of neoantigens in tumor vaccines, neoantigens in the tumor predicted to bind the major histocompatibility complex protein HLA-A*02:01 are identified for individual patients with a cancer, such as melanoma. Dendritic cells from the patient are matured ex vivo, then incubated with neoantigens. The activated dendritic cells are then administered to the patient. In some embodiments, following administration of the cancer vaccine, robust T-cell immunity against the neoantigen is detectable.

In some such embodiments, the cancer vaccine is developed using a neoantigen. In some embodiments, the cancer vaccine is a DNA vaccine. In some embodiments, the cancer vaccine is an engineered virus comprising a cancer antigen, such as PROSTVAC (rilimogene galvacirepvec/rilimogene glafolivec). In some embodiments, the cancer vaccine comprises engineered tumor cells, such as GVAX, which is a granulocyte-macrophage colony-stimulating factor (GM-CSF) gene-transfected tumor cell vaccine (see, e.g., Nemunaitis, 2005, Expert Rev Vaccines, 4: 259-74).

In some embodiments, an anti-ICOS antibody described herein is administered before, concurrently, and/or after a cancer vaccine. In some embodiments, cancer vaccines developed using neoantigens are used in combination with the anti-ICOS antibodies described herein. In some such embodiments, the combination is used to treat a cancer with a high mutational burden, such as melanoma, lung, bladder, or colorectal cancer.

In some embodiments, an anti-ICOS antibody provided herein is administered in combination with a chimeric antigen receptor T cell therapy (CAR-T therapy).

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Bioinformatics Analysis of ICOS mRNA Expression in Human Tumors

Utilizing RNA sequencing data collected as part of TCGA, ICOS expression in 7500 tumors was compared across 24 different indications. High ICOS mRNA levels were found in subsets of head & neck squamous cell cancer (HNSCC), non-small cell lung cancer (NSCLC) and triple negative breast cancer (TNBC). See FIG. 1A.

Figure 2:
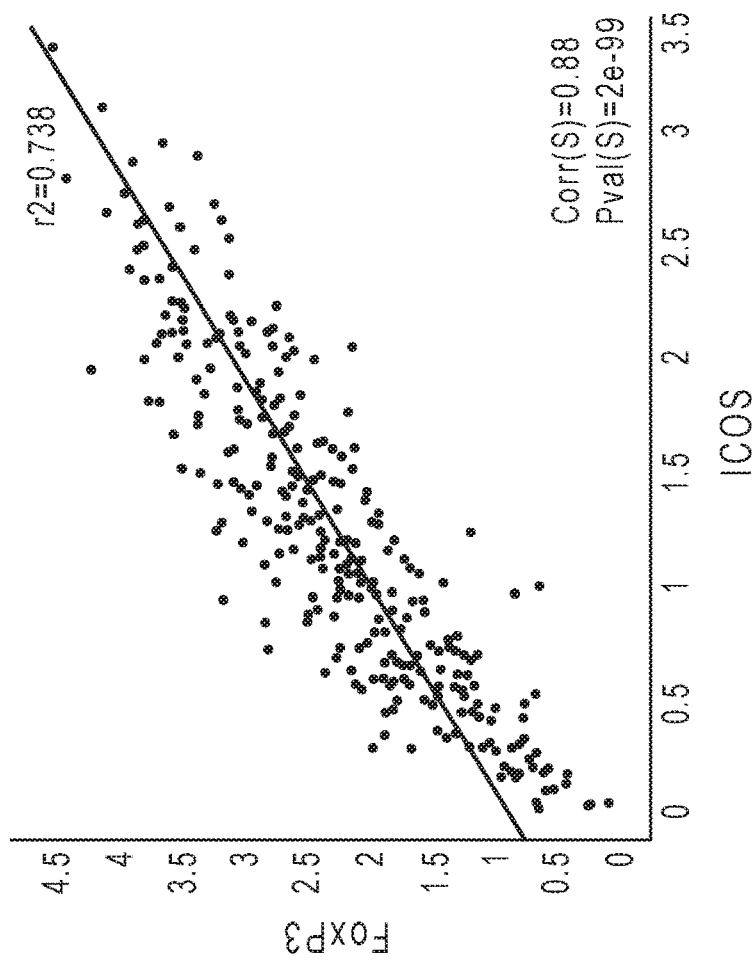
FIG. 2. Correlation of ICOS expression with T-cell infiltration. ICOS mRNA levels from ~450 HNSCC tumors were compared with a 12 gene T-cell associated chemokine signature score or FoxP3 mRNA levels. Levels of normalized chemokine signature or FoxP3 mRNA for each tumor is plotted on the Y axis, mRNA levels of ICOS are plotted in the X-axis. The Spearman correlation (R) of the association is show on the graph [Corr(S)]. A correlation of >0.75 (Spearman R) is viewed as cut-off for strong correlation.
Figure 2:
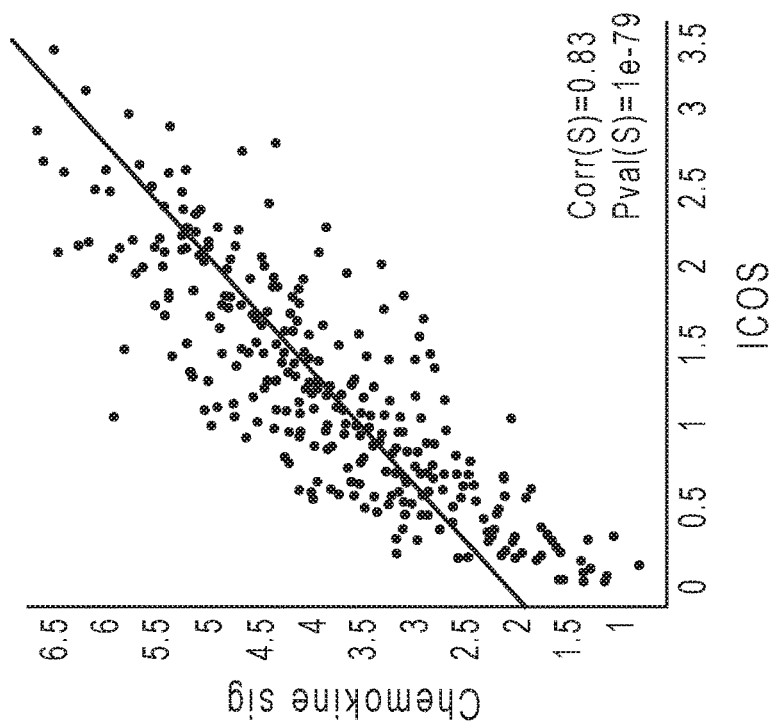

The association between T cell infiltration and levels of ICOS expression was investigated. Expression of a set of 12 chemokine genes has been associated with high levels of T cell infiltration and formation of lymph node-like structures (Messina et al., 2012, Sci Reports. 2:765-771). The chemokine signature score was computed for each sample based on the average expression of these 12 chemokine genes. This signature score was calculated across all of the head and neck squamous cell cancer samples (HNSCC). Levels of the chemokine signature or a Treg cell marker (FoxP3) with ICOS levels in HNSCC tumors were correlated. See FIG. 2. There was a strong correlation between chemokine signature and ICOS levels (R=0.83; Spearman correlation) or ICOS and FoxP3, a Treg cell marker (R=0.88; Spearman correlation). These data demonstrate that ICOS expression is closely associated with T cell infiltration and Treg cells. Similar data was observed in NSCLC and TNBC.

Figure 3:
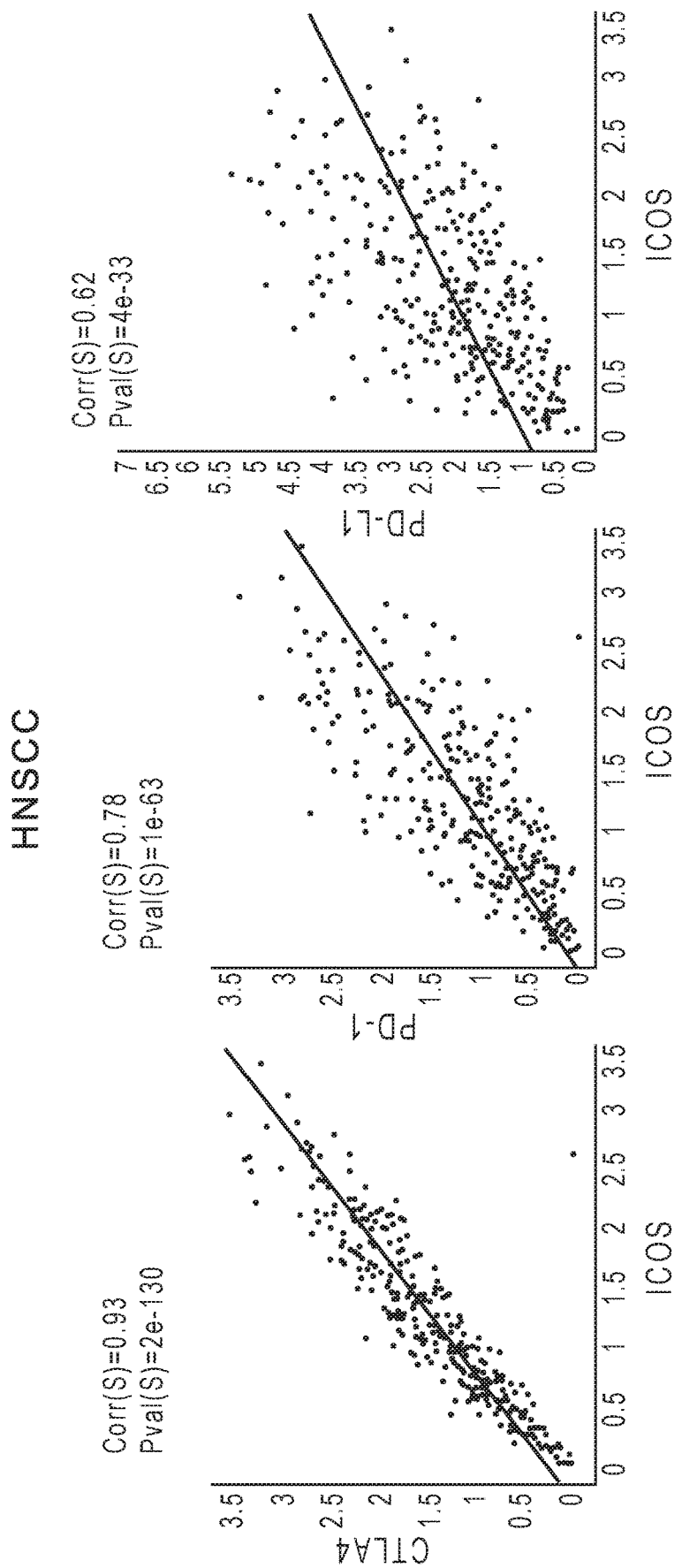
FIG. 3. ICOS mRNA expression was compared for ~450 HNSCC tumors using TCGA RNA sequencing data (NCI). Levels of normalized CTLA-4 or PD-1 or PD-L1 mRNA for each tumor is plotted on the Y axis, mRNA levels of ICOS are plotted in the X-axis. The Spearman correlation (R) of the association is show on the graph [Corr(S)]. ICOS expression levels significantly correlated with expression of checkpoint molecules CTLA-4, PD-1. A weak correlation between ICOS and PD-L1 was observed. A correlation of >0.75 (Spearman R) is viewed as cut-off for strong correlation.

In the HNSCC tumors, ICOS expression was significantly correlated (R=0.93 and 0.78 respectively) with expression levels of other check point molecules such as CTLA-4 and PD-1. See FIG. 3. The correlation of ICOS with PD-L1 was weak (R=0.62). Similar data was observed in other indications such as NSCLC. These data suggest that ICOS may be expressed on the same T cells that are expressing other checkpoint molecules such as CTLA-4 and PD-1. The weaker correlation with PD-L1 and ICOS suggest that there could be a subset of ICOS high patients that could be PD-L1 low or negative. These data are supportive of ICOS as a single agent in PD-L1 negative patients and also a combination strategy with anti-PD-1 or anti-CTLA-4 therapies.

Example 2: IHC Analysis of Human Tumors

Figure 1B:
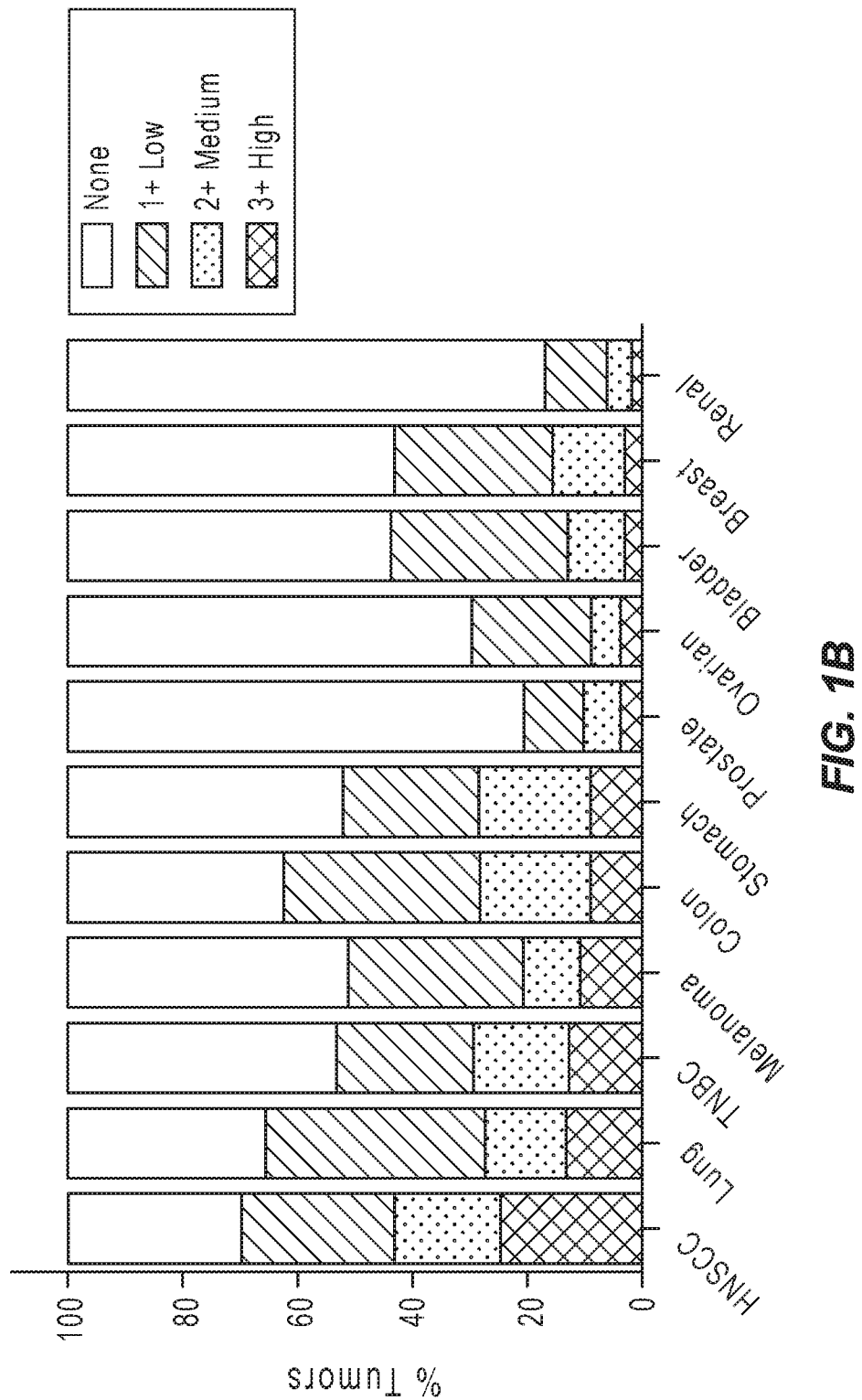

ICOS protein expression levels were determined using an immunohistochemistry (IHC) assay. This assay, using a rabbit anti-ICOS monoclonal antibody (SP98, Spring Biosciences, Pleasanton, Calif.), was validated for assay specificity, assay precision (intra-run and inter-run, and lot-to-lot reproducibility), and sensitivity. The validation studies were performed using formalin-fixed, paraffin embedded (FFPE) tissue sections and control cell lines (CHO engineered to express human ICOS (positive control) or non-ICOS expressing CHO vector control cell line (negative control)). The assay was performed on a Leica-Bond Rx automated staining platform and specific staining of ICOS was detected in the positive control CHO cells and in T cell subsets in normal human tonsil.

age of high ICOS+ immune cell infiltration (i.e., 3+). See FIG. 1B. In addition to these tumors, subsets of patients from melanoma, colorectal cancer and gastric adenocarcinoma had moderate levels of ICOS-positive cell infiltration. See FIG. 1B.

To evaluate the prevalence and nature of T cells that express ICOS, a multiplex immuno-fluorescence IHC assay for detecting ICOS, FOXP3 and CD8 was developed. A DNA marker (DAPI) to count the total number of nuclei in the human tumor sections was utilized.

ICOS expression was determined using immunohistochemistry analysis with the rabbit monoclonal antibody clone that recognizes human ICOS (Spring Biosciences Inc. Pleasanton, Calif.). The specificity and sensitivity of the ICOS IHC assay was confirmed using human tonsil and cell lines constitutively over-expressing ICOS. The staining intensity was scored by a trained pathologist using the following criteria. All positive staining was score based on membrane expression in at least two-thirds of the cells.

Figure 4:
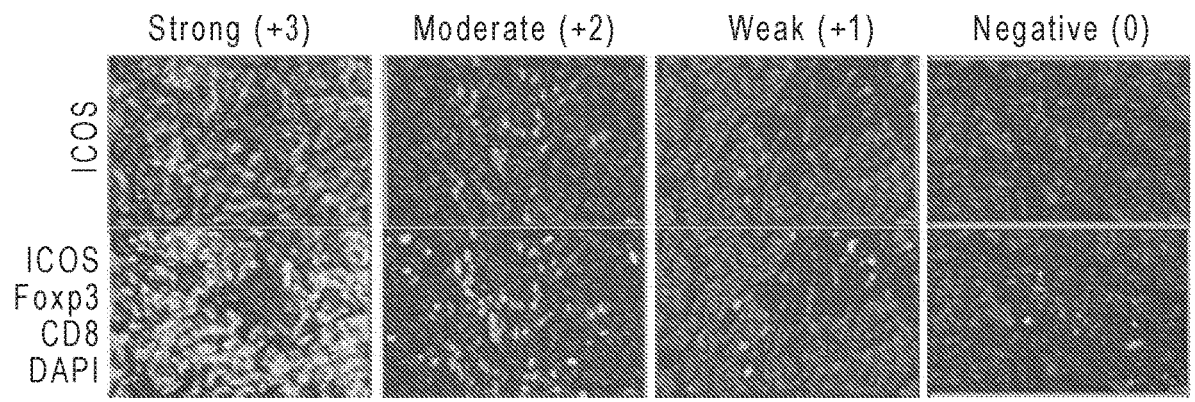
FIG. 4. Representative images of the varying intensities of ICOS staining in human NSCLC tumor.

A representative image for the scoring schema is shown in FIG. 4. The scoring was performed based on the following criteria for immunofluorescence:

0 (negative)=No or less than 0.1% of cells have membrane staining

1+(mild)=0.1 to 5% of the cells are positive

2+(moderate)=5 to 10% of the cells are positive

3+(Strong)=>10 to 50% in cells are positive

Prevalence of ICOS expression in various subsets of NSCLC or adjacent normal lung samples are summarized in Table 2. Strong ICOS expression was not observed in adjacent normal lung tissue in cancer patients. Strong ICOS expression was observed in all major sub-types of lung cancer. About 29-31% of the most common NSCLC sub-types (adenocarcinoma or squamous cell carcinoma) had strong ICOS staining.

TABLE 2

Distribution of ICOS staining in various subsets of NSCLC samples based on pathological scoring.

| Tumor sub-type | N | Strong (3+) | Moderate (2+) | Weak (1+) | Negative (0) |
|---|---|---|---|---|---|
| SCLC | 2 | 0 (0%) | 0 (0%) | 2 (100%) | 0 (0%) |
| Squamous | 49 | 14 (29%) | 14 (29%) | 17 (35%) | 4 (8%) |
| Adenocarcinoma | 16 | 5 (31%) | 2 (13%) | 8 (50%) | 1 (6%) |
| Adenosquamous | 9 | 3 (11%) | 2 (11%) | 3 (11%) | 1 (67%) |
| Brochiolalveolar carcinoma | 9 | 2 (22%) | 2 (22%) | 5 (56%) | 0 (0%) |
| Undifferentiated | 5 | 1 (20%) | 0 (0%) | 3 (60%) | 1 (20%) |
| Normal | 3 | | 1 (33%) | 2 (67%) | 0 (0%) |

Slides were scored by a trained pathologist using the following criteria for chromogenic staining:

| Frequency of ICOS-positive cells | Score |
|---|---|
| <1% cells are ICOS positive | 0 |
| >1% but <5% cells are ICOS positive | 1+ |
| >5% but <15% cells are ICOS positive | 2+ |
| >15% cells are ICOS positive | 3+ |

Figure 5:
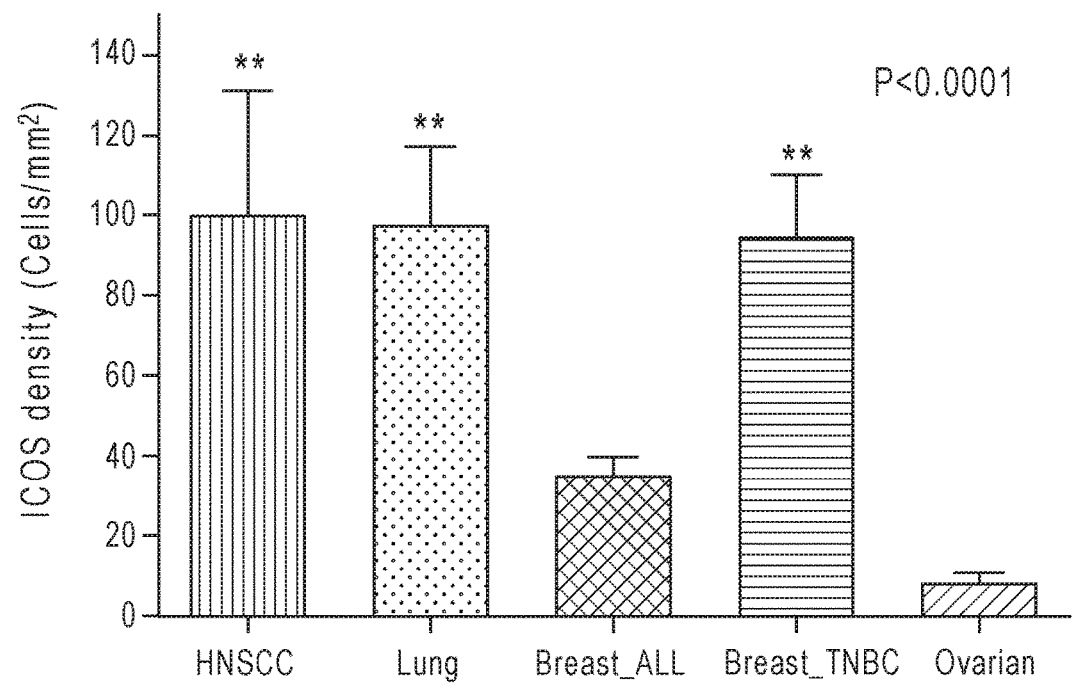
FIG. 5. Distribution of ICOS cell density from human tumors. ICOS cell density was determined in each of the human tumors, and mean ICOS density from each tumor type is plotted in Y axis [NSCLC (N=100); HNSCC (N=102); Breast cancer, all major subtypes (N=94); triple negative subtype of breast cancer, TNBC (N=95); ovarian cancer (N=94)]. The statistical analysis was performed using ANOVA.

Tissue microarrays from 11 different tumor types were stained and classified using this scoring system. See FIG. 1B. The IHC data confirmed the mRNA based data in that HNSCC, NSCLC and TNBC contained the greatest percent- An automated methodology to measure ICOS positive cells was also employed, using image analysis software (Strataquest from Tissuegnostics Inc., Tarzana, Calif.). The density of ICOS positive cells in a fixed area of tumor tissue was determined by determining the number of ICOS positive cells in the viable region of human tumor tissue as defined by the DAPI staining region. ICOS cell density was determined from a separate set of approximately 500 individual patients across 4 major tumor types [NSCLC (N=100); HNSCC (N=102); breast cancer, all major sub-types (N=94); triple negative subtype of breast cancer, TNBC (N=95); ovarian cancer (N=94)]. A summary of the results of the analysis are shown in FIG. 5. Consistent with the ICOS mRNA analysis, the HNSCC and NSCLC tumors had a significantly higher density of ICOS positive tumors as compared to ovarian or breast cancer. Although ICOS expression is low in breast cancer, high levels of ICOS expression was observed in the TNBC subtype, which constitutes about 10% of breast cancer. See FIG. 5. This TNBC subtype of breast cancer is the most aggressive subtype with limited treatment options and highest unmet medical need.

Figure 6A:
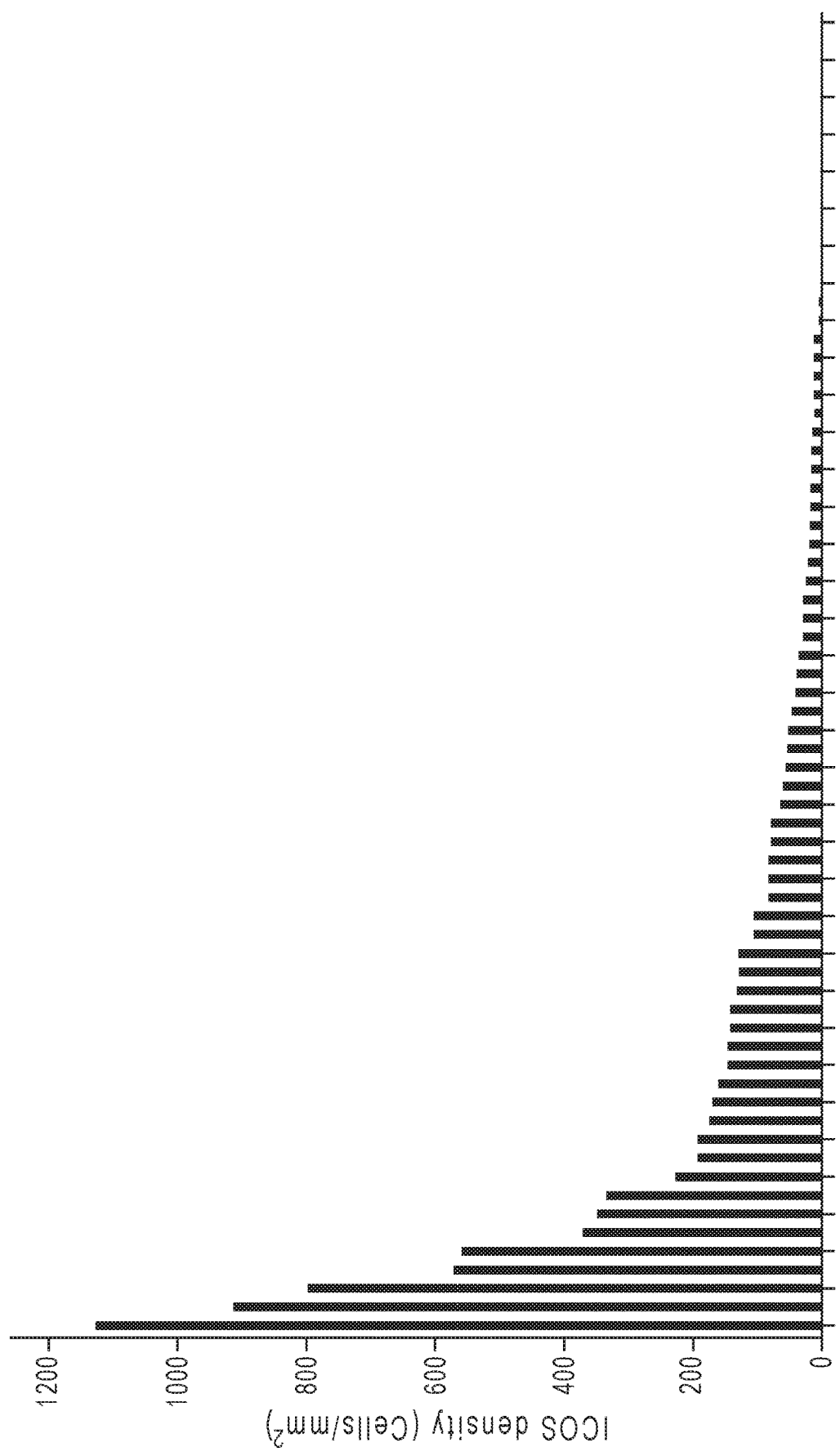
FIG. 6A-B. Diversity of ICOS cell density in NSCLC samples. A) The density of ICOS expression was evaluated in a panel of lung tumor samples (N=98) and tumors were ranked based on ICOS+ density of positive cells/mm2. B) Diversity of ICOS expression in a second independent cohort of NSCLC clinical samples (N=204).
Figure 6B:
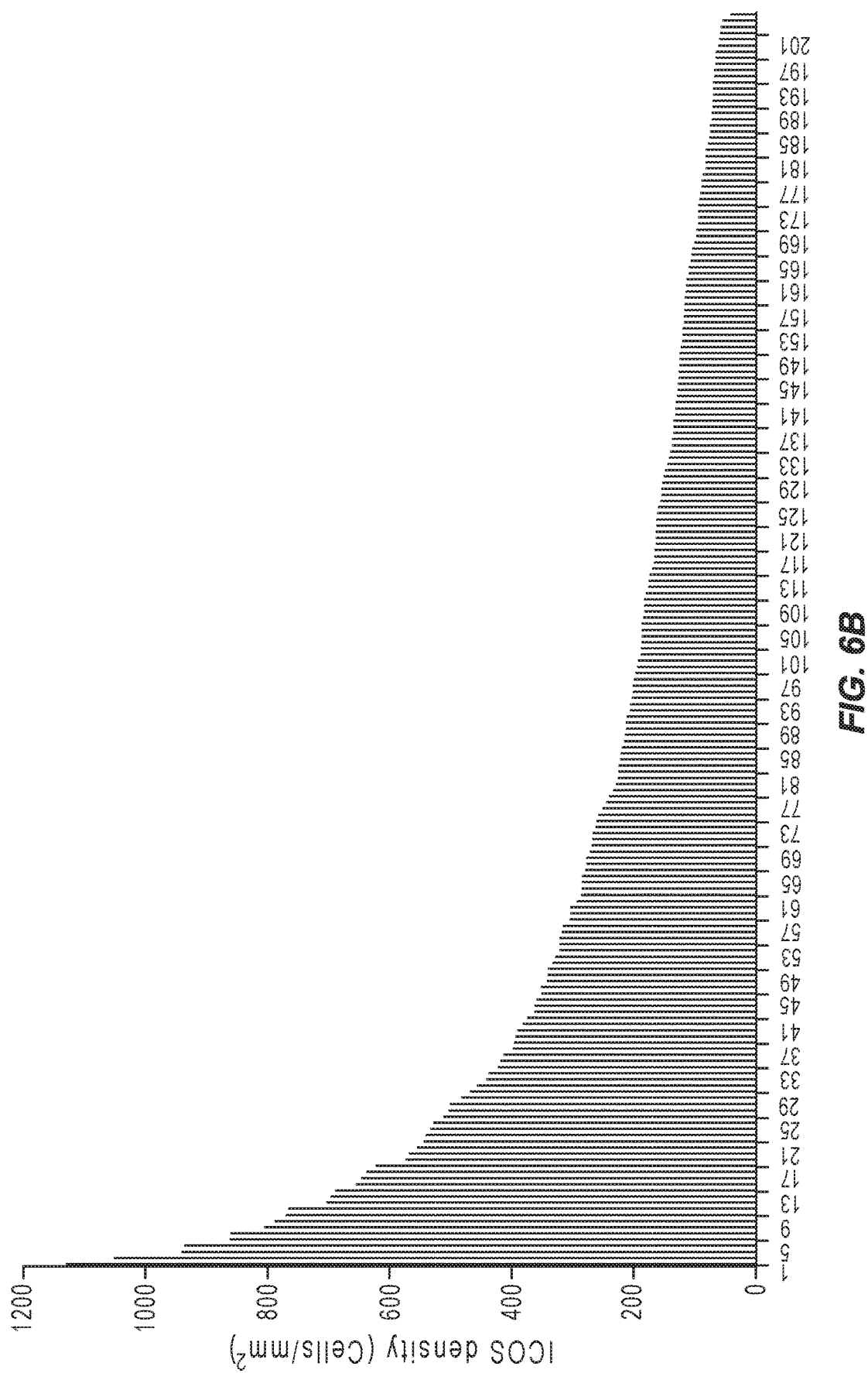

The patient to patient variability in ICOS expression in two different cohorts of a high ICOS expressing tumor types (NSCLC) is shown in FIGS. 6A and 6B. A range of ICOS cell density was observed in NSCLC from 98 lung cancer samples (FIG. 6A) available from a commercial vendor. Similar diversity in ICOS expression was observed using an independent clinical cohort (FIG. 6B) of NSCLC (N=204).

Figure 7A:
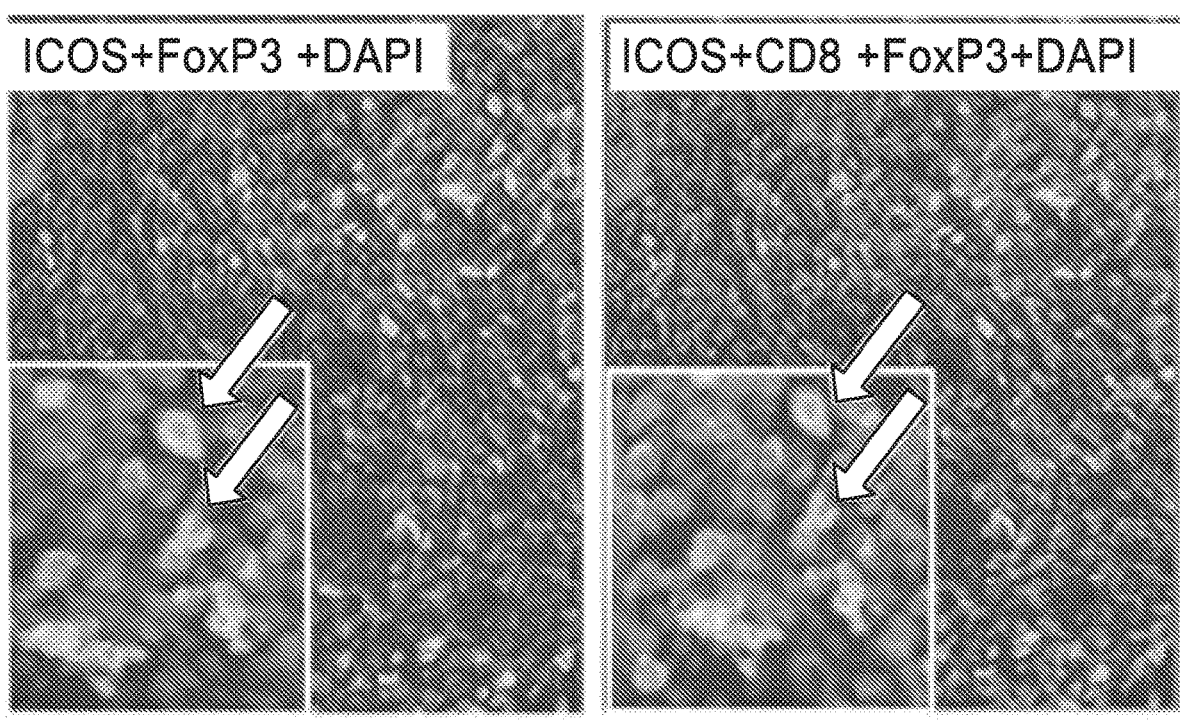
FIG. 7A-B. Distribution of ICOS cell density in different T cell subsets from human cancer. A) Representative image depicting the ICOS staining in the distinct T cell compartments. The arrows point to ICOS+ FOXP3+ Treg cells or ICOS+ CD8– CD4 effectors. B) ICOS cell density from individual tumors was analyzed in FoxP3 positive CD4 Tregs or CD8 positive T cells are CD8 negative and FoxP3 negative CD4 effs. The mean ICOS density and standard deviation from each of these tumor types are plotted. [Lung cancer (N=100); HNSCC (N=102); Triple negative subtype of breast cancer, TNBC (N=95); Ovarian cancer (N=94)].
Figure 7B:
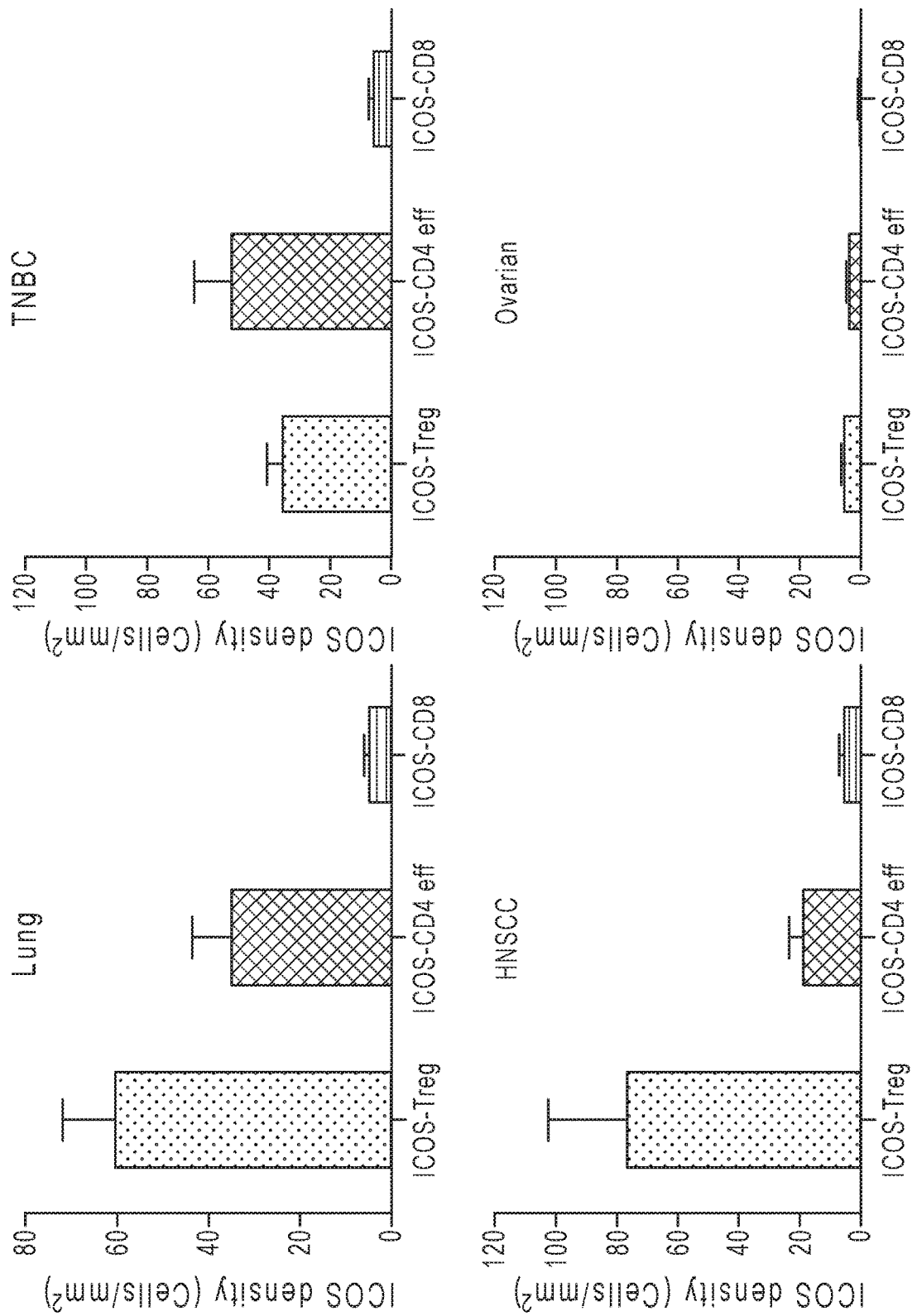

A multiplex IHC with ICOS, FoxP3 (a Treg cell marker) and CD8 from the human tumor samples described above was analyzed and quantified using image analysis software (Strataquest from Tissuegnostics Inc., Tarzana, Calif.). A representative image of the multiplex ICOS staining with these T cell markers is shown in FIG. 7A. The ICOS positive cells that are also FOXP3 positive are called ICOS+ CD4 Treg cells. The ICOS positive and CD8 positive cells are called ICOS+ CD8 cells. The ICOS positive but negative for CD8 and FoxP3 are called ICOS+ CD4 Teffs. The density of the different sub-sets of ICOS positive T cells were quantified using the image analysis software as described above. In lung (N=100) and TNBC (n=95) samples there was a high number of both CD4 effectors and CD4 Treg cell that were ICOS positive (FIG. 7B). In contrast, not many ICOS positive cells were observed in ovarian cancer (n=94). HNSCC tumors (N=102) had a large population of ICOS positive CD4 Treg cells. There was only a small population of ICOS positive CD8 T cells observed in all the tumor types examined. These data suggest that ICOS is predominantly expressed in the CD4 compartment as compared to the CD8 T cells, and that variation in the relative proportions of Treg vs Teff can be seen across indications.

Figure 8A:
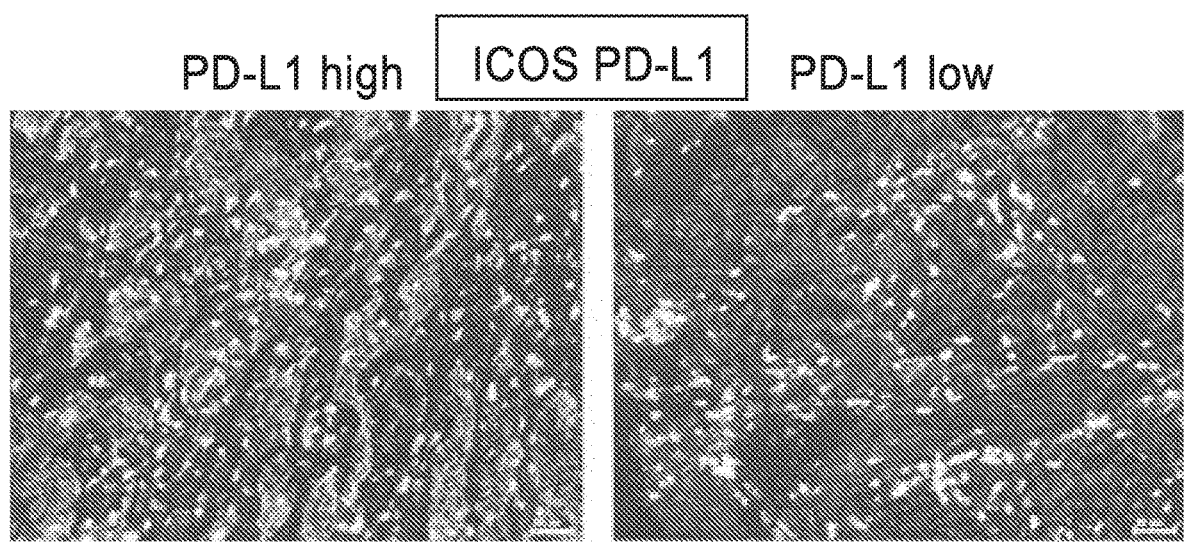
FIG. 8A-B. High ICOS expression is observed in PD-L1 high NSCLC tumors. By utilizing the PD-L1/ICOS/PD-1 multiplex IHC ICOS and PD-L1 levels were evaluated in a set of adenocarcinoma of NSCLC (n=150). A) Representative images of a PD-L1 high (left panel) or a PD-L1 low (right panel) tumor stained with ICOS, PD-1 and PD-L1. B) Quantification of ICOS cell density in PD-L1 high (>5% of cells are PD-L1 positive or PD-L1 low (<5% of the cells are PD-L1 positive) squamous cell carcinoma (left panel) and adenocarcinoma (right panel).
Figure 8B:
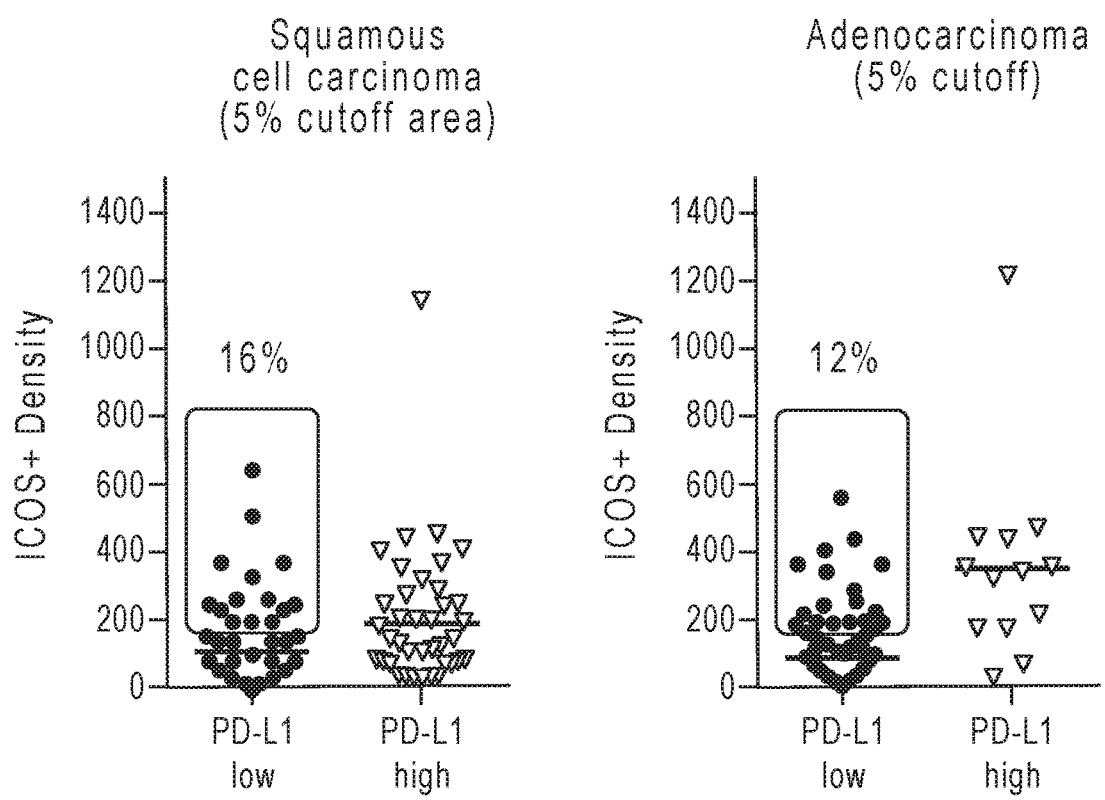

In order to understand if ICOS expression is directly associated with PD-L1 status, the correlation between PD-L1 levels and ICOS expression was evaluated. Bioinformatics analysis suggested that PD-L1 expression and ICOS levels were weakly correlated (R=0.62). PD-L1, ICOS and PD-1 levels were evaluated by a multiplex IHC. A representative image of the multiplex IHC from a PD-L1 high and low lung tumor is shown. See FIG. 8. PD-L1 and ICOS in 154 adenocarcinoma sub-type of NSCLC tumors were evaluated. The tumors were subdivided into PD-L1 high or low tumors based on 5% of the cells that are PD-L1 positive. Results indicate that PD-L1 positive tumors had a higher density of ICOS expression.

Example 3: Flow Cytometry Analysis

Figure 9B:
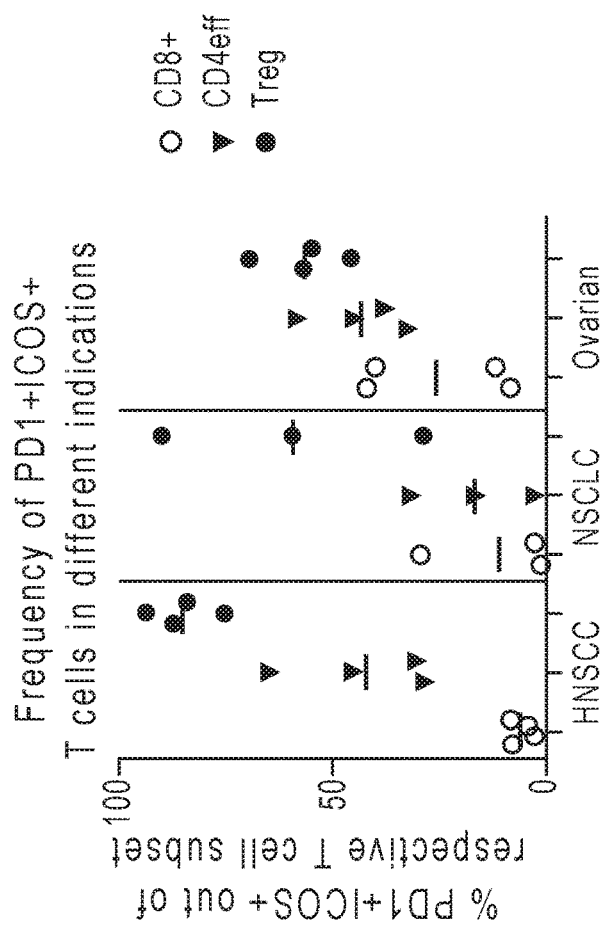
Figure 9C:
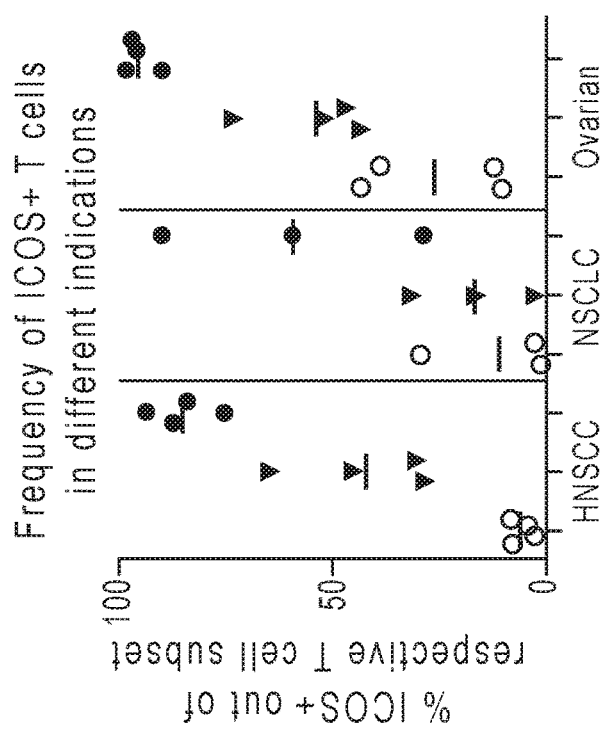
Figure 9C:
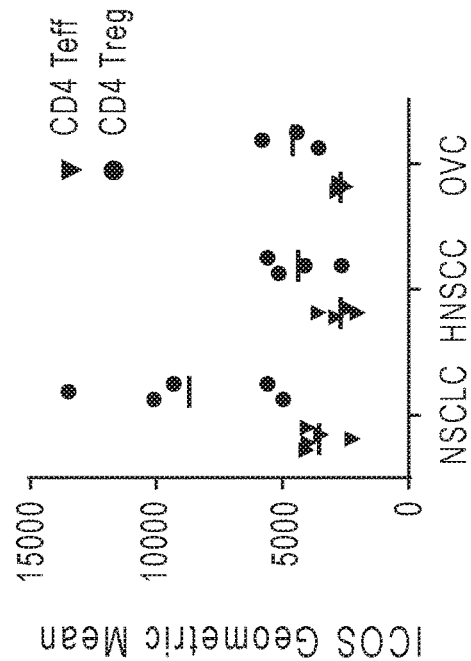

To confirm the ICOS expression data obtained by IHC and to compare relative intensities of ICOS expressed in different T cell populations, ICOS expression in tumor infiltrating lymphocytes was evaluated using multi-color flow cytometry. Samples from four HNSCC patients, three lung cancer, and four ovarian cancer patients were analyzed. Consistent with the IHC data, ICOS expression was predominantly observed on CD4 T cells. See FIG. 9 (HNSCC). The frequency of ICOS positive cells in the CD8 population is very low in a majority of these tumors. It was also observed that the majority of CD4 effector cells co-express ICOS and PD-1. These data support developing an ICOS therapeutic in the clinic alone or in combination with anti-PD-1 therapies.

The mean fluorescence intensity (MFI) of ICOS staining provides a measure of ICOS expression in the different T-cell population. The MFI of ICOS positive cells in the Treg cells was 2-3 fold higher than the CD4 effectors. See FIG. 9C. It should be noted that there are small populations of CD4 effectors that have high ICOS MFI. Confirmation of the difference in ICOS receptor densities in Teffs versus Tregs, coupled with data from ongoing ADCC assays to evaluate differential Teff and Treg sensitivity to depletion, would support development of agonistic antibody with an active Fc that could potentially deplete the Treg cells.

Translational studies show high levels of tumor infiltrating ICOS positive T cells in a subset of human tumors (such as HNSCC, NSCLC etc.). ICOS expression is correlated with expression of other check-point regulators such as CTLA-4 and PD-1. Analysis of the T cell subsets showed that ICOS expression is predominantly restricted to the CD4 T cell compartment. ICOS is expressed in both FoxP3 positive Treg cells as well as CD4 Teff cells. Studies show, consistent with the literature, that the level of ICOS expression is higher in the Treg cells as compared to CD4 Teff cells.

Example 4: Antibody Generation

Reagents

ICOS proteins representing human, mouse, rat, and cynomolgus species were produced as homodimeric, Fc fusions (IgG1 backbone), and the human and mouse ICOS-hFc were used as antigens for rodent immunizations. Human ICOS-hFc included human ICOS amino acids 1 to 141 (21 to 141 in mature construct); mouse ICOS-hFc included mouse ICOS amino acids 1 to 142 (21 to 142 in mature construct).

ICOS-Fc was generated as both bivalent and monovalent Fc fusion molecules to assess avid and monovalent binding of antibodies to ICOS, respectively.

For screening purposes, CHO stable cell lines overexpressing full length human or mouse ICOS (ICOS+ CHO cells, or "CHO-ICOS cells") were generated as were constructs encoding full length cynomolgus monkey or rat ICOS to enable screening following transient transfection.

Rodent Antibody Campaign

Rodent campaigns were performed at Precision Antibody. Mice (10), rats (6), Syrian hamsters (6), and Armenian hamsters (6) were immunized with hICOS-hFc or mICOS-hFc. Hybridomas were generated, and supernatants screened by ELISA for binding to hICOS and mICOS, as well as multiplex screening by FACS for binding to CHO-hICOS and CHO-mICOS cells. Hybridomas were additionally assessed for the ability to block ICOSL binding to the CHO-ICOS cells. Clones that scored positive for binding to mouse and human ICOS were selected for protein purification. Purified antibodies were subsequently re-screened in the binding and blocking assays, and antibodies that scored positive proceeded to in vitro assessment as outlined below. All antibodies selected for further investigation from the immunization approach originated from Armenian hamster fusions.

Biochemical Characterization of Antibodies

Affinity measurements were conducted using Bio-Layer Interferometry (BLI) technology (ForteBio Octet® RED96). The monovalent affinities were generated with IgG versions of the antibodies with monovalent, heterodimeric forms of the ICOS receptor. The avid affinities were generated using full-length IgGs against homodimeric forms of the ICOS receptor. The monomeric and bivalent hICOS affinities of the selected hamster antibodies are shown in Table 3.

TABLE 3

Hamster-derived antibody affinity.

| | Monomeric hICOS Affinity | | | Bivalent hICOS Affinity | | |
|---|---|---|---|---|---|---|
| mAb | $K_D$ | $K_{on}$ (1/Ms) | $K_{dis}$ (1/s) | $K_D$ (M) | $K_{on}$ (1/Ms) | $K_{dis}$ (1/s) |
| 7F12 | 1.32E−08 | 1.33E+05 | 1.75E−03 | 3.42E−11 | 6.74E+05 | 2.30E−05 |
| 35A9 | 2.45E−09 | 1.78E+05 | 4.38E−04 | <1.0E−12 | 6.25E+05 | <1.0E−07 |
| 36E10 | 1.59E−09 | 1.43E−05 | 2.28E−04 | <1.0E−12 | 6.26E+05 | <1.0E−07 |
| 37A10 | 3.18E−09 | 1.51E+05 | 4.79E−04 | 3.42E−11 | 6.74E+05 | 2.30E−05 |
| 16G10 | 4.37E−09 | 1.63E+05 | 7.12E−04 | <1.0E−12 | 1.01E+06 | <1.0E−07 |

Binding affinity of the antibodies for cynomolgus monkey, mouse, and rat ICOS was also determined, and the antibodies were found to bind all species with comparable affinity. Cross-reactivity measurements were conducted using BLI technology with antibody panels being screened for binding to human, mouse, and cynomolgus ICOS-Fc fusions (homodimeric, bivalent forms). Table 4 shows representative binding data for several hamster antibodies for human and cynomolgus monkey ICOS.

TABLE 4

Bivalent binding affinities of several hamster antibodies to human and cyno ICOS-Fc.

| | hICOS-Fc | | | cynoICOS-Fc | | |
|---|---|---|---|---|---|---|
| ligand/mAb | $K_D$ (M) | $K_{on}$ (1/Ms) | $K_{dis}$ (1/s) | $K_D$ (M) | $K_{on}$ (1/Ms) | $K_{dis}$ (1/s) |
| hICOSL-mG2a | 3.62E−10 | 9.41E+05 | 3.41E−04 | | | |
| 7F12 | 3.42E−11 | 6.74E+05 | 2.30E−05 | <1.0E−12 | 5.85E+05 | <1.0E−07 |
| 35A9 | <1.0E−12 | 1.01E+06 | <1.0E−07 | <1.0E−12 | 7.40E+05 | <1.0E−07 |
| 36E10 | <1.0E−12 | 6.17E+05 | <1.0E−07 | <1.0E−12 | 6.97E+05 | <1.0E−07 |
| 37A10 | <1.0E−12 | 6.25E+05 | <1.0E−07 | <1.0E−12 | 7.12E+05 | <1.0E−07 |
| 16G10 | <1.0E−12 | 6.26E+05 | <1.0E−07 | <1.0E−12 | 6.47E+05 | <1.0E−07 |

To assess specificity, binding to human ICOS+ CHO cells and mouse ICOS+ CHO cells was individually analyzed by flow cytometry. As a control to screen out pan-reactive antibodies, staining on CHO cells lacking ICOS receptor expression was also examined. All of the selected antibodies bound to human and mouse ICOS+ CHO cells, and not to CHO cells lacking ICOS expression.

To further assess the specificity of the anti-ICOS antibodies, the antibodies were screened for binding to additional members of the CD28 protein family (CD28, BTLA, PD-1 and CTLA-4). No cross-reactivity was observed for the selected antibodies to human or mouse CD28, BTLA, PD-1 or CTLA4. Specifically, binding to Fc fusions (of CD28, BTLA, PD-1 and CTLA-4) in dimeric forms was evaluated, and no binding was observed. For a subset of the CD28 family members, mouse or human protein was over-expressed on the surface of HEK293 and CHOK1 cells. No binding of antibody above background relative to untransduced parental cells was observed.

Antibodies were also found to not bind to abundant serum proteins nor to platelets or red blood cells.

Epitope binning was conducted using BLI. Antibodies were also binned against an ICOSL-Fc fusion (homodimeric, bivalent form). All of the selected antibodies were found to be in the same epitope bin, and all blocked binding of ICOS to ICOS ligand.

Humanization

Selected antibodies were humanized by performing homology studies between the antibody variable framework regions of human and hamster origin. A panel of primary designs for analysis was provided and antibodies were then produced for comparison with wild-type antibody (hamster or chimera form). Once humanized panels were produced, leads were characterized and ranked based on affinity and in vitro activity. Additional humanization designs were executed to reduce sequence liabilities and low-scoring immunogenic sites resulting in minor sequence variations. The sequence liabilities considered included the presence of free cysteines and potential sites for chemical degradation (asparagine deamidation, aspartate isomerization, methionine/tryptophan, and non-enzymatic lysine glycation).

The affinity of a humanized antibody having the variable regions of 37A10S713 for monomeric forms of ICOS from human, cynomolgus monkey and rat was measured by Bio-Layer Interferometry (BLI) technology (ForteBio Octet® RED96) and $K_D$'s are shown in Table 5. The $K_D$'s were deemed comparable across the species as they were within 2 to 5-fold. Functionality of binding was confirmed by assessing potency of inducing proliferation of primary CD4+ T cells isolated from each species.

TABLE 5

Monovalent binding affinity of 37A10S713 to human, cynomolgus monkey, and rat ICOS.

| | Human | Cynomolgus Monkey | Rat |
|---|---|---|---|
| Binding Affinity ($K_D$ nM)[A] | 1.50 ± 0.39 | 0.66 ± 0.16 | 7.20 ± 2.55 |
| Potency in primary CD4+ T cell proliferation (EC50 nM)[B] | 4.27-49.75 | 8.25-13.14 | 10.7-30.0 |

[A] affinities shown as mean ± SEM from 6 experiments;
[B] range of 4 donors is shown Example 5: In Vitro Functional Characterization of Anti-ICOS Antibodies A number of cell-based in vitro assays were used to assess the activity of the anti-ICOS mAbs. The main purpose was to screen for antibodies with agonistic/co-stimulatory properties. Since the cell system (primary cell versus transfected cell line) and the method of antibody presentation (soluble versus plate-bound or cross-linked) can influence agonistic activity, a number of different assay formats were employed. In addition, an assay to detect undesired super-agonistic activity (see Suntharalingam et al., 2006, *N. Eng. J. Med.*, 355: 1018-28) was also used.

The assays designed to look for agonistic/co-stimulatory activity of the anti-ICOS mAbs were performed on the cell types outlined below, with the first signal to the T cells (signal 1) provided using either sub-optimal concentrations of anti-CD3 or PMA or in the PBMC assay with stimulation with super-antigen (SEB):
1. Primary human CD4+ T cell assay
   a. Plate-bound/cross-linked antibody format co-stimulated with anti-CD3
   b. Soluble antibody format co-stimulated with PMA
2. Jurkat assay (reporter cell line with transfected human or mouse ICOS constructs)
   a. Plate-bound/cross-linked format with either anti-CD3 or PMA
   b. Soluble antibody format co-stimulated with PMA
3. Human PBMC assay
   a. Soluble antibody format with super-antigen (SEB)

Figure 10A:
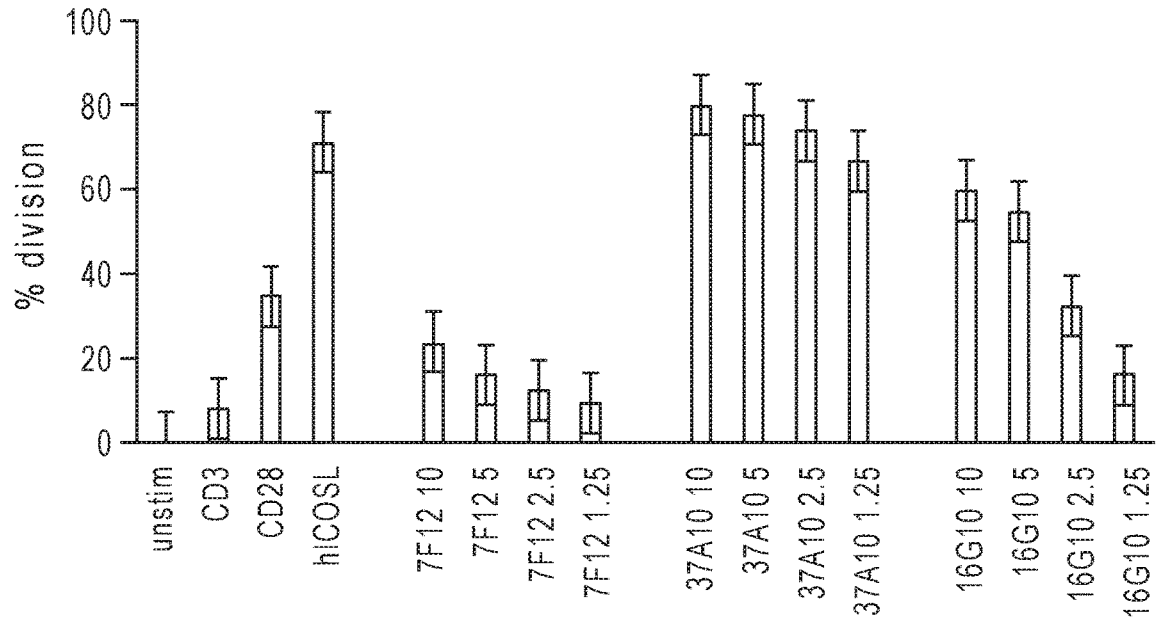
FIG. 10A-C. A) Effect of anti-ICOS antibodies on proliferation of primary human CD4+ T cells in a plate-bound format in the presence of suboptimal anti-CD3 is shown. Percent of cells divided is graphed. B) Effect of anti-ICOS antibodies on proliferation of human CD4+ T cells in soluble format in the presence of suboptimal PMA is shown. Percent of cells divided is graphed. C) Effect of anti-ICOS antibody 37A10S713-hIgG1 on proliferation of primary human CD4+ T cells in a plate-bound format in the presence of suboptimal anti-CD3.
Figure 10B:
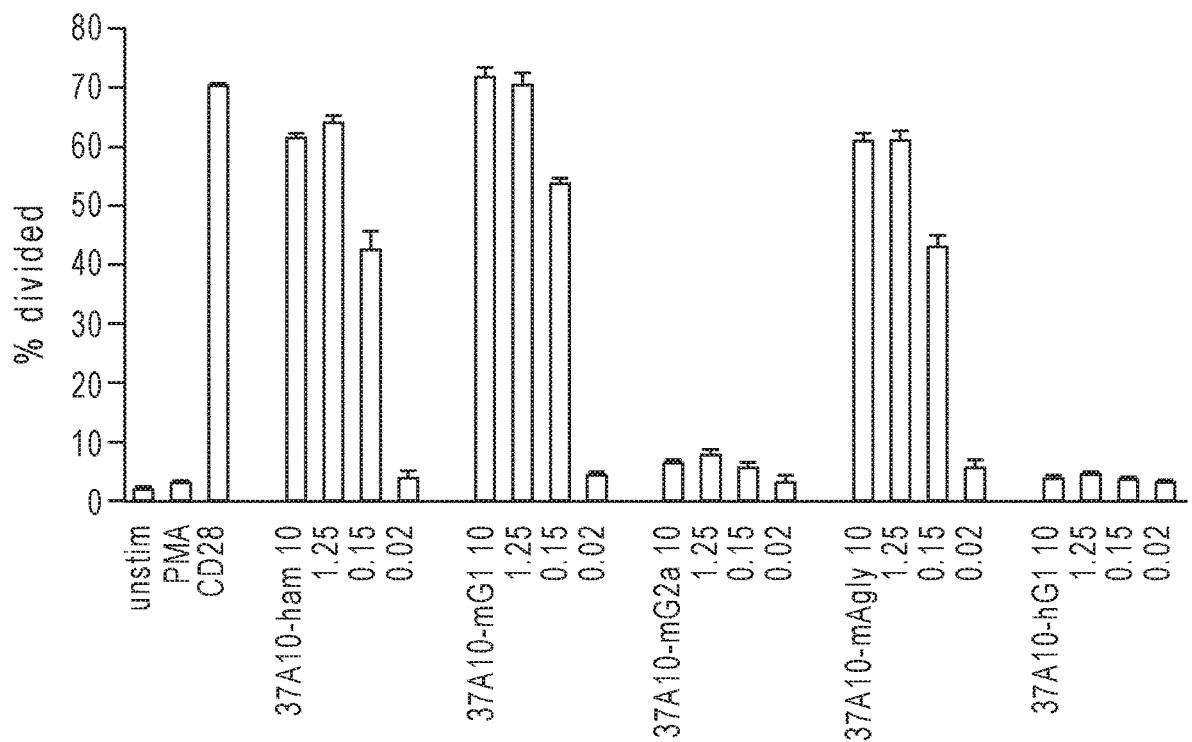

Panels of hamster anti-ICOS mAbs were screened in the above assays to identify antibodies with agonistic properties. An example of the agonistic activity observed in an assay using primary human CD4+ T cells co-stimulated with suboptimal anti-CD3 with addition of plate-bound anti-ICOS antibody is shown in FIG. 10A for a selection of hamster anti-ICOS antibodies. In this assay, human CD4+ T cell isolated from PBMCs are activated with suboptimal plate-bound anti-CD3 in the presence of plate-bound hamster anti-ICOS antibodies (7F12, 37A10 and 16G10) at four concentrations (µg/ml). Plate-bound hICOSL and soluble anti-CD28 in the presence of anti-CD3 are used as positive controls. % divided cells is graphed. Multiple anti-ICOS antibodies exhibit activity in this assay. FIG. 10B shows the results of the assay using soluble antibody and costimulation with sub-optimal PMA. Human CD4+ T cells were isolated from PBMCs by negative selection and labeled with CFSE. Cells were activated in 96-well plates with suboptimal PMA (0.25 ng/ml) alone or in the presence of different Fc versions (hamster, mG1, mG2a, mG1Agly or hG1) of anti-ICOS antibody 37A10 at indicated concentrations (µg/ml). Soluble anti-CD28 antibody was used as a control. Proliferation was analyzed on day 3 by flow cytometry. The mouse IgG1 and mouse IgG1-agly versions showed activity in the assay, along with the parental fully hamster antibody. At least antibody 37A10 showed agonist activity in both soluble and plate-bound formats. See FIGS. 10A and 10B.

Figure 10C:
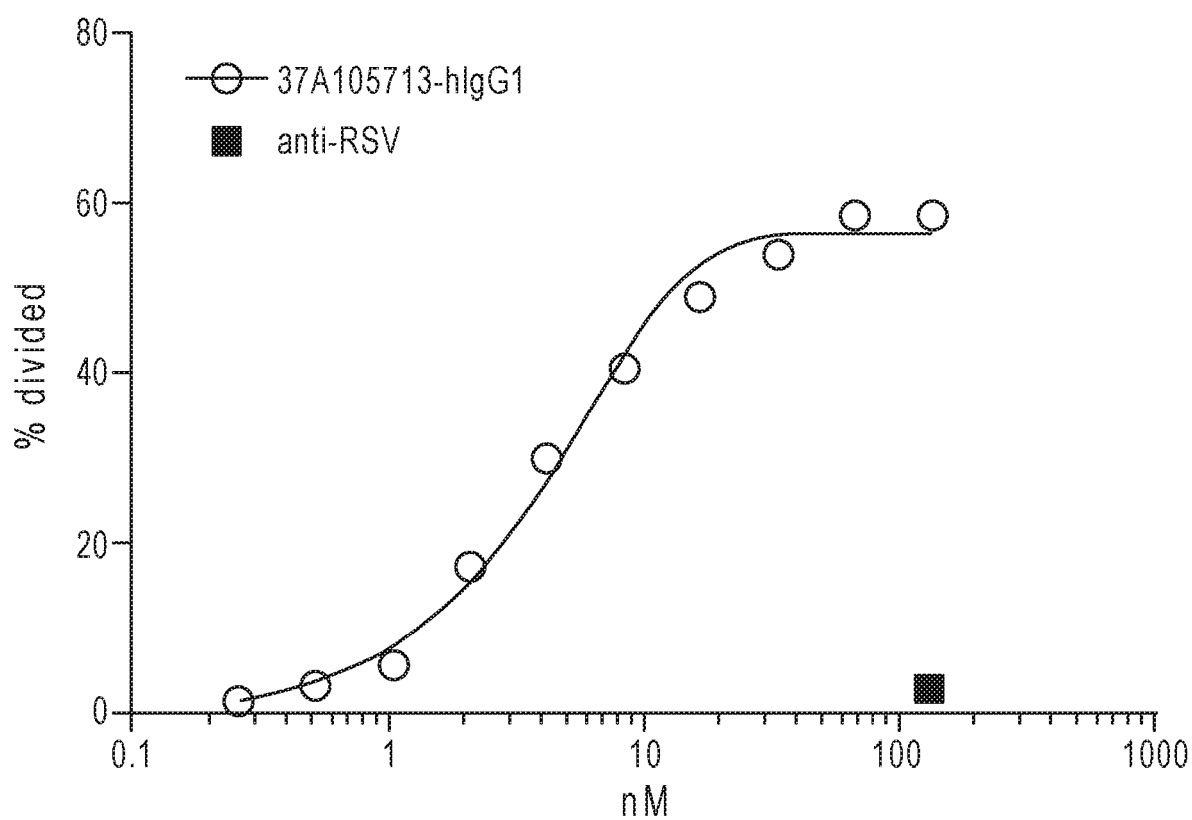

FIG. 10C shows the agonist activity of results of 37A10S713 antibody with a human IgG1 in the primary human CD4+ T cell assay. CD4+ T cells were isolated from PBMC from 4 healthy donors, labeled with CFSE dye and then incubated in plates coated with a sub-optimal concentration of anti-CD3 and various concentrations of either 37A105713-hIgG1 or a negative control human IgG1 antibody (anti-respiratory syncytial virus (RSV)). After 3 days, the percentage of divided cells was determined using flow cytometry. The EC50 values ranged from 4.27-49.75 nM for the 4 donors tested. Proliferation is plotted as the percentage of divided cells (measured by CFSE dilution using flow cytometry) and are means of duplicates. FIG. 10C shows data from a representative donor.

Figure 11A:
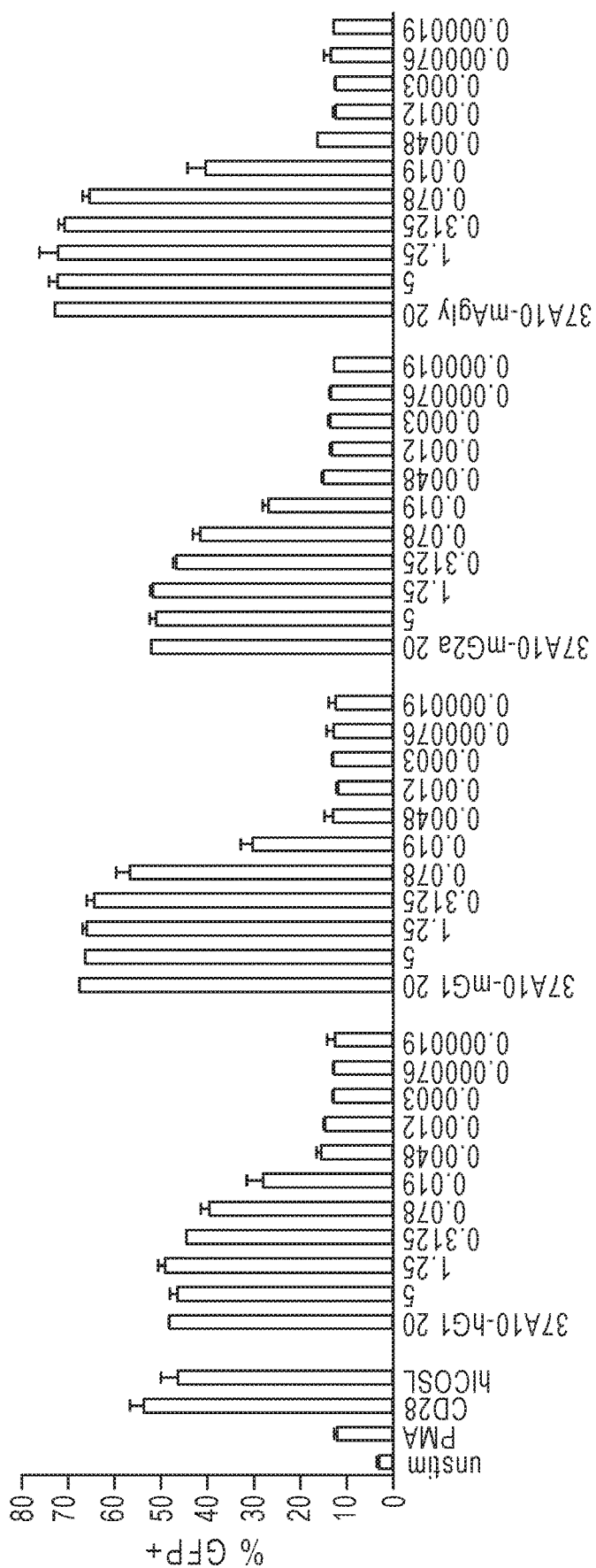
FIG. 11A-B. Evaluation of anti-ICOS antibodies in an NF-kB reporter assay is shown. The graphs show percent GFP+ cells.
Figure 11B:
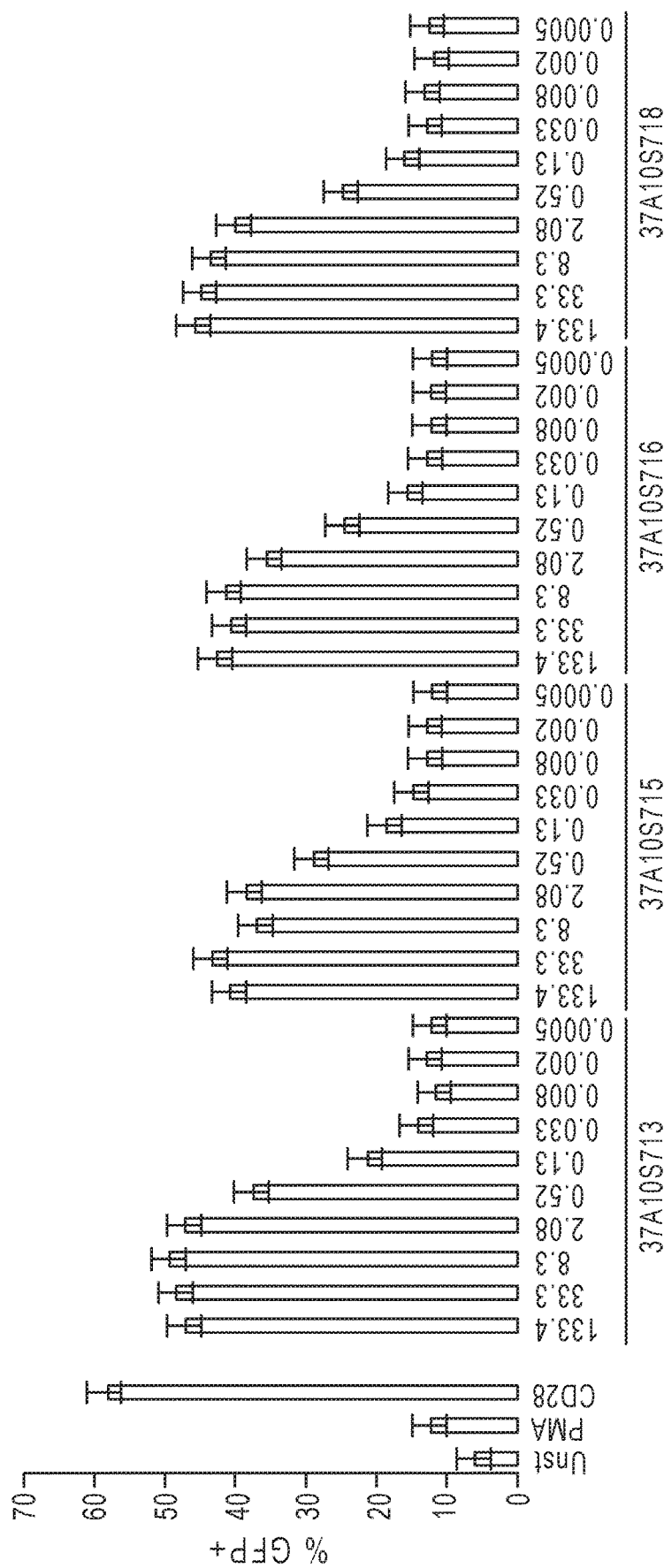

Another example of an assay in which the hamster antibodies demonstrated agonistic activity is the Jurkat reporter assay. A Jurkat reporter assay was developed in-house by transducing a hICOS-hCD28 chimeric expression construct into a Jurkat NFkB reporter cell line. Jurkat-hICOS-hCD28 reporter cells were activated for 5 hours with PMA and soluble hamster anti-ICOS 37A10 antibody with different Fc ends at 11 concentrations (µg/ml). Soluble anti-CD28 and hICOSL-Fc are used as controls. % GFP+ cells is graphed. Representative data from the Jurkat reporter assay using the hamster anti-ICOS antibodies is shown in FIG. 11. FIG. 11A shows the results for different Fc versions of anti-ICOS antibody 37A10 (hG1, mG1, mG2a, mG1Agly) at the indicated concentrations (µg/ml). All Fc versions of the anti-ICOS antibody, including the mG1-agly version (i.e. minimal Fc effector function) shows activity in this assay. FIG. 11B shows the results for humanized antibodies 37A10S713, 37A10S715, 37A10S716, and 37A10S718 at the indicated concentrations (µg/ml). All four humanized antibodies tested showed agonist activity in the assay.

Figure 12:
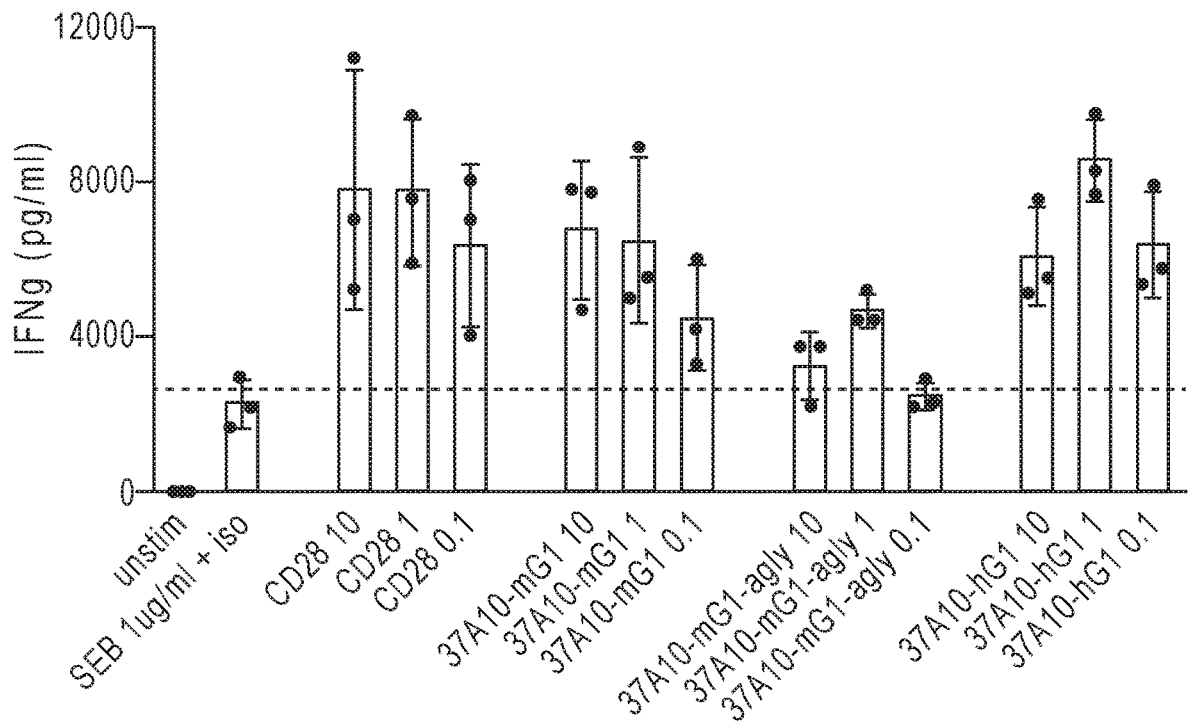
FIG. 12. Evaluation of soluble anti-ICOS antibodies in a PBMC assay with super-antigen (SEB) stimulation is shown. The readout is IFNg production.

Another assay format showing agonistic activity is the PBMC assay with the superantigen staphylococcal enterotoxin B (SEB) using cytokine production (e.g., IFNg) as a readout. This assay typically has a small window of a 1.5-3 fold effect on cytokine release. Consistent with published anti-PD-1 data, cytokine induction with the anti-ICOS antibodies is ~2 fold but is reproducibly observed in this assay across multiple donors. See, e.g., Korman et al., 2014, *Cancer Res.*, 2: 846-856. A representative assay is shown in FIG. 12. Frozen PBMCs from healthy donors were stimulated with SEB and soluble anti-ICOS 37A10 antibody (with mG1, mG1-agly or hG1 Fc) at indicated concentrations (µg/ml) for 3 days. Supernatants were collected and IFNg levels were measured by cytokine bead array using flow cytometry. Anti-CD28 and mouse IgG1 isotype antibodies were used as controls. IFNg is induced by PBMCs following stimulation with SEB in the presence of soluble anti-ICOS antibodies. In this assay format, an mG1-agly version of 37A10 showed reduced activity.

Figure 13:
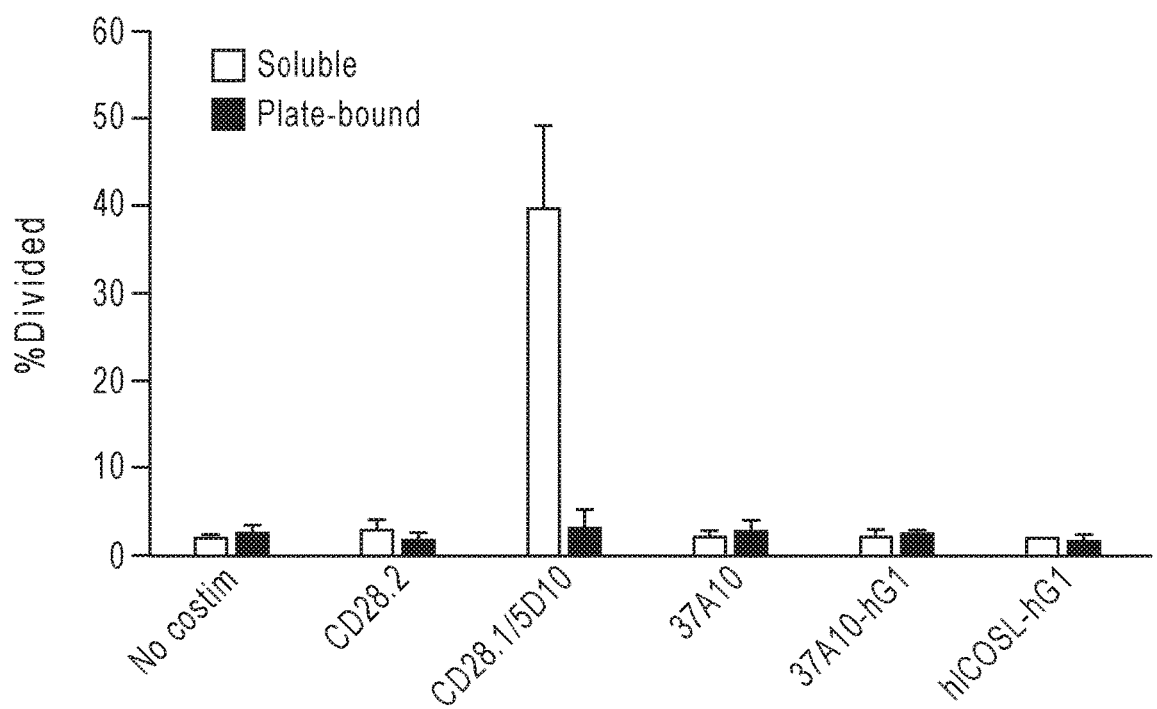
FIG. 13. Anti-ICOS antibodies were evaluated for potential superagonism in a human T cell proliferation assay in the absence anti-CD3. The readout in this assay is percent proliferation.

To screen out any potential super-agonists, an assay in which primary human CD4+ T cells were incubated with soluble or plate-bound anti-ICOS antibodies in the absence of a signal 1 was employed using a known anti-CD28 super-agonist antibody as the positive control. Human CD4 T cells activated in the absence of anti-CD3 will proliferate only when treated with an anti-CD28 superagonist antibody (clone CD28.2/5D10) in soluble form, but not when treated with ICOSL-Fc or anti-ICOS antibody 37A10 (hamster and hG1 Fc versions), or a non-superagonist anti-CD28 (CD28.2) antibody. None of the anti-ICOS mAbs tested exhibited super-agonistic activity in this assay. Representative data is depicted in FIG. 13.

It is well established that ICOS can signal through the AKT signaling pathway (reviewed in Simpson et al., 2010, *Curr. Opin. Immunol.*, 22: 326-332). The ability of the anti-ICOS antibody to induce signaling through AKT was evaluated as an additional means to demonstrate agonistic activity of the antibody.

CD4 T cells isolated from human PBMCs were stimulated for 24 hours with anti-CD3/anti-CD28, and then rested for 24 hours in culture media. Cells were then incubated with anti-ICOS 37A10-mG2a, hICOSL-mG2a Fc or PBS for 2, 5, 15 or 30 minutes with or without anti-mouse IgG cross-linking antibody. Following incubation, cells were fixed, permeabilized and then stained with an anti-phospho-AKT antibody. The percentage of pAKT-positive cells was analyzed by flow cytometry.

Figure 14A:
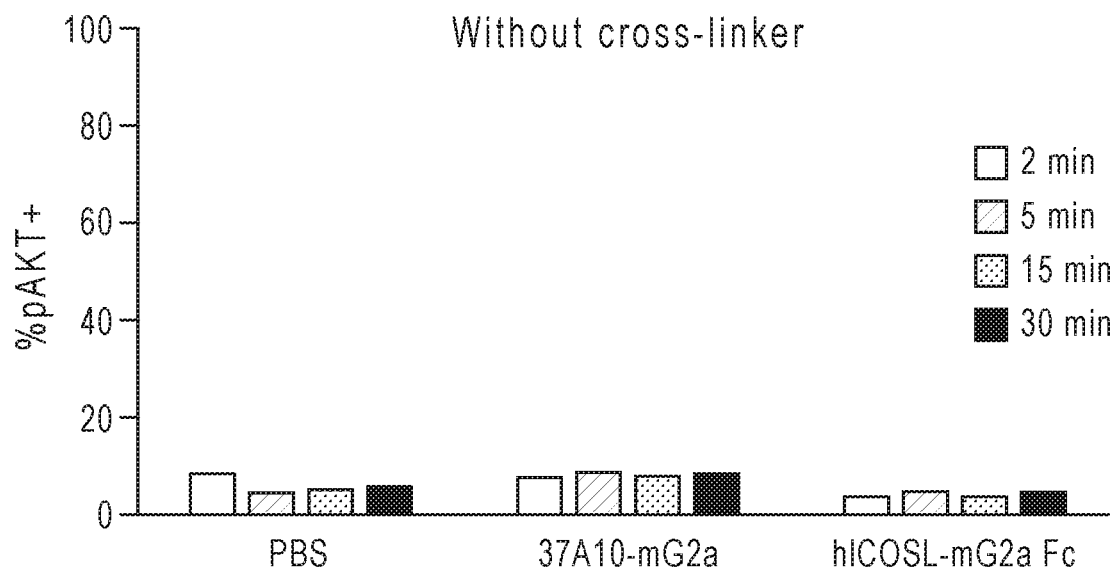
FIG. 14A-B. Evaluation of an anti-ICOS antibody in a phospho-AKT (pAKT) assay in the presence or absence of a secondary cross-linker. The readout is percent of CD4 T cells that are pAKT-positive. A) Results in the absence of secondary cross-linker. B) Results in the presence of secondary cross-linker.
Figure 14B:
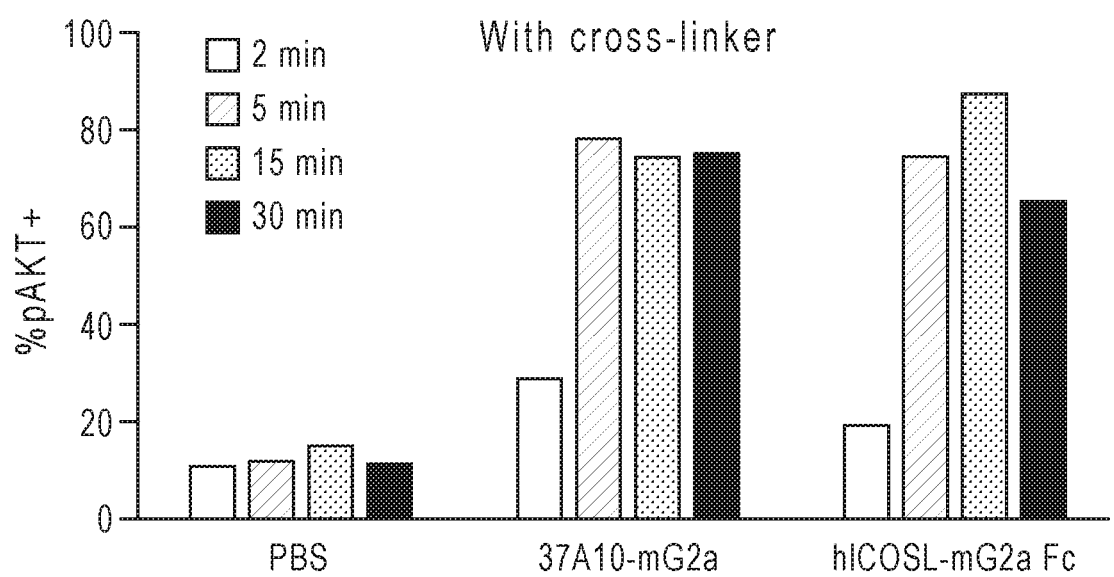

As shown in FIGS. 14A-B, pAKT was induced on CD4 T cells following treatment with 37A10-mG2a with similar kinetics as compared to treatment with hICOSL-mG2a. Induction of pAKT signaling was only observed in the presence of secondary cross-linking agent.

Example 6: In Vivo Functional Characterization of Anti-ICOS Antibodies

Antibodies selected from the screening assays described above were evaluated in vivo using syngeneic tumor models.

The Sa1N fibrosarcoma model (Ostrand-Rosenberg, 2001, *Curr. Protoc. Immunol.*, Chapter 20) may be used for evaluating anti-ICOS antibodies in vivo. Immune profiling of the Sa1/N mouse model shows that it is highly infiltrated with CD4 T cells, and that the CD4 T cells express high levels of ICOS. This immune profile is similar to immune profiles of the NSCLC patient samples in which high levels of CD4 infiltration were observed, with ICOS expression largely restricted to the CD4 compartment.

A second model used for evaluating efficacy of anti-ICOS antibodies is the CT26 colon carcinoma model (Wang et al., 1995, *J. Immunol.*, 9: 4685-4692). Immune profiling of the CT26 mouse model showed high levels of CD8 infiltration. ICOS expression was observed in the CD8 T cell subset in this model. A small proportion of human NSCLC samples similarly show ICOS expression in the CD8 T cells.

Antibody Formats for In Vivo Evaluation

Human IgG1 (hIgG1) can bind across multiple Fc receptors, including strong binding to the activating Fc receptors which are capable of receptor cross-linking and mediating ADCC and CDC. Given the ability to bind the activating Fc receptors, hIgG1 is typically capable of depleting cells that express a high level of target. The closest mouse equivalent to hIgG1 is mouse IgG2a (mIgG2a). Thus, as an example, in vivo experiments to evaluate an ICOS agonist antibody with depleting capacity would utilize mIgG2a to mimic properties of hIgG1.

Human IgG4 (hIgG4) is utilized in therapeutic situations where depletion is not desired, although hIgG4 is capable of some level of depletion. It is roughly, although not perfectly, aligned to mouse IgG1 (mIgG1), which almost exclusively binds the inhibitory FcγRII receptors, and is thus capable of cross-linking but not particularly competent at depletion.

Regarding the anti-ICOS antibodies, the hamster antibodies were initially evaluated in vivo as fully hamster Abs. The hamster Abs have a hamster IgG1, which has FcR binding characteristics similar to mIgG1. Hamster antibodies of interest were cloned as chimeras with mouse Fc regions, either as mIgG2a or mIgG1.

Sa1N Fibrosarcoma Model

Figure 15A:
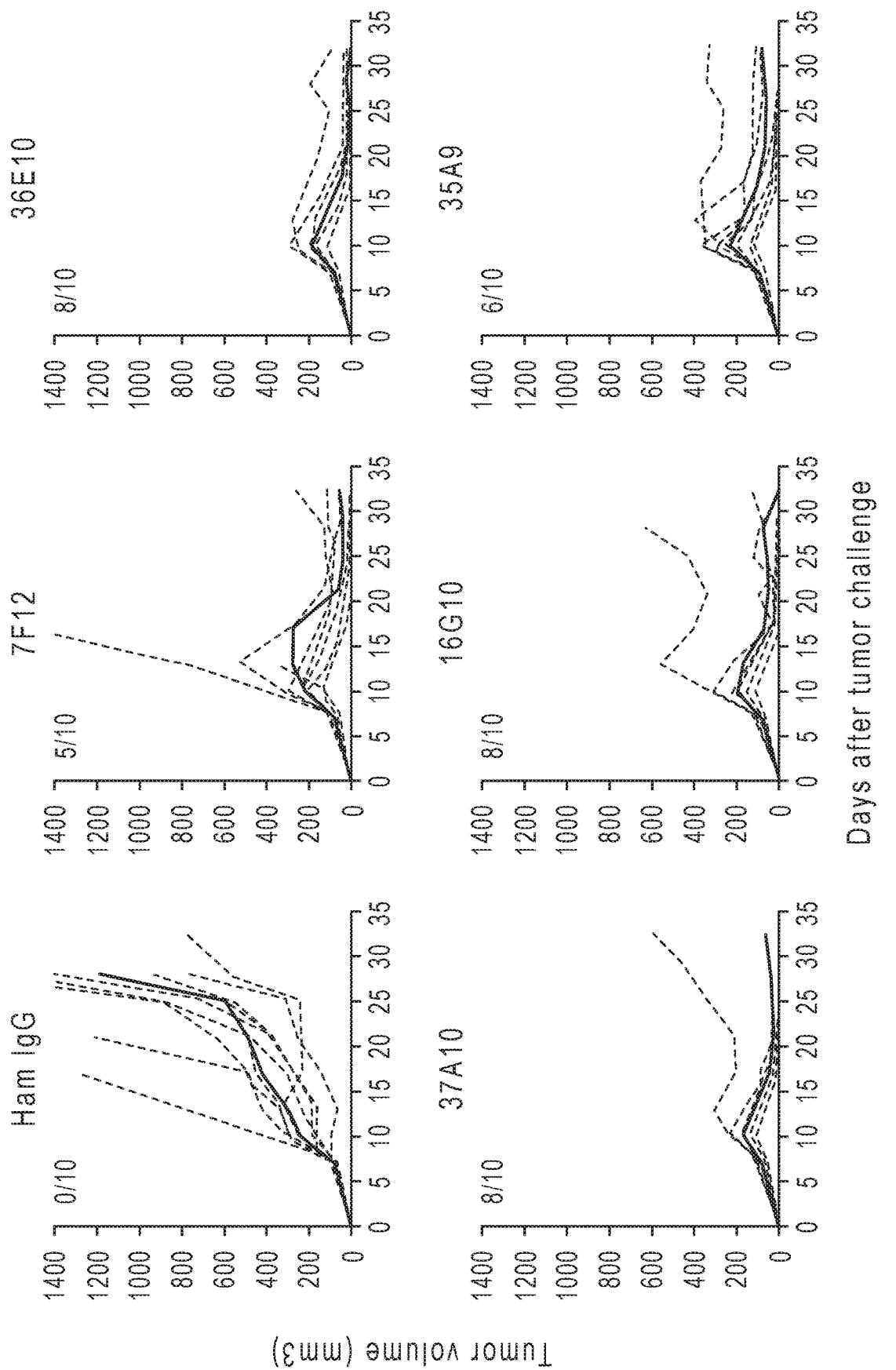
FIG. 15A-B. Anti-ICOS antibodies were evaluated in the Sa1/N fibrosarcoma syngeneic tumor model. Tumor growth is plotted on the y-axis. A) Dashed lines indicate tumor growth of individual mice; solid line indicates average growth curve for the group. Number of tumor-free mice per group is indicated. B) Average tumor volume in each treatment group.
Figure 15B:
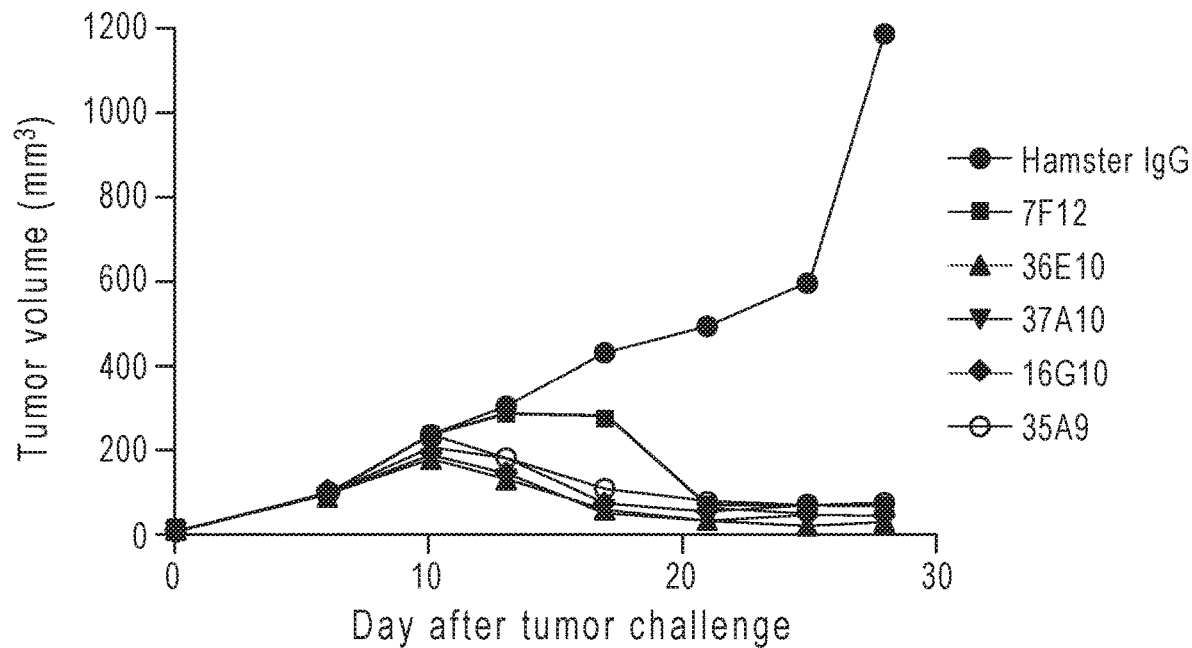

The primary in vivo model used for screening anti-ICOS antibody candidates for efficacy is the Sa1N fibrosarcoma model. Thus, antibodies selected from the screening assays described above were assessed in the Sa1N model. In initial studies, several hamster antibodies (clones 7F12, 36E10, 37A10, 16G10 and 35A9) demonstrated robust anti-tumor activity when administered as single agents at an 8 mg/kg dose in the Sa1N model. See FIG. 15. Sa1N fibrosarcoma cells ($1\times10^6$) were injected s.c. to right flank of naïve A/J mice (6-8 weeks old, female). When tumor volumes reached 50-100 mm³ on day 7, mice were randomized. Mice received dose of hamster anti-ICOS (7F12, 36E10, 37A10, 16G10 and 35A9) or hamster IgG isotype antibody i.p. on days 7, 10, 14 and 17. Tumor growth was monitored twice weekly. N=10.

Figure 16:
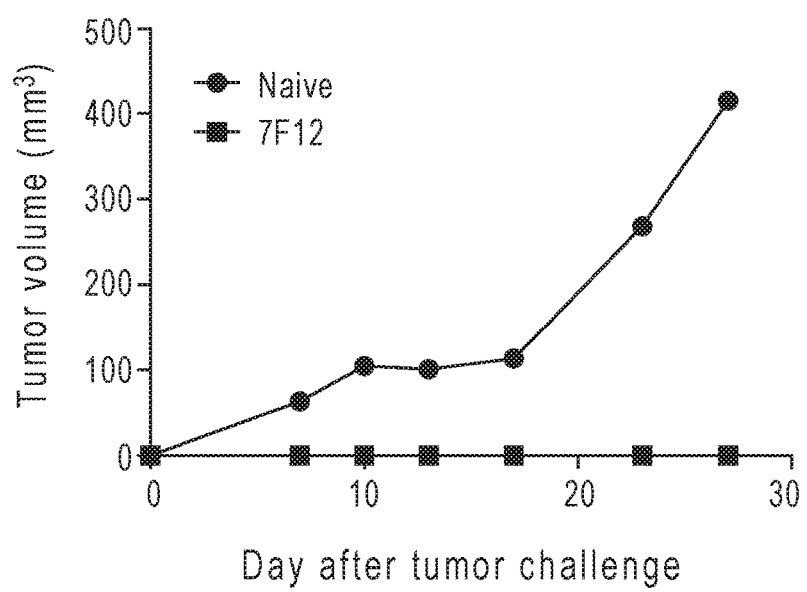
FIG. 16. Tumor-free mice previously treated with anti-ICOS 7F12 were re-challenged with Sa1/N tumors Tumor growth is plotted on the y-axis.

A potentially beneficial feature of a cancer immunotherapeutic is the ability to mount a sustained and durable immune response against the tumor. The ability of a mouse previously treated with an anti-ICOS antibody to subsequently reject a tumor was determined. Mice were treated at 8 mg/kg antibody on day 7, 10, 14, and 17. Subsequently, mice that were tumor-free were then re-implanted with a tumor on day 60. All of the mice pre-treated with anti-ICOS antibody 7F12 (n=7) rejected the newly implanted tumor, in contrast to naïve mice (n=10) in which tumors grew out in all of the mice. See FIG. 16.

Figure 17:
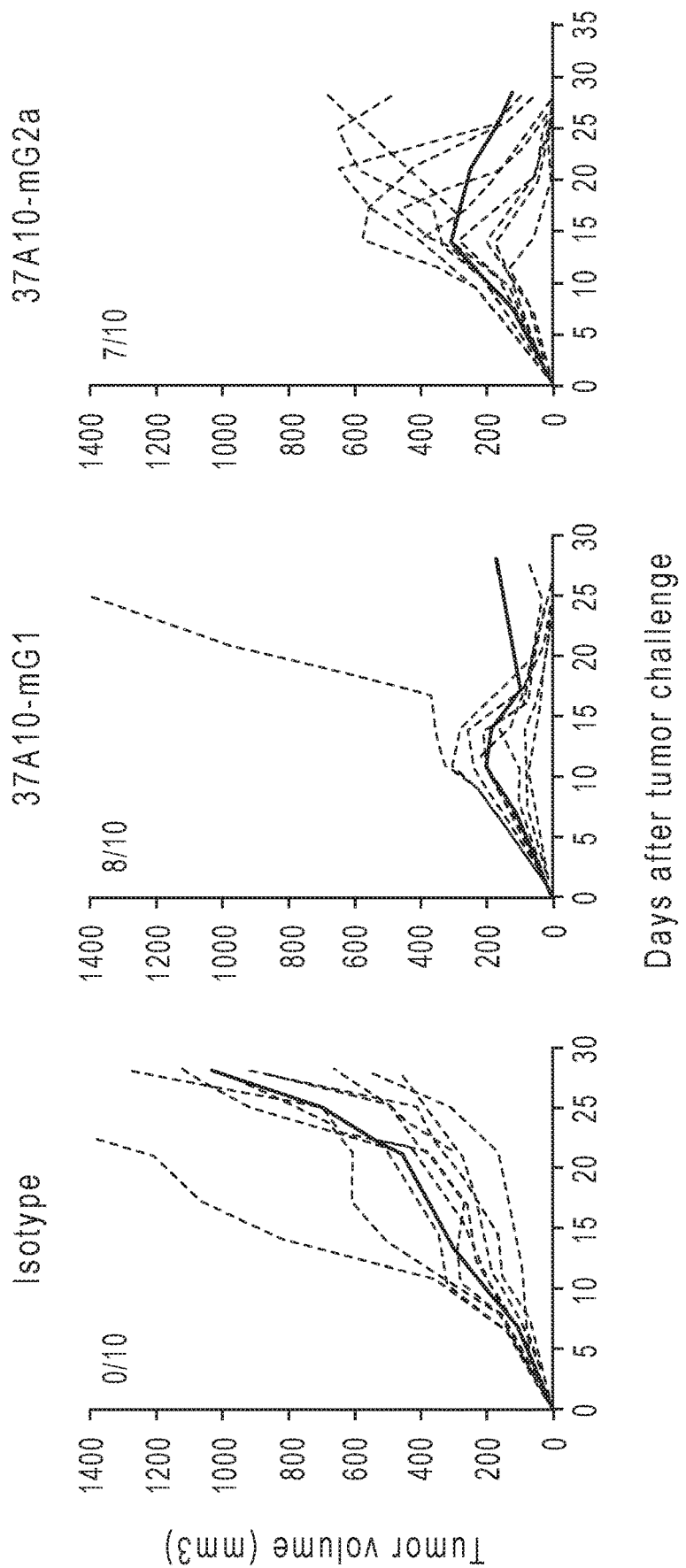
FIG. 17. Effect of hamster anti-ICOS antibody 37A10 with mG1 and mG2a Fc on Sa1/N tumor growth. Dashed lines indicate individual tumor growth of individual mice; solid line indicates average tumor growth curve for the group. Number of tumor-free mice per group is indicated.

The hamster antibodies were cloned as chimeric antibodies with mouse Fc regions (mG1 or mG2a) to enable assessment of the contribution of Fc effector function to in vivo activity. Mice received a total of 4 doses biweekly of 4 mg/kg antibody starting on day 11. Anti-CTLA-4 antibody was included as a positive control. The initial screening experiment was performed at a dose of 4 mg/kg dose, and efficacy was observed with both the mG1 and mG2a formats. Representative data for one of the hamster antibodies, 37A10, is shown in FIG. 17.

Colon CT26 Syngeneic Tumor Model

The colon CT26 syngeneic tumor model was used both to assess single agent activity, as well as combination therapy with anti-PD-1 antibody.

Figure 18:
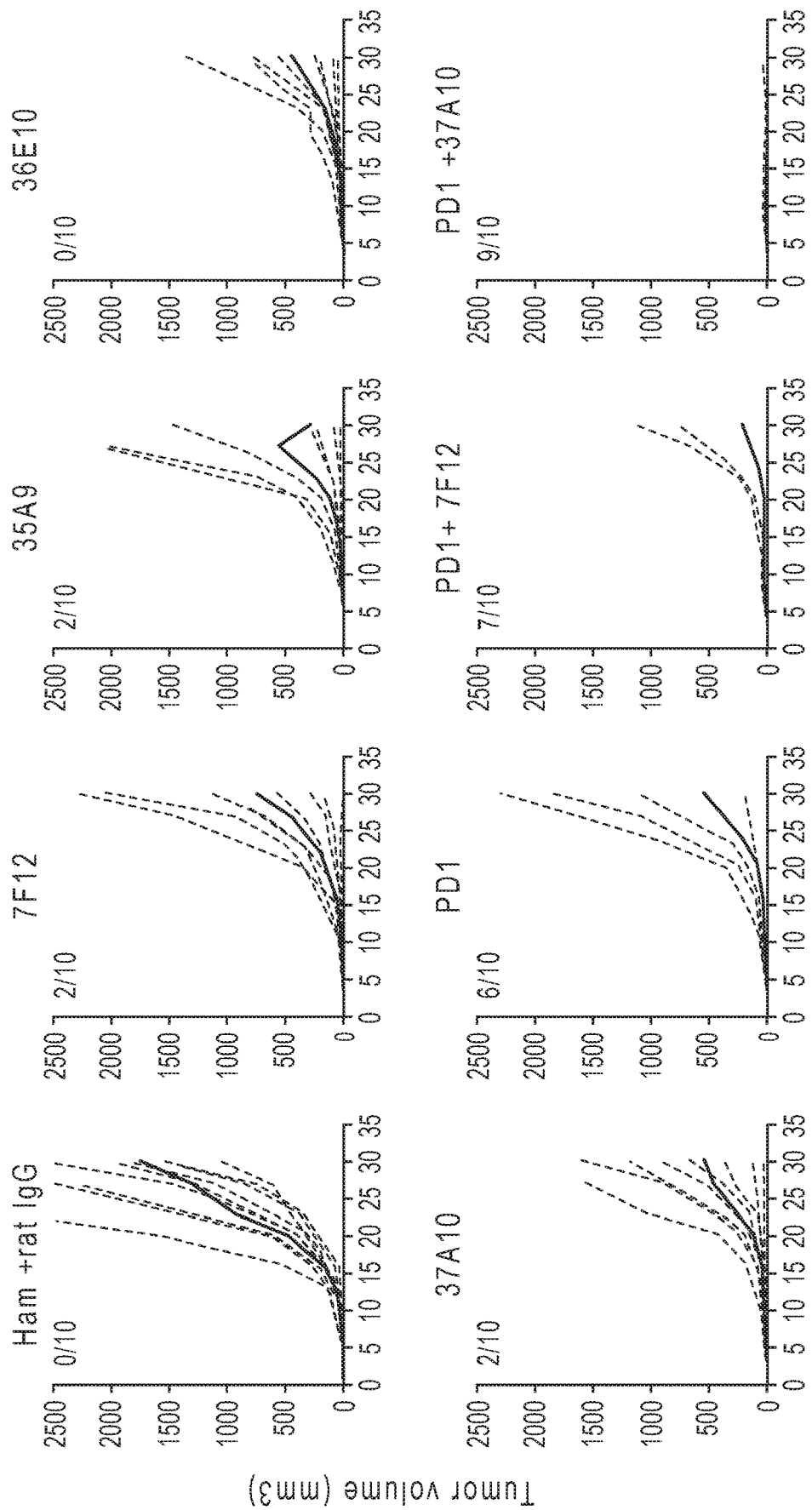
FIG. 18. Evaluation of anti-ICOS antibodies as single agents or in combination with anti-PD1 in the CT26 syngeneic tumor model. Dashed lines indicate individual mice; solid line indicates average growth curve for the group. Number of tumor-free mice per group is indicated.

In the CT26 model, several of the anti-ICOS hamster antibodies (e.g., 7F12, 35A9, 36E10, 37A10) exhibited single agent activity. See FIG. 18. The CT26 model was also used to assess potential combination activity with anti-PD-1. When the anti-ICOS antibodies were combined with an anti-PD-1 antibody, anti-tumor efficacy was markedly enhanced. CT26 tumor-bearing mice were treated biweekly (4 doses starting on day 3) with hamster anti-ICOS antibodies (8 mg/kg) alone or in combination with anti-PD-1 antibody (8 mg/kg). Notably, combination of anti-PD-1 with anti-ICOS antibody 37A10 resulted in 9/10 mice tumor free. See FIG. 18.

Example 7: Selective Treg Depletion Contributes to Anti-ICOS Antibody Efficacy

Figure 19:
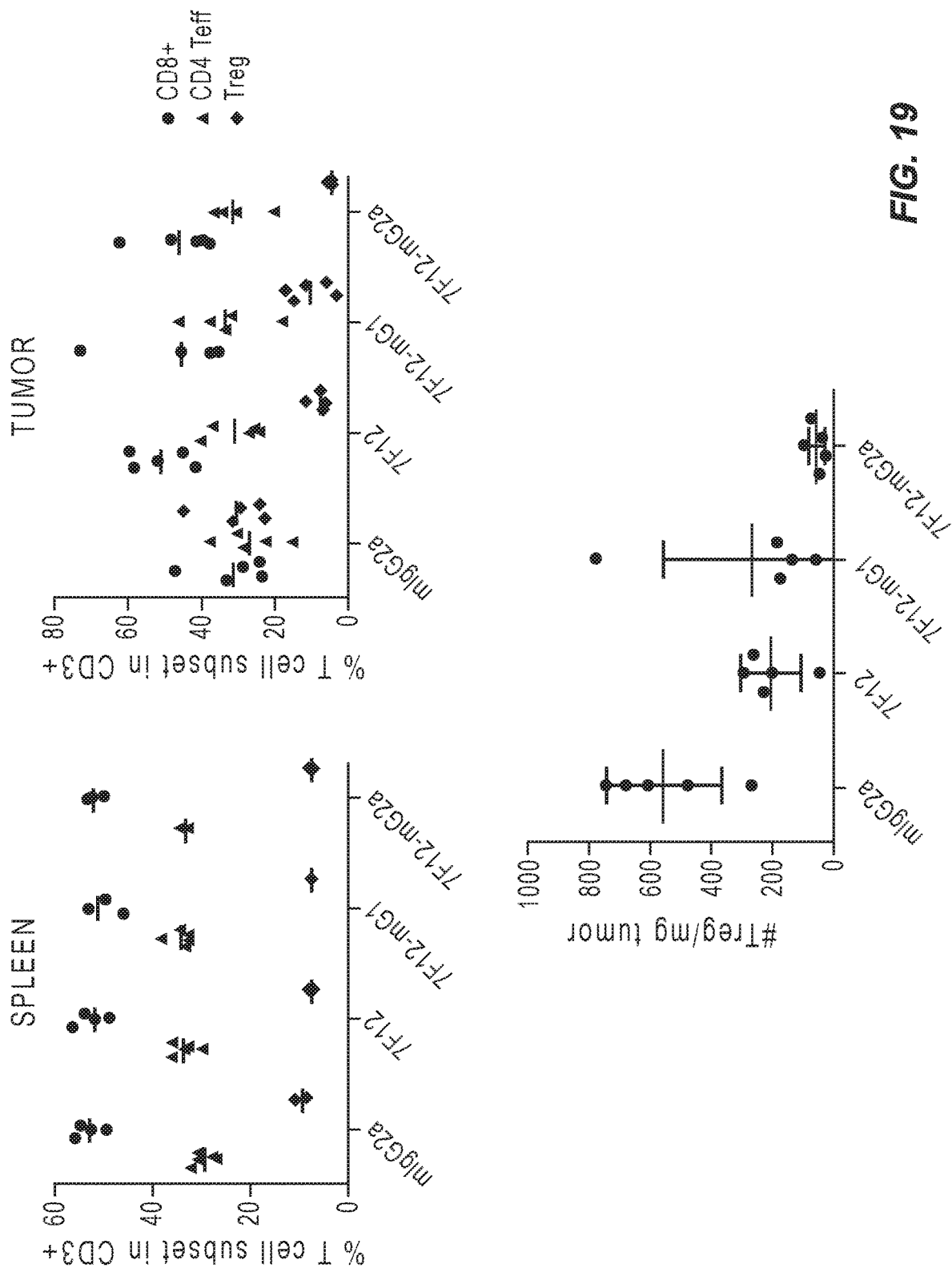
FIG. 19. Depletion of FoxP3+ Tregs in Sa1/N tumors upon anti-ICOS antibody treatment. Frequency of CD8, CD4 Teff and Treg cells in spleen and tumor, and number of Tregs per mg of tumor is shown. Each shape indicates an individual mouse.

Ex vivo studies were performed to characterize the status of immune cell infiltrates following dosing with anti-ICOS antibodies. Studies in the Sa1N model showed a decrease in the Treg population following treatment with 7F12. Mice received two doses of anti-ICOS hamster 7F12, 7F12-mG1 or 7F12-mG2a at 8 mg/kg on days 7 and 10. Tumors and spleens were harvested and analyzed on day 12. There was a marked reduction in Tregs but not in Teff cells, but little impact on T cell populations in lymphoid organs such as the spleen or lymph node. See FIG. 19.

Figure 20:
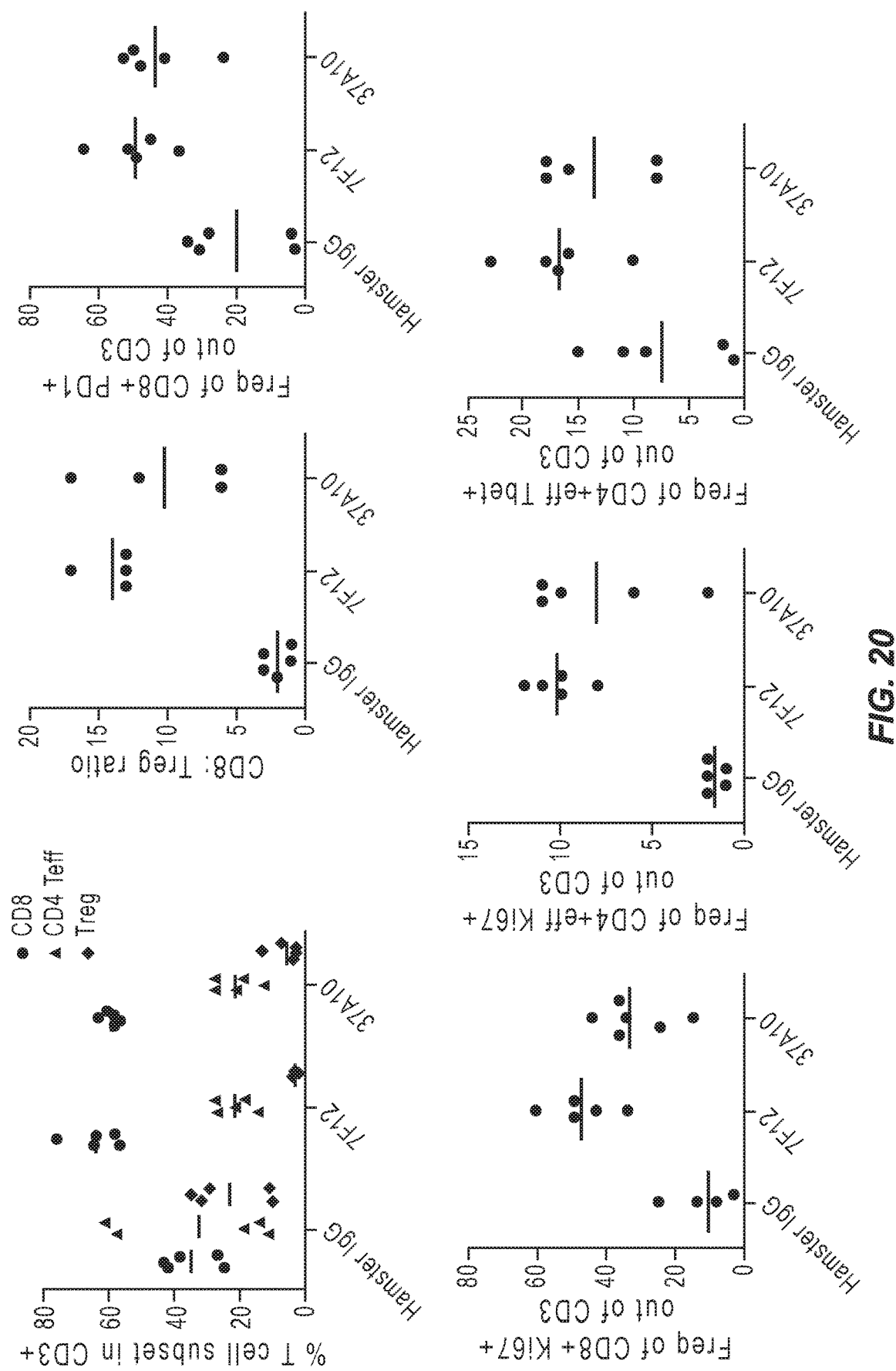
FIG. 20. Depletion of Tregs and activation of Teff cells in Sa1/N tumors upon anti-ICOS antibody treatment. Top row: Frequency of CD8, CD4 Teff and Treg cells, CD8 to Treg ratio and frequency of PD-1+ CD8 T cells in tumors. Bottom row: Frequency of dividing Ki-67+ CD8 and CD4 Teff cells, and Tbet+ CD4 Teff cells among CD3+ cells in tumors. Each shape indicates an individual mouse.

Similar results have also been observed with other anti-ICOS antibodies, such as 37A10. See FIG. 20. Mice received two doses of anti-ICOS antibodies at 8 mg/kg on days 7 and 10. Tumors were harvested and analyzed on day 12. A similar reduction in the Treg population has also been observed in the CT26 model following dosing with the anti-ICOS antibody.

Taken together, the TIL (tumor-infiltrating lymphocytes) studies support the hypothesis that Treg cells are selectively depleted by the anti-ICOS antibodies described herein, without corresponding depletion of Teff cell populations, and specifically in tumors but not in other organs or in the periphery.

To formally demonstrate the contribution of the immune system to efficacy of the anti-ICOS antibody, cell depletion experiments were performed in the context of the tumor model, Sa1N. Specifically, mice were depleted of CD8 T cells, CD4 T cells, or a combination of CD4+ CD8 T cells. At days 6 and 13 post-tumor implantation, mice were treated with anti-CD8, anti-CD4, anti-CD4+ anti-CD8 or control Ig antibody (n=10 per group). Anti-ICOS antibody 7F12 was administered at 8 mg/kg antibody on day 7, 10, 14, and 17. Tumor growth was monitored twice weekly.

Figure 21:
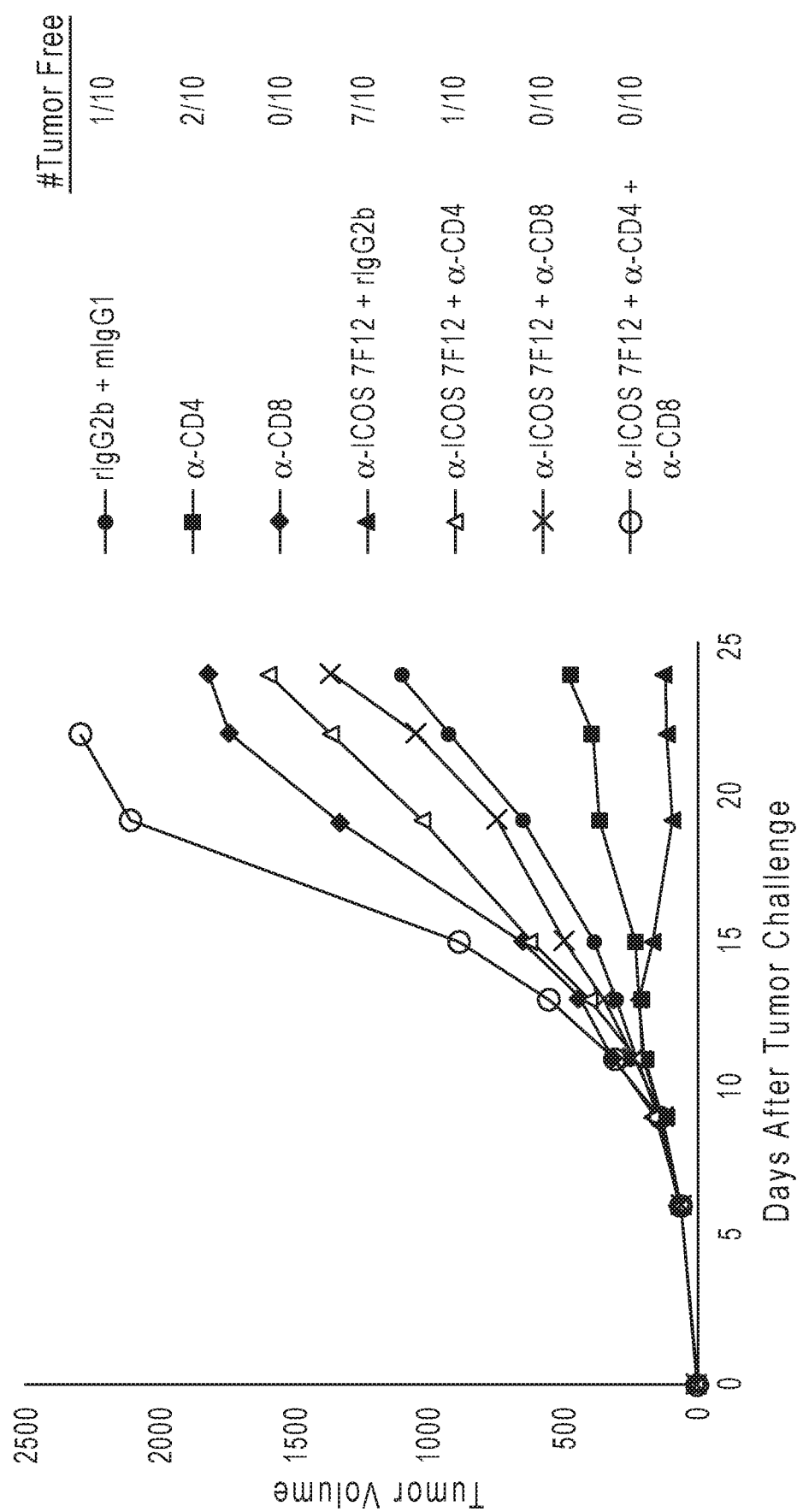
FIG. 21. Evaluation of an anti-ICOS antibody in the Sa1/N tumor model following depletion of T cells. Tumor growth over time is plotted. Number of tumor free mice is indicated.

A marked reduction in anti-tumor efficacy of 7F12 was observed when mice were depleted of CD4, CD8, or CD4+ CD8 T cells. See FIG. 21.

Example 8: Selective Treg Reduction by Humanized Anti-ICOS Antibody

Human PBMCs were incubated at 37° C. with 100 ng/ml recombinant human IL-2 for 48 hours in a humidified incubator with 5% $CO_2$. After 48 hours, antibody 37A10S713 was added at the indicated concentrations. Antibody was prepared as 10-fold serial dilutions in culture media containing IL-2. The antibody/cell mixture was allowed to incubate an additional 72 hours. Following incubation, cells were stained for CD3, CD4, CD8, CD25, and FoxP3 per standard methods and analyzed by flow cytometry. Quantification of Treg (CD4+ CD25+ FoxP3+) and Teff (CD4+ CD25− FoxP3−) cells was carried out for each concentration and treatment. Data were normalized to percent of each subset in a trastuzumab-treated group for each concentration.

Figure 22A:
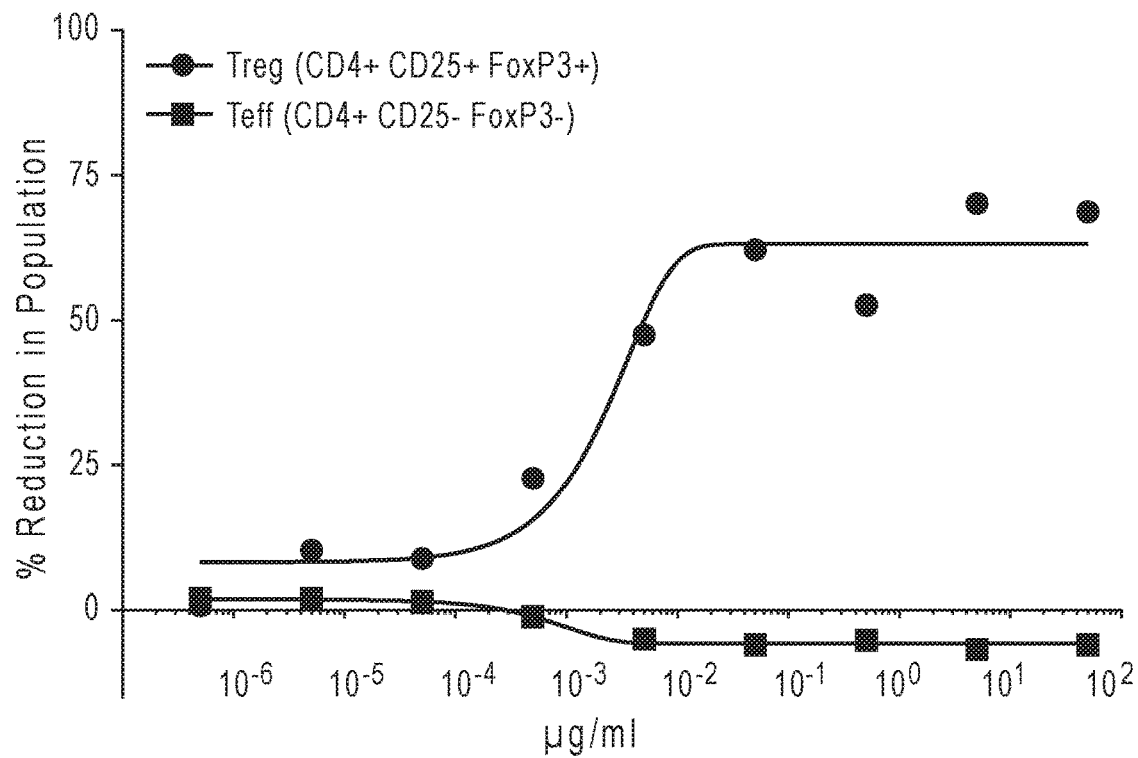
FIG. 22A-B. A) Reduction of Tegs cells in a PBMC assay upon treatment with a humanized anti-ICOS antibody. B) Treg and Teff cells express similar levels of ICOS following five days of IL-2 treatment.
Figure 22B:
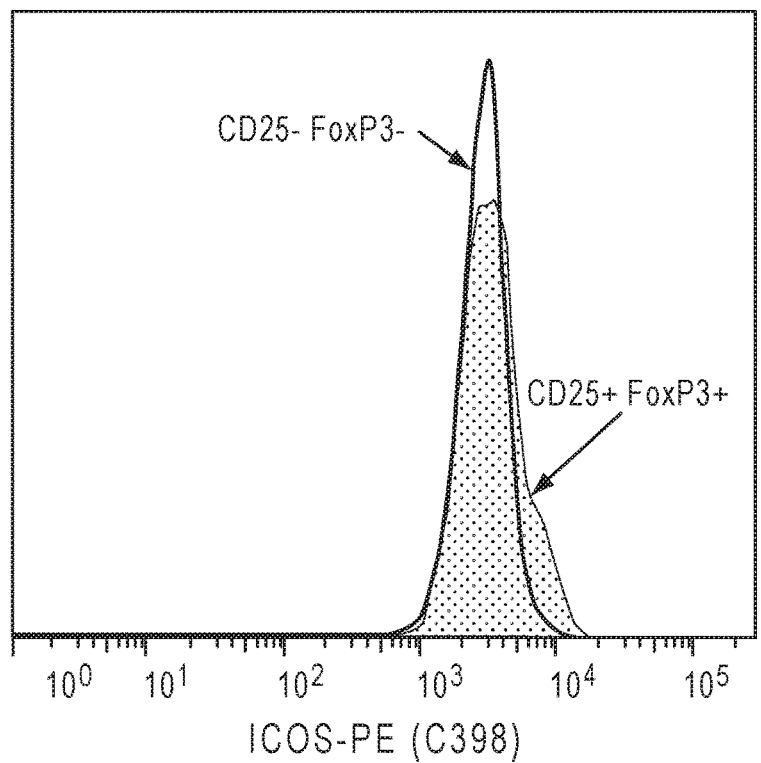

The results of that experiment are shown in FIG. 22A. Antibody 37A10S713 caused a dose-dependent reduction of Treg cells. As shown in FIG. 22B, Teff and Treg cells expressed similar levels of ICOS after five days of IL-2 treatment.

Example 9: Tumor Re-Challenge Following Treatment with Anti-ICOS Antibody

Six to eight week old female A/J mice were inoculated subcutaneously on the right flank with 1×10⁶ Sa1/N cells in 100 µl PBS using tuberculin syringes with 27-gauge needles. Tumor growth was monitored and on day 7, animals were redistributed into new cages after normalizing the average tumor volume to 100-150 mm³ for each treatment group. Ten mice were included in each treatment group. Animals were treated with antibodies via intraperitoneal injections of 0.25 mg/kg anti-ICOS antibody (37A10S713 VH and VL (SEQ ID NOs: 60 and 61) with a mouse IgG2a) or an isotype control. Dosing was performed on day 7 for single dose or days 7 and 14 for 2 doses. Tumor growth and animal body weights were monitored twice weekly. Mice were sacrificed when tumor volumes reached ~2000 mm³ or if there were signs of clinical distress such as severe ulcerations as pursuant to IACUC protocol.

Figure 23:
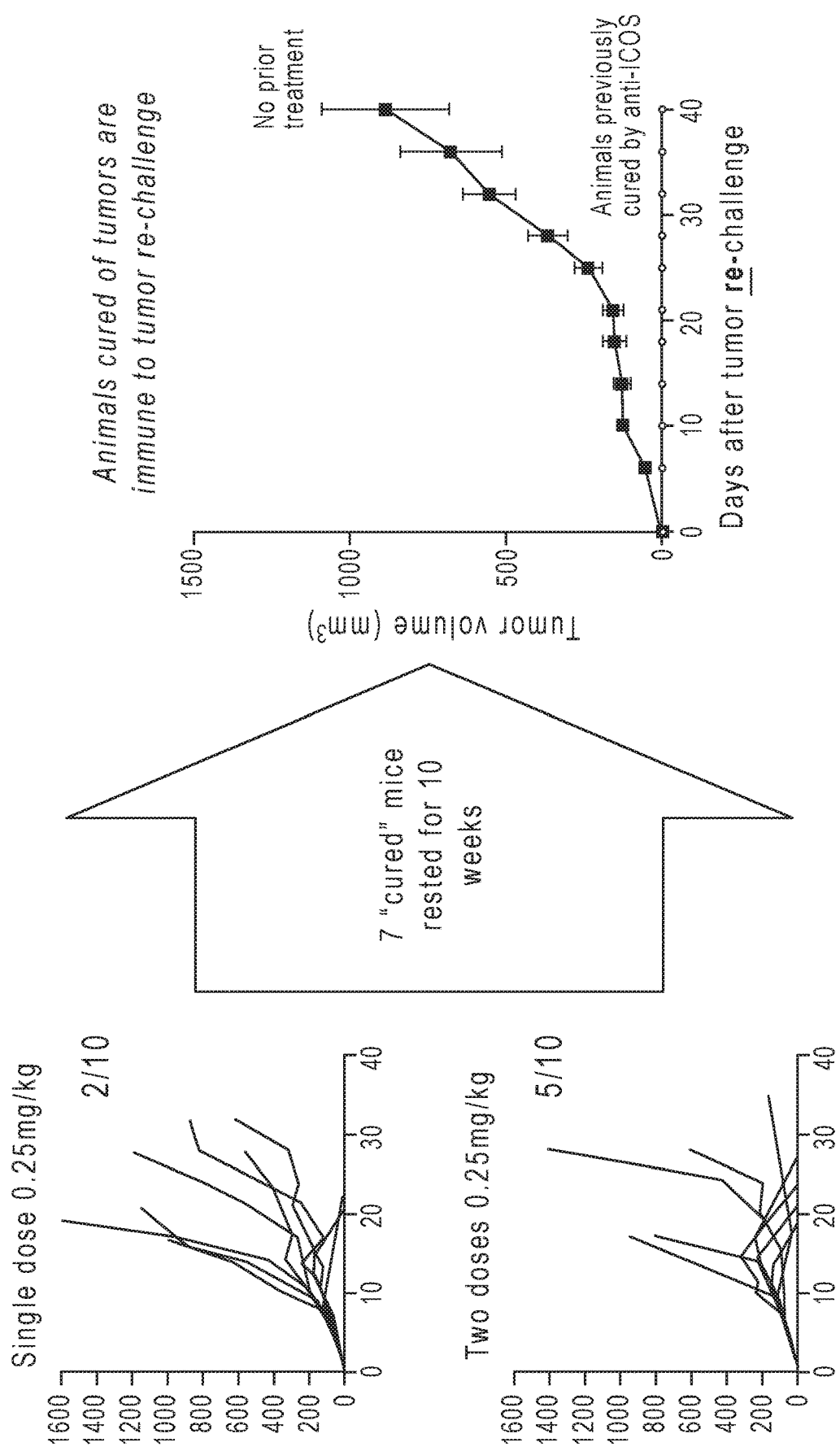
FIG. 23. Tumor re-challenge following treatment with anti-ICOS antibody. Left panel shows tumor volume in mice following administration of one or two doses of anti-ICOS antibody. Right panel shows tumor volume in control mice or mice that were tumor free following administration of anti-ICOS antibody, following tumor re-challenge.

FIG. 23, left panel, shows tumor volume in mice administered a single dose of anti-ICOS antibody (n=10) or two doses of anti-ICOS antibody (n=10).

A tumor re-challenge experiment was performed to assess durability of the response. The 7 mice previously challenged with Sa1/N cells whose tumors were eradicated with a single dose or two doses of 0.25 mg/kg 37A10S713-mIgG2a antibody were re-challenged on the contralateral flank with Sa1/N cells 10 weeks after the initial tumor challenge. As a control, naïve mice were also challenged with Sa1/N cells (N=10). Animals were assessed for tumor growth on a bi-weekly basis.

As shown in FIG. 23, right panel, none of the mice that had previously had their tumors eradicated with anti-ICOS antibody treatment showed tumor growth in the re-challenge experiment.

Example 10: ICOS Ligand (ICOSL) Expression in Sa1/N Tumor-Bearing Mice and Cynomolgus Monkeys Administered Anti-ICOS Antibody Eight week old female A/J mice were inoculated with Sa1/N tumor cells at day zero. At day 7, when tumors reached ~100 mm³, mice were administered a single 5 or 100 µg i.p. dose of antibody 37A10 with either a mouse IgG1 or IgG2a, or isotype control antibody. Mice were administered a subsequent dose of antibody on day 10, and tissue (blood, spleen, and tumor) were harvested at day 12. Following tissue processing, cells were incubated with 5% Fc block (5% reconstituted normal rat, mouse and human serum, 5% Fetal Calf Serum, 0.1 mg/mL Fc blocking Ab 2.4G2, 0.01% sodium azide) for 15 min on ice in flow staining buffer (FSB: 5% FBS, 0.01% sodium azide in 1×PBS). Following Fc block, cells were stained with an extracellular staining cocktail (anti-CD45-BV510, anti-CD19-BV605, anti-ICOSL-PE, Fixable Viability Dye eFluor 780) in FSB for 1 hr on ice. Cells were washed twice with FSB. Cells were fixed with Fixation/Permeabilization solution for 30 min on ice. Cells were washed twice with 1× Permeabilization Buffer, then stained with an intracellular staining cocktail (anti-CD3-BUV496, in Permeabilization Buffer for 1 hr on ice. Cells were washed twice with Permeabilization Buffer, then re-suspended in 1.5% PFA FSB solution. Cells were run on the BD Fortessa and data was analyzed using FlowJo software.

Samples were analyzed on a BD Fortessa flow cytometer. For analysis of ICOSL expression, staining of ICOSL was analyzed on viable CD45+ CD3− CD19+ B cells. ICOSL mean fluorescent intensities (MFIs) are reported.

Antibody 37A10S713 with a human IgG1 was administered via 1 hour intravenous infusion to three cynolmolgus monkeys per dose group (0.5 mg/kg, 5 mg/kg, 75 mg/kg, and vehicle alone). Blood was obtained pre-first dose (day 1), 48 hours post-first dose (day 3), 7 days post-first dose (pre-second dose; day 8), and 48 hours post-second dose (day 10). 95 µL samples of whole blood were first Fc blocked with 5 µL Human TruStain for 15 min on ice. Following Fc block, 100 µL of an antibody mix containing anti-CD3 FITC, anti-CD20 PE, anti-CD14 PE/Cy7, viability dye e780, and cynoICOS-Fc DyLight 650 was added. Blood and antibody mix was incubated on ice for 60 min. Following incubation, samples were centrifuged at 500×g for 5 min. Supernatant was decanted, and samples were resuspended in 200 µL of FACS staining buffer. Wash steps were repeated three times, with final resuspension in 200 µL staining buffer+0.1% paraformaldehyde.

Samples were analyzed on a BD Fortessa flow cytometer. For analysis of ICOSL expression, staining of ICOSL by DyLight 650 labeled cynoICOS-Fc was analyzed on viable CD3− CD20+ B cells. ICOSL MFIs were normalized to vehicle at each time point.

Figure 24A:
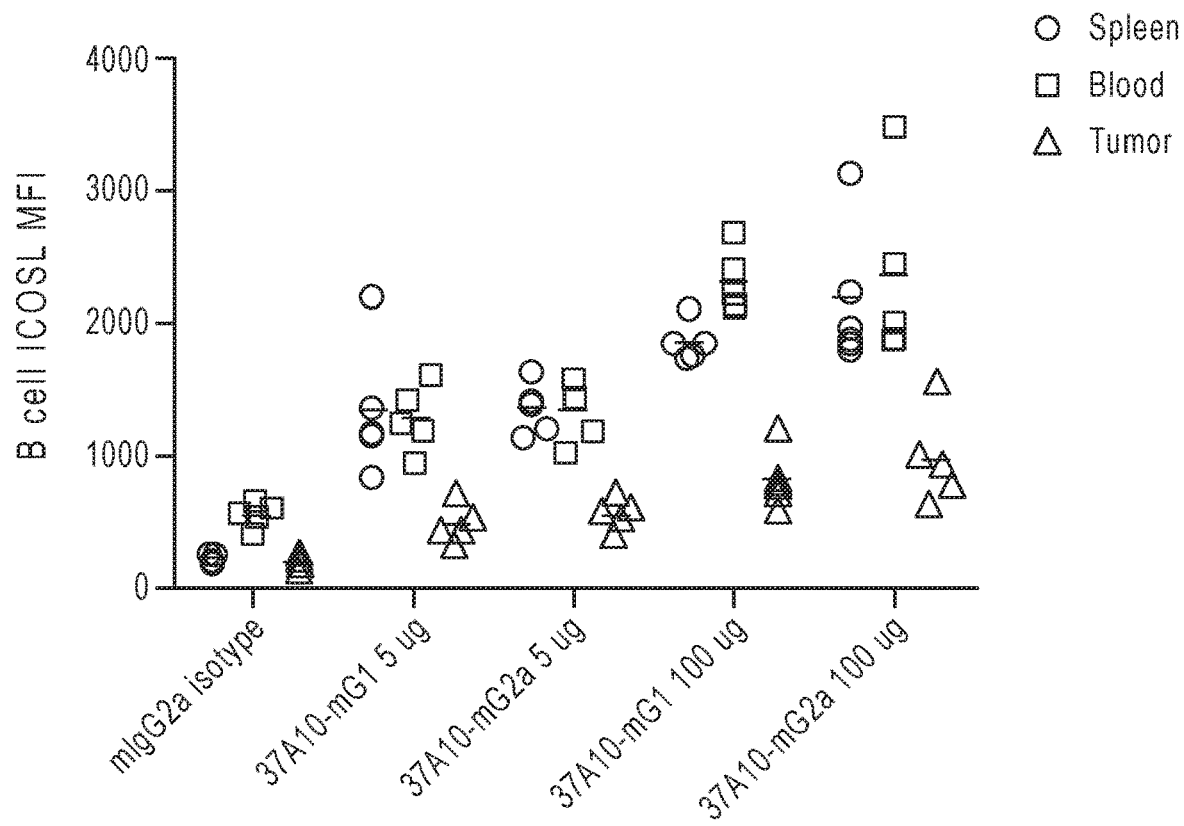
FIG. 24A-B. Increase in ICOSL expression in Sa1/N tumor bearing mice (A) and cynomolgus monkeys (B) administered anti-ICOS antibody.
Figure 24B:
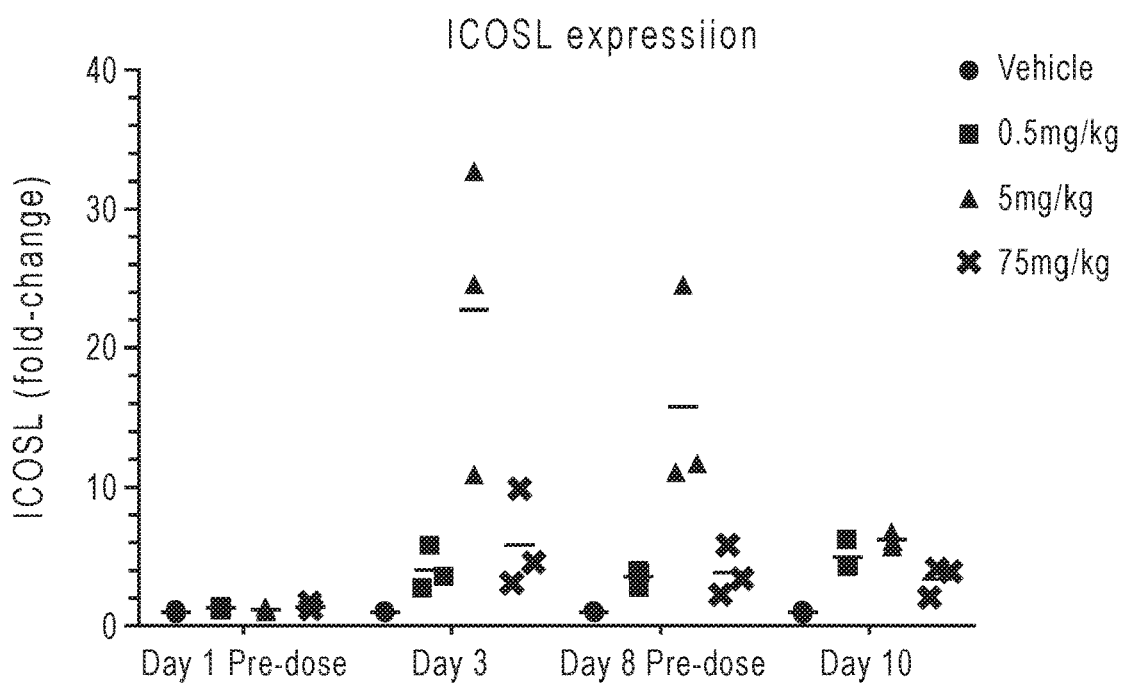

The results of those experiments are shown in FIGS. 24A and 24B. A dose-dependent increase in ICOS-L expression was observed across all antibody treatments and doses and in all tissues relative to isotype control treated mice. See FIG. 24A. Similarly, a dose-dependent increase in ICOS-L expression was observed across all time points for the 0.5 and 5 mg/kg dose groups in cynomolgus monkeys relative to vehicle and pre-study samples. See FIG. 24B. Induction of ICOSL was also observed in the 75 mg/kg group, but the observed expression may be an underrepresentation due to potential drug interference as the anti-ICOS antibody is capable of binding the staining reagent (cynoICOS-Fc).

ICOS target engagement may also be assessed as measured by receptor availability assay, for example, as follows. Naive mice were i.p. injected with either the isotype control mIgG2a at 2.5 mg/kg or 37A10S713 with a mouse IgG2a at 2.5 mg/kg. At various time-points post-injection, blood was collected in EDTA coated microtubes via submandibular draw.

Whole blood was Fc blocked using mouse TruStain (BioLegend) for 5 minutes on ice. Following incubation, 100 µl of 2× concentrated extracellular staining antibody mixture was added to each sample for 30 minutes at 4° C. Samples were spun down and fixed and permeabilized in Foxp3 staining buffer (eBioSciences) for 30 minutes at 4° C. Samples were then spun down and resuspended in intracellular antibody stain for 30 minutes at 4° C. Samples were spun down and resuspended in 0.1% PFA. Samples were analyzed on a BD LSRII Fortessa. Tregs were identified as live CD45+ CD3+ CD4+ Foxp3+. Teff cells were identified as live CD45+ CD3+ CD4+ Foxp3−. CD8+ cells were identified as live CD45+ CD3+ CD8+. Fluorescently labeled 37A10S713-mG2a (DyLight 650 conjugated) was used as the staining reagent for ICOS. Receptor availability at each time point was determined using the following formula:

% Receptor Available at time $t$=((MFI of 37$A$10S713−$mG2aDy$650 at time $t$−MFI of isotype$Dy$650 at time $t$))/((MFI of 37$A$10S713−$mG2aDy$650 prestudy−MFI of isotype$Dy$650 prestudy))×100

Results showed that following administration of anti-ICOS antibodies, the levels of free receptor are undetectable, suggesting antibodies saturate all available target ICOS molecules.

Example 11: Identification of Genes Correlating with ICOS Expression

The level of ICOS across various tumor types was assessed at both the mRNA and the protein level. To specifically quantify ICOS levels across patient tumor samples, a novel RNA signature based approach was used. Analysis of high-dimensional gene expression was performed to define the immune component of tumors in an unbiased manner, using the high-dimensional data set from The Cancer Genome Atlas (TCGA) that include DNA mutational data, gene-expression data and gene-amplification data from ~7,500 human tumors representing 24 different indications. Raw sequence data was prepared and gene expression values utilizing the fragments per kilobase of exon per million fragments mapped (FPKM) were computed by OmicSoft Corporation utilizing their proprietary data normalization and expression analysis pipeline. All the FPKM values were converted using a logarithmic function with a base 2 and analyzed. Before using the data for discovery of immune related signatures, the quality of the data was assessed using known biological patterns. For example, estrogen receptor expression was associated with the first principal component of the breast data, while microsatellite instability related signatures was associated with the third principal component of the colon data.

Figure 25:
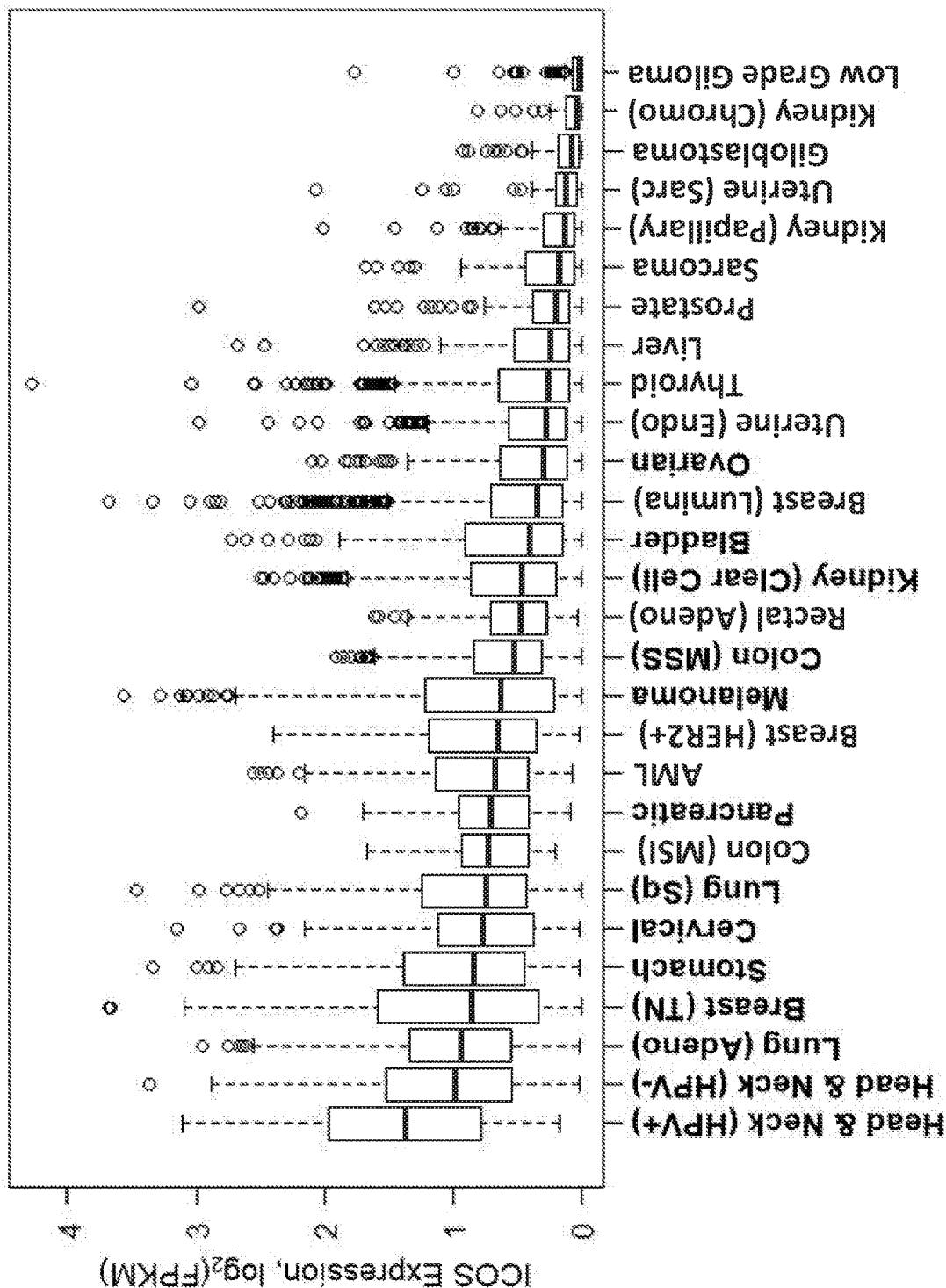
FIG. 25. Box plot of the analysis of ICOS expression across TCGA human tumor indications. Boxes indicate the upper and lower quartiles of expression, with the median line being shown. Outliers are plotted for any tumor in which ICOS expression expressed at a level that is more than the interquartile range outside of the upper or lower quartile. Indications shown in bold were selected for follow-up analysis to identify genes associated with ICOS expression. Expression is shown as $\log_2(FPKM)$.

To identify a multigene signature to quantify the degree of ICOS expression in tumors, indications in which ICOS was overexpressed with a high coefficient of variance were first identified. FIG. 25 shows the results of the analysis of ICOS expression across TCGA human tumor indications. Boxes indicate the upper and lower quartiles of expression, with the median line being shown. Outliers are plotted for any tumor in which ICOS expression expressed at a level that is more than the interquartile range outside of the upper or lower quartile. Indications shown in bold were selected for follow-up analysis to identify genes associated with ICOS expression. Expression is shown as $\log_2$(FPKM).

Figure 26:
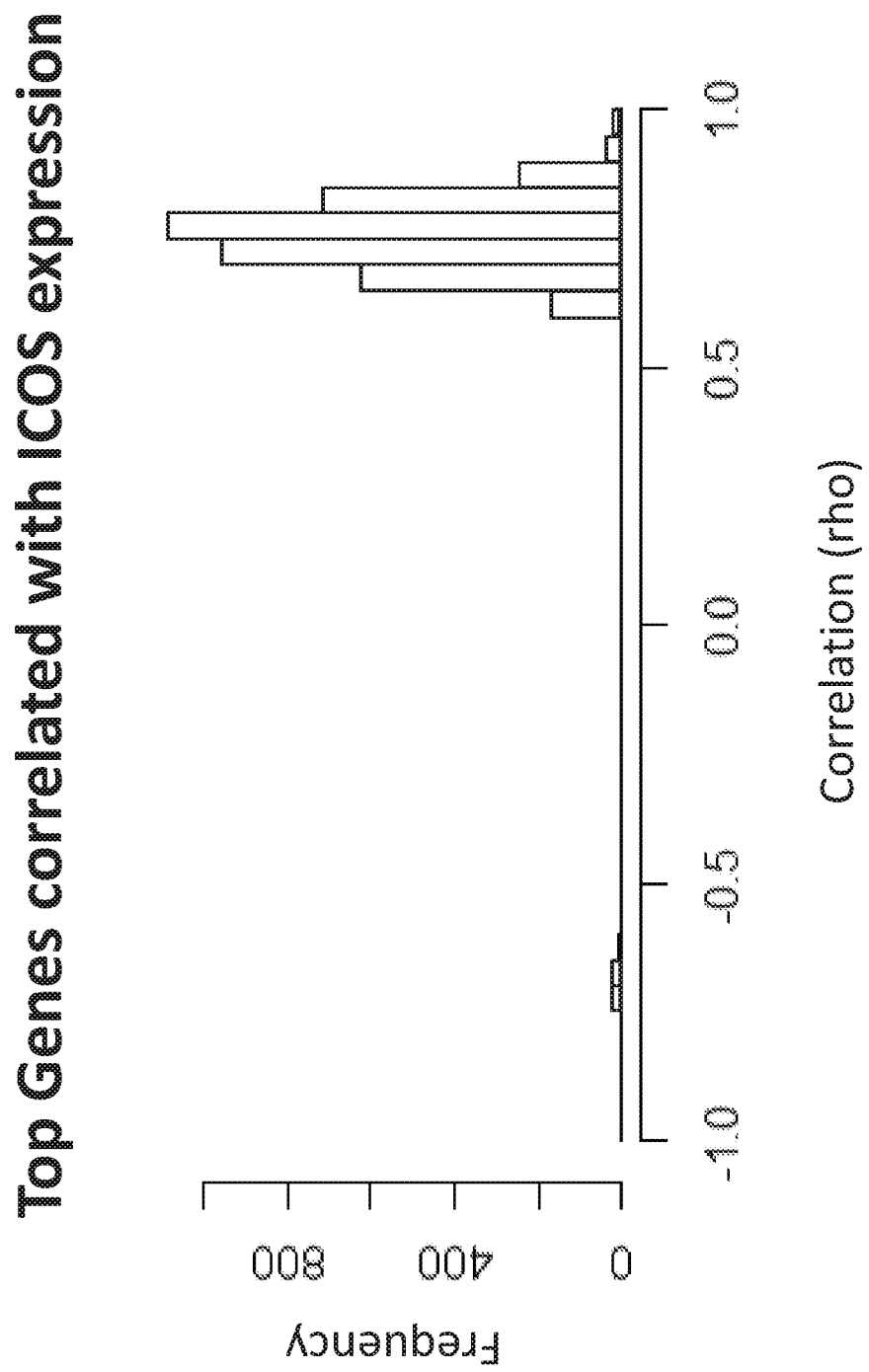
FIG. 26. Histogram of correlation (ρ) values between a given gene and ICOS expression for genes correlated with ICOS expression.

To identify a novel gene signature of ICOS expression, other genes tightly correlated with ICOS across the 13 major subtypes of cancer that had high and variable ICOS expression were examined. The spearman rank correlation ($\rho$) between a given gene and ICOS expression was calculated within each indication. The 300 genes most significantly associated with ICOS expression were retained for each indication, correlation $\rho$ and nominal p-values retained for secondary analysis. All associations with ICOS were found to be significant at $p<0.005$. See FIG. 26. The average correlation rank was then computed across all indications for each gene, excluding values that had dropped during the first phase of analysis.

Genes selected to remain within the signature were those that were a) part of the top 300 genes associated with ICOS in at least 10 of the 13 indications tested and b) were, on average, within the top 75 genes associated with ICOS across indications in which they were part of the top 300 correlated genes. The genes identified using these metrics, along with the criteria for selection including the spearman correlation and the mean rank of correlation with ICOS are shown in Table 6. This analysis identified 39 genes, which can be used individually or in combination to predict the expression of ICOS across these 13 indications by RNA expression profiling. Table 6 shows the Spearman correlation coefficients ($\rho$) for 39 genes identified as correlating with ICOS expression. If a gene was not part of the top 300 genes correlated with ICOS expression no value is shown for the correlation coefficient. The average rank of correlation with ICOS is shown in the left most column across all indications in which the gene was part of the top 300 genes correlated with ICOS. Genes were selected that were found to be within the top 300 genes associated with ICOS expression in at least 10 of the indications shown above. ICOS signature genes also were required to have a mean rank within the top 75 genes of any indication in which why were in the top 300 genes. Indication abbreviations are: Bladder Cancer (BLCA), triple negative breast cancer (BRCA TN), cervical cancer (CESC), microsatellite stable colorectal cancer (CO MSS), head & neck cancer (HNSC), clear cell kidney cancer (KIRC) lung adenocarcinoma (LUAD, a sub-type of non-small cell lung cancer (NSCLC)), lung squamous cell carcinoma (LUSC, a sub-type of non-small cell lung cancer (NSCLC)), ovarian cancer (OV), pancreatic cancer (PAAD), melanoma (SKCM), stomach cancer (STAD).

TABLE 6 mRNAs correlated with ICOS expression

| Gene | Exemplary mRNA Acc. No. | BLCA | BRCA TN | CESC | CO MSS | HNSC HPV− | HNSC HPV+ | KIRC | LUAD | LUSC | OV | PAAD | SKCM | STAD | Mean Rank |
|---|---|---|---|---|---|---|---|---|---|---|---|---|---|---|---|
| CCR5 | NM_000579.3 | 0.876 | 0.901 | 0.887 | | 0.847 | 0.789 | 0.880 | 0.817 | 0.866 | 0.834 | 0.799 | 0.841 | 0.820 | 23 |
| CD2 | NM_001767.3 | 0.905 | 0.941 | 0.858 | 0.680 | 0.858 | 0.780 | 0.889 | 0.881 | 0.903 | 0.896 | 0.849 | 0.881 | 0.841 | 26 |
| CD3D | NM_000732.4 | 0.822 | 0.891 | 0.805 | 0.738 | 0.827 | 0.792 | 0.852 | 0.833 | 0.878 | 0.836 | 0.848 | 0.860 | 0.759 | 40 |
| CD3E | NM_000733.3 | 0.896 | 0.903 | 0.849 | | 0.841 | 0.795 | 0.853 | 0.847 | 0.883 | 0.855 | 0.837 | 0.839 | 0.750 | 26 |
| CD3G | NM_000073.2 | 0.833 | 0.912 | 0.795 | 0.765 | 0.833 | 0.890 | 0.855 | 0.812 | 0.839 | 0.795 | 0.783 | 0.879 | 0.822 | 33 |
| CD48 | NM_001256030.1 | 0.833 | 0.882 | 0.877 | 0.749 | 0.794 | 0.764 | 0.742 | 0.775 | 0.834 | 0.781 | 0.730 | 0.826 | 0.743 | 71 |
| CD5 | NM_014207.3 | 0.851 | 0.889 | 0.849 | | 0.788 | 0.820 | 0.803 | 0.771 | 0.832 | 0.830 | 0.807 | 0.830 | | 45 |
| CD96 | NM_198196.2 | | 0.880 | 0.775 | 0.690 | 0.774 | 0.765 | 0.872 | 0.803 | 0.829 | 0.797 | 0.815 | 0.797 | 0.843 | 73 |
| CTLA4 | NM_005214.4 | 0.942 | 0.925 | 0.892 | | 0.944 | 0.853 | 0.825 | 0.860 | 0.910 | 0.889 | 0.876 | | 0.804 | 10 |
| CXCR6 | NM_006564.1 | 0.862 | 0.904 | 0.790 | 0.741 | 0.853 | 0.900 | 0.845 | 0.830 | 0.869 | 0.872 | 0.798 | 0.853 | 0.824 | 27 |
| FOXP3 | NM_014009.3 | 0.905 | 0.886 | 0.816 | | 0.886 | 0.845 | 0.715 | 0.778 | 0.858 | 0.812 | 0.749 | | 0.763 | 50 |
| ICOS | NM_012092.3 | 1.000 | 1.000 | 1.000 | 1.000 | 1.000 | 1.000 | 1.000 | 1.000 | 1.000 | 1.000 | 1.000 | 1.000 | 1.000 | 1 |
| IKZF1 | NM_006060.5 | 0.821 | 0.869 | 0.799 | 0.752 | 0.807 | 0.901 | 0.829 | 0.782 | 0.808 | 0.690 | 0.752 | 0.841 | 0.792 | 67 |
| IL21R | NM_181078.2 | 0.898 | 0.868 | 0.912 | 0.711 | 0.874 | 0.833 | 0.687 | 0.787 | 0.874 | 0.838 | | 0.817 | 0.764 | 53 |
| IL2RB | NM_000878.3 | 0.885 | 0.894 | 0.729 | | 0.822 | 0.862 | 0.788 | 0.791 | 0.819 | 0.827 | 0.803 | 0.826 | 0.829 | 51 |
| ITGAL | NM_002209.2 | 0.853 | 0.894 | 0.867 | | 0.834 | 0.848 | 0.801 | 0.785 | 0.830 | 0.794 | 0.692 | 0.834 | 0.769 | 50 |
| ITK | NM_005546.3 | 0.893 | 0.916 | 0.770 | 0.767 | 0.828 | 0.804 | 0.850 | 0.843 | 0.876 | 0.881 | 0.832 | 0.808 | 0.811 | 35 |
| KIAA0748 | NM_001136030.2 | | 0.892 | 0.849 | | 0.816 | 0.783 | 0.783 | 0.792 | 0.825 | 0.786 | 0.755 | 0.828 | 0.707 | 62 |
| LCP2 | NM_005565.3 | 0.862 | 0.877 | 0.841 | | 0.838 | 0.833 | 0.766 | 0.810 | 0.854 | 0.795 | 0.728 | | 0.828 | 44 |
| LTA | NM_001159740.2 | 0.816 | 0.901 | 0.843 | 0.741 | 0.796 | 0.763 | 0.837 | 0.810 | 0.819 | 0.808 | 0.775 | 0.805 | 0.695 | 69 |
| P2RY10 | NM_014499.2 | 0.889 | 0.902 | 0.826 | 0.780 | 0.806 | 0.802 | 0.874 | 0.804 | 0.867 | 0.859 | 0.835 | 0.865 | 0.823 | 24 |
| PTPRC | NM_002838.4 | 0.904 | 0.880 | 0.829 | 0.764 | 0.836 | 0.872 | 0.784 | 0.820 | 0.867 | 0.798 | 0.740 | 0.840 | 0.838 | 34 |
| PYHIN1 | NM_152501.4 | 0.850 | 0.906 | 0.807 | | 0.770 | 0.758 | 0.839 | 0.836 | 0.845 | 0.810 | 0.844 | 0.814 | 0.818 | 52 |
| SASH3 | NM_018990.3 | 0.876 | 0.880 | 0.881 | 0.674 | 0.850 | 0.863 | 0.803 | 0.815 | 0.866 | 0.755 | 0.712 | 0.795 | 0.735 | 66 |
| SH2D1A | NM_002351.4 | 0.884 | 0.907 | 0.898 | 0.681 | 0.805 | 0.900 | 0.860 | 0.881 | 0.868 | 0.848 | 0.843 | 0.859 | 0.795 | 28 |
| SIRPG | NM_018556.3 | 0.760 | 0.891 | 0.831 | | 0.842 | 0.796 | 0.872 | 0.848 | 0.862 | 0.814 | 0.848 | 0.847 | 0.780 | 43 |
| SIT1 | NM_014450.2 | 0.824 | 0.852 | 0.851 | 0.761 | 0.781 | 0.796 | 0.848 | 0.794 | 0.811 | 0.822 | 0.794 | 0.838 | 0.636 | 73 |
| SLA2 | NM_032214.3 | 0.894 | 0.900 | 0.751 | | 0.837 | 0.796 | 0.867 | 0.804 | 0.864 | 0.839 | 0.762 | 0.873 | 0.797 | 39 |
| SLAMF1 | NM_003037.3 | 0.901 | 0.897 | 0.888 | 0.684 | 0.807 | 0.798 | 0.764 | 0.817 | 0.864 | 0.880 | 0.885 | 0.770 | 0.799 | 54 |
| SLAMF6 | NM_001184714.1 | 0.843 | 0.891 | 0.791 | | 0.760 | 0.896 | 0.847 | 0.769 | 0.836 | 0.855 | 0.761 | 0.862 | 0.759 | 53 |
| SNX20 | NM_182854.2 | 0.796 | 0.888 | 0.814 | 0.738 | 0.817 | 0.770 | 0.794 | 0.773 | 0.849 | 0.764 | 0.700 | 0.838 | 0.747 | 75 |
| SP140 | NM_007237.4 | 0.801 | 0.912 | 0.851 | | | 0.761 | | | | | | | | |
| TCR-α | NG_001332.2* | 0.828 | 0.904 | 0.731 | 0.762 | 0.821 | 0.805 | | | | | | | | |
| TCRVB | NG_001333.2* | | 0.872 | 0.848 | 0.701 | 0.812 | 0.810 | | | | | | | | |
| TIGIT | NM_173799.3 | 0.888 | 0.920 | 0.872 | 0.738 | 0.861 | 0.827 | | | | | | | | |
| TRA | NG_001332.2* | 0.841 | 0.911 | 0.765 | 0.666 | 0.810 | 0.778 | | | | | | | | |
| TRAC | NG_001332.2* | 0.891 | 0.909 | 0.850 | 0.684 | 0.853 | 0.791 | | | | | | | | |
| TRAT1 | NM_016388.2 | 0.802 | 0.917 | 0.810 | 0.770 | 0.737 | 0.781 | | | | | | | | |
| UBASH3A | NM_018961.3 | 0.849 | 0.902 | 0.766 | | 0.812 | 0.758 | | | | | | | | |
| Average ρ | | 0.863 | 0.899 | 0.832 | 0.739 | 0.828 | 0.820 | | | | | | | | |

TABLE 6-continued

| mRNAs correlated with ICOS expression | | | | | | | | |
|---|---|---|---|---|---|---|---|---|
| SP140 | 0.838 | 0.755 | 0.818 | 0.771 | 0.789 | 0.843 | 0.693 | 73 |
| TCR-α | 0.788 | 0.835 | 0.848 | 0.816 | 0.827 | 0.837 | 0.802 | 51 |
| TCRVB | 0.826 | 0.832 | 0.884 | 0.853 |  | 0.840 | 0.745 | 47 |
| TIGIT | 0.906 | 0.868 | 0.849 | 0.888 | 0.918 | 0.893 | 0.830 | 14 |
| TRA | 0.793 | 0.805 | 0.839 | 0.807 | 0.762 | 0.843 | 0.772 | 70 |
| TRAC | 0.845 | 0.868 | 0.877 | 0.849 | 0.841 | 0.840 | 0.794 | 33 |
| TRAT1 | 0.882 | 0.851 | 0.839 | 0.851 | 0.842 | 0.867 | 0.804 | 48 |
| UBASH3A | 0.872 | 0.789 | 0.839 | 0.758 | 0.715 | 0.855 | 0.771 | 67 |
| Average ρ | 0.830 | 0.820 | 0.856 | 0.827 | 0.801 | 0.844 | 0.787 |  |

*Accessions for genomic loci provided for TCR genes.

The list of mRNAs in Table 6 may be used to form a panel of mRNAs for determining the expression level of ICOS, e.g., to create a more robust assay than an assay that detects ICOS alone. In some embodiments, a panel is formed from the set of mRNAs: CCR5, CD2, CD96, CTLA4, CXCR6, FOXP3, ICOS, ITK, P2RY10, SIRPG, and TIGIT.

Example 12: Induction of Th-1 Chemokines and Cytokines Following Anti-ICOS Antibody Treatment Fresh patient lung tumors were obtained 24 hours post-surgery. Soft tissue was manually removed from the tumor, and the remaining solid tumor was embedded in 4% low melting agar in a cast container and allowed to solidify on ice. The gel-embedded tumor was cut by vibratome (Leica) (speed: 2, frequency: 9) to generate slices with a thickness of 300 µm. If the tumor was too soft and unable to be sliced by vibratome, the tissue was manually cut with a blade.

Tumor slices were placed in a 40 µm transwell filter (Millipore) (~1 slice/well), and the unit was moved to the wells of a 6-well plate, which contained 1.5 mL of histoculture media (complete RPMI 1640/AIM-V). The appropriate treatment was then added into the medium of the corresponding well. Treatments included 10 µg/mL anti-RSV hIgG1 (Lake Pharma, lot #3086-849598) as an isotype control, 10 µg/mL antibody 37A10S713 with a human IgG1 (SEQ ID NOs: 188 and 189), or 10 µg/ml of anti-PD-1 (IgG4) antibody. Replicate plates were prepared for various time points, ranging from 6-72 hours. The plates were placed in an incubator at 37° C., 5% CO$_2$.

At the desired time points, tumor slices were collected and immersed in RNALater (Ambion). RNA was extracted using a RNeasy Mini kit (Qiagen, cat #74106) according to the manufacturer's instructions. Following RNA extraction, 1 µg of RNA was used for reverse transcription using a Bio-Rad iScript cDNA Synthesis Kit (cat #170-8891). The RT product was diluted 1 to 7, and 3 µl was used for each qPCR reaction. The qPCR was carried out by using TaqMan Gene Expression Master Mix from Thermo Fisher Scientific (cat #4369016) using a Bio-Rad Real-Time System. The TaqMan assays used are listed in Table 7.

Expression was normalized to CD45, with fold change calculated as:

$$\text{fold change} = \frac{1/2^{(\text{exp. target } Ct - \text{exp. } CD45\ Ct)}}{1/2^{(\text{Iso. target } Ct - \text{Iso. } CD45\ Ct)}}$$

TABLE 7

| TaqMan chemokine and cytokine assays | | |
|---|---|---|
| Target | Assay ID | Source |
| CD8B | Hs00174762_m1 | ThermoFisher Scientific |
| CSF2 | Hs00929873_m1 | ThermoFisher Scientific |
| PRF1 | Hs00169473_m1 | ThermoFisher Scientific |
| GZMA | Hs00989184_m1 | ThermoFisher Scientific |
| GZMB | Hs00188051_m1 | ThermoFisher Scientific |
| IL2 | Hs00174114_m1 | ThermoFisher Scientific |
| CXCL9 | Hs00171065_m1 | ThermoFisher Scientific |
| CXCL10 | Hs01124251_g1 | ThermoFisher Scientific |
| CXCL11 | Hs04187682_g1 | ThermoFisher Scientific |
| FOXP3 | Hs01085834_m1 | ThermoFisher Scientific |
| CTLA4 | Hs00175480_m1 | ThermoFisher Scientific |
| CD45 | Hs04189704_m1 | ThermoFisher Scientific |
| CXCL13 | Hs00757930_m1 | ThermoFisher Scientific |

Figure 27:
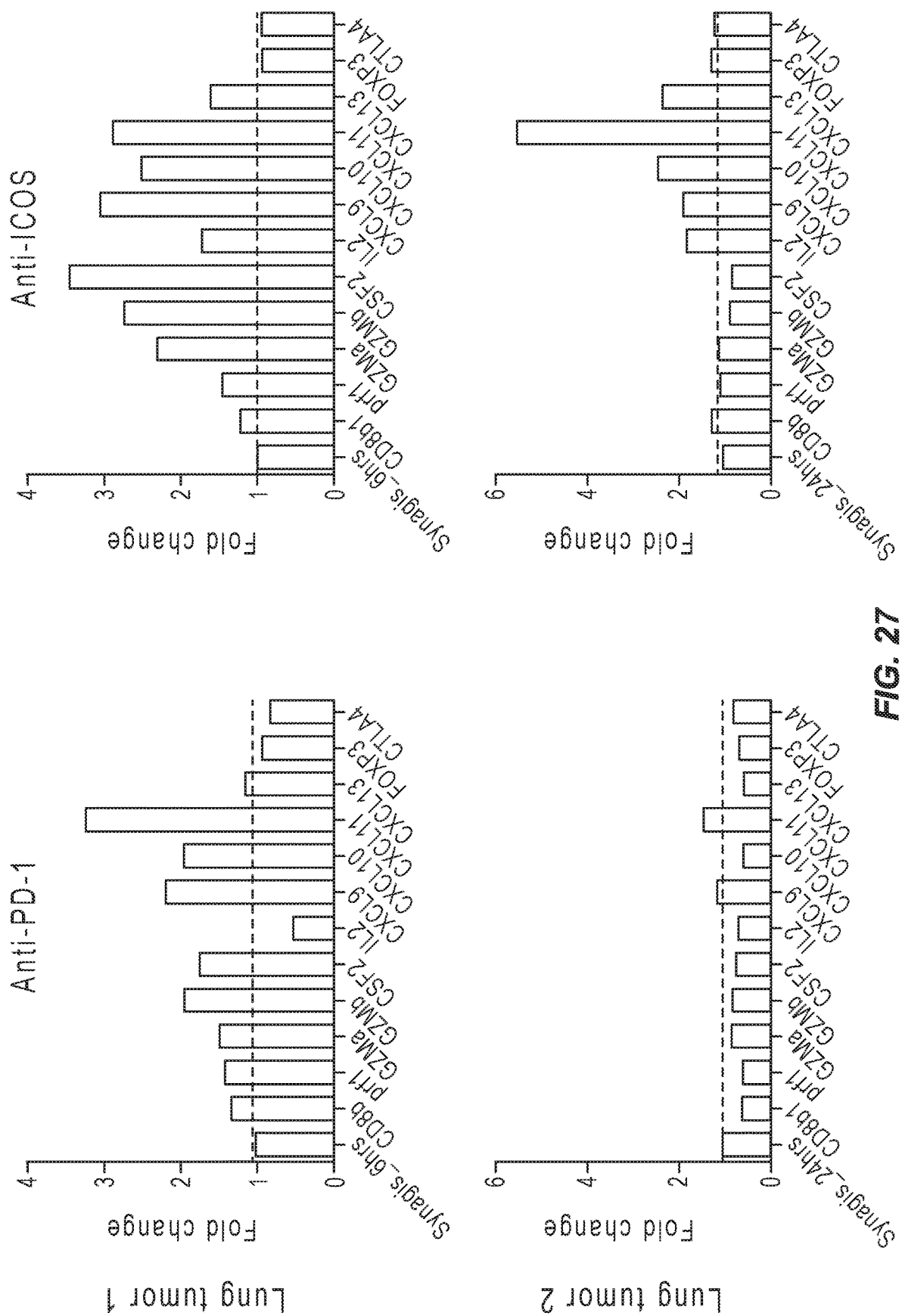
FIG. 27. Change in Th-1 chemokine and cytokine expression following treatment of lung tumor tissue with anti-ICOS antibody (right panels) or anti-PD-1 antibody (left panels), at 6 hours (top panels) or 24 hours (bottom panels).
Figure 28A:
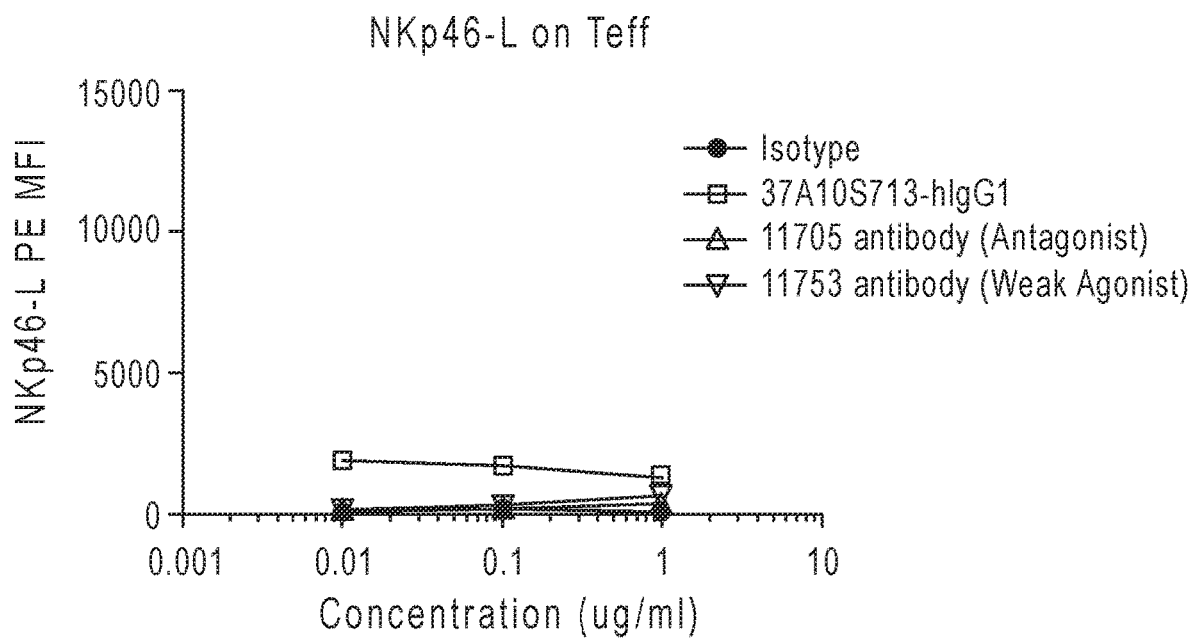
FIG. 28A-F. NKp46 ligand levels on Teff cells (A, C, E) and Treg cells (B, D, F) from three different donors, following treatment with agonist and antagonist anti-ICOS antibodies.
Figure 28B:
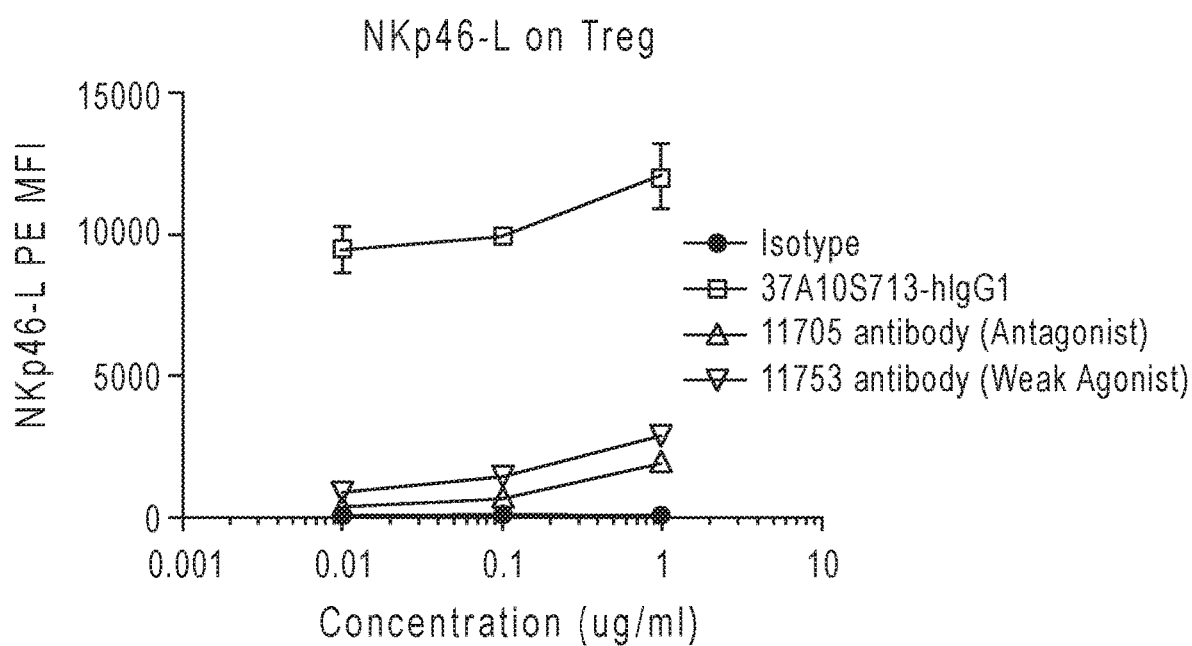
Figure 28C:
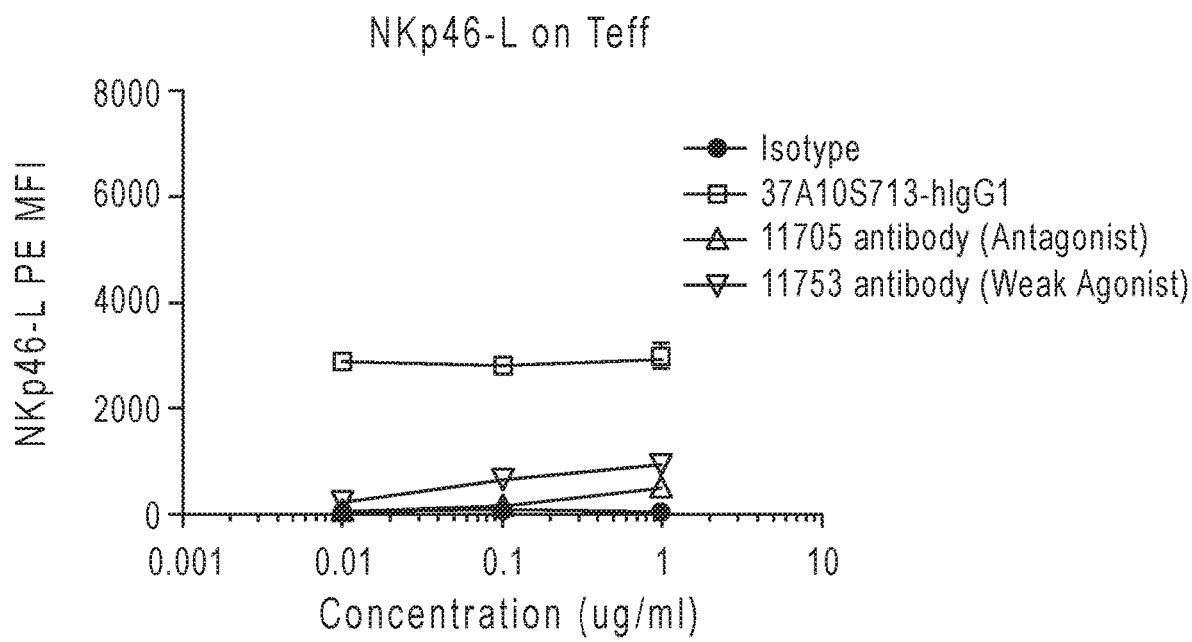
Figure 28D:
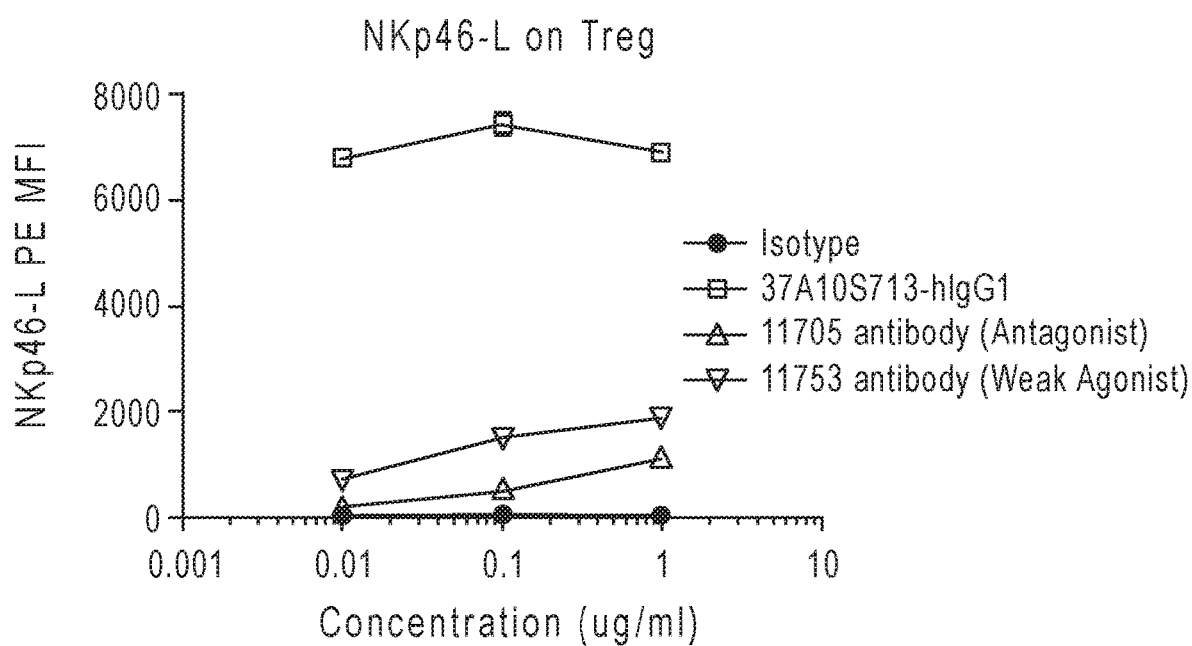
Figure 28E:
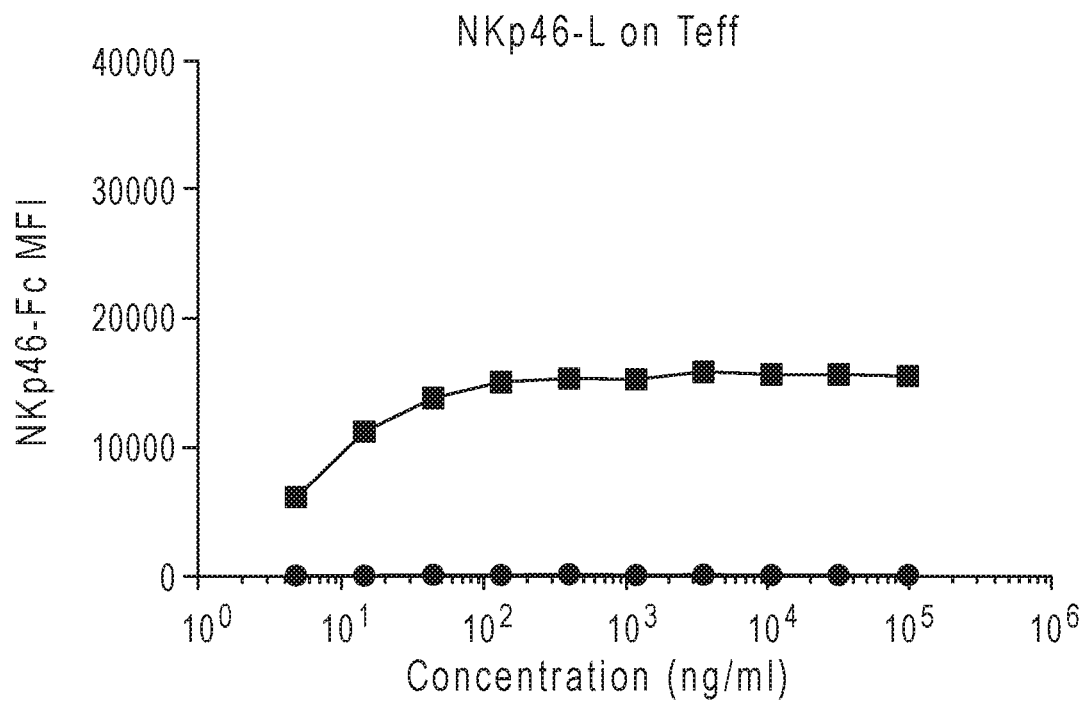
Figure 28F:
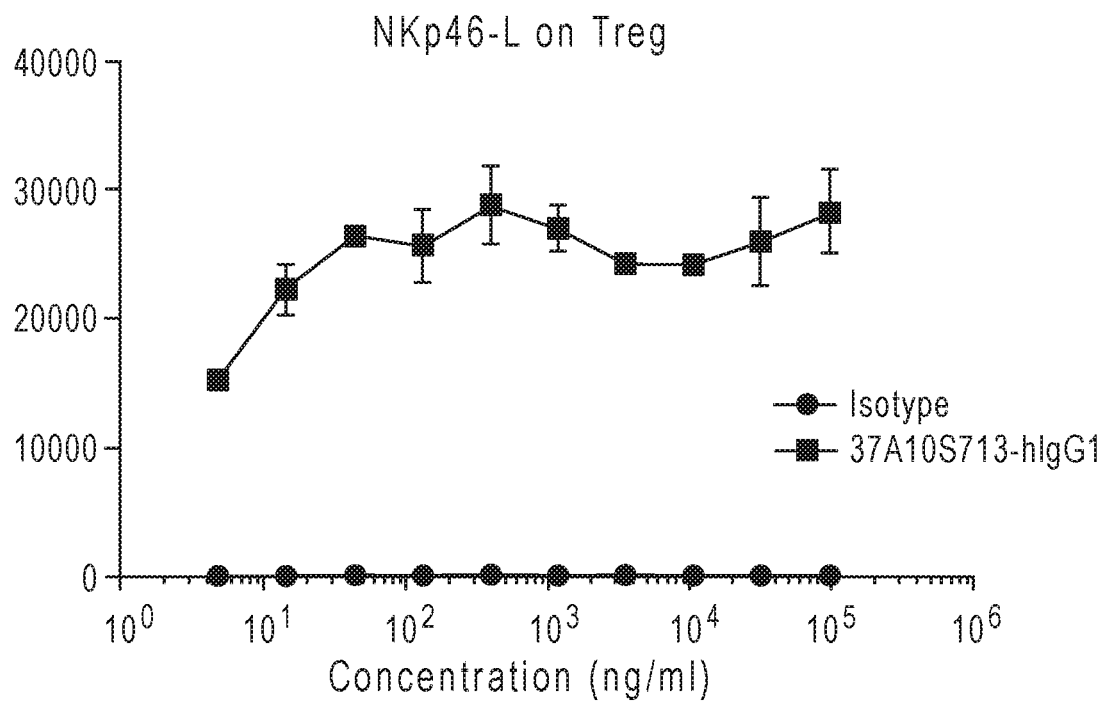

The results of that experiment are shown in FIG. 27. At the 6 hour time point with lung tumor 1, the anti-ICOS antibody resulted in increased expression of GZMa, GZMb, CSF2, IL2, CXCL9, CXCL10, CXCL11, and CXCL13. Anti-PD-1 antibody also increased expression of GZMa, GZMb, CSF2, CXCL9, and CXCL10, although to a lesser extent, and showed a similar increase in CXCL11. For lung tumor 2 at the 24 hour time point, anti-ICOS antibody treatment showed a sustained increase in CXCL11, and some continued elevation of IL2, CXCL9, and CXCL10. The anti-PD-1 antibody showed only a slight elevation in CXCL11 at 24 hours.

Example 13: Induction of NKp46 Ligand on Treg Cells Following Agonist Anti-ICOS Antibody Treatment Peripheral blood mononuclear cells were isolated from healthy human donors (Research Blood Components) using Ficoll (GE Life Sciences) centrifugation, frozen in Bam-Banker (Wako-Chem) and stored at −150° C. until use. PBMCs were incubated with soluble anti-ICOS antibody and plate bound anti-human CD3 (1 µg/ml coating, Biolegend, OKT3) at 37° C. in RPMI (Gibco) supplemented with 10% fetal bovine serum (Sigma-Aldrich) and 1% penicillin/streptomycin (Gibco). Three antibodies were tested in the assay: the strong agonist antibody 37A10S713, a weak agonist antibody, and a weak antagonist antibody. After four days, PBMCs were gently scraped from plates and washed with DPBS (Gibco) containing 1% fetal bovine serum, 0.05% sodium azide (Ricco) and 2 mM EDTA (Ambion). Cells were then blocked with Human TruStain FcX (Biolegend). To detect NKp46 ligand, cells were incubated with 2 µg/mL NKp46-hIgG1 Fc (R&D Systems, 1850-NK). NKp46-hIgG1 Fc bound to cells was detected using a PE conjugated anti-human IgG (Biolegend, polyclonal). Cells were again blocked with Human TruStain FcX and then stained with anti-human CD56 (Biolgend, Brilliant Violet 711, HCD56), anti-human CD16 (Biolegend, Brilliant Violet 785, 3G8), anti-human CD4 (Biolegend, Brilliant Violet 510, OKT4), anti-human CD8 (BD Biosciences, BUV395, RPA-T8), anti-human CD25 (Biolegend, Brilliant Violet 605, BC96), and fixable viability dye (eBioscience, eFluor 780). Following staining, cells were fixed and permeabilized with Foxp3/Transcription Factor Staining Buffer Set (eBioscience). Following permeabilization, cells were stained intracellularly with anti-human CD3 (BD Biosceinces, PE-CF594, UCHT1) and anti-human Foxp3 (eBioscience, APC, PCH101). Cells were then fixed in paraformaldehyde (Alfa Aesar). Data was acquired on a BD LSRII Fortessa and analyzed on FlowJo v10.1 software.

Figure 29:
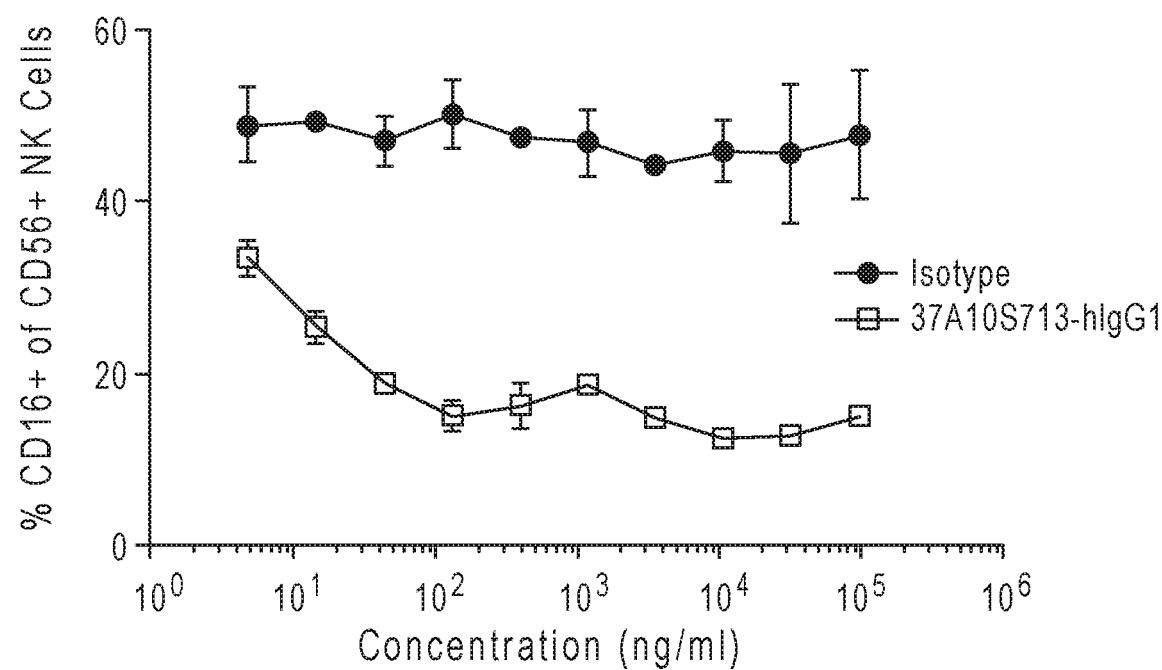
FIG. 29. Loss of CD16 (CD16 shedding) from NK cells treated with agonist anti-ICOS antibody.

The results of that experiment are shown in FIG. 28 and FIG. 29. Treatment with the agonist anti-ICOS antibody 37A10S713 resulted in strong induction of NKp46 ligand on Treg cells from three different donors. See FIGS. 28A-F (FIGS. 28A-B show data from donor 1, FIGS. 28C-D show data from donor 2, and FIGS. 28E-F show data from donor 3). Induction of NKp46 ligand on Teff cells was not as strong as on Treg cells. See FIGS. 28A-F. In addition, treatment with agonist anti-ICOS antibody 37A10S713 leads to loss of CD16 (CD16 shedding) on NK cells, suggesting activation of the NK cells. See FIG. 29.

Without intending to be bound by any particular theory, it is postulated that the agonist anti-ICOS antibody 37A10S713 significantly increases NKp46 ligand levels on Treg cells and also activates NK cells, leading to selective Treg depletion.

Example 14: Intratumoral Expression of ICOS can Predict Response to Anti-ICOS Antibody To test whether high ICOS+ tumor infiltrating T cells at baseline would respond better to anti-ICOS antibody as a monotherapy, mouse syngeneic tumor models were used to correlate the expression of mICOS using immunohistochemical (IHC) staining and with in vivo efficacy of anti-ICOS antibody.

In vivo efficacy studies were performed in several mouse syngeneic tumor models by treating tumor bearing animals with 2 doses of 37A10S713 with mG2a Fc at 0.25 mg/kg, dosed once a week. Mice were sacrificed when tumor volumes reached ~2000 mm³ or if there were signs of clinical distress such as severe ulcerations as pursuant to IACUC protocol.

Tumor Samples for IHC Analysis.

Tumor tissues were generated by inoculating cell lines in syngeneic animals (n≥4). Tumors were harvested at an average volume of 150 (±50) mm³, fixed in 4% paraformaldehyde followed by embedding into Optimal Cutting Temperature (OCT) medium.

Immunohistochemistry for mICOS.

IHC analysis was performed on 8 μm sections. Anti-mICOS antibody was used to detect mICOS expression on tumor infiltrating T cells. Chromogenic detection was performed using the ImmPRESS™ HRP (Peroxidase) system (Vector Labs, Burlingame, Calif.) according to manufacturer's recommended protocol. ICOS staining was scored by a trained pathologist using the 0-3+ scale, where 3+=>4%, 2+=>2% but <4%, 1+=>0.5% but <2%, and 0=<0.5% mICOS positive cells.

The results are shown in the following table.

TABLE 8

In vivo efficacy results

| Tumor | ICOS IHC Score | Single Agent Efficacy | Combination Efficacy (+anti-PD-1) |
|---|---|---|---|
| Sa1/N | 3+ | ++++ | Not Done |
| B16-SIY | 2+ | +++ | ++++ |
| MC38 | 1+ | + | +++ |
| CT26 | 1+ | + | ++++ |
| EMT6 | 1+ | + | +/− |
| LLC1 | 0 | − | + |
| 4T1 | 2+ | − | − |

++++: ≥70% animals responded to treatment with 37A10S713 with mG2a Fc

As shown in Table 8, single agent efficacy was observed in mouse models with high frequency of intratumoral mICOS+ T cells. Lack of response in the 4T1 model was due to restricted localization of mICOS+ cells to the tumor periphery.

Example 15: Generation of Anti-ICOS Antibodies and Detection of Inducible T-Cell Co-Stimulator (ICOS) in Normal and Tumor Human Tissue Samples Using Immunohistochemistry Immunization and Initial Screen.

6 mice (3 BALB/c and 3 SJL) were immunized with peptides from the cytoplasmic domain of ICOS at the CRO Antibody Solutions. Sera from each animal was screened using a peptide ELISA, and a subset of the mice (BALB/c) were fused to create a hybridoma library. Supernatant from the hybridoma library and subsequent single clones were screened using a peptide ELISA assay. Positive antibody clones (mAbs) were further screened using a cell based ELISA assay.

Cell-Based ELISA for Identification of IHC Antibodies.

Chinese Hamster ovary (CHO) cells stably transfected with ICOS overexpressing plasmid (CHO-ICOS) or control plasmid (CHO-vector) were used to screen positive clones from the peptide ELISA assay using established protocols. Briefly, cells grown in 96 well plates were fixed and permeabilized using 10% formalin with 0.1% Triton X-100. Following blocking, cells were incubated with primary antibody, followed by HRP-conjugated anti-mouse antibody. Detection was carried out using chemiluminescence substrate. Commercial anti-ICOS antibody, SP98 (Spring Biosciences) was used as a positive control and mouse IgG1 was used as a negative control for the assay.

Sequencing of Antibody Sequences.

Total RNA was extracted from the three hybridoma clones. Antibodies were cloned and sequenced following RT-PCR amplification of the cDNA sequences using degenerate primers for variable heavy ($V_H$) and non-degenerate primers for the variable light (VKL) chains.

Test and Control Articles.

Purified mouse monoclonal antibodies (mAbs), 2M13, 2M19, and 2M24 were produced from a clonal hybridoma cell line and tested for use in detection of ICOS-positive cells in human tissues. FFPE blocks of CHO cells pellets stably transfected with ICOS overexpressing plasmid (CHO-ICOS) or control plasmid (CHO-vector) were generated using standard protocols. Briefly, cells were collected by scraping, fixed in 10% buffered formalin, and embedded in Histogel. After the Histogel pellet solidified, it was processed as FFPE blocks using routine histology embedding techniques. 5 µm sections were used for antibody staining.

Tissues Samples for IHC Analysis.

Formalin Fixed Paraffin Embedded (FFPE) blocks of normal human tonsil (positive control), Non-small cell lung cancer (NSCLC) and Head and Neck Squamous Cell Carcinoma (HNSCC) tissues were purchased from commercial sources. 5 µm sections of FFPE tissues were used for validation of antibody staining.

Immunohistochemistry for ICOS.

IHC analysis was performed on 5 µm FFPE sections. Antigen expression was enhanced by heat treatment of sections using buffer ER2 (pH 10). IHC was performed using an indirect method using the DAB chromogen, employing standard protocols on the Leica Bond Rx automated system (Leica Microsystems Inc., Chicago, Ill.).

ICOS staining was scored by a trained pathologist using the 0-3+ scale as shown in Table 9.

TABLE 9

ICOS Scoring guidelines.

| Score | % ICOS$^+$ positivity |
|---|---|
| 0 | <1% ICOS positive cells |
| 1 | >1% but <5% |
| 2 | >5% but <15% |
| 3 | >15% |

Identification of ICOS-Specific IHC Antibodies.

Figure 30:
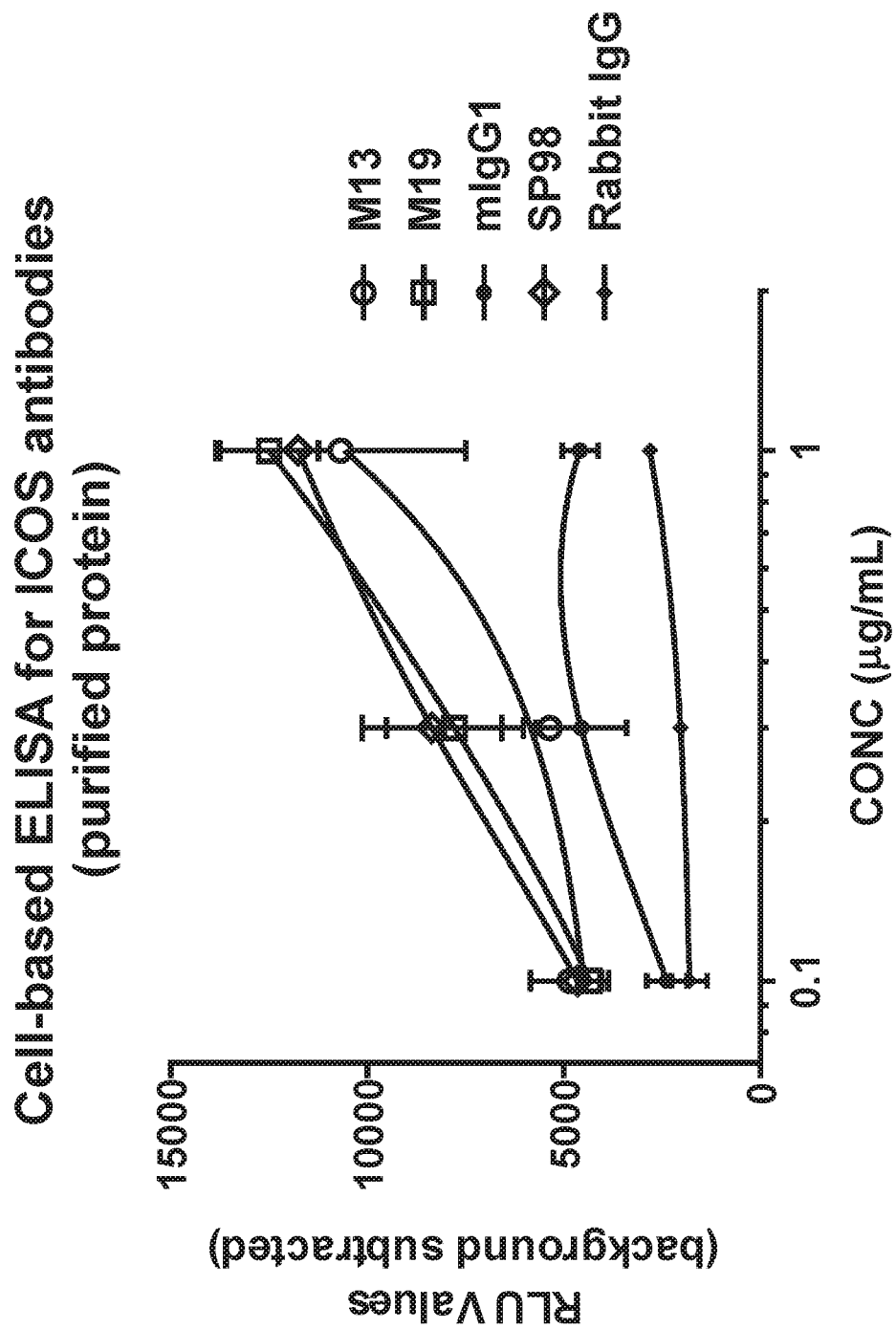
FIG. 30. Representative data showing binding of antibodies in Cell-based ELISA. Increasing binding as reflected by relative light units (RLU) from detection of monoclonal antibodies 2M13 and 2M19 binding to ICOS expressing CHO-K1 cells. This binding was significantly higher than that observed with IgG isotype control antibody. Similar data was seen for control anti-ICOS antibodies, SP98 and 2M24 (data not shown).

Antibodies 2M13, 2M19, and 2M24 were identified by screening a hybridoma library generated by immunization of peptides mapping to the intracellular domain of human ICOS protein. Positive antibodies were identified by progressively screening the hybridoma clones using a peptide ELISA, Cell-based ELISA, and IHC on FFPE tissue sections. Representative data from the Cell-based ELISA is shown in FIG. 30.

Validation of mAbs in IHC Analysis of FFPE Tissues.

Figure 31:
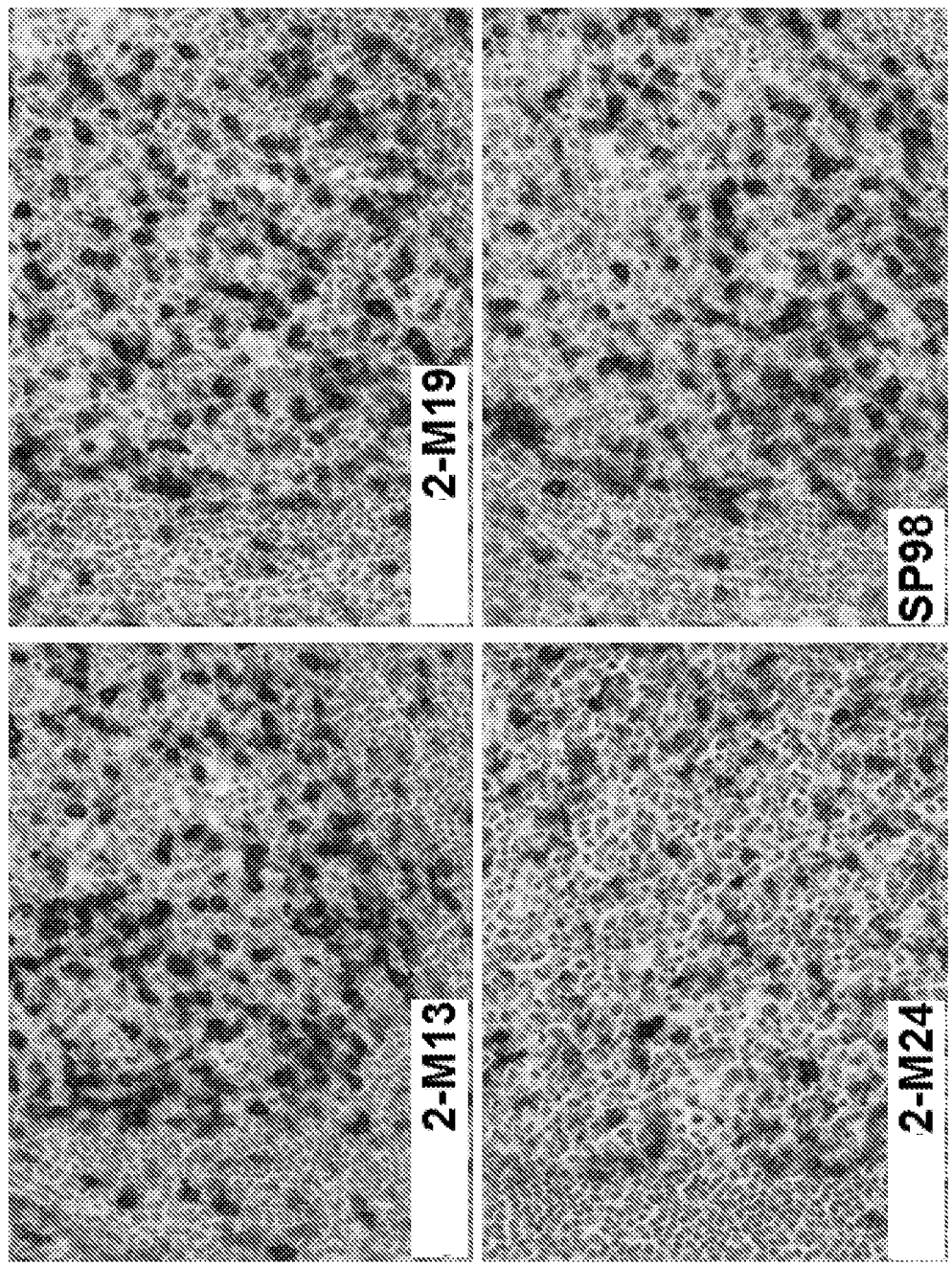
FIG. 31. Representative images of tonsil sections stained with anti-ICOS mAbs. Sections of human tonsil samples were stained with anti-ICOS antibodies 2M13, 2M19, 2M24, and SP98. 2M13, 2M19, and 2M24 antibodies were used at 0.5 μg/mL, while SP98 was used at 0.66 μg/mL. Specific and intense staining of cells was observed in the lymphatic areas known to be populated by T cells. No staining was observed in non-T cell regions of the tissue. A control antibody did not show any staining in the tissue section (data not shown).

2M13, 2M19, and 2M24 were further tested on human tonsil tissue sections. As seen in FIG. 31, all 3 antibodies showed specific membrane or cytosolic staining in normal human tonsil tissue. This staining pattern was consistent with known localization of T cells, which predominantly populate the lymphatic nodules surrounding the germinal centers in normal tonsil, and are distributed at a lower frequency within the germinal centers and in the follicular regions of the tonsil. Very little to no background was observed in other cell types in the tissues. These data together confirm specificity of the 2M13 antibody. Furthermore, antibody 2M13 yielded the most intense staining compared to both 2M19 and 2M24. Based on these data, 2M13 was used for further studies.

Specificity.

Figure 32:
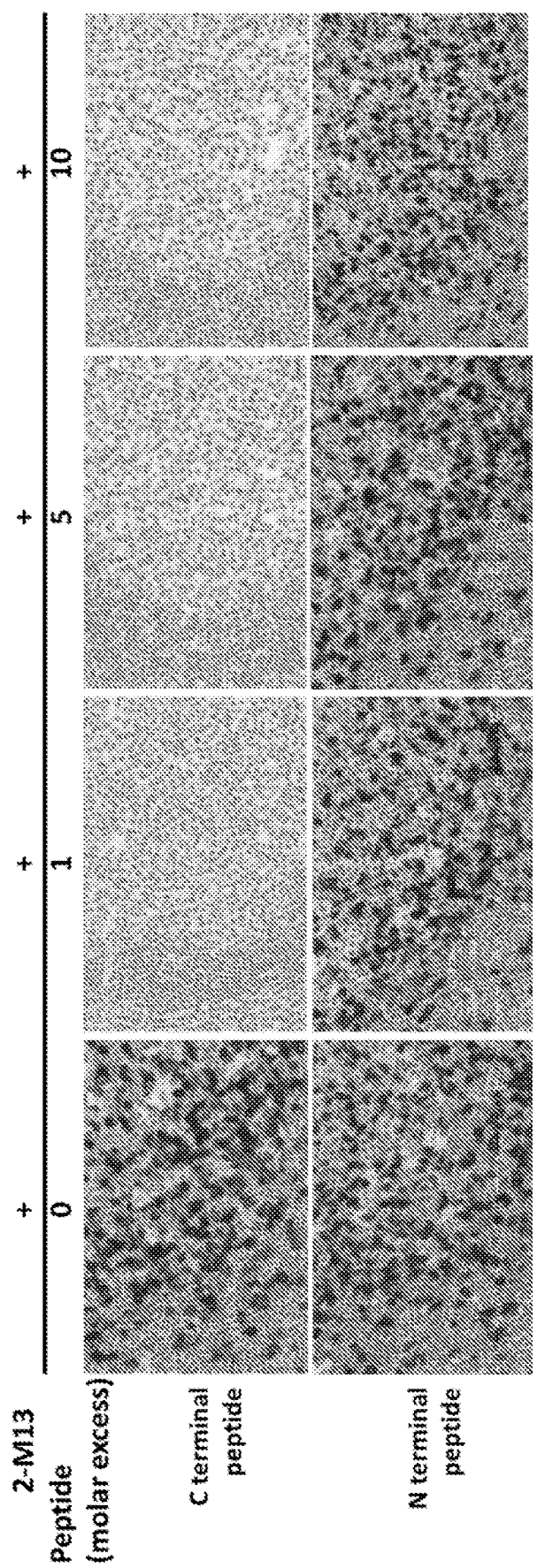
FIG. 32. Competition studies shows that 2M13 specifically detects ICOS expression. Staining of tonsil tissue samples is blocked by a (C-terminal) peptide encompassing the antigen epitope used to generate the antibody (upper panels). An adjacent N-terminal peptide was unable to block staining of ICOS positive cells by 2M13 (lower panels). The two left panels show staining of tonsil tissue with 2M13 alone.

As seen in FIGS. 31 and 32, anti-ICOS antibody (2M13) specifically detected expression of ICOS on T cells in tonsil tissues, with minimal non-specific background staining. To further confirm specificity, staining of ICOS expression was blocked using a peptide corresponding to the antigen used to generate the antibody. As seen in FIG. 32, ICOS staining of tonsil samples with the 2M13 antibody was completely competed off using molar excess of the ICOS (C-terminal) peptide (upper panels). ICOS specific staining was retained when 2M13 was competed using an adjacent (N-terminal) peptide further supporting specificity of the antibody for detection of ICOS. Importantly, background staining was low in all experiments. Similar specificity was observed for 2M19 antibody (data not shown).

Figure 33:
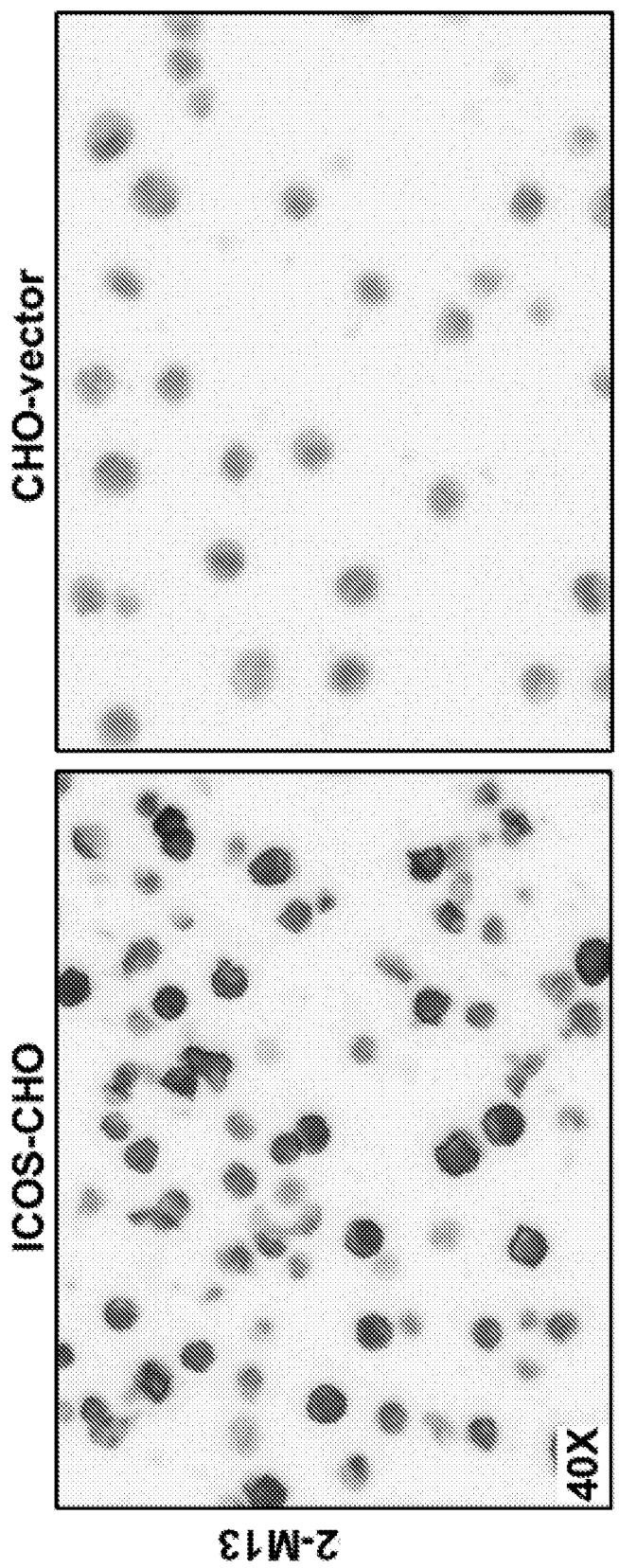
FIG. 33. 2M13 specifically stained CHO cells expressing ICOS but not cells transfected with empty vector. Similar staining was observed for anti-ICOS antibodies 2M19 and 2M24 (data not shown).

Antibody specificity was further tested using FFPE processed CHO cells stably expressing ICOS or empty vector. As seen in FIG. 33, 2M13 only stained CHO cells expressing ICOS. No staining was observed on CHO cells expressing empty vector.

Assay Precision.

Figure 34:
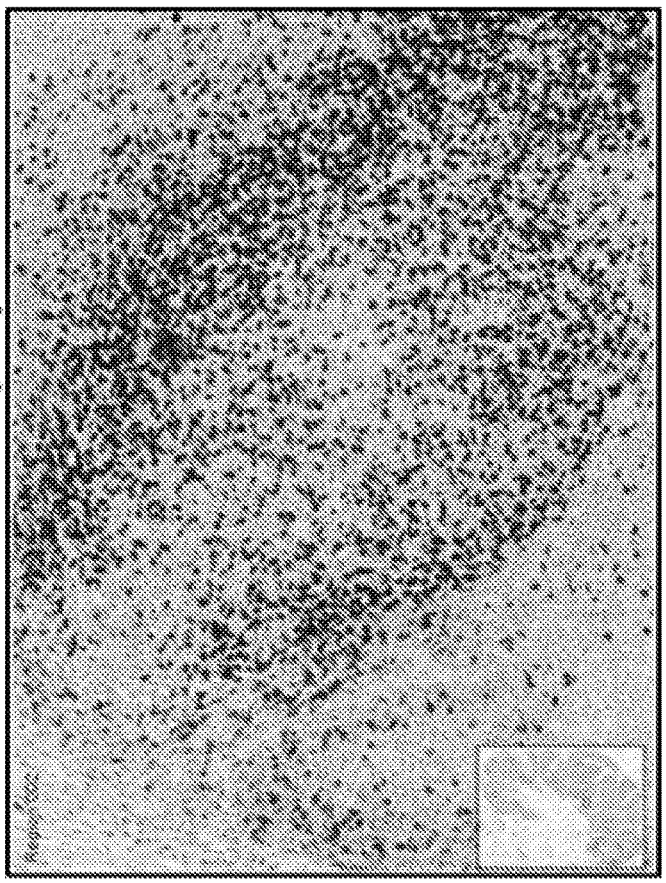
FIG. 34. Representative images demonstrating inter-run assay consistency. Representative photomicrographs of duplicate slides stained on two different days using the developed IHC protocol. Antibody was used at 0.5 μg/mL. Pathology scores are indicated in parentheses.
Figure 34:
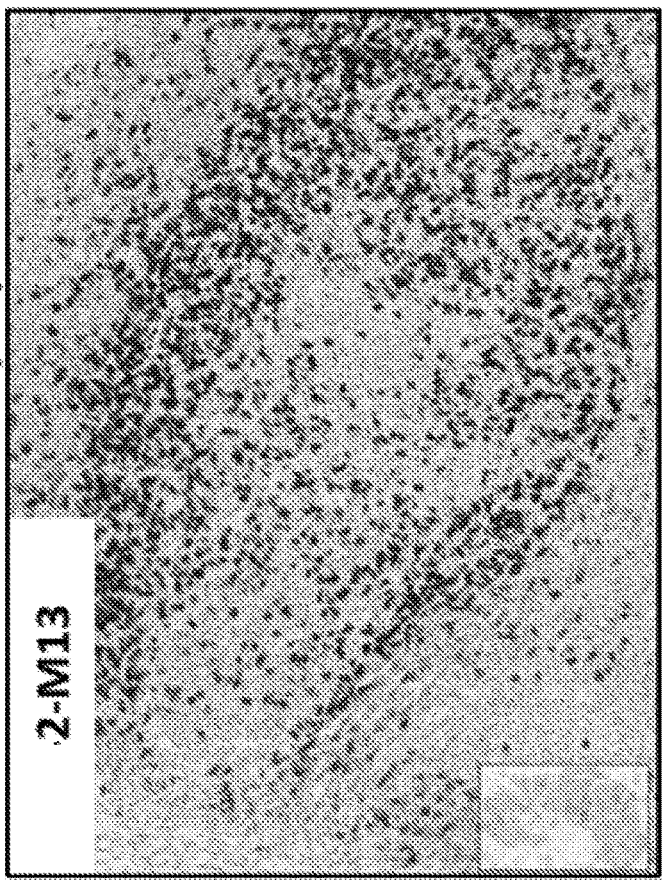

Pathology review of anti-ICOS (2M13) antibody reactivity showed consistent staining intensities in both inter- and intra-assay runs. These results are readily observed in the photomicrographs of the tonsil (FIG. 34). Staining with the negative control was minimal in these assays (data not shown).

Range.

Figure 35:
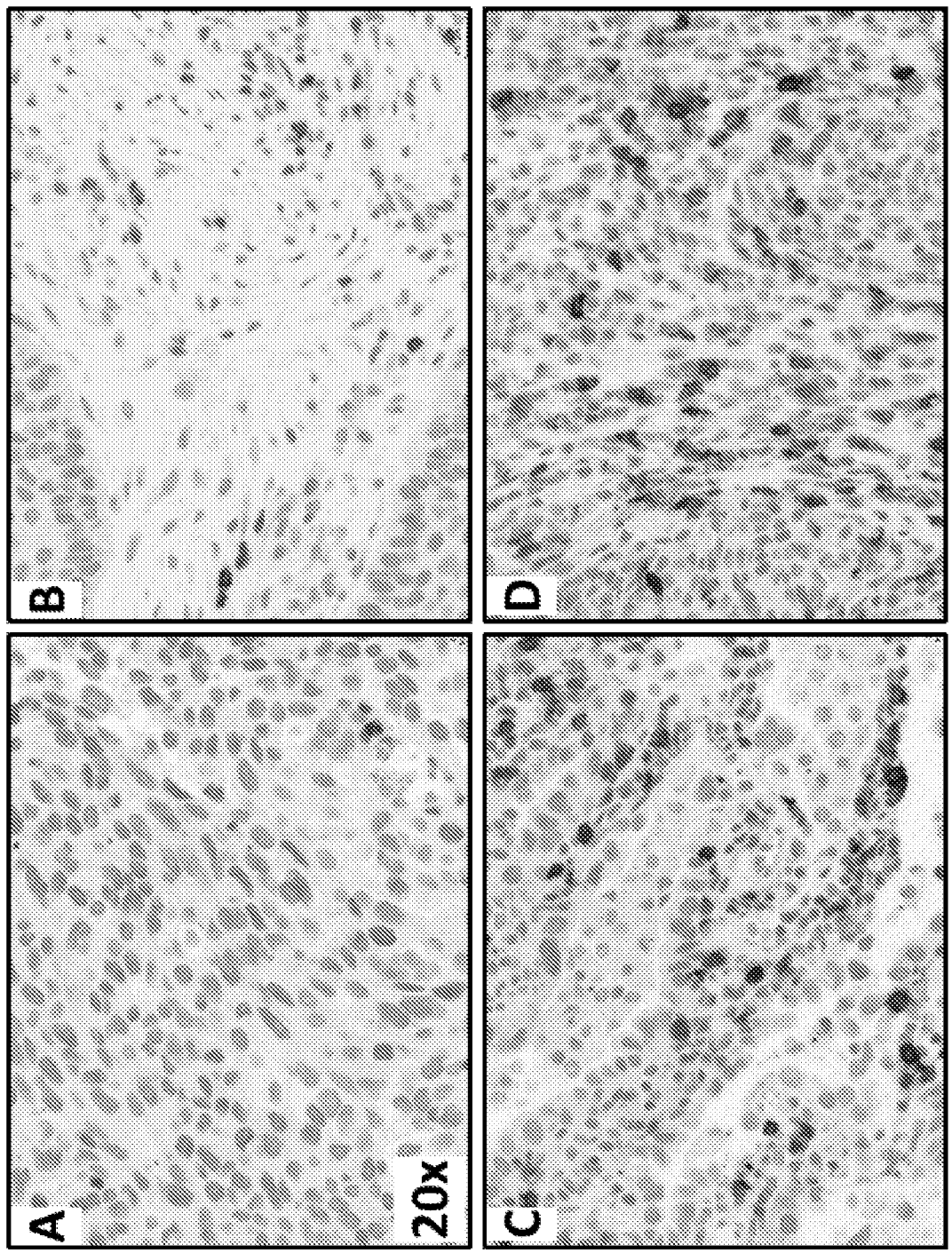
FIG. 35. Representative photomicrograph of samples depicting a range of ICOS expression levels. IHC assay for detection of ICOS expression has a wide range of detection. Panel D shows tumor sample with high number of ICOS expressing cells (3+). Panels B & C show representative samples with low ICOS positive cells (1+) or medium (2+) ICOS expression respectively. Panel A shows a tumor sample with no ICOS expressing cells (score 0).

Multiple NSCLS and HNSCC tumor samples were stained with the anti-ICOS antibody using the developed protocol. These samples showed a wide range of ICOS expression levels and membrane intensities. As shown in FIG. 35, this assay can detect a wide spectrum of physiologically relevant expression levels.

Example 16: Determination of Microsatellite Instability (MSI) in Tumors and Correlation with ICOS Levels Mismatch repair deficiency is associated with a deficiency in the DNA repair pathways in certain fraction of human tumors. These mismatch repair deficient, microsatellite instable (MSI) tumors accumulate 10-100 fold more mutations in the tumors as compared to the microsatellite stable counterparts (Nature 513: 202-209 (2014)). An MSI high tumor may display more non-self or neo-antigens to the surrounding tumor microenvironment, and therefore be immunologically recognized as foreign. These non-self-antigens may attract cells of the immune system such that they infiltrate the tumor. Thus as a consequence of a higher number of mutations, MSI high tumors tend to have higher levels of infiltrate than those that are MSS (Jass et al., 1998, Gut 42: 673-679). Because ICOS is expressed on infiltrating immune cells, ICOS RNA levels in MSI tumors were compared to ICOS RNA levels in MSS tumors.

The high-dimensional Cancer Genome Atlas (TCGA) dataset, which includes DNA mutational data, gene expression data, and gene amplification data from ~10,000 human tumors representing 30 different cancers, was used for the analysis. Raw sequence data was prepared and gene expression values utilizing the fragments per kilobase of exon per million fragments mapped (FPKM) were computed by OmicSoft Corporation utilizing their proprietary data normalization and expression analysis pipeline. All the FPKM values were converted using a logarithmic function with a base 2 and analyzed.

For this analysis, the data set was limited to those indications and tumors with known MSI status as measured by PCR according to manufacture specifications using NCI guidelines for designation of MSI status similar to that shown in Table 10 (see Nature 287: 330-337 (2012); Nature 497: 67-73 (2013); Nature 513: 202-209 (2014)).

TABLE 10

Guidelines for evaluation of MSI in colorectal cancer via PCR analysis

Reference Panel

| Marker | Repeating Unit | GenBank accession no. |
|---|---|---|
| BAT25 | Mononucleotide | 9834508 |
| BAT26 | Mononucleotide | 9834505 |
| D5S346 | Dinucleotide | 181171 |
| D2S123 | Dinucleotide | 187953 |
| D17S250 | Dinucleotide | 177030 |

Criteria for interpretation

| 5 loci analyzed | >5 loci analyzed | Interpretation |
|---|---|---|
| >=2 | >=30-40% | MSI-H |
| 1 | <30-40% | MSI-L |
| 0 | 0 | MSS or MSI-L |

ICOS levels (log 2 FPKM) were obtained from 731 tumor samples from colon adenocarcinoma (COAD), stomach adenocarcinoma (STAD) also known as gastric cancer, and uterine corpus endometrial carcinoma (UCEC). The ICOS levels are plotted as box plots in FIG. 36, grouped first by indication and then by MSI status (MSI-high, MSI-low, and MSS). Boxes indicate the upper and lower quartiles of expression, with the median line being shown by a dashed line. Outliers are plotted for any tumor in which ICOS was expressed at a level that is more than the interquartile range outside of the upper or lower quartile. The distribution of individual tumors is shown by the histogram in darker grey displayed vertically across each individual box. Expression is shown as log 2(FPKM). A Kruskal-Wallis test was applied across MSI/MSS status groups within each indication to obtain a p-value for significance of differential expression of ICOS across MSI/MSS groups.

Figure 36:
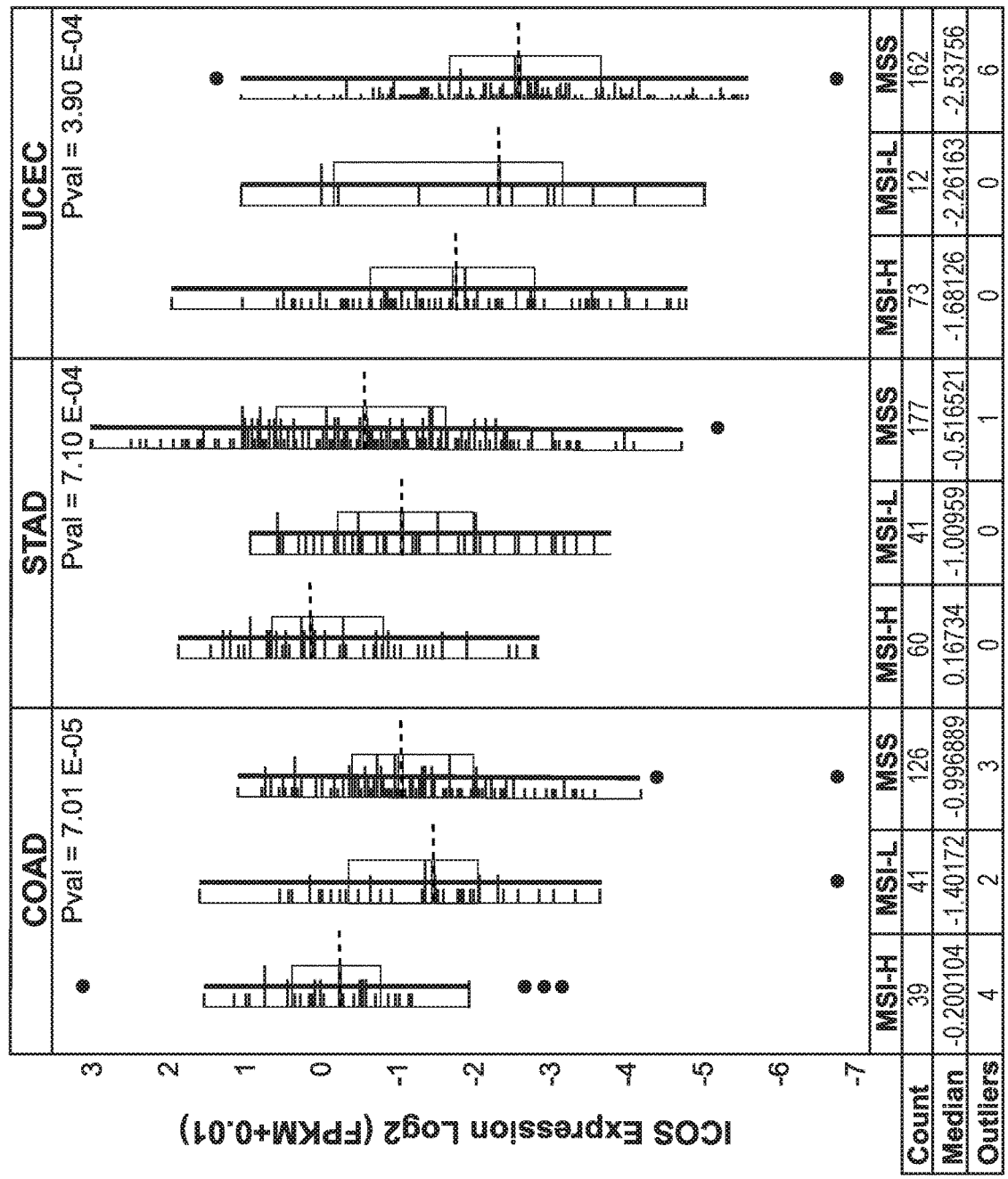
FIG. 36. Higher ICOS levels are observed on Micosatellite Instability high (MSI-high) tumors than on MSI-low or Microsatellite Stable (MSS) tumors. The expression of ICOS is shown across colon adenocarcinoma (COAD), stomach adenocarcinoma (STAD; also known as gastric cancer), and uterine corpus endometrial carcinoma (UCEC) subdivided by MSI/MSS status.

As shown in FIG. 36, ICOS levels are generally higher in the MSI-high groups than in the MSI-low or MSS groups in all indications when comparing the medians (dashed line) of each group. Kruskal-Wallis analysis provides p-values of <0.001, suggesting the differential expression is significant.

These results indicate that MSI positive patients may benefit from agonist anti-ICOS antibody therapy.

MSI can be assayed by PCR, for example, according to NCI guidelines, as discussed above (Boland et al., 1998, *Cancer Res.* 58: 5248-5257; see also Table 10). IHC analysis can also be performed to detect MLH1, MSH2, MSH6, and/or PMS2, as the loss of expression of these genes may contribute to the MSI phenotype (See, e.g., Umar et al., 2004, *J. Natl. Cancer Inst.* 96: 261-268; AMA and NCHPEG Colorectal Cancer Fact Sheets: 11-0456:2/12:jt:Updated February 2012; Mayo clinic guidelines: mayomedicallaboratories.com/test-catalog/Clinical+and+Interpretive/35458).

Example 17: Stratification of Cancer Subtypes According to ICOS Expression

The level of ICOS expression in various tumor subtypes may be assessed using the high-dimensional data set from The Cancer Genome Atlas (TCGA). Raw sequence data is prepared and gene expression values utilizing the fragments per kilobase of exon per million fragments mapped (FPKM) are computed by OmicSoft Corporation utilizing their proprietary data normalization and expression analysis pipeline. FPKM values are converted using a logarithmic function with a base 2 and analyzed.

The ICOS expression in various human tumor subtypes is shown in Table 11. As shown in that table, certain subtypes of tumors have higher expression levels of ICOS than other subtypes of the same tumor. For example, terminal respiratory unit (TRU) and prox-inflammatory subtypes of lung adenocarcinoma have higher ICOS expression than prox-proliferation subtype of lung adenocarcinoma. Similary, secretory lung squamous cell carcinoma (lung SCC) has higher ICOS expression than primordial, classical, or basal subtypes of lung SCC. Of the head and neck subtypes, only classical had low ICOS expression levels. Of the breast invasive carcinoma subtypes tested, HER2+ and triple negative had the highest ICOS expression. Of the uterine corpus endometrial carcinoma subtypes tested, POLE mutation subtype has the highest ICOS expression. HPV+ cervical squamous cell carcinoma and endocervical adenocarcinoma had higher ICOS expression than HPV-. All of the stomach adenocarcinoma subtypes tested had high ICOS expression. Of the bladder urothelial carcinoma subtypes tested, basal IV (mesenchymal) subtype had the higheste ICOS expression. Of the pancreatic adenocarcinoma subtypes tested, only immunogenic showed high ICOS expression levels. Of the liver hepatocellular carcinoma subtypes tested, S1 subtype had the highest ICOS expression.

TABLE 11

Cancer subtype ICOS expression

| | | ICOS expression | | | |
|---|---|---|---|---|---|
| Cancer type | Subtype | $Log_2(FPKM) \geq 1.06$ (ICOS high) | $Log_2(FPKM) =$ 0.21-1.06 | $Log_2(FPKM) =$ (-1.01)-0.21 | $Log_2(FPKM) \leq$ (-1.01) (ICOS low) |
| Lung adenocarcinoma (LUAD) | Terminal respiratory unit (TRU) | 10.8% | 20.1% | 39.6% | 29.5% |
| | Prox-Proliferation | 0.9% | 8.9% | 28.6% | 61.6% |
| | Prox-Inflammatory | 17.7% | 30.0% | 37.7% | 14.6% |
| Lung squamous cell carcinoma (LUSC) | Primordial | 1.8% | 10.7% | 26.8% | 60.7% |
| | Classical | 0% | 10.4% | 24.4% | 65.3% |
| | Secretory | 26.0% | 34.1% | 30.1% | 9.8% |
| | Basal | 3.1% | 14.7% | 34.1% | 48.1% |
| Head and Neck Squamous Cell Carcinoma (HNSCC) | HPV+ | 36.4% | 22.7% | 22.7% | 18.2% |
| | HPV- | 22.8% | 19.2% | 33.9% | 24.1% |
| | Basal | 14.7% | 25.3% | 42.7% | 17..3% |
| | Atypical | 26.9% | 17.3% | 36.5% | 19.2% |
| | Classical | 0% | 4.5% | 31.1% | 64.4% |
| | Mesenchymal | 45.9% | 24.3% | 21.6% | 8.1% |

TABLE 11-continued

Cancer subtype ICOS expression

| Cancer type | Subtype | ICOS expression | | | |
|---|---|---|---|---|---|
| | | $Log_2(FPKM) \geq 1.06$ (ICOS high) | $Log_2(FPKM) =$ 0.21-1.06 | $Log_2(FPKM) =$ (−1.01)-0.21 | $Log_2(FPKM) \leq$ (−1.01) (ICOS low) |
| Breast invasive | Luminal A | 5.1% | 5.7% | 15.5% | 73.7% |
| carcinoma (BRCA) | Luminal B | 7.2% | 10.4% | 24.0% | 58.4% |
| | HER2+ | 10.3% | 13.8% | 27.6% | 48.3% |
| | Triple Negative (basal) | 22.7% | 18.2% | 24.5% | 34.5% |
| Uterine Corpus | POLE mutation | 8.9% | 11.8% | 24.6% | 52.9% |
| Endometrial | MSI | 3.1% | 7.7% | 24.6% | 64.6% |
| Carcinoma | CN low | 0% | 0% | 7.7% | 92.3% |
| (UCEC) | CN high | 3.1% | 3.2% | 17.5% | 76.2% |
| Cervical squamous | HPV+ | 8.9% | 15.6% | 35.8% | 39.7% |
| cell carcinoma and endocervical adenocarcinoma (CESC) | HPV− | 4.3% | 8.7% | 8.7% | 78.3% |
| Stomach | MSI-H | 13.3% | 31.7% | 36.7% | 18.3% |
| adenocarcinoma | CN stable | 9.1% | 27.3% | 32.7% | 30.9% |
| (Gastric, STAD) | EBV+ | 24.0% | 36.0% | 24.0% | 16.0% |
| | CN Instable | 6.5% | 15.9% | 29.7% | 47.8% |
| Bladder Urothelial | Luminal I (Papillary) | 1.4% | 3.5% | 7.6% | 87.5% |
| Carcinoma (BLCA) | Luminal II | 4.5% | 9.0% | 22.6% | 63.9% |
| | Basal III (Squamous) | 2.3% | 16.3% | 31.4% | 50.0% |
| | Basal IV (Mesenchymal) | 29.2% | 37.5% | 20.8% | 12.5% |
| Pancreatic | ADEX | 0.0% | 9.4% | 24.5% | 66.0% |
| adenocarcinoma | Immunogenic | 14.3% | 19.0% | 38.1% | 28.6% |
| (PAAD) | Progenitor | 0.0% | 0.0% | 11.1% | 88.9% |
| | Squamous | 0.0% | 0.0% | 28.2% | 71.8% |
| Liver hepatocellular | S1 Subtype | 3.6% | 17.3% | 23.6% | 55.5% |
| carcinoma (LIHC) | S2 | 0.0% | 4.3% | 12.0% | 83.7% |
| | S3 | 0.6% | 0.0% | 6.4% | 93.0% |

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

Table of Sequences

| SEQ ID NO | Description | Sequence |
|---|---|---|
| 1 | Human ICOS precursor (with signal sequence); UniProtKB/Swiss-Prot: Q9Y6W8.1 07-JAN-2015 | MKSGLWYFFL FCLRIKVLTG EINGSANYEM FIFHNGGVQI LCKYPDIVQQ FKMQLLKGGQ ILCDLTKTKG SGNTVSIKSL KFCHSQLSNN SVSFFLYNLD HSHANYYFCN LSIFDPPPFK VTLTGGYLHI YESQLCCQLK FWLPIGCAAF VVVCILGCIL ICWLTKKKYS SSVHDPNGEY MFMRAVNTAK KSRLTDVTL |
| 2 | Human mature ICOS (without signal sequence) | EINGSANYEM FIFHNGGVQI LCKYPDIVQQ FKMQLLKGGQ ILCDLTKTKG SGNTVSIKSL KFCHSQLSNN SVSFFLYNLD HSHANYYFCN LSIFDPPPFK VTLTGGYLHI YESQLCCQLK FWLPIGCAAF VVVCILGCIL ICWLTKKKYS SSVHDPNGEY MFMRAVNTAK KSRLTDVTL |
| 3 | Mouse ICOS precursor (with signal sequence); UniProtKB/Swiss-Prot: Q9WVS0.2; 07-JAN-2015 | MKPYFCRVFV FCFLIRLLTG EINGSADHRM FSFHNGGVQI SCKYPETVQQ LKMRLFRERE VLCELTKTKG SGNAVSIKNP MLCLYHLSNN SVSFFLNNPD SSQGSYYFCS LSIFDPPPFQ ERNLSGGYLH IYESQLCCQL KLWLPVGCAA FVVVLLFGCI LIIWFSKKKY GSSVHDPNSE YMFMAAVNTN KKSRLAGVTS |
| 4 | Mouse mature ICOS (without signal sequence) | EINGSADHRM FSFHNGGVQI SCKYPETVQQ LKMRLFRERE VLCELTKTKG SGNAVSIKNP MLCLYHLSNN SVSFFLNNPD SSQGSYYFCS LSIFDPPPFQ ERNLSGGYLH IYESQLCCQL KLWLPVGCAA FVVVLLFGCI LIIWFSKKKY GSSVHDPNSE YMFMAAVNTN KKSRLAGVTS |

-continued

| SEQ ID NO | Description | Sequence |
|---|---|---|
| 5 | Cynomolgus monkey ICOS precursor (with signal sequence) | MKSGLWYFFL FCLHMKVLTG EINGSANYEM FIFHNGGVQI LCKYPDIVQQ FKMQLLKGGQ ILCDLTKTKG SGNKVSIKSL KFCHSQLSNN SVSFFLYNLD RSHANYYFCN LSIFDPPPFK VTLTGGYLHI YESQLCCQLK FWLPIGCATF VVVCIFGCIL ICWLTKKKYS STVHDPNGEY MFMRAVNTAK KSRLTGTTP |
| 6 | Cynomolgus mature ICOS (without signal sequence) | EINGSANYEM FIFHNGGVQI LCKYPDIVQQ FKMQLLKGGQ ILCDLTKTKG SGNKVSIKSL KFCHSQLSNN SVSFFLYNLD RSHANYYFCN LSIFDPPPFK VTLTGGYLHI YESQLCCQLK FWLPIGCATF VVVCIFGCIL ICWLTKKKYS STVHDPNGEY MFMRAVNTAK KSRLTGTTP |
| 10 | 7F12 heavy chain variable region | E V Q L V E S G G G L V K P G G S L T L S C A A S G F T F S D Y W M D W V R Q G P G K G L E W V G N I D E D G S T T Y Y A P F V K G R F T I S R D N A K K T L Y L Q M N S V K S E D T A T Y Y C T R W G R Y A F D S W G Q G T L V T V S S |
| 11 | 7F12 light chain variable region | D I V M T Q S P S S L A V S P G D K V T I N C K S S Q S L L S G N Y N Y L A W Y Q Q K T G Q A P K L L I F Y A S T R H T G V P D R F M G S G S G T D F S L T I N S F Q T E D L G D Y Y C Q H H Y S T P P T F G P G T K L E I K |
| 12 | 7F12 VH CDR1 | G F T F S D Y W M D |
| 13 | 7F12 VH CDR2 | N I D E D G S T T Y Y A P F V K G |
| 14 | 7F12 VH CDR3 | W G R Y A F D S |
| 15 | 7F12 VL CDR1 | K S S Q S L L S G N Y N Y L A |
| 16 | 7F12 VL CDR2 | Y A S T R H T |
| 17 | 7F12 VL CDR3 | Q H H Y S T P P T |
| 20 | 37A10 heavy chain variable region | E V Q L V E S G G G L V K P G G S L K L S C A A S G F T F S D Y W M D W V R Q A P G K G L E W V G N I D E D G S I T E Y S P F V K G R F T I S R D N V K N T L Y L Q M N S V K S E D T A T Y Y C T R W G R F G F D S W G Q G T L V T V S S |
| 21 | 37A10 light chain variable region | D I V M T Q S P S S L A V S A G D R V T I N C K S S Q S L L S G S F N Y L T W Y Q Q K T G Q A P K L L I F Y A S T R H T G V P D R F M G S G S G T D F T L T I N S F Q T E D L G D Y Y C H H H Y N A P P T F G P G T K L E L R |
| 22 | 37A10 VH CDR1 | G F T F S D Y W M D |
| 23 | 37A10 VH CDR2 | N I D E D G S I T E Y S P F V K G |
| 24 | 37A10 VH CDR3 | W G R F G F D S |
| 25 | 37A10 VL CDR1 | K S S Q S L L S G S F N Y L T |
| 26 | 37A10 VL CDR2 | Y A S T R H T |
| 27 | 37A10 VL CDR3 | H H H Y N A P P T |
| 30 | 35A9 heavy chain variable region | E V Q L V E S G G G L V K P G G S L K L S C A A S G F T F S D Y W M D W V R Q A P G K G L E W V G N I D E D G S I A E Y S P F V K G R F T I S R D N V K N T L Y L Q M N S V K S E D T A T Y Y C S R W G R F A F D S W G Q G T L V T V S S |
| 31 | 35A9 light chain variable region | D I V M T Q S P S S L A V S A G D R V T I N C K S S Q S L L S G S F N Y L T W Y Q Q K T G Q A P K L L I F Y A S T R H T G V P D R F M G S G S G T D F T L T I N S F Q T E D L G D Y Y C H H H Y N A P P T F G P G T K L E L R |

-continued

Table of Sequences

| SEQ ID NO | Description | Sequence |
|---|---|---|
| 32 | 35A9 VH CDR1 | G F T F S D Y W M D |
| 33 | 35A9 VH CDR2 | N I D E D G S I A E Y S P F V K G |
| 34 | 35A9 VH CDR3 | W G R F A F D S |
| 35 | 35A9 VL CDR1 | K S S Q S L L S G S F N Y L T |
| 36 | 35A9 VL CDR2 | Y A S T R H T |
| 37 | 35A9 VL CDR3 | H H H Y N A P P T |
| 40 | 36E10 heavy chain variable region | E V Q L V E S G G G L V K P G G S L K L S C A A S G F T F S D Y W M D W V R Q A P G K G L E W V G N I D E D G S I T E Y S P F V K G R F T I S R D N V K N I L Y L Q M N S V K S E D T A T Y Y C T R W G R F A F D S W G Q G T L V T V S S |
| 41 | 36E10 light chain variable region | D I V M T Q S P S S L A V S P G D R V T I N C K S S Q S L L S G S F H Y L T W Y Q Q K T G Q A P K L L I F Y A S T R H T G V P D R F M G S G S G T D F T L T I N S F Q T E D L G D Y Y C H H H Y N A P P T F G P G T K L E L R |
| 42 | 36E10 VH CDR1 | G F T F S D Y W M D |
| 43 | 36E10 VH CDR2 | N I D E D G S I T E Y S P F V K G |
| 44 | 36E10 VH CDR3 | W G R F A F D S |
| 45 | 36E10 VL CDR1 | K S S Q S L L S G S F H Y L T |
| 46 | 36E10 VL CDR2 | Y A S T R H T |
| 47 | 36E10 VL CDR3 | H H H Y N A P P T |
| 50 | 16G10 heavy chain variable region | E V Q L V E S G G G L V K P G G S L K L S C A A S G F T F S D Y W M D W V R Q A P G K G L E W V G N I D H D G N I I N F A P S V K G R F T I S R D N A K N T L Y L Q M N S V K S E D T A T Y Y C A R W G H Y A F D S W G Q G T L V T V S S |
| 51 | 16G10 light chain variable region | D I V M T Q S P S S L A V S A G D K V T I N C K S S Q S L L S S G Y N Y L I W Y Q Q K T G Q A P K L L I F Y A S T R H T G V P D R F I G S G S G T D F T L T I T S F Q T E D L G D Y Y C Q H H Y S S P P T F G P G T K L E I K |
| 52 | 16G10 VH CDR1 | G F T F S D Y W M D |
| 53 | 16G10 VH CDR2 | N I D H D G N I I N F A P S V K G |
| 54 | 16G10 VH CDR3 | W G H Y A F D S |
| 55 | 16G10 VL CDR1 | K S S Q S L L S S G Y N Y L I |
| 56 | 16G10 VL CDR2 | Y A S T R H T |
| 57 | 16G10 VL CDR3 | Q H H Y S S P P T |
| 60 | 37A10S713 heavy chain variable region | EVQLVESGGG LVQPGGSLRL SCAASGFTFS DYWMDWVRQA PGKGLVWVSN IDEDGSITEY SPFVKGRFTI SRDNAKNTLY LQMNSLRAED TAVYYCTRWG RFGFDSWGQG TLVTVSS |
| 61 | 37A10S713 light chain variable region | DIVMTQSPDS LAVSLGERAT INCKSSQSLL SGSFNYLTWY QQKPGQPPKL LIFYASTRHT GVPDRFSGSG SGTDFTLTIS SLQAEDVAVY YCHHHYNAPP TFGPGTKVDI K |
| 62 | 37A10S713 VH CDR1 | GFTFSDYWMD |
| 63 | 37A10S713 VH CDR2 | NIDEDGSITEYSPFVKG |

-continued

Table of Sequences

| SEQ ID NO | Description | Sequence |
|---|---|---|
| 64 | 37A10S713 VH CDR3 | WGRFGFDS |
| 65 | 37A10S713 VL CDR1 | KSSQSLLSGSFNYLT |
| 66 | 37A10S713 VL CDR2 | YASTRHT |
| 67 | 37A10S713 VL CDR3 | HHHYNAPPT |
| 70 | 37A10S714 heavy chain variable region | EVQLVESGGG LVQPGGSLRL SCAASGFTFS DYWMDWVRQA PGKGLVWVSN IDEDGSITEY SPFVKGRFTI SRDNAKNTLY LQMNSLRAED TAVYYCTRWG RFGFDSWGQG TLVTVSS |
| 71 | 37A10S714 light chain variable region | DIVMTQSPDS LAVSLGERAT INCKSSQSLL SGSFNYLTWY QQKPGQPPKL LIFYASTRET GVPDRFSGSG SGTDFTLTIS SLQAEDVAVY YCHHHYNAPP TFGPGTKVDI K |
| 72 | 37A10S714 VH CDR1 | GFTFSDYWMD |
| 73 | 37A10S714 VH CDR2 | NIDEDGSITEYSPFVKG |
| 74 | 37A10S714 VH CDR3 | WGRFGFDS |
| 75 | 37A10S714 VL CDR1 | KSSQSLLSGSFNYLT |
| 76 | 37A10S714 VL CDR2 | YASTRET |
| 77 | 37A10S714 VL CDR3 | HHHYNAPPT |
| 80 | 37A10S715 heavy chain variable region | EVQLVESGGG LVQPGGSLRL SCAASGFTFS DYWMDWVRQA PGKGLVWVSN IDEDGSITEY SPFVKGRFTI SRDNAKNTLY LQMNSLRAED TAVYYCTRWG RFGFDSWGQG TLVTVSS |
| 81 | 37A10S715 light chain variable region | DIVMTQSPDS LAVSLGERAT INCKSSQSLL SGSFNYLTWY QQKPGQPPKL LIFYASTRQT GVPDRFSGSG SGTDFTLTIS SLQAEDVAVY YCHHHYNAPP TFGPGTKVDI K |
| 82 | 37A10S715 VH CDR1 | GFTFSDYWMD |
| 83 | 37A10S715 VH CDR2 | NIDEDGSITEYSPFVKG |
| 84 | 37A10S715 VH CDR3 | WGRFGFDS |
| 85 | 37A10S715 VL CDR1 | KSSQSLLSGSFNYLT |
| 86 | 37A10S715 VL CDR2 | YASTRQT |
| 87 | 37A10S715 VL CDR3 | HHHYNAPPT |
| 90 | 37A10S716 heavy chain variable region | EVQLVESGGG LVQPGGSLRL SCAASGFTFS DYWMDWVRQA PGKGLVWVSN IDESGSITEY SPFVKGRFTI SRDNAKNTLY LQMNSLRAED TAVYYCTRWG RFGFDSWGQG TLVTVSS |
| 91 | 37A10S716 light chain variable region | DIVMTQSPDS LAVSLGERAT INCKSSQSLL SGSFNYLTWY QQKPGQPPKL LIFYASTRHT GVPDRFSGSG SGTDFTLTIS SLQAEDVAVY YCHHHYNAPP TFGPGTKVDI K |
| 92 | 37A10S716 VH CDR1 | GFTFSDYWMD |
| 93 | 37A10S716 VH CDR2 | NIDESGSITEYSPFVKG |
| 94 | 37A10S716 VH CDR3 | WGRFGFDS |
| 95 | 37A10S716 VL CDR1 | KSSQSLLSGSFNYLT |
| 96 | 37A10S716 VL CDR2 | YASTRHT |
| 97 | 37A10S716 VL CDR3 | HHHYNAPPT |
| 100 | 37A10S717 heavy chain variable region | EVQLVESGGG LVQPGGSLRL SCAASGFTFS DYWMDWVRQA PGKGLVWVSN IDESGSITEY SPFVKGRFTI SRDNAKNTLY LQMNSLRAED TAVYYCTRWG RFGFDSWGQG TLVTVSS |

| SEQ ID NO | Description | Sequence |
|---|---|---|
| 101 | 37A10S717 light chain variable region | DIVMTQSPDS LAVSLGERAT INCKSSQSLL SGSFNYLTWY QQKPGQPPKL LIFYASTRET GVPDRFSGSG SGTDFTLTIS SLQAEDVAVY YCHHHYNAPP TFGPGTKVDI K |
| 102 | 37A10S717 VH CDR1 | GFTFSDYWMD |
| 103 | 37A10S717 VH CDR2 | NIDESGSITEYSPFVKG |
| 104 | 37A10S717 VH CDR3 | WGRFGFDS |
| 105 | 37A10S717 VL CDR1 | KSSQSLLSGSFNYLT |
| 106 | 37A10S717 VL CDR2 | YASTRET |
| 107 | 37A10S717 VL CDR3 | HHHYNAPPT |
| 110 | 37A10S718 heavy chain variable region | EVQLVESGGG LVQPGGSLRL SCAASGFTFS DYWMDWVRQA PGKGLVWVSN IDESGSITEY SPFVKGRFTI SRDNAKNTLY LQMNSLRAED TAVYYCTRWG RFGFDSWGQG TLVTVSS |
| 111 | 37A10S718 light chain variable region | DIVMTQSPDS LAVSLGERAT INCKSSQSLL SGSFNYLTWY QQKPGQPPKL LIFYASTRQT GVPDRFSGSG SGTDFTLTIS SLQAEDVAVY YCHHHYNAPP TFGPGTKVDI K |
| 112 | 37A10S718 VH CDR1 | GFTFSDYWMD |
| 113 | 37A10S718 VH CDR2 | NIDESGSITEYSPFVKG |
| 114 | 37A10S718 VH CDR3 | WGRFGFDS |
| 115 | 37A10S718 VL CDR1 | KSSQSLLSGSFNYLT |
| 116 | 37A10S718 VL CDR2 | YASTRQT |
| 117 | 37A10S718 VL CDR3 | HHHYNAPPT |
| 120 | 16G10S71 heavy chain variable region | EVQLVESGGG LVQPGGSLRL SCAASGFTFS DYWMDWVRQA PGKGLVWVSN IDHDGNIINF APSVKGRFTI SRDNAKNTLY LQMNSLRAED TAVYYCARWG HYAFDSWGQG TLVTVSS |
| 121 | 16G10S71 light chain variable region | DIVMTQSPDS LAVSLGERAT INCKSSQSLL SSGYNYLIWY QQKPGQPPKL LIFYASTRHT GVPDRFSGSG SGTDFTLTIS SLQAEDVAVY YCQHHYSSPP TFGPGTKVDI K |
| 122 | 16G10S71 VH CDR1 | GFTFSDYWMD |
| 123 | 16G10S71 VH CDR2 | NIDHDGNIINFAPSVKG |
| 124 | 16G10S71 VH CDR3 | WGHYAFDS |
| 125 | 16G10S71 VL CDR1 | KSSQSLLSSGYNYLI |
| 126 | 16G10S71 VL CDR2 | YASTRHT |
| 127 | 16G10S71 VL CDR3 | QHHYSSPPT |
| 130 | 16G10S72 heavy chain variable region | EVQLVESGGG LVQPGGSLRL SCAASGFTFS DYWMDWVRQA PGKGLVWVSN IDHDGNIINF APSVKGRFTI SRDNAKNTLY LQMNSLRAED TAVYYCARWG HYAFDSWGQG TLVTVSS |
| 131 | 16G10S72 light chain variable region | DIVMTQSPDS LAVSLGERAT INCKSSQSLL SSGYNYLIWY QQKPGQPPKL LIFYASTRET GVPDRFSGSG SGTDFTLTIS SLQAEDVAVY YCQHHYSSPP TFGPGTKVDI K |
| 132 | 16G10S72 VH CDR1 | GFTFSDYWMD |
| 133 | 16G10S72 VH CDR2 | NIDHDGNIINFAPSVKG |
| 134 | 16G10S72 VH CDR3 | WGHYAFDS |
| 135 | 16G10S72 VL CDR1 | KSSQSLLSSGYNYLI |

Table of Sequences

| SEQ ID NO | Description | Sequence |
|---|---|---|
| 136 | 16G10S72 VL CDR2 | YASTRET |
| 137 | 16G10S72 VL CDR3 | QHHYSSPPT |
| 140 | 16G10S73 heavy chain variable region | EVQLVESGGG LVQPGGSLRL SCAASGFTFS DYWMDWVRQA PGKGLVWVSN IDHDGNIINF APSVKGRFTI SRDNAKNTLY LQMNSLRAED TAVYYCARWG HYAFDSWGQG TLVTVSS |
| 141 | 16G10S73 light chain variable region | DIVMTQSPDS LAVSLGERAT INCKSSQSLL SSGYNYLIWY QQKPGQPPKL LIFYASTRQT GVPDRFSGSG SGTDFTLTIS SLQAEDVAVY YCQHHYSSPP TFGPGTKVDI K |
| 142 | 16G10S73 VH CDR1 | GFTFSDYWMD |
| 143 | 16G10S73 VH CDR2 | NIDHDGNIINFAPSVKG |
| 144 | 16G10S73 VH CDR3 | WGHYAFDS |
| 145 | 16G10S73 VL CDR1 | KSSQSLLSSGYNYLI |
| 146 | 16G10S73 VL CDR2 | YASTRQT |
| 147 | 16G10S73 VL CDR3 | QHHYSSPPT |
| 150 | 16G10S83 heavy chain variable region | EVQLVESGGG LVQPGGSLRL SCAASGFTFS DYWMDWVRQA PGKGLEWVSN IDHDGNIINF APSVKGRFTI SRDNAKNSLY LQMNSVRAED TAVYYCARWG HYAFDSWGQG TLVTVSS |
| 151 | 16G10S83 light chain variable region | DIVMTQSPDS LAVSAGERVT INCKSSQSLL SSGYNYLIWY QQKPGQPPKL LIFYASTRQT GVPDRFSGSG SGTDFTLTIS SLQAEDVAVY YCQHHYSSPP TFGQGTKLEI K |
| 152 | 16G10S83 VH CDR1 | GFTFSDYWMD |
| 153 | 16G10S83 VH CDR2 | NIDHDGNIINFAPSVKG |
| 154 | 16G10S83 VH CDR3 | WGHYAFDS |
| 155 | 16G10S83 VL CDR1 | KSSQSLLSSGYNYLI |
| 156 | 16G10S83 VL CDR2 | YASTRQT |
| 157 | 16G10S83 VL CDR3 | QHHYSSPPT |
| 160 | 35A9S79 heavy chain variable region | EVQLVESGGG LVQPGGSLRL SCAASGFTFS DYWMDWVRQA PGKGLVWVSN IDEDGSIAEY SPFVKGRFTI SRDNAKNTLY LQMNSLRAED TAVYYCSRWG RFAFDSWGQG TLVTVSS |
| 161 | 35A9S79 light chain variable region | DIVMTQSPDS LAVSLGERAT INCKSSQSLL SGSFNYLTWY QQKPGQPPKL LIFYASTRQT GVPDRFSGSG SGTDFTLTIS SLQAEDVAVY YCHHHYNAPP TFGPGTKVDI K |
| 162 | 35A9S79 VH CDR1 | GFTFSDYWMD |
| 163 | 35A9S79 VH CDR2 | NIDEDGSIAEYSPFVKG |
| 164 | 35A9S79 VH CDR3 | WGRFAFDS |
| 165 | 35A9S79 VL CDR1 | KSSQSLLSGSFNYLT |
| 166 | 35A9S79 VL CDR2 | YASTRQT |
| 167 | 35A9S79 VL CDR3 | HHHYNAPPT |
| 170 | 35A9S710 heavy chain variable region | EVQLVESGGG LVQPGGSLRL SCAASGFTFS DYWMDWVRQA PGKGLVWVSN IDESGSIAEY SPFVKGRFTI SRDNAKNTLY LQMNSLRAED TAVYYCSRWG RFAFDSWGQG TLVTVSS |
| 171 | 35A9S710 light chain variable region | DIVMTQSPDS LAVSLGERAT INCKSSQSLL SGSFNYLTWY QQKPGQPPKL LIFYASTRHT GVPDRFSGSG SGTDFTLTIS SLQAEDVAVY YCHHHYNAPP TFGPGTKVDI K |
| 172 | 35A9S710 VH CDR1 | GFTFSDYWMD |

-continued

Table of Sequences

| SEQ ID NO | Description | Sequence |
|---|---|---|
| 173 | 35A9S710 VH CDR2 | NIDESGSIAEYSPFVKG |
| 174 | 35A9S710 VH CDR3 | WGRFAFDS |
| 175 | 35A9S710 VL CDR1 | KSSQSLLSGSFNYLT |
| 176 | 35A9S710 VL CDR2 | YASTRHT |
| 177 | 35A9S710 VL CDR3 | HHHYNAPPT |
| 180 | 35A9S89 heavy chain variable region | EVQLVESGGG LVQPGGSLRL SCAASGFTFS DYWMDWVRQA PGKGLEWVSN IDEDGSIAEY SPFVKGRFTI SRDNSKNTLY LQMNSLRAED TAVYYCSRWG RFAFDSWGQG TLVTVSS |
| 181 | 35A9S89 light chain variable region | DIVMTQSPDS LAVSAGERVT INCKSSQSLL SGSFNYLTWY QQKPGQPPKL LIFYASTRQT GVPDRFSGSG SGTDFTLTIS SLQAEDVAVY YCHHHYNAPP TFGQGTKLEI K |
| 182 | 35A9S89 VH CDR1 | GFTFSDYWMD |
| 183 | 35A9S89 VH CDR2 | NIDEDGSIAEYSPFVKG |
| 184 | 35A9S89 VH CDR3 | WGRFAFDS |
| 185 | 35A9S89 VL CDR1 | KSSQSLLSGSFNYLT |
| 186 | 35A9S89 VL CDR2 | YASTRQT |
| 187 | 35A9S89 VL CDR3 | HHHYNAPPT |
| 188 | 37A10S713 human IgG1 heavy chain | EVQLVESGGG LVQPGGSLRL SCAASGFTFS DYWMDWVRQA PGKGLVWVSN IDEDGSITEY SPFVKGRFTI SRDNAKNTLY LQMNSLRAED TAVYYCTRWG RFGFDSWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 189 | 37A10S713 human κ light chain | DIVMTQSPDS LAVSLGERAT INCKSSQSLL SGSFNYLTWY QQKPGQPPKL LIFYASTRHT GVPDRFSGSG SGTDFTLTIS SLQAEDVAVY YCHHHYNAPP TFGPGTKVDI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 190 | Rat ICOS precursor (with signal sequence); UniProt Q9R1T7 | MKPYFSCVFV FCFLIKLLTG ELNDLANHRM FSFHDGGVQI SCNYPETVQQ LKMQLFKDRE VLCDLTKTKG SGNTVSIKNP MSCPYQLSNN SVSFFLDNAD SSQGSYFLCS LSIFDPPPFQ EKNLSGGYLL IYESQLCCQL KLWLPVGCAA FVAALLFGCI FIVWFAKKKY RSSVHDPNSE YMFMAAVNTN KKSRLAGMTS |
| 191 | Mature rat ICOS (without signal sequence) | ELNDLANHRM FSFHDGGVQI SCNYPETVQQ LKMQLFKDRE VLCDLTKTKG SGNTVSIKNP MSCPYQLSNN SVSFFLDNAD SSQGSYFLCS LSIFDPPPFQ EKNLSGGYLL IYESQLCCQL KLWLPVGCAA FVAALLFGCI FIVWFAKKKY RSSVHDPNSE YMFMAAVNTN KKSRLAGMTS |
| 192 | 2M13 heavy chain variable region | EVQLQQSGAE LVRPGAVVKL SCKASGFDIK DYYMHWVQQR PEQGLEWIGW IDPENGNAVY DPQFQGKASI TADTSSNTAY LQLSSLTSED TAVYYCASDY YGSKGYLDVW GAGTTVTSS |
| 193 | 2M13 light chain variable region | QIVLTQSPTI MSASPGEKVT ITCSASSSVS YMHWFQQKPG TSPKLWIYST SNLASGVPAR FGGSRSGTSY SLTISRMEAE DAATYYCQQR SSYPFTFGSG TKLEIK |
| 194 | 2M13 VH CDR1 | DYYMH |

Table of Sequences

| SEQ ID NO | Description | Sequence |
|---|---|---|
| 195 | 2M13 VH CDR2 | WIDPENGNAVYDPQFQG |
| 196 | 2M13 VH CDR3 | DYYGSKGYLDV |
| 197 | 2M13 VL CDR1 | SASSSVSYMH |
| 198 | 2M13 VL CDR2 | STSNLAS |
| 199 | 2M13 VL CDR3 | QQRSSYPFT |
| 200 | 2M19 heavy chain variable region | EVQLQQSGAE LVRSGASVKL SCTTSAFNII DYYMHWVIQR PEQGLEWIAW IDPENGDPEY APKFQDKATM TTDTSSNTAY LQLSSLTSED TAVYYCTAWR GFAYWGQGTL VTVSA |
| 201 | 2M19 light chain variable region | DVVMTQTPLS LPVSLGDQAS ISCRSSQSLV HSNGNTYLHW YLQKPGQSPK LLIYKVSNRF SGVPDRFSGS GSGTDFTLKI SRVEAEDLGV YFCSQSIHVP PTFGGGTKLE IK |
| 202 | 2M19 VH CDR1 | DYYMH |
| 203 | 2M19 VH CDR2 | WIDPENGDPEYAPKFQD |
| 204 | 2M19 VH CDR3 | WRGFAY |
| 205 | 2M19 VL CDR1 | RSSQSLVHSNGNTYLH |
| 206 | 2M19 VL CDR2 | KVSNRFS |
| 207 | 2M19 VL CDR3 | SQSIHVPPT |
| 208 | 2M24 heavy chain variable region | EVQLQQSGAE LVRSGASVKL SCTASGFNIR DYYMHWVRQR PEQGLEWIGW IDPENGDIDY APKFQDKATM TADTSSNTAY LQLSSLTSED SAVYYFTAWK GLAYWGQGTL VTVSA |
| 209 | 2M24 light chain variable region | DVVMTQTPLS LPVSLGDQAS MSCRSSQSLV HSNGNTYLQW YLQKPGQSPK LLIYKVFNRF SGVPDRFSGS GSGTDFTLKI SRVEAEDLGV YFCSQSTHVP PTFGGGTKLE IK |
| 210 | 2M24 VH CDR1 | DYYMH |
| 211 | 2M24 VH CDR2 | WIDPENGDIDYAPKFQD |
| 212 | 2M24 VH CDR3 | WKGLAY |
| 213 | 2M24 VL CDR1 | RSSQSLVHSNGNTYLQ |
| 214 | 2M24 VL CDR2 | KVFNRFS |
| 215 | 2M24 VL CDR3 | SQSTHVPPT |

What is claimed is:

1. An isolated antibody comprising:
   a. (a) HCDR1 comprising the amino acid sequence of SEQ ID NO: 194; (b) HCDR2 comprising the amino acid sequence of SEQ ID NO: 195; (c) HCDR3 comprising the amino acid sequence of SEQ ID NO: 196; (d) LCDR1 comprising the amino acid sequence of SEQ ID NO: 197; (e) LCDR2 comprising the amino acid sequence of SEQ ID NO: 198; and (f) LCDR3 comprising the amino acid sequence of SEQ ID NO: 199; or
   b. (a) HCDR1 comprising the amino acid sequence of SEQ ID NO: 202; (b) HCDR2 comprising the amino acid sequence of SEQ ID NO: 203; (c) HCDR3 comprising the amino acid sequence of SEQ ID NO: 204; (d) LCDR1 comprising the amino acid sequence of SEQ ID NO: 205; (e) LCDR2 comprising the amino acid sequence of SEQ ID NO: 206; and (f) LCDR3 comprising the amino acid sequence of SEQ ID NO: 207; or
   c. (a) HCDR1 comprising the amino acid sequence of SEQ ID NO: 210; (b) HCDR2 comprising the amino acid sequence of SEQ ID NO: 211; (c) HCDR3 comprising the amino acid sequence of SEQ ID NO: 212; (d) LCDR1 comprising the amino acid sequence of SEQ ID NO: 213; (e) LCDR2 comprising the amino acid sequence of SEQ ID NO: 214; and (f) LCDR3 comprising the amino acid sequence of SEQ ID NO: 215.

2. The isolated antibody of claim 1, wherein the antibody comprises a heavy chain variable region ($V_H$) and a light chain variable region ($V_L$), wherein:
   a. the $V_H$ is at least 90%, 91%, 92%, 93%, 94%, 95%, 96%, 97%, 98%, 99%, or 100% identical to the amino acid sequence of SEQ ID NO: 192 and the $V_L$ is at least 90%, 91%, 92%, 93%, 94%, 95%, 96%, 97%, 98%, 99%, or 100% identical to the amino acid sequence of SEQ ID NO: 193; or
   b. the $V_H$ is at least 90%, 91%, 92%, 93%, 94%, 95%, 96%, 97%, 98%, 99%, or 100% identical to the amino acid sequence of SEQ ID NO: 200 and the $V_L$ is at least 90%, 91%, 92%, 93%, 94%, 95%, 96%, 97%, 98%, 99%, or 100% identical to the amino acid sequence of SEQ ID NO: 201; or
   c. the $V_H$ is at least 90%, 91%, 92%, 93%, 94%, 95%, 96%, 97%, 98%, 99%, or 100% identical to the amino acid sequence of SEQ ID NO: 208 and the $V_L$ is at least 90%, 91%, 92%, 93%, 94%, 95%, 96%, 97%, 98%, 99%, or 100% identical to the amino acid sequence of SEQ ID NO: 209.

3. The isolated antibody of claim 1, wherein the antibody comprises a heavy chain variable region ($V_H$) and a light chain variable region ($V_L$), wherein:
   a. the $V_H$ comprises the amino acid sequence of SEQ ID NO: 192 and the $V_L$ comprises the amino acid sequence of SEQ ID NO: 193; or
   b. the $V_H$ comprises the amino acid sequence of SEQ ID NO: 200 and the $V_L$ comprises the amino acid sequence of SEQ ID NO: 201; or
   c. the $V_H$ comprises the amino acid sequence of SEQ ID NO: 208 and the $V_L$ comprises the amino acid sequence of SEQ ID NO: 209.

4. A nucleic acid encoding the antibody of claim 1.

5. A host cell comprising the nucleic acid of claim 4.

6. A method of producing an antibody comprising culturing the host cell of claim 5 under conditions wherein the antibody is expressed.

7. The method of claim 6, further comprising purifying the antibody.

8. A method of detecting ICOS in a sample from a subject, comprising contacting the sample with the antibody of claim 1.

9. The method of claim 8, wherein the method comprises immunohistochemistry.

10. A method of selecting a subject with cancer for treatment with an anti-ICOS antibody, comprising contacting a sample from the subject with the antibody of claim 1.

11. The method of claim 10, wherein the subject has a cancer selected from melanoma, non-small cell lung cancer (NSCLC), renal cell carcinoma (RCC), gastric cancer, bladder cancer, endometrial cancer, diffuse large B-cell lymphoma (DLBCL), Hodgkin's lymphoma, ovarian cancer, head & neck squamous cell cancer (HNSCC), and triple negative breast cancer (TNBC).

12. The method of claim 11, wherein the sample is a tumor sample.

13. The method of claim 12, wherein the method comprises immunohistochemistry.

14. The method of claim 11, wherein the method comprises immunohistochemistry.

15. The method of claim 10, wherein the subject has a cancer selected from melanoma, gastric cancer, endometrial cancer, head & neck squamous cell cancer (HNSCC), non-small cell lung cancer (NSCLC), and triple negative breast cancer (TNBC).

16. The method of claim 15, wherein the sample is a tumor sample.

17. The method of claim 16, wherein the method comprises immunohistochemistry.

18. The method of claim 15, wherein the method comprises immunohistochemistry.

19. The method of claim 10, wherein the sample is a tumor sample.

20. The method of claim 19, wherein the method comprises immunohistochemistry.

21. The method of claim 10, wherein the method comprises immunohistochemistry.

* * * * *